(12) United States Patent
Ohashi et al.

(10) Patent No.: US 6,476,021 B1
(45) Date of Patent: Nov. 5, 2002

(54) COMPOUNDS HAVING CGMP-PDE INHIBITORY EFFECT

(75) Inventors: Masayuki Ohashi; Hidemitsu Nishida; Toshiyuki Shudo, all of Tokyo (JP)

(73) Assignee: Mochida Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 09/580,657

(22) Filed: May 26, 2000

Related U.S. Application Data

(63) Continuation of application No. PCT/JP98/05350, filed on Nov. 27, 1998.

(30) Foreign Application Priority Data

Nov. 28, 1997 (JP) ............................................. 9-344164

(51) Int. Cl.⁷ ................ A61K 31/4375; A61K 31/5365; C07D 471/08; C07D 491/08; C07D 491/18
(52) U.S. Cl. ............................... 514/224.5; 514/229.5; 514/284; 514/287; 514/288; 544/14; 544/31; 544/99; 546/64; 546/66; 546/68; 546/72
(58) Field of Search ............................. 544/14, 31, 99; 546/64, 66, 68, 72; 514/224.5, 229.5, 287, 288, 284

(56) References Cited

U.S. PATENT DOCUMENTS

| | | | |
|---|---|---|---|
| 5,482,941 A | | 1/1996 | Terrett ......................... 514/253 |
| 6,018,046 A | * | 1/2000 | Ohashi et al. ................. 546/62 |
| 6,197,768 B1 | * | 3/2001 | Ohashi et al. ............ 514/233.2 |

FOREIGN PATENT DOCUMENTS

| | | |
|---|---|---|
| CS | 261 338 B | 6/1989 |
| EP | 0 722 936 A1 | 7/1996 |
| EP | 0 985 671 A1 | 3/2000 |
| EP | 0 992 240 A1 | 4/2000 |
| JP | 0710843 | 1/1995 |
| JP | 08253484 | 10/1996 |
| WO | WO94/22855 | 10/1994 |
| WO | WO9616644 | 6/1996 |
| WO | WO99/26946 A1 | 6/1999 |

OTHER PUBLICATIONS

Vishwakarma et al., Chemical Abstracts, vol. 97:162163, 1982.*
Huang et al., Chemical Abstracts, vol.71:49875, 1969.*
Rosenkranz et al., Chemical Abstracts, vol. 68:105409, 1968.*
Daniel Chu; J. Heterocycl. Chem., vol. 25, No. 3, (1988), pp. 927–930, XP001013439.
Stanisl Radl; Collect. Czech. Chem. Commun., vol. 54, No. 2, (1989), pp. 506–515; XP001013437.
Daniel Chu; J. Heterocycl. Chem., vol. 24, No. 2, (1987), pp. 453–456, XP001013634.

* cited by examiner

*Primary Examiner*—Richard L. Raymond
(74) *Attorney, Agent, or Firm*—Birch, Stewart, Kolasch & Birch, LLP

(57) ABSTRACT

Novel fused tetracyclic heterocyclic compounds having a potent and highly selective effect of inhibiting cyclic GMP phosphodiesterase (cGMP-PDE) and a high safety; a process for producing the same; drugs characterized by containing at least one of these compounds as the active ingredient, in particular, preventives and/or remedies for pulmonary hypertension, ischemic heart diseases, erectile insufficiency, female sexual dysfunction or diseases against which cGMP-PDE inhibitory effects are efficacious and intermediates useful in producing the above compounds.

24 Claims, 3 Drawing Sheets

Reaction Scheme 1

Process 1    Process 2

Reaction Scheme 2

Process 1

EX.No. 4

EX.No. 8

EX.No. 81

COMPOUNDS HAVING CGMP-PDE INHIBITORY EFFECT

Figure 1:
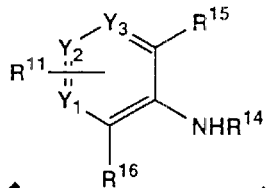
Figure 1:
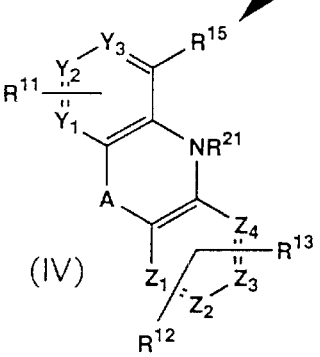
Figure 1:
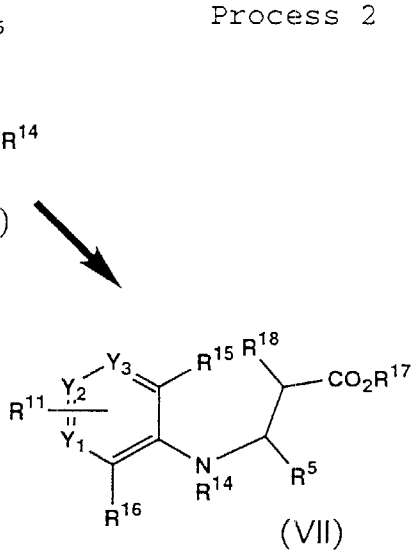
Figure 1:
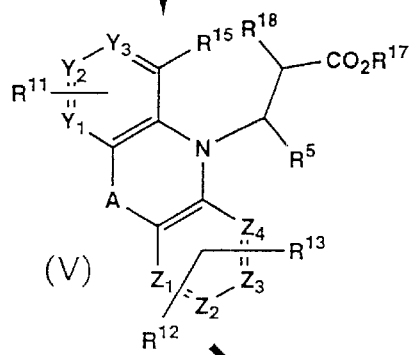
Figure 1:
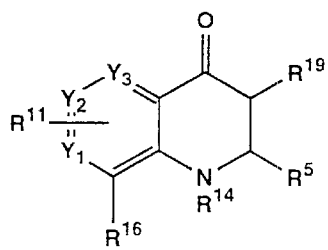
Figure 1:
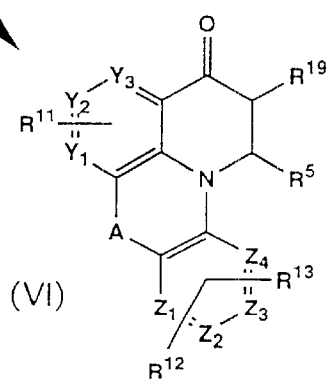

This application is a Continuation of PCT International Application No. PCT/JP98/05350 filed on Nov. 27, 1998, which designated the United States, and on which priority is claimed under 35 U.S.C. §120, the entire contents of which are hereby incorporated by reference.

TECHNICAL FIELD

This invention relates to novel condensed tetracyclic hetero-ring compounds having action in inhibiting strongly and highly selectively cyclic GMP-phosphodiesterase (hereinafter abbreviated as cGMP-PDE), featuring high safety, processes for producing such compounds, pharmaceuticals containing at least one of such compounds as an active ingredient, in particular, agents for preventing and/or treating pulmonary hypertension, ischemic heart diseases, erectile dysfunction, female sexual dysfunction or diseases against which the cGMP-PDE inhibition is effective, and intermediates useful for the production of the condensed tetracyclic hetero-ring compounds.

BACKGROUND ART

The identity of vascular endothelial cell derived relaxing factors has been found to be nitric oxide (hereinafter abbreviated as NO) which, like nitroglycerin used to treat angina pectoris, manifests its vascular relaxing action as mediated by the increase in cyclic GMP (hereinafter abbreviated as cGMP). Briefly, nitrites-like relaxing factors exist endogenously and counteract catecholamine and other endogenous vasoconstricting factors to adjust the tone of blood vessels and contribute to the retention of adequate blood flow. Therefore, the decrease in NO or cGMP is believed to enhance vasotonia and reduce the blood flow in tissue, eventually causing circulatory disorders or ischemic heart diseases. Increase in vasotonia resulting from damage to coronary endothelial cells which are in the class of NO producing cells is believed to induce insufficiency in the blood flow in myocardial tissue, thereby causing anginal attacks. This results from disorders in the NO-cGMP system working as an endogenous relaxing factor. The vasodilating action of nitrites depends on the diameter of blood vessels for the degree of relaxation and because of their active site specificity (i.e., thicker coronary arteries are relaxed more intensely), nitrites have so far been in common use. However, the nitrites have a disadvantage in that their action is transient and attenuated during prolonged use. In addition, it has been pointed out that among vasodilators, adenosine enhancers such as dipyridamole which dilate narrow portions of coronary arteries to increase the coronary blood flow increase the myocardial blood flow at normal sites rather than at the lesion, thereby aggravating the ischemia (this phenomenon is generally referred to as "steal") and, hence, showing side effects such as aggravation of angina pectoris and pectoralgia.

While no effective therapeutics have been available for the various pathogenic conditions that manifest pulmonary hypertension, it has recently been reported that NO gas inhalation therapy has certain utility. Since NO gas relaxes blood vessels and lower the pulmonary arterial pressure through the increase in cGMP, it is anticipated that activation of the cGMP producing system dilates selectively pulmonary arteries in the pulmonary circulation, thereby contributing to the treatment of pulmonary hypertension. Calcium blockers and many other vasodilating drugs have so far been used in attempts to treat pulmonary hypertension, none have been commercialized since every one of them is more potent in lowering the systemic blood pressure than the pulmonary arterial pressure. An oxygen therapy has been verified to be effective in achieving improvements after its application. However, oxygen intoxication occurs as a serious side effect and the occurrence of pulmonary lesions such as pulmonary edema and fibrosis has been reported with patients who were on prolonged oxygen therapy at home. The NO gas inhalation therapy is not an exception and the NO gas used in this therapy is one of the air pollutants $NO_x$ and will easily generate $NO_2$ in the presence of oxygen, thereby potentially causing adverse effects on the airway and lungs; hence, utmost care is required in applying the NO gas and many problems are involved in its prolonged use. On the other hand, suppressing the cGMP degradation system is believed another way to maintain the concentration of cGMP, thereby allowing for selective decrease in the pulmonary arterial pressure. Briefly, an inhibitor of phosphodiesterase (hereinafter abbreviated as PDE) which is an enzyme catalyzing specific hydrolyzation of cyclic GMP holds promise as a new therapeutic free from the aforementioned side effects.

With the inhibition of PDE, cGMP increases, possibly leading to the treatment of these diseases. As of today, PDE has been verified to exist in at least seven isozyme types (Physiological Reviews, 75, 725–748, 1995). Of these, five types of isozymes distribute in many diverse tissues. Two isozymes are capable of selective hydrolyzation of cGMP and they are PDE type I (calmodulin-dependent PDE) and PDE type V (cGMP-PDE). On the other hand, PDE types III and IV hydrolyse cyclic AMP (hereinafter abbreviated as cAMP) selectively and PDE type II has no substrate selectivity. If the last three isozymes are inhibited, cAMP is increased to cause various obvious side effects including enhanced myocardial contraction and heart rate and depression of systemic blood pressure. Among other things, it is well known that with the inhibition of type III PDE, cAMP increases resulting in enhanced myocardial contraction. It has been also reported that increased cGMP in cardiac muscle reduced myocardial contraction but the distribution of PDE type V has not been recognized in cardiac muscle. Furthermore, PDE type VI is distributed in the retina, and it is expected that the inhibition of this PDE type VI will cause defect in vision such as changes in blue/green color and increased sensitivity to light. Therefore, it is anticipated that selective inhibition of PDE type V will produce selective action that is limited in the decrease in systemic blood pressure and side effects on the heart and the retina. It has recently been found that NO releasing compounds show an inhibition of vascular smooth muscle cell proliferation with the intermediary of cGMP. For example, Garg et al. (J. Clin. Invest., 83, 1774–1777, 1989) and Nakaki et al. (Eur. J. Pharmacol., 189, 347–353, 1990) reported that the proliferation of cultured vascular smooth muscle cells isolated from aortic media in rats was suppressed by the treatment of NO releasing compounds nitroprusside, nitroglycerin, isosorbide dinitrate or 8-bromo-cGMP. Therefore, it is suggested that increased cGMP could suppress the proliferation of vascular smooth muscle cells in arteriosclerosis and post-PTCA restenosis. It is also known that the NO-cGMP system is involved in the mechanism of penile erection. When the sexual center in the brain is excited by sexual stimulation from the eyes or ears or by direct stimulation of the penis, the stimulation is transmitted to the nerves in corpus cavernosum penis via parasympathetic pelvic nerves, whereupon acetylcholine, vasoactive intestinal peptides and nitrogen monoxide (hereinafter abbreviated as NO) are released from the corpus cavernosum to relax the smooth muscle forming the valve structure in the spiral artery so that the arterial blood supplied from the penile deep artery and dorsal artery suddenly flows into the cavities of corpora cavernosa, causing the pressure in the corpus cavernosum penis to rise so that the fibrous trabeculae that have relaxed under the action of acetylcholine, vasoactive intestinal peptides and NO clog the flux veins or the cavities of corpora cavernosa will themselves increase in volume. In addition, the tension under the pressure of the tunica albuginea compresses the veins running obliquely across the tunica albuginea to obstruct the blood outflow. As the result, blood stays within the cavities of corpora cavernosa and the tunica albuginea becomes rigid under tension to establish penile erection.

It has been unravelled that the entity of the vascular endothelial cell derived relaxing factor is NO and develops its vasohypotonic action with the intermediary of an increased cGMP level. Therefore, it is postulated that suppressing the CGMP decomposing system is another way to maintain the CGMP level and achieve selective erection.

The cGMP-PDE inhibitors so far disclosed in the art include pyrazolopyrimidone derivatives (see EP-A-526004), purinone derivatives (JP-A 2-88577), phenylpyrimidone derivatives (JP-A 2-295978), quinazoline derivatives (JP-A 6-192235 and JP-A 7-10843 and WO 93/12095) and phthalazine derivatives (WO 96/05176). However, there is no prior art disclosure of the fact that compounds such as the ones claimed in the present invention which have a condensed tetracyclic hetero-ring have the cGMP-PDE inhibitory action. As for the PDE isozyme selectivity, EP-A 526004 and WO 93/12095 teach isozyme selectivity between types V and III but the selectivity has not yet been commercialized in clinical fields to demonstrate a satisfactory action.

Recently, there is a report on the clinical test results of a therapeutic agent for impotence through oral administration of 5-[2-ethoxy-5-(4-methylpiperazin-1-ylsulphonyl) phenyl]-1-methyl-3-propyl-6,7-dihydro-1H-pyrazolo[4,3-d] pyrimidin-7-one citrate (hereinafter, abbreviated as sildenafil) which is a PDE type V inhibitor (cf. Drugs of the Future, volume 22, page 138–143, 1997). However side effect such as headache, flushing, dyspepsia, muscular pain, and visual. disability were reported.

Referring to condensed tetracyclic hetero-ring compounds, Ohmoto et al., Chem. Pharm. Bull., 36, 11, 4588–4592, 1988 and Song et al., Chem. Pharm. Bull., 32, 5, 1872–1877, 1984 have reported the cAMP-PDE inhibitory activity of canthin-6-one derivatives. JP-A 60-12791 teaches the phosphodiesterase inhibitory activity of 5-hydroxymethyl-canthin-6-one. However, these compounds have different structures than the compounds of the invention and there has been no teaching at all as to whether they have a selective cGMP-PDE inhibitory action.

DISCLOSURE OF THE INVENTION

An object, therefore, of the invention is to provide novel compounds that have high isozyme selectivity and potent cGMP-PDE inhibitory action and that cause less side effects to feature high safety.

Other objects of the invention are to provide processes for producing such compounds, intermediates useful for producing them, as well as pharmaceuticals and pharmaceutical compositions containing said compounds. In particular, the invention aims at providing agents for preventing and/or treating pulmonary hypertension, ischemic heart diseases, erectile dysfunction, female sexual dysfunction or diseases against which the cGMP-PDE inhibitory action is effective, said agents having solved at least one of the aforementioned problems with the prior art.

The present inventors conducted intensive studies with a view to obtaining drugs that are capable of potent and selective inhibition of type V PDE while featuring high safety. As a result, they found that novel condensed tetracyclic hetero-ring compounds and salts thereof have potent and selective type V PDE inhibiting activity and this finding has eventually led to the accomplishment of the present invention.

According to its first aspect, the invention provides compounds represented by the following formula (I) or salts thereof or pharmaceuticals containing said compounds or salts as an active ingredient:

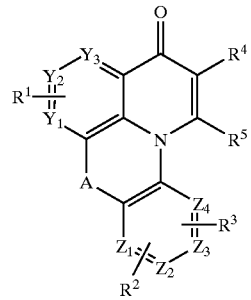

(I)

where A represents a single bond, a methylene group, a carbonyl group, an oxygen atom, a group: —SO$_n$— (n is 0–2), a group: —N(R$^6$)—, a group: —CR$^7$(OR$^8$)— or a group: —C(=N—R$^9$)—; Y$^1$–Y$^3$ and Z$^1$–Z$^4$ represent each a methine group or a nitrogen atom; R$^1$ represents a hydrogen atom, a halogen atom, a cyano group, an optionally protected carboxyl group, an optionally protected carboxymethyl group, an alkoxycarbonyl group having 1–4 carbon atoms, a carbamoyl group, an acetylamino group, a 3-carboxy-1-propenyl group, a 2-hydroxypentyloxy group, a 2,2-diethoxyethoxy group, an optionally protected hydroxyl group, an optionally protected mercapto group, a straight- or branched-chain alkanoyloxy group having 1–4 carbon atoms, a carbonyloxy group substituted by a phenyl group or a pyridyl group, a straight- or branched-chain alkyl group having 1–4 carbon atoms which may be substituted by one hydroxyl group, an amino group which may be mono- or disubstituted by an alkyl group having 1–4 carbon atoms, an alkylthio group having 1–3 carbon atoms which may be monosubstituted by any group selected from the group consisting of a hydroxyl group, a carboxyl group, a phenyl group and a pyridyl group, a 1-methyl-hexahydroazepin-4-yl-oxy group, or represented by the following formula (II):

—O—(CH$_2$)$_n$—Q (II)

(where Q represents a hydrogen atom, a carboxyl group, an alkoxy group having 1 or 2 carbon atoms which may be substituted by one hydroxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or one mercapto group, a piperidinylcarbonyl group which may be substituted by one carboxyl group or alkoxycarbonyl group having 1 or 2 carbon atoms, a morpholylcarbonyl group, a hydroxyl group, a mercapto group, a group: —NR$^{24}$R$^{24}$ (R$^{24}$ represents a hydrogen atom or an alkyl group having 1–4 carbon atoms; the two R$^{24}$s may be the same or different, or may combine each other to form a ring), a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyridyl group which may be monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyrazinyl group, a pyrimidinyl group, a furyl group, a thienyl group, an oxadiazolyl group, a 4-methoxyphenoxy group, a 1-benzotriazolyl group, a 4-morpholinyl group, or 2-benzimidazolyl group; n is 1–6); R$^2$ represents a hydrogen atom, a halogen atom, an optionally protected hydroxyl group, an optionally protected mercapto group, an optionally protected amino group, a cyano group, a nitro group, a trifluoromethyl group, a trifluoromethoxy group, an optionally protected carboxyl group, a 4-morpholylacetyl group, a straight- or branched-chain alkanoyloxy group having 1–4 carbon atoms, a straight- or branched-chain alkanoyl group having 1–4 carbon atoms, a straight- or branched-chain alkyl group having 1–4 carbon atoms, an alkylthio group having 1–3 carbon atoms which may be monosubstituted by any group selected from the group consisting of a hydroxyl group, a carboxyl group, a phenyl group and a pyridyl group, or a straight- or branched-chain alkoxy group having 1–4 carbon atoms which may be monosubstituted by any group selected from the group consisting of an alkoxycarbonyl group having 1–4 carbon atoms, a hydroxyl group, a carboxyl group, a phenyl group and a pyridyl group; R$^3$ represents a hydrogen atom, a halogen atom, an optionally protected hydroxyl group or a straight- or branched-chain alkoxy group having 1–4 carbon atoms; R$^4$ represents a hydrogen atom, a halogen atom, a group: —M—G (where M represents an oxygen atom, an imino group or a group: —N(CH$_3$)—, and G represents a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group), an alkyl group having 1 or 2 carbon atoms which may be substituted by a cyclic alkyl group having 3–6 carbon atoms, a benzyl group which may be mono- or disubstituted in the benzene ring by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group,) a pyridylmethyl group which may be monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a morpholylmethyl group, a triazolylmethyl group, a furylmethyl group, a thienylmethyl group, a pyrimidinylmethyl group, a pyrazinylmethyl group, a pyrrolylmethyl group, an imidazolylmethyl group, a quinolylmethyl group, an indolylmethyl group, a naphthylmethyl group, a benzoyl group or an α-hydroxybenzyl group; R$^5$ represents a hydrogen atom or a methyl group; R$^6$ represents a hydrogen atom, a straight- or branched-chain alkyl group having 1–4 carbon atoms or a straight- or branched-chain alkanoyl group having 1–4 carbon atoms; R$^7$ represents a hydrogen atom or a straight- or branched-chain alkoxy group having 1–4 carbon atoms; R$^8$ represents a hydrogen atom or an alkyl group having 1–4 carbon atoms, provided that the alkoxy group as R$^7$ and the alkyl group as R$^8$ may combine to form a ring; R$^9$ represents a hydrogen atom, a hydroxyl group, an alkyl group having 1–4 carbon atoms, an alkoxy group having 1–4 carbon atoms, a carboxymethyloxy group or a group: —NR$^{10}$R$^{10}$ (the two R$^{10}$s may be the same or different); R$^{10}$ represents a hydrogen atom or an alkyl group having 1 or 2 carbon atoms; provided that are limited the compounds wherein, when A represents a single bond, and all of Y$^1$–Y$^3$ and Z$^1$–Z$^4$ represent a methine group, R$^1$ represents a 1-methyl-hexahydroazepin-4-yl-oxy group, or represented by the following formula (II):

$$-O-(CH_2)_n-Q \qquad (II)$$

(where Q represents a group: —NR$^{24}$R$^{24}$ (R$^{24}$ represents a hydrogen atom or an alkyl group having 1–4 carbon atoms; R$^{24}$ may not be hydrogen atom at the same time, or may combine each other to form a ring), a phenyl group which was mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyridyl group which was monosubstituted by any group selected from the group consisting of a halogen atom, a hydroxyl group, a mercapto group, an alkoxy group having 1 or 2 carbon atoms, an alkylthio group having 1 or 2 carbon atoms, an acetylamino group, a carboxyl group, an amino group, a cyano group, a nitro group, an amino group mono- or disubstituted by a lower alkyl group and a carbamoyl group, a 1-benzotriazolyl group, a 4-morpholinyl group, or 2-benzimidazolyl group; n is 1–6); or R$^2$ represents a straight- or branched-chain alkoxy group having 1–4 carbon atoms which was monosubstituted by any group selected from the group consisting of a hydroxyl group, a carboxyl group, a phenyl group and a pyridyl group; or $R^4$ represents a group: —M—G (where M represents an oxygen atom, an imino group or a group: —N(CH$_3$)—, and G represents a phenyl group which was mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group), a benzyl group which was mono- or disubstituted in the benzene ring by any group selected from the group consisting of a cyano group, a nitro group, an amino group mono- or disubstituted by a lower alkyl group, a carbamoyl group, an alkyl group having 1–4 carbon atoms, a hydroxymethyl group and an acetoxymethyl group, a pyridylmethyl group which was monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, a hydroxymethyl group and an acetoxymethyl group; and it is also noted that the compounds other than the above described limited compounds represented by the formula (I), if the compounds are useful as a pharmaceutical agent of the present invention, the other compounds are included in the present pharmaceutical invention, and that are excluded the compounds wherein, A represents a single bond, $Y^1$ and $Y^2$ represent a methine group, $Y^3$ represents a nitrogen atom, $Z^1$–$Z^4$ represent a methine group, $R^1$, $R^2$ and $R^3$ represent respectively a hydrogen atom, and $R^4$ represents a hydrogen atom and $R^5$ represents a hydrogen atom or a methyl group, or $R^4$ represents an ethyl group and $R^5$ represents a hydrogen atom, or $R^4$ represents a chlorine atom and $R^5$ represents a methyl group; the compounds wherein A represents a sulfur atom, and all of $Y^1$–$Y^3$ and $Z^1$–$Z^4$ represent a methine group, $R^1$, $R^2$, $R^3$ and $R^5$ represent respectively a hydrogen atom, and $R^4$ represents a hydrogen atom, a benzyl group, a 4-methoxybenzyl group, a 4-dimethylaminobenzyl group, a 4-chlorobenzyl group, a 3-nitrobenzyl group, or a bromine atom; the compounds wherein A represents an oxygen atom, and all of $Y^1$–$Y^3$ and $Z^1$–$Z^4$ represent a methine group, $R^1$, $R^2$, $R^3$ and $R^5$ represent respectively a hydrogen atom, and $R^4$ represents a hydrogen atom, a benzyl group, a 4-methoxybenzyl group, a 4-dimethylaminobenzyl group, a 4-chlorobenzyl group, or a 3-nitrobenzyl group; the compounds wherein A represents a carbonyl group, and all of $Y^1$–$Y^3$ and $Z^1$–$Z^4$ represent a methine group, $R^2$, $R^3$, $R^4$ and $R^5$ represent respectively a hydrogen atom, and $R^1$ represents a methoxy group at position 5; the compounds wherein A represents a carbonyl group, and all of $Y^1$–$Y^3$ and $Z^1$–$Z^4$ represent a methine group, $R^1$, $R^4$ and $R^5$ represent respectively a hydrogen atom, and one of $R^2$ and $R^3$ represents a hydrogen atom and the other one of $R^2$ and $R^3$ represents a methoxy group at position 9; the compounds wherein A represents a group: SO$_n$ (n is 1), and all of $Y^1$–$Y^3$ and $Z^1$–$Z^4$ represent a methine group, and $R^1$, $R^2$, $R^3$, $R^4$ and $R^5$ represent respectively a hydrogen atom, and it is noted that as to the above described compounds excluded from the compounds represented by the formula (I), if the compounds are useful as a pharmaceutical agent of the present invention, the excluded compounds are included in the present pharmaceutical invention.

The preferred substituents in the compounds represented by the above formula (I) or the preferred combinations thereof are shown below but the invention is by no means limited thereto.

Speaking of $R^1$, it is preferably substituted at position 2 in the case of the formula (I)-a and position 5 in the case of the formula (I)-b, and is preferably a hydroxyl group or represented by the following formula (II):

$$—O—(CH_2)_n—Q \qquad (II)$$

where Q represents a hydrogen atom, a carboxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or one mercapto group, a hydroxyl group, a group: —NR$^{24}$R$^{24}$ (R$^{24}$ represents a hydrogen atom or an alkyl group having 1–4 carbon atoms; the two R$^{24}$s may be the same or different, or may combine each other to form a ring), a phenyl group, a pyridyl group which may be monosubstituted by a hydroxymethyl group, an acetoxymethyl group, an alkyl group having 1–4 carbon atoms or an alkoxycarbonyl group having 1 or 2 carbon atoms, pyrazinyl group, a pyrimidinyl group, or a 1-benzotriazolyl group; n is 1–4.

More preferably, $R^1$ is substituted at position 2 in the case of the formula (I)-a and position 5 in the case of the formula (I)-b, and is either a hydroxyl group or represented by the following formula (II):

$$—O—(CH_2)_n—Q \qquad (II)$$

where Q represents a hydrogen atom, a carboxyl group, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or one mercapto group, a hydroxyl group, a group: —NR$^{24}$R$^{24}$ (R$^{24}$ represents a hydrogen atom or an alkyl group having 1–4 carbon atoms; the two R$^{24}$s may be the same or different, or may combine each other to form a ring), a phenyl group, a pyridyl group which may be monosubstituted by a hydroxymethyl group, an acetoxymethyl group, an alkyl group having 1–4 carbon atoms or an alkoxycarbonyl group having 1 or 2 carbon atoms, a pyrazinyl group, a pyrimidinyl group, or a 1-benzotriazolyl group; n is 1–4.

Preferably, $R^2$ and $R^3$ are not a hydrogen atom at the same time; it is preferred that $R^2$ is substituted at position 9 or 10 and is a hydrogen atom, a halogen atom, a hydroxyl group, a cyano group, a trifluoromethyl group or a straight- or branched-chain alkoxy group having 1–4 carbon atoms and that $R^3$ is a hydrogen atom.

Preferably, $R^4$ is a hydrogen atom, an alkyl group having 1 or 2 carbon atoms, a pyrimidinylmethyl group or a pyridylmethyl group which may be substituted by a methyl group. Further, it is more preferred that $R^4$ is a methyl group, a pyrimidinylmethyl group or a pyridylmethyl group. Preferably, $R^5$ is a hydrogen atom.

The preferred combinations of the substituents are as follows: $R^1$ is substituted at position 2 in the formula (I)-a and position 5 in the formula (I)-b, and is either a hydroxyl group or represented by the following formula (II):

$$—O—(CH_2)_n—Q \qquad (II)$$

where Q represents a hydrogen atom, a carboxyl group, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or one mercapto group, a hydroxyl group, a group: —NR$^{24}$R$^{24}$ (R$^{24}$ represents a hydrogen atom or an alkyl group having 1–4 carbon atoms; the two R$^{24}$s may be the same or different, or may combine each other to form a ring), a phenyl group, a pyridyl group which may be monosubstituted by a hydroxymethyl group, an acetoxymethyl group, an alkyl group having 1–4 carbon atoms or an alkoxycarbonyl group having 1 or 2 carbon atoms, a pyrazinyl group, a pyrimidinyl group, or a 1-benzotriazolyl group; n is 1–4; R$^2$ is a halogen atom, a cyano group or a trifluoromethyl group which is substituted at position 9 or 10; R$^3$ is a hydrogen atom; R$^4$ is a methyl group, a pyrimidinylmethyl group or a pyridylmethyl group; and R$^5$ is a hydrogen atom.

The specific individual compounds of the invention include:

(1) 10-bromo-5-(3-hydroxypropyloxy)-2-(3-pyridylmethyl)-3H-pyrido[3,2,1-kl]phenoxazin-3-one
(2) 9-bromo-5-(3-hydroxypropyloxy)-2-(3-pyridylmethyl)-3H-pyrido[3,2,1-kl]phenoxazin-3-one
(3) 10-bromo-5-(3-hydroxypropyloxy)-2-(3-pyridylmethyl)-3H-pyrido[3,2,1-kl]phenothiazin-3-one
(4) 9-bromo-5-(3-hydroxypropyloxy)-2-(3-pyridylmethyl)-3H-pyrido[3,2,1-kl]phenothiazin-3-one
(5) 10-bromo-5-(3-hydroxypropyloxy)-2-(3-pyridylmethyl)-3H,7H-pyrido[3,2,1-de]phenazin-3-one
(6) 9-bromo-5-(3-hydroxypropyloxy)-2-(3-pyridylmethyl)-3H,7H-pyrido[3,2,1-de]phenazin-3-one
(7) 7-acetyl-10-bromo-5-(3-hydroxypropyloxy)-2-(3-pyridylmethyl)-3H,7H-pyrido[3,2,1-de]phenazin-3-one
(8) 7-acetyl-9-bromo-5-(3-hydroxypropyloxy)-2-(3-pyridylmethyl)-3H,7H-pyrido[3,2,1-de]phenazin-3-one
(9) 10-bromo-5-(3-hydroxypropyloxy)-7-methyl-2-(3-pyridylmethyl)-3H,7H-pyrido[3,2,1-de]phenazin-3-one
(10) 9-bromo-5-(3-hydroxypropyloxy)-7-methyl-2-(3-pyridylmethyl)-3H,7H-pyrido[3,2,1-de]phenazin-3-one
(11) 10-bromo-5-(3-hydroxypropyloxy)-2-(3-pyridylmethyl)-3H,7H-pyrido[3,2,1-de]acridin-3,7-dione
(12) 9-bromo-5-(3-hydroxypropyloxy)-2-(3-pyridylmethyl)-3H,7H-pyrido[3,2,1-de]acridin-3,7-dione
(13) 10-bromo-7-hydroxy-5-(3-hydroxypropyloxy)-2-(3-pyridylmethyl)-3H,7H-pyrido[3,2,1-de]acridin-3-one
(14) 9-bromo-7-hydroxy-5-(3-hydroxypropyloxy)-2-(3-pyridylmethyl)-3H,7H-pyrido[3,2,1-de]acridin-3-one
(15) 10-bromo-7-(hydroxyimino)-5-(3-hydroxypropyloxy)-2-(3-pyridylmethyl)-3H,7H-pyrido[3,2,1-de]acridin-3-one
(16) 9-bromo-7-(hydroxyimino)-5-(3-hydroxypropyloxy)-2-(3-pyridylmethyl)-3H,7H-pyrido[3,2,1-de]acridin-3-one
(17) 9-bromo-2-(3-hydroxypropyloxy)-5-(3-pyridylmethyl)-4H-indolo[3,2,1-de][1,5]naphthyridin-4-one
(18) 10-bromo-2-(3-hydroxypropyloxy)-5-(3-pyridylmethyl)-4H-indolo[3,2,1-de][1,5]naphthyridin-4-one
(19) 9-bromo-2-(3-hydroxypropyloxy)-5-(3-pyridylmethyl)-4H[7]-azaindolo[3,2,1-ij]quinolin-4-one
(20) 10-bromo-2-(3-hydroxypropyloxy)-5-(3-pyridylmethyl)-4H[7]-azaindolo[3,2,1-ij]quinolin-4-one
(21) 9-bromo-2-(3-hydroxypropyloxy)-5-(3-pyridylmethyl)-4H[5]-azaindolo[3,2,1-ij]quinolin-4-one
(22) 10-bromo-2-(3-hydroxypropyloxy)-5-(3-pyridylmethyl)-4H[6]-azaindolo[3,2,1-ij]quinolin-4-one
(23) 9-bromo-2-(3-hydroxypropyloxy)-5-(3-pyridylmethyl)-4H[4]-azaindolo[3,2,1-ij]quinolin-4-one
(24) 10-bromo-2-(3-hydroxypropyloxy)-5-(3-pyridylmethyl)-4H[4]-azaindolo[3,2,1-ij]quinolin-4-one <A=O>
(25) 10-bromo-2-(3-pyridylmethyl)-5-(3-pyridylmethyloxy)-3H-pyrido[3,2,1-kl]phenoxazin-3-one
(26) 5-(1-benzotriazolylmethyloxy)-10-bromo-2-(3-pyridylmethyl)-3H-pyrido[3,2,1-kl]phenoxazin-3-one
(27) 10-bromo-5-(2-(1-piperidyl)ethyloxy)-2-(3-pyridylmethyl)-3H-pyrido[3,2,1-kl]phenoxazin-3-one
(28) 9-bromo-5-(3-pyridylmethyloxy)-2-(3-pyridylmethyl)-3H-pyrido[3,2,1-kl]phenoxazin-3-one
(29) 5-(1-benzotriazolylmethyloxy)-9-bromo-2-(3-pyridylmethyl)-3H-pyrido[3,2,1-kl]phenoxazin-3-one
(30) 9-bromo-5-(2-(1-piperidyl)ethyloxy)-2-(3-pyridylmethyl)-3H-pyrido[3,2,1-kl]phenoxazin-3-one <A=S>
(31) 10-bromo-2-(3-pyridylmethyl)-5-(3-pyridylmethyloxy)-3H-pyrido[3,2,1-kl]phenothiazin-3-one
(32) 5-(1-benzotriazolylmethyloxy)-10-bromo-2-(3-pyridylmethyl)-3H-pyrido[3,2,1-kl]phenothiazin-3-one
(33) 10-bromo-5-(2-(1-piperidyl)ethyloxy)-2-(3-pyridylmethyl)-3H-pyrido[3,2,1-kl]phenothiazin-3-one
(34) 9-bromo-2-(3-pyridylmethyl)-5-(3-pyridylmethyloxy)-3H-pyrido[3,2,1-kl]phenothiazin-3-one
(35) 9-bromo-5-(1-benzotriazolylmethyloxy)-2-(3-pyridylmethyl)-3H-pyrido[3,2,1-kl]phenothiazin-3-one
(36) 9-bromo-5-(2-(1-piperidyl)ethyloxy)-2-(3-pyridylmethyl)-3H-pyrido[3,2,1-kl]phenothiazin-3-one <A=NH>
(37) 10-bromo-2-(3-pyridylmethyl)-5-(3-pyridylmethyloxy)-3H,7H-pyrido[3,2,1-de]phenazin-3-one
(38) 5-(1-benzotriazolylmethyloxy)-10-bromo-2-(3-pyridylmethyl)-3H,7H-pyrido[3,2,1-de]phenazin-3-one
(39) 10-bromo-5-(2-(1-piperidyl)ethyloxy)-2-(3-pyridylmethyl)-3H,7H-pyrido[3,2,1-de]phenazin-3-one
(40) 9-bromo-2-(3-pyridylmethyl)-5-(3-pyridylmethyloxy)-3H,7H-pyrido[3,2,1-de]phenazin-3-one
(41) 9-bromo-5-(1-benzotriazolylmethyloxy)-2-(3-pyridylmethyl)-3H,7H-pyrido[3,2,1-de]phenazin-3-one
(42) 9-bromo-5-(2-(1-piperidyl)ethyloxy)-2-(3-pyridylmethyl)-3H,7H-pyrido[3,2,1-de]phenazin-3-one <A=N—Ac>
(43) 7-acetyl-10-bromo-2-(3-pyridylmethyl)-5-(3-pyridylmethyloxy)-3H,7H-pyrido[3,2,1-de]phenazin-3-one
(44) 7-acetyl-5-(1-benzotriazolylmethyloxy)-10-bromo-2-(3-pyridylmethyl)-3H,7H-pyrido[3,2,1-de]phenazin-3-one
(45) 7-acetyl-10-bromo-5-(2-(1-piperidyl)ethyloxy)-2-(3-pyridylmethyl)-3H,7H-pyrido[3,2,1-de]phenazin-3-one
(46) 7-acetyl-9-bromo-2-(3-pyridylmethyl)-5-(3-pyridylmethyloxy)-3H,7H-pyrido[3,2,1-de]phenazin-3-one
(47) 7-acetyl-5-(1-benzotriazolylmethyloxy)-9-bromo-2-(3-pyridylmethyl)-3H,7H-pyrido[3,2,1-de]phenazin-3-one
(48) 7-acetyl-9-bromo-5-(2-(1-piperidyl)ethyloxy)-2-(3-pyridylmethyl)-3H,7H-pyrido[3,2,1-de]phenazin-3-one <A=N—Me>
(49) 10-bromo-7-methyl-2-(3-pyridylmethyl)-5-(3-pyridylmethyloxy)-3H,7H-pyrido[3,2,1-de]phenazin-3-one
(50) 5-(1-benzotriazolylmethyloxy)-10-bromo-7-methyl-2-(3-pyridylmethyl)-3H,7H-pyrido[3,2,1-de]phenazin-3-one
(51) 10-bromo-7-methyl-5-(2-(1-piperidyl)ethyloxy)-2-(3-pyridylmethyl)-3H,7H-pyrido[3,2,1-de]phenazin-3-one

(52) 9-bromo-7-methyl-2-(3-pyridylmethyl)-5-(3-pyridylmethyloxy)-3H,7H-pyrido[3,2,1-de]phenazin-3-one
(53) 5-(1-benzotriazolylmethyloxy)-9-bromo-7-methyl-2-(3-pyridylmethyl)-3H,7H-pyrido[3,2,1-de]phenazin-3-one
(54) 9-bromo-7-methyl-5-(2-(1-piperidyl)ethyloxy)-2-(3-pyridylmethyl)-3H,7H-pyrido[3,2,1-de]phenazin-3-one
<A=CO>
(55) 10-bromo-2-(3-pyridylmethyl)-5-(3-pyridylmethyloxy)-3H,7H-pyrido[3,2,1-de]acridin-3,7-dione
(56) 5-(1-benzotriazolylmethyloxy)-10-bromo-2-(3-pyridylmethyl)-3H,7H-pyrido[3,2,1-de]acridin-3,7-dione
(57) 10-bromo-5-(2-(1-piperidyl)ethyloxy)-2-(3-pyridylmethyl)-3H,7H-pyrido[3,2,1-de]acridin-3,7-dione
(58) 9-bromo-2-(3-pyridylmethyl)-5-(3-pyridylmethyloxy)-3H,7H-pyrido[3,2,1-de]acridin-3,7-dione
(59) 5-(1-benzotriazolylmethyloxy)-9-bromo-2-(3-pyridylmethyl)-3H,7H-pyrido[3,2,1-de]acridin-3,7-dione
(60) 9-bromo-5-(2-(1-piperidyl)ethyloxy)-2-(3-pyridylmethyl)-3H,7H-pyrido[3,2,1-de]acridin-3,7-dione
<A=CH—OH>
(61) 10-bromo-7-hydroxy-2-(3-pyridylmethyl)-5-(3-pyridylmethyloxy)-3H,7H-pyrido[3,2,1-de]acridin-3-one
(62) 5-(1-benzotriazolylmethyloxy)-10-bromo-7-hydroxy-2-(3-pyridylmethyl)-3H,7H-pyrido[3,2,1-de]acridin-3-one
(63) 10-bromo-7-hydroxy-5-(2-(1-piperidyl)ethyloxy)-2-(3-pyridylmethyl)-3H,7H-pyrido[3,2,1-de]acridin-3-one
(64) 9-bromo-7-hydroxy-2-(3-pyridylmethyl)-5-(3-pyridylmethyloxy)-3H,7H-pyrido[3,2,1-de]acridin-3-one
(65) 5-(1-benzotriazolylmethyloxy)-9-bromo-7-hydroxy-2-(3-pyridylmethyl)-3H,7H-pyrido[3,2,1-de]acridin-3-one
(66) 9-bromo-7-hydroxy-5-(2-(1-piperidyl)ethyloxy)-2-(3-pyridylmethyl)-3H,7H-pyrido[3,2,1-de]acridin-3-one
<A=N—OH>
(67) 10-bromo-7-(hydroxyimino)-2-(3-pyridylmethyl)-5-(3-pyridylmethyloxy)-3H,7H-pyrido[3,2,1-de]acridin-3-one
(68) 5-(1-benzotriazolylmethyloxy)-10-bromo-7-(hydroxyimino)-2-(3-pyridylmethyl)-3H,7H-pyrido[3,2,1-de]acridin-3-one
(69) 10-bromo-7-(hydroxyimino)-5-(2-(1-piperidyl)ethyloxy)-2-(3-pyridylmethyl)-3H,7H-pyrido[3,2,1-de]acridin-3-one
(70) 9-bromo-7-(hydroxyimino)-2-(3-pyridylmethyl)-5-(3-pyridylmethyloxy)-3H,7H-pyrido[3,2,1-de]acridin-3-one
(71) 9-bromo-7-(hydroxyimino)-5-(1-benzotriazolylmethyloxy)-2-(3-pyridylmethyl)-3H,7H-pyrido[3,2,1-de]acridin-3-one
(72) 9-bromo-7-(hydroxyimino)-5-(2-(1-piperidyl)ethyloxy)-2-(3-pyridylmethyl)-3H,7H-pyrido[3,2,1-de]acridin-3-one
(73) 10-bromo-5-hydroxy-2-(3-pyridylmethyl)-3H-pyrido[3,2,1-kl]phenothiazin-3-one
(74) 2-benzyl-10-bromo-5-(3-hydroxypropyloxy)-3H-pyrido[3,2,1-kl]phenothiazin-3-one
(75) 2-benzyl-10-bromo-5-(3-pyridylmethyloxy)-3H-pyrido[3,2,1-kl]phenothiazin-3-one
(76) 2-benzyl-10-bromo-5-(1-benzotriazolylmethyloxy)-3H-pyrido[3,2,1-kl]phenothiazin-3-one
(77) 2-benzyl-10-bromo-5-(2-(1-piperidyl)ethyloxy)-3H-pyrido[3,2,1-kl]phenothiazin-3-one
(78) 10-bromo-5-(3-hydroxypropyloxy)-2-(5-pyrimidinylmethyl)-3H-pyrido[3,2,1-kl]phenothiazin-3-one
(79) 10-bromo-5-(3-pyridylmethyloxy)-2-(5-pyrimidinylmethyl)-3H-pyrido[3,2,1-kl]phenothiazin-3-one
(80) 5-(1-benzotriazolylmethyloxy)-10-bromo-2-(5-pyrimidinylmethyl)-3H-pyrido[3,2,1-kl]phenothiazin-3-one
(81) 10-bromo-5-(2-(1-piperidyl)ethyloxy)-2-(5-pyrimidinylmethyl)-3H-pyrido[3,2,1-kl]phenothiazin-3-one.

According to its second aspect, the present invention provides compounds represented by the above formula (I) where all of $Y^1$–$Y^3$ and $Z^1$–$Z^4$ represents a methine group, or salts thereof. A, the substituents and $R^1$–$R^5$ in this formula as well as the substituents $R^6$–$R^{10}$ defined in A are the same as in the above formula (I).

The preferred substituents in this particular case or the preferred combinations thereof are shown below but the invention is by no means limited thereto.

Speaking of $R^1$, it is preferably substituted at position 2 in the case of the formula (I)-a and position 5 in the case of the formula (I)-b, and is preferably a hydroxyl group or represented by the following formula (II):

—O—(CH$_2$)$_n$—Q       (II)

where Q represents a hydrogen atom, a carboxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or one mercapto group, a hydroxyl group, a group: —NR$^{24}$R$^{24}$ (R$^{24}$ represents a hydrogen atom or an alkyl group having 1–4 carbon atoms; R$^{24}$ may not be hydrogen atom at the same time, or may combine each other to form a ring), a phenyl group, a pyridyl group which may be monosubstituted by a hydroxymethyl group, an acetoxymethyl group, an alkyl group having 1–4 carbon atoms or an alkoxycarbonyl group having 1 or 2 carbon atoms, a pyrazinyl group, a pyrimidinyl group, or a 1-benzotriazolyl group; n is 1–4.

More preferably, $R^1$ is substituted at position 2 in the case of the formula (I)-a and position 5 in the case of the formula (I)-b, and is either a hydroxyl group or represented by the following formula (II):

—O—(CH$_2$)$_n$—Q       (II)

where Q represents a hydrogen atom, a carboxyl group, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or one mercapto group, a hydroxyl group, a group: —NR$^{24}$R$^{24}$ (R$^{24}$ represents a hydrogen atom or an alkyl group having 1–4 carbon atoms; R$^{24}$ may not be hydrogen atom at the same time, or may combine each other to form a ring), a phenyl group, a pyridyl group which may be monosubstituted by a hydroxymethyl group, an acetoxymethyl group, an alkyl group having 1–4 carbon atoms or an alkoxycarbonyl group having 1 or 2 carbon atoms, a pyrazinyl group, a pyrimidinyl group, or a 1-benzotriazolyl group; n is 1–4.

Preferably, $R^2$ and $R^3$ are not a hydrogen atom at the same time; it is preferred that $R^2$ is substituted at position 9 or 10 and is a hydrogen atom, a halogen atom, a hydroxyl group, a cyano group, a trifluoromethyl group or a straight- or branched-chain alkoxy group having 1–4 carbon atoms and that $R^3$ is a hydrogen atom.

Preferably, $R^4$ is a hydrogen atom, an alkyl group having 1 or 2 carbon atoms, a pyrimidinylmethyl group or a pyridylmethyl group which may be substituted by a methyl group. Further, it is more preferred that $R^4$ is a methyl group, a pyrimidinylmethyl group or a pyridylmethyl group. Preferably, $R^5$ is a hydrogen atom.

The preferred combinations of the substituents are as follows: $R^1$ is substituted at position 2 in the formula (I)-a and position 5 in the formula (I)-b, and is either a hydroxyl group or represented by the following formula (II):

$$—O—(CH_2)_n—Q \quad (II)$$

where Q represents a hydrogen atom, a carboxyl group, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or one mercapto group, a hydroxyl group, a group: $—NR^{24}R^{24}$ ($R^{24}$ represents a hydrogen atom or an alkyl group having 1–4 carbon atoms; the two $R^{24}$s may be the same or different, or may combine each other to form a ring), a phenyl group, a pyridyl group which may be monosubstituted by a hydroxymethyl group, an acetoxymethyl group, an alkyl group having 1–4 carbon atoms or an alkoxycarbonyl group having 1 or 2 carbon atoms, a pyrazinyl group, a pyrimidinyl group, or a 1-benzotriazolyl group; n is 1–4; $R^2$ is a halogen atom, a cyano group or a trifluoromethyl group which is substituted at position 9 or 10; $R^3$ is a hydrogen atom; $R^4$ is a methyl group, a pyrimidinylmethyl group or a pyridylmethyl group; and $R^5$ is a hydrogen atom.

According to its third aspect, the invention provides compounds of the above formula (I) where all of $Y^1$–$Y^3$ and $Z^1$–$Z^4$ represent a methine group, A is an oxygen atom, a group: $—SO_n—$ (n is 0–2), or a group: $—N(R^6)—$, or salts thereof. The other elements of the formula, namely, A, substituents $R^1$–$R^5$, and substituents $R^6$–$R^{10}$ defined in A are identical to those defined for the above formula (I). In this particular case, preferably A is a group: $—SO_n—$ (n is 0–2), and then more preferably A is a sulfur atom. The substituents that are preferred in this particular case or preferred combinations thereof are the same as its second aspect but the invention is by no means limited thereto.

According to its fourth aspect, the invention provides compounds of the above formula (I) where all of $Y^1$–$Y^3$ and $Z^1$–$Z^4$ represent a methine group, A is a carbonyl group, or salts thereof. The other elements of the formula, namely, A, substituents $R^1$–$R^5$, and substituents $R^6$–$R^{10}$ defined in A are identical to those defined for the above formula (I). The substituents that are preferred in this particular case or preferred combinations thereof are the same as its second aspect but the invention is by no means limited thereto.

According to its fifth aspect, the invention provides compounds of the above formula (I) where all of $Y^1$–$Y^3$ and $Z^1$–$Z^4$ represent a methine group, A is a single bond, or salts thereof. The other elements of the formula, namely, A, substituents $R^1$–$R^5$, and substituents $R^6$–$R^{10}$ defined in A are identical to those defined for the above formula (I). The substituents that are preferred in this particular case or preferred combinations thereof are the same as its second aspect but the invention is by no means limited thereto.

Speaking of $R^1$, it is preferably substituted at position 2, and is preferably a hydroxyl group, a 1-methylhexahydroazepin-4-yl-oxy group, or represented by the following formula (II):

$$—O—(CH_2)_n—Q \quad (II)$$

where Q represents a hydrogen atom, a carboxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or one mercapto group, a hydroxyl group, a group: $—NR^{24}R^{24}$ ($R^{24}$ represents a hydrogen atom or an alkyl group having 1–4 carbon atoms; the two $R^{24}$s may not be hydrogen atom at the same time, or may combine each other to form a ring), a pyrazinyl group, a pyrimidinyl group, a 1-benzotriazolyl group, a 4-morpholinyl group, or 2-benzimidazolyl group; n is 1–4.

More preferably, $R^1$ is substituted at position 2, and is either a hydroxyl group or represented by the following formula (II):

$$—O—(CH_2)_n—Q \quad (II)$$

where Q represents a group: $—NR^{24}R^{24}$ ($R^{24}$ represents a hydrogen atom or an alkyl group having 1–4 carbon atoms; the two $R^{24}$s may not be hydrogen atom at the same time, or may combine each other to form a ring); n is 1–4.

Preferably, $R^2$ and $R^3$ are not a hydrogen atom at the same time; it is preferred that $R^2$ is substituted at position 9 or 10 and is a hydrogen atom, a halogen atom, a hydroxyl group, a cyano group, a trifluoromethyl group or a straight- or branched-chain alkoxy group having 1–4 carbon atoms and that $R^3$ is a hydrogen atom.

Preferably, $R^4$ is a hydrogen atom, an alkyl group having 1 or 2 carbon atoms, a pyrimidinylmethyl group or a pyridylmethyl group which may be substituted by a methyl group. Further, it is more preferred that $R^4$ is a methyl group, a pyrimidinylmethyl group or a pyridylmethyl group. Preferably, $R^5$ is a hydrogen atom.

The preferred combinations of the substituents are as follows: $R^1$ is substituted at position 2, and is either a hydroxyl group or represented by the following formula (II):

$$—O—(CH_2)_n—Q \quad (II)$$

where Q represents a group: $—NR^{24}R^{24}$ ($R^{24}$ represents a hydrogen atom or an alkyl group having 1–4 carbon atoms; the two $R^{24}$s may be the same or different, or may combine each other to form a ring); n is 1–4; $R^2$ is a halogen atom, a cyano group or a trifluoromethyl group which is substituted at position 9 or 10; $R^3$ is a hydrogen atom; $R^4$ is a methyl group, a pyrimidinylmethyl group or a pyridylmethyl group; and $R^5$ is a hydrogen atom.

According to its sixth aspect, the invention provides compounds of the above formula (I) where $Y^1$ is a nitrogen atom and all of $Y^2$, $Y^3$ and $Z^1$–$Z^4$ represent a methine group, or salts thereof. The other elements of the formula, namely, A, substituents $R^1$–$R^5$, and substituents $R^6$–$R^{10}$ defined in A are identical to those defined for the above formula (I). The substituents that are preferred in this particular case or preferred combinations thereof are the same as set forth above.

According to its seventh aspect, the invention provides compounds of the above formula (I) where $Y^3$ is a nitrogen atom and all of $Y^1$, $Y^2$ and $Z^1$–$Z^4$ represent a methine group, or salts thereof. The other elements of the formula, namely, A, substituents $R^1$–$R^5$, and substituents $R^6$–$R^{10}$ defined in A are identical to those defined for the above formula (I). The substituents that are preferred in this particular case or preferred combinations thereof are the same as set forth above.

According to its eighth aspect, the invention provides compounds of the above formula (I) where $Z^1$ is a nitrogen atom and all of $Y^1$–$Y^3$ and $Z^2$, $Z^3$ and $Z^4$ represent a methine group, or salts thereof. The other elements of the formula, namely, A, substituents $R^1$–$R^5$, and substituents $R^6$–$R^{10}$ defined in A are identical to those defined for the above formula (I). The substituents that are preferred in this particular case or preferred combinations thereof are the same as set forth above.

According to its ninth aspect, the invention provides compounds of the above formula (I) where $Z^2$ is a nitrogen atom, all of $Y^1$–$Y^3$ and $Z^1$, $Z^3$ and $Z^4$ represent a methine group, or salts thereof. The other elements of the formula, namely, A, substituents $R^1$–$R^5$, and substituents $R^6$–$R^{10}$ defined in A are identical to those defined for the above formula (I). The substituents that are preferred in this particular case or preferred combinations thereof are the same as set forth above.

According to its tenth aspect, the invention provides compounds of the above formula (I) where $Z^3$ is a nitrogen atom, all of $Y^1$–$Y^3$ and $Z^1$, $Z^2$ and $Z^4$ represent a methine group, or salts thereof. The other elements of the formula, namely, A, substituents $R^1$–$R^5$, and substituents $R^6$–$R^{10}$ defined in A are identical to those defined for the above formula (I). The substituents that are preferred in this particular case or preferred combinations thereof are the same as set forth above.

According to its eleventh aspect, the invention provides compounds of the above formula (I) where $Z^4$ is a nitrogen atom, all of $Y^1$–$Y^3$ and $Z^1$, $Z^2$ and $Z^3$ represent a methine group, or salts thereof. The other elements of the formula, namely, A, substituents $R^1$–$R^5$, and substituents $R^6$–$R^{10}$ defined in A are identical to those defined for the above formula (I). The substituents that are preferred in this particular case or preferred combinations thereof are the same as set forth above.

According to its twelfth aspect, the invention provides compounds of the formula (I) where the total number of nitrogen atoms in $Y^1$–$Y^3$ and $Z^1$–$Z^4$ is 0, A is a methylene group, a carbonyl group, an oxygen atom, a group: —$SO_n$— (n is 0–2), a group: —N($R^6$)—, a group: —$CR^7(OR^8)$— or a group: —C(=N—$R^9$)—, or salts thereof. In this particular case, A, substituents $R^1$–$R^5$, and $R^{6-R10}$ defined in A are the same as defined for the above formula (I).

According to its thirteenth aspect, the invention provides compounds of the formula (I) where the total number of nitrogen atoms in $Y^1$–$Y^3$ and $Z^1$–$Z^4$ is 1, and A is a single bond, or salts thereof. In this particular case, A, substituents $R^1$–$R^5$, and $R^6$–$R^{10}$ defined in A are the same as defined for the above formula (I).

According to its fourteenth aspect, the invention provides compounds of the formula (I) where the total number of nitrogen atoms in $Y^1$–$Y^3$ and $Z^1$–$Z^4$ is 2, and A is a single bond, a methylene group, a carbonyl group, an oxygen atom, a group: —$SO_n$— (n is 0–2), a group: —N($R^6$)—, a group: —$CR^7(OR^8)$— or a group: —C(=N—$R^9$)—, or salts thereof. In this particular case, A, substituents $R^1$–$R^5$, and $R^6$–$R^{10}$ defined in A are the same as defined above.

According to its fifteenth aspect, the invention provides intermediates represented by the following formula (VI) or salts thereof which are useful for the synthesis of compounds of the above formula (I) or salts thereof:

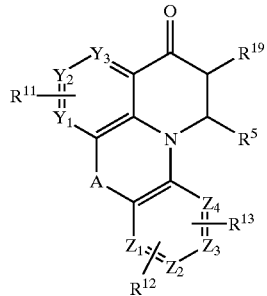

(VI)

(where A represents a single bond, a methylene group, a carbonyl group, an oxygen atom, a group: —$SO_n$— (n is 0–2), a group: —N($R^6$)—, a group: —$CR^7(OR^8)$— or a group: —C(=N—$R^9$)—; $Y^1$–$Y^3$ and $Z^1$–$Z^4$ represent each a methine group or a nitrogen atom; $R^5$ represents a hydrogen atom or a methyl group; $R^6$ represents a hydrogen atom, a straight- or branched-chain alkyl group having 1–4 carbon atoms or a straight- or branched-chain alkanoyl group having 1–4 carbon atoms; $R^7$ represents a hydrogen atom or a straight- or branched-chain alkoxy group having 1–4 carbon atoms; $R^8$ represents a hydrogen atom or an alkyl group having 1–4 carbon atoms, provided that the alkoxy group as $R^7$ and the alkyl group as $R^8$ may combine to form a ring; $R^9$ represents a hydrogen atom, a hydroxyl group, an alkyl group having 1–4 carbon atoms, an alkoxy group having 1–4 carbon atoms, a carboxymethyloxy group or a group: —$NR^{10}R^{10}$ (the two $R^{10}$s may be the same or different); $R^{10}$ represents a hydrogen atom or an alkyl group having 1 or 2 carbon atoms; $R^{11}$ represents a hydrogen atom, a halogen atom, a cyano group, an optionally protected carboxyl group, an optionally protected carboxymethyl group, an alkoxycarbonyl group having 1–4 carbon atoms, a carbamoyl group, an acetylamino group, an optionally protected hydroxyl group, an optionally protected mercapto group, a straight- or branched-chain alkyl group having 1–4 carbon atoms which may optionally be substituted by one hydroxyl group, an amino group which may optionally be mono- or disubstituted by an alkyl group having 1–4 carbon atoms, an alkylthio group having 1–3 carbon atoms, or a straight-chain alkoxy group having 1–6 carbon atoms which may optionally be substituted by a 4-methoxyphenoxy group; $R^{12}$ represents a hydrogen atom, a halogen atom, an optionally protected hydroxyl group, an optionally protected mercapto group, an optionally protected amino group, a cyano group, a nitro group, a trifluoromethyl group, a trifluoromethoxy group, an optionally protected carboxyl group, a straight- or branched-chain alkanoyl group having 1–4 carbon atoms, a straight- or branched-chain alkyl group having 1–4 carbon atoms, or a straight- or branched-chain alkoxy group having 1–4 carbon atoms; $R^{13}$ represents a hydrogen atom, a halogen atom, an optionally protected hydroxyl group or a straight- or branched-chain alkoxy group having 1–4 carbon atoms; $R^{19}$ represents a hydrogen atom, a halogen atom, a group: —M—G (where M represents an oxygen atom, an imino group or a group: —N($CH_3$)—, and G represents a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group), an α-hydroxybenzyl group, a methyl group or a halogenomethyl group; provided that are excluded the compounds wherein, when A represents a single bond, and all of $Y^1$–$Y^3$ and $Z^1$–$Z^4$ represent a methine group; the compounds wherein, A represents an oxygen atom or a group: —$SO_n$— (n is 0–2), all of $Y^1$–$Y^3$ and $Z^1$–$Z^4$ represent a methine group, and all of $R^5$, $R^{11}$, $R^{12}$, $R^{13}$ and $R^{19}$ represent respectively a hydrogen atom; the compounds wherein, A represents a sulfur atom, all of $Y^1$–$Y^3$ and $Z^1$–$Z^4$ represent a methine group, $R^5$, $R^{11}$ and $R^{19}$ represent respectively a hydrogen atom, and one of $R^{12}$ and $R^{13}$ represents a hydrogen atom and the other one of $R^{12}$ and $R^{13}$ represents a fluorine atom, a chlorine atom or a bromine atom at position 10, or a chlorine atom at position 11; the compounds wherein, A represents a sulfur atom, all of $Y^1$–$Y^3$ and $Z^1$–$Z^4$ represent a methine group, $R^5$, $R^{11}$, $R^{12}$ and $R^{13}$ represent respectively a hydrogen atom, and $R^{19}$ represents a bromine atom or a methyl group; the compounds wherein, A represents a sulfur atom, all of $Y^1$–$Y^3$ and $Z^1$–$Z^4$ represent a methine group, $R^5$, $R^{12}$, $R^{13}$ and $R^{19}$ represent respectively a hydrogen atom, and $R^{11}$ represents a chlorine atom at position 4; the compounds wherein, A represents a sulfur atom, all of $Y^1$–$Y^3$ and $Z^1$–$Z^4$ represent a methine group, $R^5$, $R^1$, $R^{13}$ and $R^{19}$ represent respectively a hydrogen atom, and $R^{12}$ represents a trifluoromethyl group at position 9, 10 or 11; the compounds wherein, A represents a sulfur atom, all of $Y^1$–$Y^3$ and $Z^1$–$Z^4$ represent a methine group, $R^5$, $R^{13}$ and $R^{19}$ represent respectively a hydrogen atom, $R^{11}$ represents a methyl group at position 4, and $R^{12}$ represents a trifluoromethyl group at position 10; the compounds wherein, A represents a single bond, $Y^1$ and $Y^2$ represent a methine group, $Y^3$ represents a nitrogen atom, $Z^1$–$Z^4$ represent a methine group, and all of $R^5$, $R^{11}$, $R^{12}$, $R^{13}$ and $R^{19}$ represent respectively a hydrogen atom.)

According to its sixteenth aspect, the present invention provides a process for producing said derivative compounds of the above formula (I) in which a compound represented by the following formula (VI) or a salt thereof:

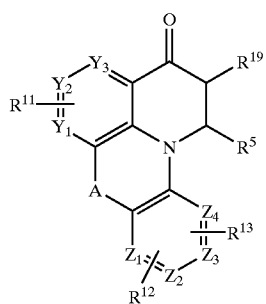

(VI)

(where A represents a single bond, a methylene group, a carbonyl group, an oxygen atom, a group: —$SO_n$— (n is 0–2), a group: —N($R^6$)—, a group: —$CR^7(OR^8)$— or a group: —C(=N—$R^9$)—; $Y^1$–$Y^3$ and $Z^1$–$Z^4$ represent each a methine group or a nitrogen atom; $R^5$ represents a hydrogen atom or a methyl group; $R^6$ represents a hydrogen atom, a straight- or branched-chain alkyl group having 1–4 carbon atoms or a straight- or branched-chain alkanoyl group having 1–4 carbon atoms; $R^7$ represents a hydrogen atom or a straight- or branched-chain alkoxy group having 1–4 carbon atoms; $R^8$ represents a hydrogen atom or an alkyl group having 1–4 carbon atoms, provided that the alkoxy group as $R^7$ and the alkyl group as $R^8$ may combine to form a ring; $R^9$ represents a hydrogen atom, a hydroxyl group, an alkyl group having 1–4 carbon atoms, an alkoxy group having 1–4 carbon atoms, a carboxymethyloxy group or a group: —$NR^{10}R^{10}$ (the two $R^{10}$s may be the same or different); $R^{10}$ represents a hydrogen atom or an alkyl group having 1 or 2 carbon atoms; $R^{11}$ represents a hydrogen atom, a halogen atom, a cyano group, an optionally protected carboxyl group, an optionally protected carboxymethyl group, an alkoxycarbonyl group having 1–4 carbon atoms, a carbamoyl group, an acetylamino group, an optionally protected hydroxyl group, an optionally protected mercapto group, a straight- or branched-chain alkyl group having 1–4 carbon atoms which may optionally be substituted by one hydroxyl group, an amino group which may optionally be mono- or disubstituted by an alkyl group having 1–4 carbon atoms, an alkylthio group having 1–3 carbon atoms, or a straight-chain alkoxy group having 1–6 carbon atoms which may optionally be substituted by a 4-methoxyphenoxy group; $R^{12}$ represents a hydrogen atom, a halogen atom, an optionally protected hydroxyl group, an optionally protected mercapto group, an optionally protected amino group, a cyano group, a nitro group, a trifluoromethyl group, a trifluoromethoxy group, an optionally protected carboxyl group, a straight- or branched-chain alkanoyl group having 1–4 carbon atoms, a straight- or branched-chain alkyl group having 1–4 carbon atoms, or a straight- or branched-chain alkoxy group having 1–4 carbon atoms; $R^{13}$ represents a hydrogen atom, a halogen atom, an optionally protected hydroxyl group or a straight- or branched-chain alkoxy group having 1–4 carbon atoms; $R^{19}$ represents a hydrogen atom, a halogen atom, a group: —M—G (where M represents an oxygen atom, an imino group or a group: —N($CH_3$)—, and G represents a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group), an α-hydroxybenzyl group, a methyl group or a halogenomethyl group) is reacted optionally, under basic conditions, with an aldehyde derivative represented by the following formula (XVII):

$R^{22}$—CHO (XVII)

(where $R^{22}$ represents a hydrogen atom, a methyl group, a cyclic alkyl group having 3–6 carbon atoms, a phenyl group which may be mono- or disubstituted in the benzene ring by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyridyl group which may be monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a morpholyl group, a triazolyl group, a furyl group, a thienyl group, a pyrimidinyl group, a pyrazinyl group, a pyrrolyl group, an imidazolyl group, a quinolyl group, an indolyl group or a naphthyl group) and then the reaction product either in an isolated form or after dehydration to yield an enone which has the double bond subsequently isomerized in the ring, is subjected to an oxidation, either immediately or after reaction with phenol, aniline, N-methylaniline, triazole, imidazole, morpholine, etc. to derive a compound represented by the following formula (XIV):

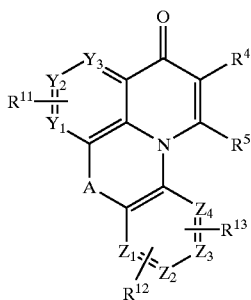

(XIV)

(where $R^4$, $R^5$, $R^{11}$, $R^{12}$, $R^{13}$, $Y^1$–$Y^3$, $Z^1$–$Z^4$ and A as well as $R^6$, $R^7$, $R^8$, $R^9$ and $R^{10}$ defined in A have the same meanings as defined above), said compound (XIV) is optionally subjected to a suitable substituent change and, after optional deprotection of $R^{11}$, reacted with a reactive halogen derivative represented by the following formula (XVIII):

$$R^{23}—X \quad \quad (XVIII)$$

(where X is a halogen atom, $R^{23}$ represents an alkoxycarbonyl group having 1–4 carbon atoms, a 3-carboxy-1-propenyl group, a 2,2-diethoxyethyl group, a straight- or branched-chain alkanoyl group having 1–4 carbon atoms, a carbonyl group substituted by a phenyl group or a pyridyl group, or a group: —$(CH_2)_n$—Q (where Q represents a hydrogen atom, a carboxyl group, an alkoxy group having 1 or 2 carbon atoms which may be substituted by one hydroxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or one mercapto group, a piperidinylcarbonyl group which may be substituted by one carboxyl group or alkoxycarbonyl group having 1 or 2 carbon atoms, a morpholylcarbonyl group, a hydroxyl group, a mercapto group, a group: —$NR^{24}R^{24}$ ($R^{24}$ represents a hydrogen atom or an alkyl group having 1–4 carbon atoms; the two $R^{24}$s may be the same or different, or may combine each other to form a ring), a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyridyl group which may be mono- substituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyrazinyl group, a pyrimidinyl group, a furyl group, a thienyl group, an oxadiazolyl group, a 4-methoxyphenoxy group, a 1-benzotriazolyl group, a 4-morpholinyl group, or 2-benzimidazolyl group; n is 1–6)) to yield a compound represented by the following formula (XV):

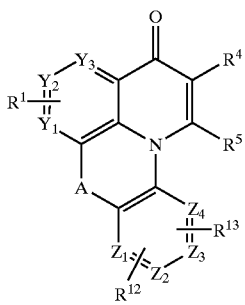

(XV)

(where $R^1$, $R^4$, $R^5$, $R^{12}$, $R^{13}$, $Y^1$–$Y^3$, $Z^1$–$Z^4$ and A as well as $R^6$, $R^7$, $R^8$, $R^9$ and $R^{10}$ defined in A have the same meanings as defined above), which is subjected to a suitable substituent change, or alternatively, the compound represented by the formula (XIV) is subjected to a suitable substituent change to yield a compound represented by the following formula (XVI):

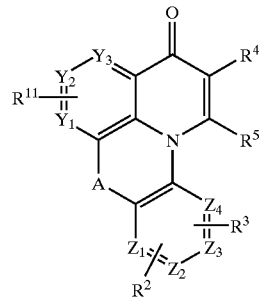

(XVI)

(where $R^2$, $R^3$, $R^4$, $R^5$, $R^{11}$, $Y^1$–$Y^3$, $Z^1$–$Z^4$ and A as well as $R^6$, $R^7$, $R^8$, $R^9$ and $R^{10}$ defined in A have the same meanings as defined above), which is optionally subjected to deprotection of $R^{11}$ and reacted with the reactive halogen derivative represented by the formula (XVIII) so as to produce the compound represented by the following formula (I) or a salt thereof:

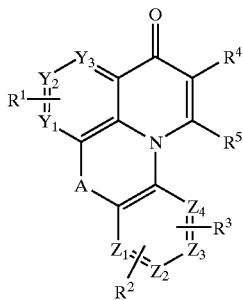

(I)

(where $R^1$, $R^2$, $R^3$, $R^4$, $R^5$, $Y^1$–$Y^3$, $Z^1$–$Z^4$ and A as well as $R^6$, $R^7$, $R^8$, $R^9$ and $R^{10}$ defined in A have the same meanings as defined above).

According to its seventeenth aspect, the present invention provides agents for preventing or treating diseases against which the cGMP-PDE inhibitory action is effective in the presence of at least one of the compounds of the above formula (I) or salts thereof as an active ingredient.

According to its eighteenth aspect, the present invention provides agents for preventing or treating pulmonary hypertension which contain at least one of the compounds of the above formula (I) or salts thereof as an active ingredient.

According to its nineteenth aspect, the present invention provides agents for preventing or treating ischemic heart diseases which contain at least one of the compounds of the above formula (I) or salts thereof as an active ingredient.

According to its twentieth aspect, the present invention provides agents for preventing or treating erectile dysfunction which contain at least one of the compounds of the above formula (I) or salts thereof as an active ingredient.

According to its twenty first aspect, the present invention provides agents for preventing or treating female sexual dysfunction which contain at least one of the compounds of the above formula (I) or salts thereof as an active ingredient.

Preferably, a pharmaceutical composition of the present invention is administered to the patient by a dosage form of oral, intranasal, intraurethral, transcutaneous or transmucomembranous preparations. More preferably, oral, intranasal or intraurethral preparations are used.

BRIEF DESCRIPTION OF THE INVENTION

FIG. 1: This is a reaction scheme showing the method of preparing a compound represented by the formula (VI) from a compound represented by the formula (III) through Process 1 or 2.

Figure 2:
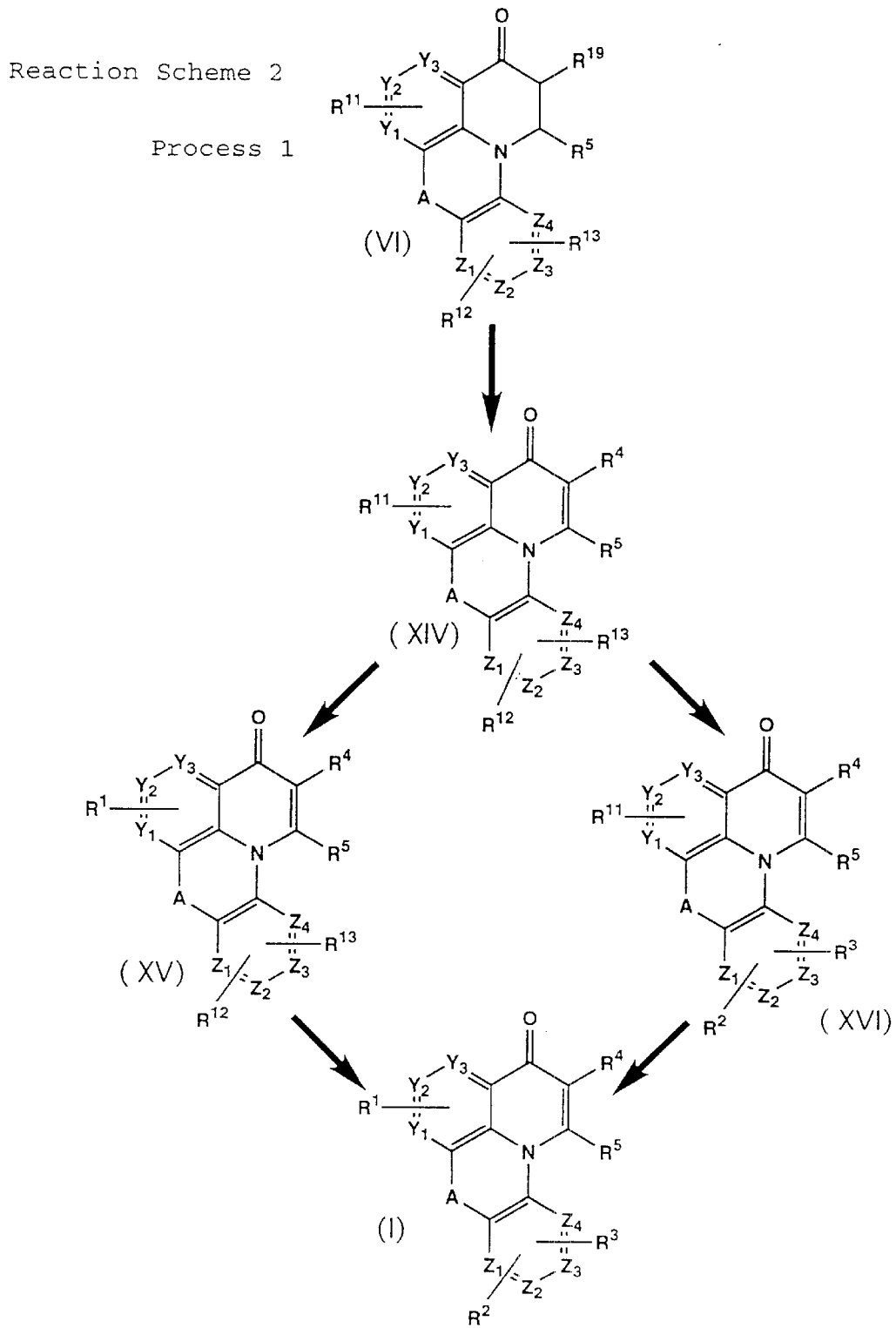

FIG. 2: This is a reaction scheme showing the method of preparing a compound represented by the formula (I) from a compound represented by the formula (VI) through Process 1.

Figure 3:
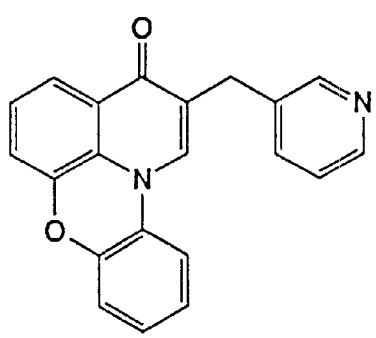
Figure 3:
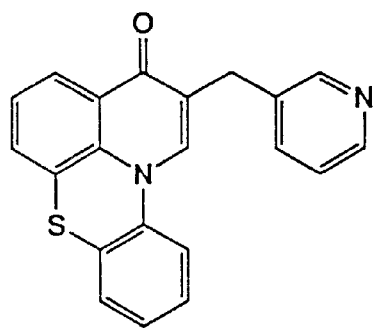
Figure 3:
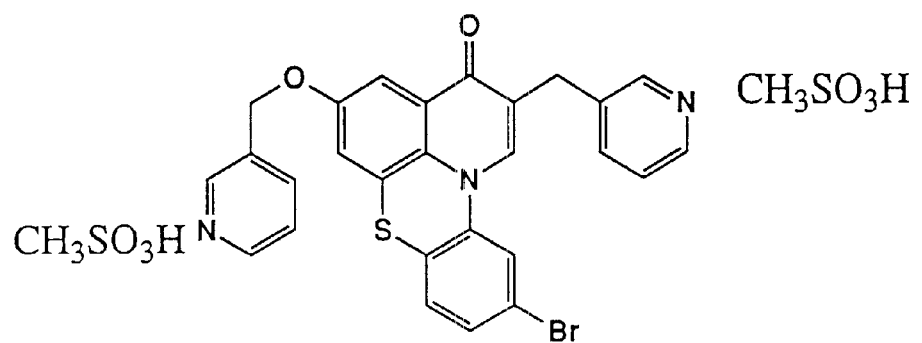

FIG. 3: This is the structural formula of Example 4, 8 and 81.

BEST MODE FOR CARRYING OUT THE INVENTION

The present invention will now be described below in detail.

The substitution position numbers assigned to the substituents in the condensed tetracyclic hetero-ring compounds of the invention are indicated below, wherein the formula (I) is expressed as formula (I)-a where A is a single bond and as formula (I)-b where A is other than a single bond (and denoted by A' in the formula).

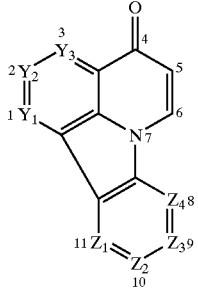

(I)-a (I)-b

In the case of the formula (I)-a, $Y^1$ is at position 1, $Y^2$ at position 2, $Y^3$ at position 3, $Z^4$ at position 8, $Z^3$ at position 9, $Z^2$ at position 10 and $Z^1$ at position 11. This means that $R^1$ is bound at position 1, 2 or 3, $R^2$ or $R^3$ at position 8, 9, 10 or 11, $R^4$ at position 5 and $R^5$ at position 6. In the case of the formula (I)-b, $Y^1$ is at position 6, $Y^2$ at position 5, $Y^3$ at position 4, $Z^1$ at position 8, $Z^2$ at position 9, $Z^3$ at position 10, $Z^4$ at position 11, and A' at position 7. This means that $R^1$ is bound at position 4, 5 or 6, $R^2$ or $R^3$ at position 8, 9, 10 or 11, $R^4$ at position 2 and $R^5$ at position 1.

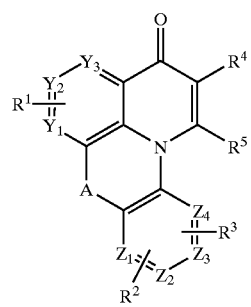

(I)

The compounds of the present invention are represented by the above formula (I) where A represents a single bond, a methylene group, a carbonyl group, an oxygen atom, a group: —$SO_n$— (n is 0–2), a group: —N($R^6$)—, a group: —$CR^7(OR^8)$— or a group: —C(=N—$R^9$)—; $Y^1$–$Y^3$ and $Z^1$–$Z^4$ represent each a methine group or a nitrogen atom; $R^1$ represents a hydrogen atom, a halogen atom, a cyano group, an optionally protected carboxyl group, an optionally protected carboxymethyl group, an alkoxycarbonyl group having 1–4 carbon atoms, a carbamoyl group, an acetylamino group, a 3-carboxy-1-propenyl group, a 2-hydroxypentyloxy group, a 2,2-diethoxyethoxy group, an optionally protected hydroxyl group, an optionally protected mercapto group, a straight- or branched-chain alkanoyloxy group having 1–4 carbon atoms, a carbonyloxy group substituted by a phenyl group or a pyridyl group, a straight- or branched-chain alkyl group having 1–4 carbon atoms which may be substituted by one hydroxyl group, an amino group which may be mono- or disubstituted by an alkyl group having 1–4 carbon atoms, an alkylthio group having 1–3 carbon atoms which may be monosubstituted by any group selected from the group consisting of a hydroxyl group, a carboxyl group, a phenyl group and a pyridyl group, a 1-methyl-hexahydroazepin-4-yl-oxy group, or represented by the following formula (II):

(where Q represents a hydrogen atom, a carboxyl group, an alkoxy group having 1 or 2 carbon atoms which may be substituted by one hydroxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or one mercapto group, a piperidinylcarbonyl group which may be substituted by one carboxyl group or alkoxycarbonyl group having 1 or 2 carbon atoms, a morpholylcarbonyl group, a hydroxyl group, a mercapto group, a group: —$NR^{24}R^{24}$ ($R^{24}$ represents a hydrogen atom or an alkyl group having 1–4 carbon atoms; the two $R^{24}$s may be the same or different, or may combine each other to form a ring), a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyridyl group which may be monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyrazinyl group, a pyrimidinyl group, a furyl group, a thienyl group, an oxadiazolyl group, a 4-methoxyphenoxy group, a 1-benzotriazolyl group, a 4-morpholinyl group, or 2-benzimidazolyl group; n is 1–6).

More specifically, the term "halogen atom" refers to a fluorine atom, a chlorine atom or a bromine atom; the term "alkoxycarbonyl group having 1–4 carbon atoms" refers to a methoxycarbonyl group, an ethoxycarbonyl group, a n-propoxycarbonyl group, an i-propoxycarbonyl group, a cyclopropoxycarbonyl group, a n-butoxycarbonyl group, a t-butoxycarbonyl group or the like; the term "optionally protected hydroxyl group" refers to a hydroxyl group, a trimethylsilyloxy group, a t-butyldimethylsilyloxy group, a methoxymethyloxy group or the like; the term "optionally protected mercapto group" refers to a phenylthio group, a benzylthio group or the like; the term "straight- or branched-chain alkanoyloxy group having 1–4 carbon atoms" refers to an acetoxy group, a propionyloxy group, a butyryloxy group, a pivaloyloxy group or the like; the term "carbonyloxy group substituted by a phenyl group or a pyridyl group" refers to a benzoyloxy group, a nicotinoyloxy group, an isonicotinoyloxy group or the like; the term "straight- or branched-chain alkyl group having 1–4 carbon atoms which may be substituted by one hydroxyl group" refers to a methyl group, an ethyl group, a n-propyl group, an i-propyl group, a n-butyl group, a t-butyl group, a 1-hydroxyethyl group, a 2-hydroxyethyl group, a 1-hydroxypropyl group or the like; the term "amino group which may be mono- or disubstituted by an alkyl group having 1–4 carbon atoms" refers to a methylamino group, a dimethylamino group, an ethylamino group, a diethylamino group, a n-propylamino group, a n-butylamino group or the like; the term "alkylthio group having 1–3 carbon atoms which may be monosubstituted by any group selected from the group consisting of a hydroxyl group, a carboxyl group, a phenyl group and a pyridyl group" refers to a methylthio group, an ethylthio group, a 3-hydroxypropylthio group, a carboxymethylthio group, a 3-pyridylmethylthio group or the like; the following formula (II):

(where Q represents a hydrogen atom, a carboxyl group, an alkoxy group having 1 or 2 carbon atoms which may be substituted by one hydroxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or one mercapto group, a piperidinylcarbonyl group which may be substituted by one carboxyl group or alkoxycarbonyl group having 1 or 2 carbon atoms, a morpholylcarbonyl group, a hydroxyl group, a mercapto group, a group: —$NR^{24}R^{24}$ ($R^{24}$ represents a hydrogen atom or an alkyl group having 1–4 carbon atoms; the two $R^{24}$s may be the same or different, or may combine each other to form a ring), a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyridyl group which may be monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyrazinyl group, a pyrimidinyl group, a furyl group, a thienyl group, an oxadiazolyl group, a 4-methoxyphenoxy group, a 1-benzotriazolyl group, a 4-morpholinyl group, or 2-benzimidazolyl group; n is 1–6) refers to a methoxy group, an ethoxy group, a n-propoxy group, a n-butoxy group, a n-pentyloxy group, a n-hexyloxy group, a carboxymethyloxy group, a 2-carboxyethyloxy group, a 3-carboxypropyloxy group, a methoxymethoxy group, an ethoxymethoxy group, a 2-methoxyethoxy group, a 2-ethoxyethoxy group, a 2-(2-hydroxyethoxy)ethoxy group, a methoxycarbonylmethyloxy group, an ethoxycarbonylmethyloxy group, a n-propoxycarbonylmethyloxy group, an i-propoxycarbonylmethyloxy group, a n-butoxycarbonylmethyloxy group, a t-butoxycarbonylmethyloxy group, a n-pentyloxycarbonylmethyloxy group, a n-hexyloxycarbonylmethyloxy group, a cyclopropyloxycarbonylmethyloxy group, a cyclohexyloxycarbonylmethyloxy group, a 2-(methoxycarbonyl)ethyloxy group, a 2-(ethoxycarbonyl)ethyloxy group, a 2-(n-propoxycarbonyl)ethyloxy group, a 2-(i-propoxycarbonyl)ethyloxy group, a 2-(n-butoxycarbonyl)ethyloxy group, a 2-(t-butoxycarbonyl)ethyloxy group, a 2-(n-pentyloxycarbonyl)ethyloxy group, a 2-(n-hexyloxycarbonyl)ethyloxy group, a 2-(cyclopropyloxycarbonyl)ethyloxy group, a 2-(cyclohexyloxycarbonyl)ethyloxy group, a 3-(methoxycarbonyl)propyloxy group, a 3-(ethoxycarbonyl)propyloxy group, a 3-(n-propoxycarbonyl)propyloxy group, a 3-(i-propoxycarbonyl)propyloxy group, a 3-(n-butoxycarbonyl)propyloxy group, a 3-(t-butoxycarbonyl)propyloxy group, a 3-(n-pentyloxycarbonyl)propyloxy group, a 3-(n-hexyloxycarbonyl)propyloxy group, a 3-(cyclopropyloxycarbonyl)propyloxy group, a 3-(cyclohexyloxycarbonyl)propyloxy group, a N-hydroxymethylcarbamoylmethyloxy group, a N-methylcarbamoylmethyloxy group, a N,N-dimethylcarbamoylmethyloxy group, a N-ethylcarbamoylmethyloxy group, a N,N-diethylcarbamoylmethyloxy group, a N-n-propylcarbamoylmethyloxy group, a N-n-butylcarbamoylmethyloxy group, a 3-hydroxy-2-oxopropyloxy group, a 4-hydroxy-3-oxobutyloxy group, a 5-hydroxy-4-oxopentyloxy group, a 4-hydroxy-2-oxobutyloxy group, a 5-hydroxy-2-oxopentyloxy group, a 6-hydroxy-2-oxohexyloxy group, a 5-mercapto-2-oxopentyloxy group, a 4-carboxy-1-piperidinylcarbonylmethyloxy group, a 4-methoxycarbonyl-1-piperidinylcarbonylmethyloxy group, a 4-ethoxycarbonyl-1-piperidinylcarbonylmethyloxy group, a 4-morpholylcarbonylmethyloxy group, a 2-hydroxyethyloxy group, a 3-hydroxypropyloxy group, a 4-hydroxybutyloxy group, a 2-mercaptoethyloxy group, a 3-mercaptopropyloxy group, a 4-mercaptobutyloxy group, a 2-aminoethyloxy group, a 3-aminopropyloxy group, a 4-aminobutyloxy group, 2-N,N-dimethylaminoethyloxy group, 3-N,N-dimethylaminopropyloxy group, 4-N,N-dimethylaminobutyloxy group, 2-N,N-diisopropylaminoethyloxy group, 3-N,N-diisopropylaminopropyloxy group, 4-N,N-diisopropylaminobutyloxy group,2-(1-piperidyl)ethyloxy group, 3-(1-piperidyl)propyloxy group, 4-(1-piperidyl)butyloxy group, a benzyloxy group, a 2-fluorobenzyloxy group, a 2-chlorobenzyloxy group, a 2-bromobenzyloxy group, a 3-fluorobenzyloxy group, a 3-chlorobenzyloxy group, a 3-bromobenzyloxy group, a 4-fluorobenzyloxy group, a 4-chlorobenzyloxy group, a 4-bromobenzyloxy group, a 2-hydroxybenzyloxy group, a 3-hydroxybenzyloxy group, a 4-hydroxybenzyloxy group, a 2-mercaptobenzyloxy group, a 3-mercaptobenzyloxy group, a 4-mercaptobenzyloxy group, a 2-methoxybenzyloxy group, a 3-methoxybenzyloxy group, a 4-methoxybenzyloxy group, a 2-ethoxybenzyloxy group, a 3-ethoxybenzyloxy group, a 4-ethoxybenzyloxy group, a 2-methylthiobenzyloxy group, a 3-methylthiobenzyloxy group, a 4-methylthiobenzyloxy group, a 2-ethylthiobenzyloxy group, a 3-ethylthiobenzyloxy group, a 4-ethylthiobenzyloxy group, a 2-methoxycarbonylbenzyloxy group, a 3-methoxycarbonylbenzyloxy group, a 4-methoxycarbonylbenzyloxy group, a 2-ethoxycarbonylbenzyloxy group, a 3-ethoxycarbonylbenzyloxy group, a 4-ethoxycarbonylbenzyloxy group, a 2-t-butoxycarbonylbenzyloxy group, a 3-t-butoxycarbonylbenzyloxy group, a 4-t-butoxycarbonylbenzyloxy group, a 2-acetylaminobenzyloxy group, a 3-acetylaminobenzyloxy group, a 4-acetylaminobenzyloxy group, a 2-carboxybenzyloxy group, a 3-carboxybenzyloxy group, a 4-carboxybenzyloxy group, a 2-aminobenzyloxy group, a 3-aminobenzyloxy group, a 4-aminobenzyloxy group, a 2-cyanobenzyloxy group, a 3-cyanobenzyloxy group, a 4-cyanobenzyloxy group, a 2-nitrobenzyloxy group, a 3-nitrobenzyloxy group, a 4-nitrobenzyloxy group, a 2-methylainobenzyloxy group, a 3-methylaminobenzyloxy group, a 4-methylaminobenzyloxy group, a 2-ethylaminobenzyloxy group, a 3-ethylarinobenzyloxy group, a 4-ethylaminobenzyloxy group, a 2-dimethylaminobenzyloxy group, a 3-dimethylaminobenzyloxy group, a 4-dimethylaminobenzyloxy group, a 2-diethylaminobenzyloxy group, a 3-diethylaminobenzyloxy group, a 4-diethylaminobenzyloxy group, a 2-hydroxymethylbenzyloxy group, a 3-hydroxymethylbenzyloxy group, a 4-hydroxymethylbenzyloxy group, a 2-acetoxymethylbenzyloxy group, a 3-acetoxymethylbenzyloxy group, a 4-acetoxymethylbenzyloxy group, a 2-carbamoylbenzyloxy group, a 3-carbamoylbenzyloxy group, a 4-carbamoylbenzyloxy group, a 2-methylbenzyloxy group, a 3-methylbenzyloxy group, a 4-methylbenzyloxy group, a 2-ethylbenzyloxy group, a 3-ethylbenzyloxy group, a 4-ethylbenzyloxy group, 2-(n-propyl)benzyloxy group, a 3-(n-propyl )benzyloxy group, a 4-(n-propyl)benzyloxy group, a 2-(i-propyl)benzyloxy group, a 3-(i-propyl)benzyloxy group, a 4-(i-propyl)benzyloxy group, a 2-(n-butyl)benzyloxy group, a 3-(n-butyl)benzyloxy group, a 4-(n-butyl)benzyloxy group, a 2-(t-butyl)benzyloxy group, a 3-(t-butyl)benzyloxy group, a 4-(t-butyl)benzyloxy group, a 2,3-difluorobenzyloxy group, a 2,4-difluorobenzyloxy group, a 2,5-difluorobenzyloxy group, a 3,4-difluorobenzyloxy group, a 3,5-difluorobenzyloxy group, a 2,3-dichlorbenzyloxy group, a 2,4-dichlorbenzyloxy group, a 2,5-dichlorbenzyloxy group, a 3,4-dichlorbenzyloxy group, a 3,5-dichlorbenzyloxy group, a 2,3-dibromobenzyloxy group, a 2,4-dibromobenzyloxy group, a 2,5-dibromobenzyloxy group, a 3,4-dibromobenzyloxy group, a 3,5-dibromobenzyloxy group, a 2,3-dihydroxybenzyloxy group, a 2,4-dihydroxybenzyloxy group, a 2,5-dihydroxybenzyloxy group, a 3,4-dihydroxybenzyloxy group, a 3,5-dihyroxybenzyloxy group, a 2,3-dimethoxybenzyloxy group, a 2,4-dimethoxybenzyloxy group, a 2,5-dimethoxybenzyloxy group, a 3,4-dimethoxybenzyloxy group, a 3,5-dimethoxybenzyloxy group, a 2,3-diethoxybenzyloxy group, a 2,4-diethoxybenzyloxy group, a 2,5-diethoxybenzyloxy group, a 3,4-diethoxybenzyloxy group, a 3,5-diethoxybenzyloxy group, a 2-fluoro-3-methoxybenzyloxy group, a 2-fluoro-4-methoxybenzyloxy group, a 2-fluoro-5-methoxybenzyloxy group, a 3-fluoro-4-methoxybenzyloxy group, a 3-fluoro-5-methoxybenzyloxy group, a 3-fluoro-2-methoxybenzyloxy group, a 4-fluoro-2-methoxybenzyloxy group, a 5-fluoro-2-methoxybenzyloxy group, a 4-fluoro-3-methoxybenzyloxy group, a 5-fluoro-3-methoxybenzyloxy group, a 2-chloro-3-methoxybenzyloxy group, a 2-chloro-4-methoxybenzyloxy group, a 2-chloro-5-methoxybenzyloxy group, a 3-chloro-4-methoxybenzyloxy group, a 3-chloro-5-methoxybenzyloxy group, a 3-chloro-2-methoxybenzyloxy group, a 4-chloro-2-methoxybenzyloxy group, a 5-chloro-2-methoxybenzyloxy group, a 4-chloro-3-methoxybenzyloxy group, a 5-chloro-3-methoxybenzyloxy group, a 2-bromo-3-methoxybenzyloxy group, a 2-bromo-4-methoxybenzyloxy group, a 2-bromo-5-methoxybenzyloxy group, a 3-bromo-4-methoxybenzyloxy group, a 3-bromo-5-methoxybenzyloxy group, a 3-bromo-2-methoxybenzyloxy group, a 4-bromo-2-methoxybenzyloxy group, a 5-bromo-2-methoxybenzyloxy group, a 4-bromo-3-methoxybenzyloxy group, a 5-bromo-3-methoxybenzyloxy group, a 2-cyano-3- methoxybenzyloxy group, a 2-cyano-4-methoxybenzyloxy group, a 2-cyano-5-methoxybenzyloxy group, a 3-cyano-4-methoxybenzyloxy group, a 3-cyano-5-methoxybenzyloxy group, a 3-cyano-2-methoxybenzyloxy group, a 4-cyano-2-methoxybenzyloxy group, a 5-cyano-2-methoxybenzyloxy group, a 4-cyano-3-methoxybenzyloxy group, a 5-cyano-3-methoxybenzyloxy group, a 2-phenethyloxy group, a 3-phenylpropyloxy group, a 5-hydroxymethyl-3-pyridylmethyloxy group, a 5-acetoxymethyl-3-pyridylmethyloxy group, a 6-hydroxymethyl-2-pyridylmethyloxy group, a 6-acetoxymethyl-2-pyridylmethyloxy group, a 5-methyl-3-pyridylmethyloxy group, a 6-methyl-2-pyridylmethyloxy group, a 5-ethyl-3-pyridylmethyloxy group, a 5-t-butyl-3-pyridylmethyloxy group, a 5-methoxycarbonyl-3-pyridylmethyloxy group, a 5-ethoxycarbonyl-3-pyridylmethyloxy group, a 2-pyridylmethyloxy group, a 3-pyridylmethyloxy group, a 4-pyridylmethyloxy group, a 6-ethyl-2-pyridylmethyloxy group, a 6-methoxycarbonyl-2-pyridylmethyloxy group, a 5-carboxy-3-pyridylmethyloxy group, a 6-carboxy-2-pyridylmethyloxy group, a 4-amino-2-pyridylmethyloxy group, a 5-amino-3-pyridylmethyloxy group, a 2-amino-4-pyridylmethyloxy group, a 4-carboxy-2-pyridylmethyloxy group, a 5-carboxy-3-pyridylmethyloxy group, a 4-acetylamino-2-pyridylmethyloxy group, a 5-acetylamino-3-pyridylmethyloxy group, a 2-acetylamino-4-pyridylmethyloxy group, a 4-methylthio-2-pyridylmethyloxy group, a 5-methylthio-3-pyridylmethyloxy group, a 3-methylthio-4-pyridylmethyloxy group, a 4-mercapto-2-pyridylmethyloxy group, a 5-mercapto-3-pyridylmethyloxy group, a 3-mercapto-4-pyridylmethyloxy group, a 4-methoxy-2-pyridylmethyloxy group, a 5-methoxy-3-pyridylmethyloxy group, a 3-methoxy-4-pyridylmethyloxy group, a 4-hydroxy-2-pyridylmethyloxy group, a 5-hydroxy-3-pyridylmethyloxy group, a 3-hydroxy-4-pyridylmethyloxy group, a 4-fluoro-2-pyridylmethyloxy group, a 5-fluoro-2-pyridylmethyloxy group, a 4-fluoro-3-pyridylmethyloxy group, a 5-fluoro-3-pyridylmethyloxy group, a 2-fluoro-4-pyridylmethyloxy group, a 2-fluoro-4-pyridylmethyloxy group, a 4-chloro-2-pyridylmethyloxy group, a 5-chloro-2-pyridylmethyloxy group, a 4-chloro-3-pyridylmethyloxy group, a 5-chloro-3-pyridylmethyloxy group, a 2-chloro-4-pyridylmethyloxy group, a 2-chloro-4-pyridylmethyloxy group, a 4-bromo-2-pyridylmethyloxy group, a 5-bromo-2-pyridylmethyloxy group, a 4-bromo-3-pyridylmethyloxy group, a 5-bromo-3-pyridylmethyloxy group, a 2-bromo-4-pyridylmethyloxy group, a 2-bromo-4-pyridylmethyloxy group, a 4-cyano-2-pyridylmethyloxy group, a 5-cyano-2-pyridylmethyloxy group, a 4-cyano-3-pyridylmethyloxy group, a 5-cyano-3-pyridylmethyloxy group, a 2-cyano-4-pyridylmethyloxy group, a 2-cyano-4-pyridylmethyloxy group, a 4-nitro-2-pyridylmethyloxy group, a 5-nitro-3-pyridylmethyloxy group, a 4-dimethylamino-2-pyridylmethyloxy group, a 5-dimethylamino-3-pyridylmethyloxy group, a 4-carbamoyl-2-pyridylmethyloxy group, a 5-carbamoyl-3-pyridylmethyloxy group, a 2-pyrazinylmethyloxy group, a 2-pyrimidinylmethyloxy group, a 4-pyrimidinylmethyloxy group, a 5-pyrimidinylmethyloxy group, a 2-furylmethyloxy group, a 3-furylmethyloxy group, a 2-thienylmethyloxy group, a 3-thienylmethyloxy group, a 3-oxadiazolylmethyloxy group, a 2-(4-methoxyphenoxy)ethyloxy group, a 3-(4-methoxyphenoxy)propyloxy group, a 4-(4-methoxyphenoxy)butyloxy group, a 1-benzotriazolylmethyloxy group, 2-(1-benzotriazolyl)ethyloxy group, a 3-(1-benzotriazolyl)propyloxy group, a 4-(1-benzotriazolyl) butyloxy group, a 4-morpholylmethyloxy group, 2-(4-morpholyl)ethyloxy group, a 3-(4-morpholyl)propyloxy group, a 4-(4-morpholyl)butyloxy group, a 2-benzimidazolylmethyloxy group, 2-(2-benzimidazolyl)ethyloxy group, a 3-(2-benzimidazolyl)propyloxy group, a 4-(2-benzimidazolyl)butyloxy group, or the like.

Preferably, $R^1$ is substituted at position 2 in the case of the formula (I)-a and position 5 in the case of the formula (I)-b, and it represents a hydroxyl group, a methoxy group, a carboxymethyloxy group, a 2-carboxyethyloxy group, a 3-carboxypropyloxy group, a methoxycarbonylmethyloxy group, an ethoxycarbonylmethyloxy group, a n-propoxycarbonylmethyloxy group, an i-propoxycarbonylmethyloxy group, a n-butoxycarbonylmethyloxy group, a t-butoxycarbonylmethyloxy group, a N-hydroxymethylcarbamoylmethyloxy group, a N-ethylcarbamoylmethyloxy group, a 4-hydroxy-2-oxobutyloxy group, a 5-hydroxy-2-oxopentyloxy group, a 2-hydroxyethyloxy group, a 3-hydroxypropyloxy group, a 4-hydroxybutyloxy group, a 2-aminoethyloxy group, a 3-aminopropyloxy group, a 4-aminobutyloxy group, 2-N,N-dimethylaminoethyloxy group, 3-N,N-dimethylaminopropyloxy group, 4-N,N-dimethylaminobutyloxy group, 2-N,N-diisopropylaminoethyloxy group, 3-N,N-diisopropylaminopropyloxy group, 4-N,N-diisopropylaminobutyloxy group, 2-(1-piperidyl)ethyloxy group, 3-(1-piperidyl)propyloxy group, 4-(1-piperidyl)butyloxy group, a benzyloxy group, a 5-hydroxymethyl-3-pyridylmethyloxy group, a 5-acetoxymethyl-3-pyridylmethyloxy group, a 6-hydroxymethyl-2-pyridylmethyloxy group, a 6-acetoxymethyl-2-pyridylmethyloxy group, a 5-methyl-3-pyridylmethyloxy group, a 6-methyl-2-pyridylmethyloxy group, a 5-ethyl-3-pyridylmethyloxy group, a 6-ethyl-2-pyridylmethyloxy group, a 5-t-butyl-3-pyridylmethyloxy group, a 6-t-butyl-2-pyridylmethyloxy group, a 5-methoxycarbonyl-3-pyridylmethyloxy group, a 5-ethoxycarbonyl-3-pyridylmethyloxy group, a 2-pyridylmethyloxy group, a 3-pyridylmethyloxy group, a 4-pyridylmethyloxy group, a 2-pyrazinylmethyloxy group, a 2-pyrimidinylmethyloxy group, a 4-pyrimidinylmethyloxy group, a 5-pyrimidinylmethyloxy group, a 1-benzotriazolylmethyloxy group, 2-(1-benzotriazolyl)ethyloxy group, a 3-(1-benzotriazolyl)propyloxy group, a 4-(1-benzotriazolyl)butyloxy group, etc.

More preferably, $R^1$ represents a hydroxyl group, a methoxy group, a carboxymethyloxy group, a 2-carboxyethyloxy group, a 3-carboxypropyloxy group, a N-hydroxymethylcarbamoylmethyloxy group, a N-ethylcarbamoylmethyloxy group, a 4-hydroxy-2-oxobutyloxy group, a 5-hydroxy-2-oxopentyloxy group, a 2-hydroxyethyloxy group, a 3-hydroxypropyloxy group, a 4-hydroxybutyloxy group, 2-aminoethyloxy group, 3-aminopropyloxy group, 4-aminobutyloxy group, 2-N,N-dimethylaminoethyloxy group, 3-N,N-dimethylaminopropyloxy group, 4-N,N-dimethylaminobutyloxy group, 2-N,N-diisopropylaminoethyloxy group, 3-N,N-diisopropylaminopropyloxy group, 4-N,N-diisopropylaminobutyloxy group, 2-(1-piperidyl)ethyloxy group, 3-(1-piperidyl)propyloxy group, 4-(1-piperidyl)butyloxy group, a benzyloxy group, a 5-hydroxymethyl-3-pyridylmethyloxy group, a 5-acetoxymethyl-3-pyridylmethyloxy group, a 6-hydroxymethyl-2-pyridylmethyloxy group, a 6-acetoxymethyl-2-pyridylmethyloxy group, a 5-methyl-3-pyridylmethyloxy group, a 6-methyl-2-pyridylmethyloxy group, a 5-ethyl-3-pyridylmethyloxy group, a 6-ethyl-2-pyridylmethyloxy group, a 5-t-butyl-3-pyridylmethyloxy group, a 6-t-butyl-2-pyridylmethyloxy group, a 5-methoxycarbonyl-3-pyridylmethyloxy group, a 5-ethoxycarbonyl-3-pyridylmethyloxy group, a 2-pyridylmethyloxy group, a 3-pyridylmethyloxy group, a 4-pyridylmethyloxy group, a 2-pyrazinylmethyloxy group, a 2-pyrimidinylmethyloxy group, a 4-pyrimidinylmethyloxy group or a 5-pyrimidinylmethyloxy group, a 1-benzotriazolylmethyloxy group, 2-(1-benzotriazolyl) ethyloxy group, a 3-(1-benzotriazolyl)propyloxy group, a 4-(1-benzotriazolyl)butyloxy group.

In the formula (I), $R^2$ represents a hydrogen atom, a halogen atom, an optionally protected hydroxyl group, an optionally protected mercapto group, an optionally protected amino group, a cyano group, a nitro group, a trifluoromethyl group, a trifluoromethoxy group, an optionally protected carboxyl group, a 4-morpholylacetyl group, a straight- or branched-chain alkanoyloxy group having 1–4 carbon atoms, a straight- or branched-chain alkanoyl group having 1–4 carbon atoms, a straight- or branched-chain alkyl group having 1–4 carbon atoms, an alkylthio group having 1–3 carbon atoms which may be monosubstituted by any group selected from the group consisting of a hydroxyl group, a carboxyl group, a phenyl group and a pyridyl group, or a straight- or branched-chain alkoxy group having 1–4 carbon atoms which may be monosubstituted by any group selected from the group consisting of an alkoxycarbonyl group having 1–4 carbon atoms, a hydroxyl group, a carboxyl group, a phenyl group and a pyridyl group.

More specifically, the "halogen atom" refers to a fluorine atom, a chlorine atom or a bromine atom; the "optionally protected hydroxyl group" refers to a hydroxyl group, a trimethylsilyloxy group, a t-butyldimethylsilyloxy group, a methoxymethyloxy group or the like; the "optionally protected mercapto group" refers to a phenylthio group, a benzylthio group or the like; the "straight- or branched-chain alkanoyloxy group having 1–4 carbon atoms" refers to an acetoxy group, a propionyloxy group, a butyryloxy group, a pivaloyloxy group or the like; the "straight- or branched-chain alkanoyl group having 1–4 carbon atoms" refers to an acetyl group, a propionyl group, a pivaloyl group or the like; the "alkyl group having 1–4 carbon atoms" refers to a methyl group, an ethyl group, a n-propyl group, an i-propyl group, a n-butyl group, a t-butyl group or the like; the "alkylthio group having 1–3 carbon atoms which may be monosubstituted by any group selected from the group consisting of a hydroxyl group, a carboxyl group, a phenyl group and a pyridyl group" refers to a methylthio group, an ethylthio group, a 3-hydroxypropylthio group, a carboxymethylthio group, a 3-pyridylmethylthio group or the like; the "straight- or branched-chain alkoxy group having 1–4 carbon atoms which may be monosubstituted by any group selected from the group consisting of an alkoxycarbonyl group having 1–4 carbon atoms, a hydroxyl group, a carboxyl group, a phenyl group and a pyridyl group" refers to a methoxy group, an ethoxy group, a n-propoxy group, an i-propoxy group, a n-butoxy group, a t-butoxy group, a methoxycarbonylmethyloxy group, an ethoxycarbonylmethyloxy group, a n-propoxycarbonylmethyloxy group, an i-propoxycarbonylmethyloxy group, a n-butoxycarbonylmethyloxy group, a t-butoxycarbonylmethyloxy group, a 2-(methoxycarbonyl)ethyloxy group, a 2-(ethoxycarbonyl) ethyloxy group, a 2-(n-propoxycarbonyl)ethyloxy group, a 2-(i-propoxycarbonyl)ethyloxy group, a 2-(n-butoxycarbonyl)ethyloxy group, a 2-(t-butoxycarbonyl) ethyloxy group, a 2-(n-pentyloxycarbonyl)ethyloxy group, a 3-(methoxycarbonyl)propyloxy group, a 3-(ethoxycarbonyl) propyloxy group, a 3-(n-propoxycarbonyl)propyloxy group, a 3-(i-propoxycarbonyl)propyloxy group, a 3-(n-butoxycarbonyl)propyloxy group, a 3-(t-butoxycarbonyl) propyloxy group, a carboxymethyloxy group, a 2-carboxyethyloxy group, a 3-carboxypropyloxy group, a 4-carboxybutyl oxy group, a hydroxymethyloxy group, a 2-hydroxyethyloxy group, a 3-hydroxypropyloxy group, a 4-hydroxybutyloxy group, a benzyloxy group, a 2-phenethyloxy group, a 3-phenylpropyloxy group, a 4-phenylbutyloxy group, a 2-pyridylmethyloxy group, a 3-pyridylmethyloxy group, a 4-pyridylmethyloxy group, a 2-(2-pyridyl)ethyloxy group, a 2-(3-pyridyl)ethyloxy group, a 2-(4-pyridyl)ethyloxy group, a 3-(2-pyridyl)propyloxy group, a 3-(3-pyridyl)propyloxy group, a 3-(4-pyridyl) propyloxy group, a 4-(2-pyridyl)butyloxy group, a 4-(3-pyridyl)butyloxy group, a 4-(4-pyridyl)butyloxy group or the like.

Preferably, $R^2$ is substituted at position 9 or 10 in the formulae (I)-a and (I)-b and represents a hydrogen atom, a hydroxyl group, a fluorine atom, a chlorine atom, a bromine atom, a methoxy group, an ethoxy group, a n-propoxy group, an i-propoxy group, a n-butoxy group, a t-butoxy group, a trifluoromethyl group or a cyano group.

More preferably, $R^2$ is substituted at position 9 in the case of the formula (I)-a and position 9 or 10 in the case of the formula (I)-b and represents a chlorine atom, a bromine atom, a trifluoromethyl group or a cyano group.

In the formula (I), $R^3$ represents a hydrogen atom, a halogen atom, an optionally protected hydroxyl group or a straight- or branched-chain alkoxy group having 1–4 carbon atoms. More specifically, the "halogen atom" refers to a fluorine atom, a chlorine atom, a bromine atom or the like; the "optionally protected hydroxyl group" refers to a hydroxyl group, a trimethylsilyloxy group, a t-butyldimethylsilyloxy group, a methoxymethyloxy group or the like; the "straight- or branched-chain alkoxy group having 1–4 carbon atoms" refers to a methoxy group, an ethoxy group, a n-propoxy group, an i-propoxy group, a cyclopropoxy group, a n-butoxy group, a t-butoxy group, or the like.

Preferably, $R^3$ represents a hydrogen atom, a hydroxyl group, a fluorine atom, a chlorine atom, a bromine atom, a methoxy group, an ethoxy group, a n-propoxy group, an i-propoxy group, a n-butoxy group or a t-butoxy group. More preferably, $R^3$ represents a hydrogen atom.

Preferably, $R^2$ and $R^3$ are not a hydrogen atom at the same time.

The preferred combinations of $R^2$ and $R^3$ are such that $R^2$ is substituted at position 9 or 10 and represents a hydrogen atom, a halogen atom, a hydroxyl group, a cyano group, a trifluoromethyl group or a straight- or branched-chain alkoxy group having 1–4 carbon atoms and $R^3$ is a hydrogen atom.

In the formula (I), $R^4$ represents a hydrogen atom, a halogen atom, a group: —M—G (where M represents an oxygen atom, an imino group or a group: —N(CH$_3$)—, and G represents a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, an alkyl group having 1 or 2 carbon atoms which may be substituted by a cyclic alkyl group having 3–6 carbon atoms, a benzyl group which may be mono- or disubstituted in the benzene ring by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyridylmethyl group which may be monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a morpholylmethyl group, a triazolylmethyl group, a furylmethyl group, a thienylmethyl group, a pyrimidinylmethyl group, a pyrazinylmethyl group, a pyrrolylmethyl group, an imidazolylmethyl group, a quinolylmethyl group, an indolylmethyl group, a naphthylmethyl group, a benzoyl group or an α-hydroxybenzyl group.

More specifically, the "halogen atom" refers to a fluorine atom, a chlorine atom, a bromine atom or the like; the "alkyl group having 1 or 2 carbon atoms which may be substituted by a cyclic alkyl group having 3–6 carbon atoms" refers to a methyl group, an ethyl group, a cyclopropylmethyl group, a cyclohexylmethyl group or the like; G in the group: —M—G (where M represents an oxygen atom, an imino group or a group: —N(CH$_3$)—, and G represents a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group) refers to a phenyl group, a 2-fluorophenyl group, a 2-chlorophenyl group, a 2-bromophenyl group, a 3-fluorophenyl group, a 3-chlorophenyl group, a 3-bromophenyl group, a 4-fluorophenyl group, a 4-chlorophenyl group, a 4-bromophenyl group, a 2-hydroxyphenyl group, a 3-hydroxyphenyl group, a 4-hydroxyphenyl group, a 2-mercaptophenyl group, a 3-mercaptophenyl group, a 4-mercaptophenyl group, a 2-methylthiophenyl group, a 3-methylthiophenyl group, a 4-methylthiophenyl group, a 2-ethylthiophenyl group, a 3-ethylthiophenyl group, a 4-ethylthiophenyl group, a 2-methoxyphenyl group, a 3-methoxyphenyl group, a 4-methoxyphenyl group, a 2-ethoxyphenyl group, a 3-ethoxyphenyl group, a 4-ethoxyphenyl group, a 2-n-propoxypheyl group, a 3-n-propoxyphenyl group, a 4-n-propoxyphenyl group, a 2-i-propoxyphenyl group, a 3-i-propoxyphenyl group, a 4-i-propoxyphenyl group, a 2-n-butoxyphenyl group, a 3-n-butoxyphenyl group, a 4-n-butoxyphenyl group, a 2-t-butoxyphenyl group, a 3-t-butoxyphenyl group, a 4-t-butoxyphenyl group, a 2-methoxycarbonylphenyl group, a 3-methoxycarbonylphenyl group, a 4-methoxycarbonylphenyl group, a 2-ethoxycarbonylphenyl group, a 3-ethoxycarbonylphenyl group, a 4-ethoxycarbonylphenyl group, a 2-t-butoxycarbonylphenyl group, a 3-t-butoxycarbonylphenyl group, a 4-t-butoxycarbonylphenyl group, a 2-acetylaminophenyl group, a 3-acetylaminophenyl group, a 4-acetylaminophenyl group, a 2-carboxyphenyl group, a 3-carboxyphenyl group, a 4-carboxyphenyl group, a 2-aminophenyl group, a 3-aminophenyl group, a 4-aminophenyl group, a 2-cyanophenyl group, a 3-cyanophenyl group, a 4-cyanophenyl group, a 2-nitrophenyl group, a 3-nitrophenyl group, a 4-nitrophenyl group, a 2-methylaminophenyl group, a 3-methylaminophenyl group, a 4-methylaminophenyl group, a 2-ethylaminophenyl group, a 3-ethylaminophenyl group, a 4-ethylaminophenyl group, a 2-dimethylaminophenyl group, a 3-dimethylaminophenyl group, a 4-dimethylaminophenyl group, a 2-diethylaminophenyl group, a 3-diethylaminophenyl group, a 4-diethylaminophenyl group, a 2-hydroxymethylphenyl group, a 3-hydroxymethylphenyl group, a 4-hydroxymethylphenyl group, a 2-acetoxymethylphenyl group, a 3-acetoxymethylphenyl group, a 4-acetoxymethylphenyl group, a 2-carbamoylphenyl group, a 3-carbamoylphenyl group, a 4-carbamoylphenyl group, a 2-methylphenyl group, a 3-methylphenyl group, a 4-methylphenyl group, a 2-ethylphenyl group, a 3-ethylphenyl group, a 4-ethylphenyl group, a 2-(n-propyl)phenyl group, a 3-(n-propyl)phenyl group, a 4-(n-propyl)phenyl group, a 2-(i-propyl)phenyl group, a 3-(i-propyl)phenyl group, a 4-(i-propyl)phenyl group, a 2-(n-butyl)phenyl group, a 3-(n-butyl)phenyl group, a 4-(n-butyl)phenyl group, a 2-(t-butyl)phenyl group, a 3-(t-butyl)phenyl group, a 4-(t-butyl)phenyl group, a 2,3-difluorophenyl group, a 2,4-difluorophenyl group, a 2,5-difluorophenyl group, a 3,4-difluorophenyl group, a 3,5-difluorophenyl group, a 2,3-dichlorphenyl group, a 2,4-dichlorphenyl group, a 2,5-dichlorphenyl group, a 3,4-dichlorphenyl group, a 3,5-dichlorphenyl group, a 2,3-dibromophenyl group, a 2,4-dibromophenyl group, a 2,5-dibromophenyl group, a 3,4-dibromophenyl group, a 3,5-dibromophenyl group, a 2,3-dihyroxyphenyl group, a 2,4-dihydroxyphenyl group, a 2,5-dihydroxyphenyl group, a 3,4-dihydroxyphenyl group, a 3,5-dihydroxyphenyl group, a 2,3-dimethoxyphenyl group, a 2,4-dimethoxyphenyl group, a 2,5-dimethoxyphenyl group, a 3,4-dimethoxyphenyl group, a 3,5-dimethoxyphenyl group, a 2,3-diethoxyphenyl group, a 2,4-diethoxyphenyl group, a 2,5-diethoxyphenyl group, a 3,4-diethoxyphenyl group, a 3,5-diethoxyphenyl group, a 2-fluoro-3-methoxyphenyl group, a 2-fluoro-4-methoxyphenyl group, a 2-fluoro-5-methoxyphenyl group, a 3-fluoro-4-methoxyphenyl group, a 3-fluoro-5-methoxyphenyl group, a 3-fluoro-2-methoxyphenyl group, a 4-fluoro-2-methoxypnenyl group, a 5-fluoro-2-methoxyphenyl group, a 4-fluoro-3-methoxyphenyl group, a 5-fluoro-3-methoxyphenyl group, a 2-chloro-3-methoxyphenyl group, a 2-chloro-4-methoxyphenyl group, a 2-chloro-5-methoxyphenyl group, a 3-chloro-4-methoxyphenyl group, a 3-chloro-5-methoxyphenyl group, a 3-chloro-2-methoxyphenyl group, a 4-chloro-2-methoxyphenyl group, a 5-chloro-2-methoxyphenyl group, a 4-chloro-3-methoxyphenyl group, a 5-chloro-3-methoxyphenyl group, a 2-bromo-3-methoxyphenyl group, a 2-bromo-4-methoxyphenyl group, a 2-bromo-5-methoxyphenyl group, a 3-bromo-4-methoxyphenyl group, a 3-bromo-5-methoxyphenyl group, a 3-bromo-2-methoxyphenyl group, a 4-bromo-2-methoxyphenyl group, a 5-bromo-2-methoxyphenyl group, a 4-bromo-3-methoxyphenyl group, a 5-bromo-3-methoxyphenyl group, a 2-cyano-3-methoxyphenyl group, a 2-cyano-4-methoxyphenyl group, a 2-cyano-5-methoxyphenyl group, a 3-cyano-4-methoxyphenyl group, a 3-cyano-5-methoxyphenyl group, a 3-cyano-2-methoxyphenyl group, a 4-cyano-2-methoxyphenyl group, a 5-cyano-2-methoxyphenyl group, a 4-cyano-3-methoxyphenyl group or a 5-cyano-3-methoxyphenyl group; the "benzyl group which may be mono- or disubstituted in the benzene ring by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group" refers to a 2-fluorobenzyl group, a 2-chlorobenzyl group, a 2-bromobenzyl group, a 3-fluorobenzyl group, a 3-chlorobenzyl group, a 3-bromobenzyl group, a 4-fluorobenzyl group, a 4-chlorobenzyl group, a 4-bromobenzyl group, a 2-hydroxybenzyl group, a 3-hydroxybenzyl group, a 4-hydroxybenzyl group, a 2-mercaptobenzyl group, a 3-mercaptobenzyl group, a 4-mercaptobenzyl group, a 2-methoxybenzyl group, a 3-methoxybenzyl group, a 4-methoxybenzyl group, a 2-ethoxybenzyl group, a 3-ethoxybenzyl group, a 4-ethoxybenzyl group, a 2-methylthiobenzyl group, a 3-methylthiobenzyl group, a 4-methylthiobenzyl group, a 2-ethylthiobenzyl group, a 3-ethylthiobenzyl group, a 4-ethylthiobenzyl group, a 2-methoxycarbonylbenzyl group, a 3-methoxycarbonylbenzyl group, a 4-methoxycarbonylbenzyl group, a 2-ethoxycarbonylbenzyl group, a 3-ethoxycarbonylbenzyl group, a 4-ethoxycarbonylbenzyl group, a 2-t-butoxycarbonylbenzyl group, a 3-t-butoxycarbonylbenzyl group, a 4-t-butoxycarbonylbenzyl group, a 2-acetylaminobenzyl group, a 3-acetylaminobenzyl group, a 4-acetylaminobenzyl group, a 2-carboxybenzyl group, a 3-carboxybenzyl group, a 4-carboxybenzyl group, a 2-aminobenzyl group, a 3-aminobenzyl group, a 4-aminobenzyl group, a 2-cyanobenzyl group, a 3-cyanobenzyl group, a 4-cyanobenzyl group, a 2-nitrobenzyl group, a 3-nitrobenzyl group, a 4-nitrobenzyl group, a 2-methylaminobenzyl group, a 3-methylaminobenzyl group, a 4-methylaminobenzyl group, a 2-ethylaminobenzyl group, a 3-ethylaminobenzyl group, a 4-ethylaminobenzyl group, a 2-dimethylaminobenzyl group, a 3-dimethylaminobenzyl group, a 4-dimethylaminobenzyl group, a 2-diethylaminobenzyl group, a 3-diethylaminobenzyl group, a 4-diethylaminobenzyl group, a 2-hydroxymethylbenzyl group, a 3-hydroxymethylbenzyl group, a 4-hydroxymethylbenzyl group, a 2-acetoxymethylbenzyl group, a 3-acetoxymethylbenzyl group, a 4-acetoxymethylbenzyl group, a 2-carbamoylbenzyl group, a 3-carbamoylbenzyl group, a 4-carbamoylbenzyl group, a 2-methylbenzyl group, a 3-methylbenzyl group, a 4-methylbenzyl group, a 2-ethylbenzyl group, a 3-ethylbenzyl group, a 4-ethylbenzyl group, a 2-(n-propyl)benzyl group, a 3-(n-propyl)benzyl group, a 4-(n-propyl)benzyl group, a 2-(i-propyl)benzyl group, a 3-(i-propyl)benzyl group, a 4-(i-propyl)benzyl group, a 2-(n-butyl)benzyl group, a 3-(butyl)benzyl group, a 4-(n- butyl)benzyl group, a 2-(t-butyl)benzyl group, a 3-(t-butyl)benzyl group, a 4-(t-butyl)benzyl group, a 2,3-difluorobenzyl group, a 2,4-difluorobenzyl group, a 2,5-difluorobenzyl group, a 3,4-difluorobenzyl group, a 3,5-difluorobenzyl group, a 2,3-dichlorbenzyl group, a 2,4-dichlorbenzyl group, a 2,5-dichlorbenzyl group, a 3,4-dichlorbenzyl group, a 3,5-dichlorbenzyl group, a 2,3-dibromobenzyl group, a 2,4-dibromobenzyl group, a 2,5-dibromobenzyl group, a 3,4-dibromobenzyl group, a 3,5-dibromobenzyl group, a 2,3-dihydroxybenzyl group, a 2,4-dihydroxybenzyl group, a 2,5-dihydroxybenzyl group, a 3,4-dihydroxybenzyl group, a 3,5-dihydroxybenzyl group, a 2,3-dimethoxybenzyl group, a 2,4-dimethoxybenzyl group, a 2,5-dimethoxybenzyl group, a 3,4-dimethoxybenzyl group, a 3,5-dimethoxybenzyl group, a 2,3-diethoxybenzyl group, a 2,4-diethoxybenzyl group, a 2,5-diethoxybenzyl group, a 3,4-diethoxybenzyl group, a 3,5-diethoxybenzyl group, a 2-fluoro-3-methoxybenzyl group, a 2-fluoro-4-methoxybenzyl group, a 2-fluoro-5-methoxybenzyl group, a 3-fluoro-4-methoxybenzyl group, a 3-fluoro-5-methoxybenzyl group, a 3-fluoro-2-methoxybenzyl group, a 4-fluoro-2-methoxybenzyl group, a 5-fluoro-2-methoxybenzyl group, a 4-fluoro-3-methoxybenzyl group, a 5-fluoro-3-methoxybenzyl group, a 2-chloro-3-methoxybenzyl group, a 2-chloro-4-methoxybenzyl group, a 2-chloro-5-methoxybenzyl group, a 3-chloro-4-methoxybenzyl group, a 3-chloro-5-methoxybenzyl group, a 3-chloro-2-methoxybenzyl group, a 4-chloro-2-methoxybenzyl group, a 5-chloro-2-methoxybenzyl group, a 4-chloro-3-methoxybenzyl group, a 5-chloro-3-methoxybenzyl group, a 2-bromo-3-methoxybenzyl group, a 2-bromo-4-methoxybenzyl group, a 2-bromo-5-methoxybenzyl group, a 3-bromo-4-methoxybenzyl group, a 3-bromo-5-methoxybenzyl group, a 3-bromo-2-methoxybenzyl group, a 4-bromo-2-methoxybenzyl group, a 5-bromo-2-methoxybenzyl group, a 4-bromo-3-methoxybenzyl group, a 5-bromo-3-methoxybenzyl group, a 2-cyano-3-methoxybenzyl group, a 2-cyano-4-methoxybenzyl group, a 2-cyano-5-methoxybenzyl group, a 3-cyano-4-methoxybenzyl group, a 3-cyano-5-methoxybenzyl group, a 3-cyano-2-methoxybenzyl group, a 4-cyano-2-methoxybenzyl group, a 5-cyano-2-methoxybenzyl group, a 4-cyano-3-methoxybenzyl group, a 5-cyano-3-methoxybenzyl group or the like; the "pyridylmethyl group which may be monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group" refers to a 2-pyridylmethyl group, a 3-pyridylmethyl group, a 4-pyridylmethyl group, a 5-methyl-3-pyridylmethyl group, a 6-methyl-2-pyridylmethyl group, a 5-ethyl-3-pyridylmethyl group, a 6-ethyl-2-pyridylmethyl group, a 5-hydroxymethyl-3-pyridylmethyl group, a 5-t-butyl-3-pyridylmethyl group, a 6-hydroxymethyl-2-pyridylmethyl group, a 5-acetoxymethyl-3-pyridylmethyl group, a 6-acetoxymethyl-2-pyridylmethyl group, a 5-methoxycarbonyl-3-pyridylmethyl group, a 5-ethoxycarbonyl-3-pyridylmethyl group, a 6-methoxycarbonyl-2-pyridylmethyl group, a 5-carboxy-3-pyridylmethyl group, a 6-carboxy-2-pyridylmethyl group, a 4-amino-2-pyridylmethyl group, a 5-amino-3-pyridylmethyl group, a 2-amino-4-pyridylmethyl group, a 4-carboxy-2-pyridylmethyl group, a 4-acetylamino-2-pyridylmethyl group, a 5-acetylamino-3-pyridylmethyl group, a 2-acetylamino-4-pyridylmethyl group, a 4-methylthio-2-pyridylmethyl group, a 5-methylthio-3-pyridylmethyl group, a 3-methylthio-4-pyridylmethyl group, a 4-mercapto- 2-pyridylmethyl group, a 5-mercapto-3-pyridylmethyl group, a 3-mercapto-4-pyridylmethyl group, a 4-methoxy-2-pyridylmethyl group, a 5-methoxy-3-pyridylmethyl group, a 3-methoxy-4-pyridylmethyl group, a 4-hydroxy-2-pyridylmethyl group, a 5-hydroxy-3-pyridylmethyl group, a 3-hydroxy-4-pyridylmethyl group, a 4-fluoro-2-pyridylmethyl group, a 5-fluoro-2-pyridylmethyl group, a 4-fluoro-3-pyridylmethyl group, a 5-fluoro-3-pyridylmethyl group, a 2-fluoro-4-pyridylmethyl group, a 2-fluoro-4-pyridylmethyl group, a 4-chloro-2-pyridylmethyl group, a 5-chloro-2-pyridylmethyl group, a 4-chloro-3-pyridylmethyl group, a 5-chloro-3-pyridylmethyl group, a 2-chloro-4-pyridylmethyl group, a 2-chloro-4-pyridylmethyl group, a 4-bromo-2-pyridylmethyl group, a 5-bromo-2-pyridylmethyl group, a 4-bromo-3-pyridylmethyl group, a 5-bromo-3-pyridylmethyl group, a 2-bromo-4-pyridylmethyl group, a 2-bromo-4-pyridylmethyl group, a 4-cyano-2-pyridylmethyl group, a 5-cyano-2-pyridylmethyl group, a 4-cyano-3-pyridylmethyl group, a 5-cyano-3-pyridylmethyl group, a 2-cyano-4-pyridylmethyl group, a 2-cyano-4-pyridylmethyl group, a 4-nitro-2-pyridylmethyl group, a 5-nitro-3-pyridylmethyl group, 4-dimethylamino-2-pyridylmethyl group, a 5-dimethylamino-3-pyridylmethyl group, a 4-carbamoyl-2-pyridylmethyl group, a 5-carbamoyl-3-pyridylmethyl group or the like.

Preferably, $R^4$ represents a hydrogen atom, a methyl group, a 2-pyrimidinylmethyl group, a 4-pyrimidinylmethyl group, a 5-pyrimidinylmethyl group, a 2-pyridylmethyl group, a 3-pyridylmethyl group, a 4-pyridylmethyl group, a 5-methyl-3-pyridylmethyl group or a 6-methyl-2-pyridylmethyl group.

More preferably, $R^4$ represents a methyl group, a 5-pyrimidinylmethyl group, a 2-pyridylmethyl group, a 3-pyridylmethyl group or a 4-pyridylmethyl group.

In the formula (I), $R^5$ represents a hydrogen atom or a methyl group, preferably a hydrogen atom.

In the formula, $R^6$ represents a hydrogen atom, a straight- or branched-chain alkyl group having 1–4 carbon atoms, or a straight- or branched-chain alkanoyl group having 1–4 carbon atoms. Typical straight- or branched-chain alkyl groups having 1–4 carbon atoms include methyl group, ethyl group, n-propyl group, i-propyl group, n-butyl group, t-butyl group and the like; and typical straight- or branched-chain alkanoyl groups having 1–4 carbon atoms include acetyl group, propionyl group, butyryl group, pivaloyl group and the like.

$R^7$ represents a hydrogen atom, or a straight- or branched-chain alkoxy group having 1–4 carbon atoms. Typical straight- or branched-chain alkoxy groups having 1–4 carbon atoms include methoxy group, ethoxy group, n-propoxy group, i-propoxy group, n-butoxy group, t-butoxy group and the like.

$R^8$ represents a hydrogen atom, or an alkyl group having 1–4 carbon atoms. Typical straight- or branched-chain alkyl groups having 1–4 carbon atoms include methyl group, ethyl group, n-propyl group, i-propyl group, n-butyl group, t-butyl group and the like.

The alkoxy group as $R^7$ and alkyl group as $R^8$ may combine to form a ring. More illustratively, $R^7$ and $R^8$ may together represent ethylene acetal or propylene acetal.

$R^9$ represents a hydrogen atom, a hydroxyl group, an alkyl group having 1–4 carbon atoms, an alkoxy group having 1–4 carbon atoms, a carboxymethyloxy group, or a group: —N$R^{10}R^{10}$ (the two $R^{10}$s may be the same or different). Typical straight- or branched-chain alkyl groups having 1–4 carbon atoms include methyl group, ethyl group, n-prop yl group, i-propyl group, n-butyl group, t-butyl group and the like; and straight- or branched-chain alkoxy groups having 1–4 carbon atoms include methoxy group, ethoxy group, n-propoxy group, i-propoxy group, n-butoxy group, t-butoxy group and the like. $R^{10}$ represents a hydrogen atom or an alkyl group having 1 or 2 carbon atoms. Exemplary alkyl groups having 1 or 2 carbon atoms include methyl group and ethyl group.

The following compounds, however, are limited from formula (I). The compounds wherein, when A represents a single bond, and all of $Y^1$–$Y^3$ and $Z^1$–$Z^4$ represent a methine group, $R^1$ represents a 1-methyl-hexahydroazepin-4-yl-oxy group, or represented by the following formula (II):

$$-O-(CH_2)_n-Q \qquad (II)$$

(where Q represents a group: —NR$^{24}$R$^{24}$ (R$^{24}$ represents a hydrogen atom or an alkyl group having 1–4 carbon atoms; R$^{24}$ may not be hydrogen atom at the same time, or may combine each other to form a ring), a phenyl group which was mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyridyl group which was monosubstituted by any group selected from the group consisting of a halogen atom, a hydroxyl group, a mercapto group, an alkoxy group having 1 or 2 carbon atoms, an alkylthio group having 1 or 2 carbon atoms, an acetylamino group, a carboxyl group, an amino group, a cyano group, a nitro group, an amino group mono- or disubstituted by a lower alkyl group and a carbamoyl group, a 1-benzotriazolyl group, a 4-morpholinyl group, or 2-benzimidazolyl group; n is 1–6); or $R^2$ represents a straight- or branched-chain alkoxy group having 1–4 carbon atoms which was mono-substituted by any group selected from the group consisting of a hydroxyl group, a carboxyl group, a phenyl group and a pyridyl group; or $R^4$ represents a group: —M—G (where M represents an oxygen atom, an imino group or a group: —N(CH$_3$)—, and G represents a phenyl group which was mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group), a benzyl group which was mono- or disubstituted in the benzene ring by any group selected from the group consisting of a cyano group, a nitro group, an amino group mono- or disubstituted by a lower alkyl group, a carbamoyl group, an alkyl group having 1–4 carbon atoms, a hydroxymethyl group and an acetoxymethyl group, a pyridylmethyl group which was monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, a hydroxymethyl group and an acetoxymethyl group. And the following compounds, however, are excluded from formula (I). The compounds wherein A represents a single bond; $Y^1$ and $Y^2$ represent a methine group; $Y^3$ represents a nitrogen atom; $Z^1$–$Z^4$ represent a methine group; $R^1$, $R^2$ and $R^3$ represent respectively a hydrogen atom; and $R^4$ represents a hydrogen atom and $R^5$ represents a hydrogen atom or a methyl group, or $R^4$ represents an ethyl group and $R^5$ represents a hydrogen atom, or $R^4$ represents a chlorine atom and $R^5$ represents a methyl group. The compounds wherein A represents a sulfur atom, and all of $Y^1$–$Y^3$ and $Z^1$–$Z^4$ represent a methine group, $R^1$, $R^2$, $R^3$ and $R^5$ represent respectively a hydrogen atom; and $R^4$ represents a hydrogen atom, a benzyl group, a 4-methoxybenzyl group, a 4-dimethylaminobenzyl group, a 4-chlorobenzyl group, a 3-nitrobenzyl group, or a bromine atom. The compounds wherein A represents an oxygen atom, and all of $Y^1$–$Y^3$ and $Z^1$–$Z^4$ represent a methine group, $R^1$, $R^2$, $R^3$ and $R^5$ represent respectively a hydrogen atom; and $R^4$ represents a hydrogen atom, a benzyl group, a 4-methoxybenzyl group, a 4-dimethylaminobenzyl group, a 4-chlorobenzyl group, or a 3-nitrobenzyl group. The compounds wherein A represents a carbonyl group, and all of $Y^1$–$Y^3$ and $Z^1$–$Z^4$ represent a methine group, $R^2$, $R^3$, $R^4$ and $R^5$ represent respectively a hydrogen atom; and $R^1$ represents a methoxy group at position 5. The compounds wherein A represents a carbonyl group, and all of $Y^1$–$Y^3$ and $Z^1$–$Z^4$ represent a methine group, $R^1$, $R^4$ and $R^5$ represent respectively a hydrogen atom; and one of $R^2$ and $R^3$ represents a hydrogen atom and the other one of $R^2$ and $R^3$ represents a methoxy group at position 9. The compounds wherein A represents a group: $SO_n$ (n is 1), and all of $Y^1$–$Y^3$ and $Z^1$–$Z^4$ represent a methine group, and $R^1$, $R^2$, $R^3$, $R^4$ and $R^5$ represent respectively a hydrogen atom.

With regard to the combination of the substituents, the position of the substitution by $R^1$ is position 2 in the case of the formula (I)-a and position 5 in the case of the formula (I)-b, and preferably, $R^1$ represents a hydroxyl group, a carboxymethyloxy group, a 2-carboxyethyloxy group, a 3-carboxypropyloxy group, a N-hydroxymethylcarbamoylmethyloxy group, a N-ethylcarbamoylmethyloxy group, a 4-hydroxy-2-oxobutyloxy group, a 5-hydroxy-2-oxopentyloxy group, a 2-hydroxyethyloxy group, a 3-hydroxypropyloxy group, a 4-hydroxybutyloxy group, a 2-aminoethyloxy group, a 3-aminopropyloxy group, a 4-aminobutyloxy group, 2-N,N-dimethylaminoethyloxy group, 3-N,N-dimethylaminopropyloxy group, 4-N,N-dimethylaminobutyloxy group, 2-N,N-diisopropylaminoethyloxy group, 3-N,N-diisopropylaminopropyloxy group, 4-N,N-diisopropylaminobutyloxy group, 2-(1-piperidyl)ethyloxy group, 3-(1-piperidyl)propyloxy group, 4-(1-piperidyl)butyloxy group, a benzyloxy group, a 5-hydroxymethyl-3-pyridylmethyloxy group, a 5-acetoxymethyl-3-pyridylmethyloxy group, a 6-hydroxymethyl-2-pyridylmethyloxy group, a 6-acetoxymethyl-2-pyridylmethyloxy group, a 5-methyl-3-pyridylmethyloxy group, a 6-methyl-2-pyridylmethyloxy group, a 5-ethyl-3-pyridylmethyloxy group, a 6-ethyl-2-pyridylmethyloxy group, a 5-t-butyl-3-pyridylmethyloxy group, a 6-t-butyl-2-pyridylmethyloxy group, a 5-methoxycarbonyl-3-pyridylmethyloxy group, a 5-ethoxycarbonyl-3-pyridylmethyloxy group, a 2-pyridylmethyloxy group, a 3-pyridylmethyloxy group, a 4-pyridylmethyloxy group, a 2-pyrazinylmethyloxy group, a 2-pyrimidinylmethyloxy group, a 4-pyrimidinylmethyloxy group, a 5-pyrimidinylmethyloxy group, a 1-benzotriazolylmethyloxy group, 2-(1-benzotriazolyl)ethyloxy group, a 3-(1-benzotriazolyl)propyloxy group, a 4-(1-benzotriazolyl)butyloxy group; $R^2$ represents a chlorine atom, a bromine atom, a cyano group or a trifluoromethyl group at the substitution position of position 9 or 10; $R^3$ represents a hydrogen atom, $R^4$ represents a methyl group, a 5-pyrimidinylmethyl group, a 2-pyridylmethyl group, a 3-pyridylmethyl group, or a 4-pyridylmethyl group; and $R^5$ represents a hydrogen atom.

In the compounds represented by the formula (I), $Y^1$–$Y^3$ and $Z^1$–$Z^4$ represent a methine group or a nitrogen atom as described above. Total number of the nitrogen atoms in $Y^1$–$Y^3$ and $Z^1$–$Z^4$ is preferably 0–2 and more preferably 0 or 1, and total number of the nitrogen atoms is further preferably 0. The total number of the nitrogen atoms in $Y^1$–$Y^3$ and $Z^1$–$Z^4$ of 0 means that all of $Y^1$–$Y^3$ and $Z^1$–$Z^4$ represent a methine group. The total number of the nitrogen atoms in $Y^1$–$Y^3$ and $Z^1$–$Z^4$ of 1 means that one of $Y^1$–$Y^3$ and $Z^1$–$Z^4$ represents a nitrogen atom, and more illustratively, that 1) $Y^1$ represents a nitrogen atom and all of $Y^2$, $Y^3$ and $Z^1$–$Z^4$ represent a methine group; 2) $Y^2$ represents a nitrogen atom and all of $Y^1$, $Y^3$ and $Z^1$–$Z^4$ represent a methine group; 3) $Y^3$ represents a nitrogen atom and all of $Y^1$, $Y^2$ and $Z^1$–$Z^4$ represent a methine group; 4) $Z^1$ represents a nitrogen atom and all of $Y^1$–$Y^3$ and $Z^2Z^3$ and $Z^4$ represent a methine group; 5) $Z^2$ represents a nitrogen atom and all of $Y^1$–$Y^3$ and $Z^1$, $Z^3$ and $Z^4$ represent a methine group; 6) $Z^3$ represents a nitrogen atom and all of $Y^1$–$Y^3$ and $Z^1$, $Z^2$ and $Z^4$ represent a methine group; or 7) $Z^4$ represents a nitrogen atom and all of $Y^1$–$Y^3$ and $Z^1$, $Z^2$ and $Z^3$ represent a methine group. The total number of the nitrogen atoms in $Y^1$–$Y^3$ and $Z^1$–$Z^4$ of 2 means that two nitrogen atoms are present in either of $Y^1$–$Y^3$ and $Z^1$–$Z^4$, or that one nitrogen is present in both of $Y^{1=1}$–$Y^3$ and $Z^1$–$Z^4$; and more illustratively, that 1) $Y^1$ and $Y^2$ represent a nitrogen atom and all of $Y^3$ and $Z^1$–$Z^4$ represent a methine group; 2) $Y^1$ and $Y^3$ represent a nitrogen atom and all of $Y^2$ and $Z^1$–$Z^4$ represent a methine group; 3) $Y^2$ and $Y^3$ represent a nitrogen atom and all of $Y^1$ and $Z^1$–$Z^4$ represent a methine group; 4) $Z^1$ and $Z^2$ represent a nitrogen atom and all of $Y^1$–$Y^3$ and $Z^3$ and $Z^4$ represent a methine group; 5) $Z^1$ and $Z^3$ represent a nitrogen atom and all of $Y^1$–$Y^3$ and $Z^2$ and $Z^4$ represent a methine group; 6) $Z^1$ and $Z^4$ represent a nitrogen atom and all of $Y^1$–$Y^3$ and $Z^2$ and $Z^3$ represent a methine group; 7) $Z^2$ and $Z^3$ represent a nitrogen atom and all of $Y^1$–$Y^3$ and $Z^1$ and $Z^4$ represent a methine group; 8) $Z^2$ and $Z^4$ represent a nitrogen atom and all of $Y^1$–$Y^3$ and $Z^1$ and $Z^3$ represent a methine group; 9) $Z^3$ and $Z^4$ represent a nitrogen atom and all of $Y^{1-Y3}$ and $Z^1$ and $Z^2$ represent a methine group; 10) $Y^1$ and $Z^1$ represent a nitrogen atom and all of $Y^2$, $Y^3$, $Z^2$, $Z^3$ and $Z^4$ represent a methine group; 11) $Y^1$ and $Z^2$ represent a nitrogen atom and all of $Y^2$, $Y^3$, $Z^1$, $Z^3$ and $Z^4$ represent a methine group; 12) $Y^1$ and $Z^3$ represent a nitrogen atom and all of $Y^2$, $Y^3$, $Z^1$, $Z^2$ and $Z^4$ represent a methine group; 13) $Y^1$ and $Z^4$ represent a nitrogen atom and all of $Y^2$, $Y^3$, $Z^1$, $Z^2$ and $Z^3$ represent a methine group; 14) $Y^2$ and $Z^1$ represent a nitrogen atom and all of $Y^1$, $Y^3$, $Z^2$, $Z^3$ and $Z^4$ represent a methine group; 15) $Y^2$ and $Z^2$ represent a nitrogen atom and all of $Y^1$, $Y^3$, $Z^1$, $Z^3$ and $Z^4$ represent a methine group; 16) $Y^2$ and $Z^3$ represent a nitrogen atom and all of $Y^1$, $Y^3$, $Z^1$, $Z^2$ and $Z^4$ represent a methine group; 17) $Y^2$ and $Z^4$ represent a nitrogen atom and all of $Y^1$, $Y^3$, $Z^1$, $Z^2$ and $Z^3$ represent a methine group; 18) $Y^3$ and $Z^1$ represent a nitrogen atom and all of $Y^1$, $Y^2$, $Z^2$, $Z^3$ and $Z^4$ represent a methine group; 19) $Y^3$ and $Z^2$ represent a nitrogen atom and all of $Y^1$, $Y^2$, $Z^1$, $Z^3$ and $Z^4$ represent a methine group; 20) $Y^3$ and $Z^3$ represent a nitrogen atom and all of $Y^1$, $Y^2$, $Z^1$, $Z^2$ and $Z^4$ represent a methine group; or 21) $Y^3$ and $Z^4$ represent a nitrogen atom and all of $Y^1$, $Y^2$, $Z^1$, $Z^2$ and $Z^3$ represent a methine group;

A, the substituents $R^1$–$R^5$, and the substituents $R^6$–$R^{10}$ defined in A when the total number of the nitrogen atoms in $Y^{1-Y3}$ and $Z^1$–$Z^4$ is 0–2 are the same as those defined for the above formula (I).

Preferable examples of the combination of $Y^{1-Y3}$ and $Z^1$–$Z^4$ with $R^1$–$R^5$ are described below, which by no means limit the scope of the present invention.

Preferable examples of the compounds wherein the total number of the nitrogen atoms in $Y^{1-Y3}$ and $Z^1$–$Z^4$ is 0–2 include the compounds wherein all of $Y^{1-Y3}$ and $Z^1$–$Z^4$ represent a methine group; the compounds wherein the total number of the nitrogen atoms in $Y^1$–$Y^3$ and $Z^1$–$Z^4$ is 1 and 1) $Y^1$ represents a nitrogen atom and all of $Y^2$, $Y^3$ and $Z^1$–$Z^4$ represent a methine group; 3) $Y^3$ represents a nitrogen atom and all of $Y^1$, $Y^2$ and $Z^1$–$Z^4$ represent a methine group; 4) $Z^1$ represents a nitrogen atom and all of $Y^1$–$Y^3$ and $Z^2$, $Z^3$ and $Z^4$ represent a methine group; 5) $Z^2$ represents a nitrogen atom and all of $Y^1$–$Y^3$ and $Z^1$, $Z^3$ and $Z^4$ represent a methine group; 6) $Z^3$ represents a nitrogen atom and all of $Y^1$–$Y^3$ and $Z^1$, $Z^2$ and $Z^4$ represent a methine group; or 7) $Z^4$ represents a nitrogen atom and all of $Y^1$–$Y^3$ and $Z^1$, $Z^2$ and $Z^3$ represent a methine group; the compounds wherein the total number of the nitrogen atoms in $Y^1$–$Y^3$ and $Z^1$–$Z^4$ is 2 and 2) $Y^1$ and $Y^3$ represent a nitrogen atom and all of $Y^2$ and $Z^1$–$Z^4$ represent a methine group; 4) $Z^1$ and $Z^2$ represent a nitrogen atom and all of $Y^1$–$Y^3$ and $Z^3$ and $Z^4$ represent a methine group; 5) $Z^1$ and $Z^3$ represent a nitrogen atom and all of $Y^1$–$Y^3$ and $Z^2$ and $Z^4$ represent a methine group; 6) $Z^1$ and $Z^4$ represent a nitrogen atom and all of $Y^1$–$Y^3$ and $Z^2$ and $Z^3$ represent a methine group; 8) $Z^2$ and $Z^4$ represent a nitrogen atom and all of $Y^1$–$Y^3$ and $Z^1$ and $Z^3$ represent a methine group; 9) $Z^3$ and $Z^4$ represent a nitrogen atom and all of $Y^1$–$Y^3$ and $Z^1$ and $Z^2$ represent a methine group; 10) $Y^1$ and $Z^1$ represent a nitrogen atom and all of $Y^2$, $Y^3$, $Z^2$, $Z^3$ and $Z^4$ represent a methine group; 11) $Y^1$ and $Z^2$ represent a nitrogen atom and all of $Y^2$, $Y^3$, $Z^1$, $Z^3$ and $Z^4$ represent a methine group; 12) $Y^1$ and $Z^3$ represent a methine group; nitrogen atom and all of $Y^2$, $Y^3$, $Z^1$, $Z^2$ and $Z^4$ represent a methine group; 13) $Y^1$ and $Z^4$ represent a nitrogen atom and all of $Y^2$, $Y^3$, $Z^1$, $Z^2$ and $Z^3$ represent a methine group; 18) $Y^3$ and $Z^1$ represent a nitrogen atom and all of $Y^1$, $Y^2$, $Z^2$, $Z^3$ and $Z^4$ represent a methine group; 19) $Y^3$ and $Z^2$ represent a nitrogen atom and all of $Y^1$, $Y^2$, $Z^1$, $Z^3$ and $Z^4$ represent a methine group; 20) $Y^3$ and $Z^3$ represent a nitrogen atom and all of $Y^1$, $Y^2$, $Z^1$, $Z^2$ and $Z^4$ represent a methine group; or 21) $Y^3$ and $Z^4$ represent a nitrogen atom and all of $Y^1$, $Y^2$, $Z^1$, $Z^2$ and $Z^3$ represent a methine group.

The preferred substituents in this case or the preferred combinations thereof are shown below.

Speaking of $R^1$, it is preferably substituted at position 2 in the case of the formula (I)-a and position 5 in the case of the formula (I)-b, and is preferably a hydroxyl group or represented by the following formula (II):

$$-O-(CH_2)_n-Q \quad (II)$$

where Q represents a hydrogen atom, a carboxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or mercapto group, a hydroxyl group, a group: $-NR^{24}R^{24}$ ($R^{24}$ represents a hydrogen atom or an alkyl group having 1–4 carbon atoms; the two $R^{24}$s may be the same or different, or may combine each other to form a ring), a phenyl group, a pyridyl group which may be monosubstituted by a hydroxymethyl group, an acetoxymethyl group, an alkyl group having 1–4 carbon atoms or an alkoxycarbonyl group having 1 or 2 carbon atoms, a pyrazinyl group, a pyrimidinyl group, or a 1-benzotriazolyl group; n is 1–4.

More preferably, $R^1$ is substituted at position 2 in the case of the formula (I)-a and position 5 in the case of the formula (I)-b, and is either a hydroxyl group or represented by the following formula (II):

$$-O-(CH_2)_n-Q \quad (II)$$

where Q represents a hydrogen atom, a carboxyl group, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or one mercapto group, a hydroxyl group, a group: $-NR^{24}R^{24}$ ($R^{24}$ represents a hydrogen atom or an alkyl group having 1–4 carbon atoms; the two $R^{24}$s may be the same or different, or may combine each other to form a ring), a phenyl group, a pyridyl group which may be monosubstituted by a hydroxymethyl group, an acetoxymethyl group, an alkyl group having 1–4 carbon atoms or an alkoxycarbonyl group having 1 or 2 carbon atoms, a pyrazinyl group, a pyrimidinyl group, or a 1-benzotriazolyl group; n is 1–4.

Preferably, $R^2$ and $R^3$ are not a hydrogen atom at the same time; it is preferred that $R^2$ is substituted at position 9 or 10 and is a hydrogen atom, a halogen atom, a hydroxyl group, a cyano group, a trifluoromethyl group or a straight- or branched-chain alkoxy group having 1–4 carbon atoms and that $R^3$ is a hydrogen atom.

Preferably, $R^4$ is a hydrogen atom, an alkyl group having 1 or 2 carbon atoms, a pyrimidinylmethyl group or a pyridylmethyl group which may be substituted by a methyl group. Further, it is more preferred that $R^4$ is a methyl group, a pyrimidinylmethyl group or a pyridylmethyl group. Preferably, $R^5$ is a hydrogen atom.

The preferred combinations of the substituents are as follows: $R^1$ is substituted at position 2 in the formula (I)-a and position 5 in the formula (I)-b, and is either a hydroxyl group or represented by the following formula (II):

$$-O-(CH_2)_n-Q \quad (II)$$

where Q represents a hydrogen atom, a carboxyl group, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or one mercapto group, a hydroxyl group, a group: $-NR^{24}R^{24}$ ($R^{24}$ represents a hydrogen atom or an alkyl group having 1–4 carbon atoms; the two $R^{24}$s may be the same or different, or may combine each other to form a ring), a phenyl group, a pyridyl group which may be monosubstituted by a hydroxymethyl group, an acetoxymethyl group, an alkyl group having 1–4 carbon atoms or an alkoxycarbonyl group having 1 or 2 carbon atoms, a pyrazinyl group, a pyrimidinyl group, or a 1-benzotriazolyl group; n is 1–4; $R^2$ is a halogen atom, a cyano group or a trifluoromethyl group which is substituted at position 9 or 10; $R^3$ is a hydrogen atom; $R^4$ is a methyl group, a pyrimidinylmethyl group or a pyridylmethyl group; and $R^5$ is a hydrogen atom.

Exemplary preferable combinations of $Y^1$–$Y^3$, $Z^1$–$Z^4$, and A include the combination wherein the total number of the nitrogen atoms in $Y^1$–$Y^3$ and $Z^1$–$Z^4$ is 0, and A represents a single bond, a methylene group, a carbonyl group, an oxygen atom, a group: —SO$_n$— (n is 0–2), a group: —N(R$^6$)—, a group: —CR$^7$(OR$^8$)—, or a group: —C(=N—R$^9$)—.

Also preferred are the combinations wherein the total number of the nitrogen atoms in Y$^1$–Y$^3$ and Z$^1$–Z4 is 1, and A represents a single bond, a methylene group, a carbonyl group, an oxygen atom, a group: —SO$_n$— (n is 0–2), a group: —N(R$^6$)—, a group: —CR$^7$(OR$^8$)—, or a group: —C(=N—R$^9$)—.

Also preferred are the combinations wherein the total number of the nitrogen atoms in Y$^1$–Y$^3$ and Z$^1$–Z$^4$ is 2, and A represents a single bond, a methylene group, a carbonyl group, an oxygen atom, a group: —SO$_n$— (n is 0–2), a group: —N(R$^6$)—, a group: —CR$^7$(OR$^8$)—, or a group: —C(=N—R$^9$)—.

More preferable are the combinations wherein the total number of the nitrogen atoms in Y$^1$–Y$^3$ and Z$^1$–Z$^4$ is 0, and A represents a single bond, a carbonyl group, an oxygen atom, a group: —SO$_n$— (n is 0–2), or a group: —N(R$^6$)—, and the combinations wherein the total number of the nitrogen atoms in Y$^1$–Y$^3$ and Z$^1$–Z$^4$ is 1, and A represents a single bond.

Further preferable are the combinations wherein the total number of the nitrogen atoms in Y$^1$–Y$^3$ and Z$^1$–Z$^4$ is 0, and A represents a group: —SO$_n$— (n is 0–2)—, and A represents a sulfur atom is particularly preferable.

A, the substituents R$^1$–R$^5$, and the substituents R$^6$–R$^{10}$ defined in A in the above-mentioned preferable combination of Y$^1$–Y$^3$, Z$^1$–Z$^4$, and A are the same as those defined for the formula (I).

The compounds of the formula (I) wherein the total number of the nitrogen atoms in Y$^1$–Y$^3$ and Z$^1$–Z$^4$ is 0, A represents a single bond, and the substituents R$^1$, R$^2$ and R$^4$ are as described below are within the scope of the present invention.

The compounds referred in the previous paragraph are the compounds wherein the substituent R$^1$ represents a 1-methyl-hexahydroazepin-4-yl-oxy group, or represented by the following formula (II):

(where Q represents a group: —NR$^{24}$R$^{24}$ (R$^{24}$ represents a hydrogen atom or an alkyl group having 1–4 carbon atoms; R$^{24}$ may not be hydrogen atom at the same time, or may combine each other to form a ring), a phenyl group which was mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyridyl group which was monosubstituted by any group selected from the group consisting of a halogen atom, a hydroxyl group, a mercapto group, an alkoxy group having 1 or 2 carbon atoms, an alkylthio group having 1 or 2 carbon atoms, an acetylamino group, a carboxyl group, an amino group, a cyano group, a nitro group, an amino group mono- or disubstituted by a lower alkyl group and a carbamoyl group, a 1-benzotriazolyl group, a 4-morpholinyl group, or 2-benzimidazolyl group; n is 1–6); or R$^2$ represents a straight- or branched-chain alkoxy group having 1–4 carbon atoms which was mono-substituted by any group selected from the group consisting of a hydroxyl group, a carboxyl group, a phenyl group and a pyridyl group; or R$^4$ represents a group: —M—G (where M represents an oxygen atom, an imino group or a group: —N(CH$_3$)—, and G represents a phenyl group which was mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group), a benzyl group which was mono- or disubstituted in the benzene ring by any group selected from the group consisting of a cyano group, a nitro group, an amino group mono- or disubstituted by a lower alkyl group, a carbamoyl group, an alkyl group having 1–4 carbon atoms, a hydroxymethyl group and an acetoxymethyl group, a pyridylmethyl group which was monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, a hydroxymethyl group and an acetoxymethyl group.

The specific individual compounds of the invention include:

(1) 10-bromo-5-(3-hydroxypropyloxy)-2-(3-pyridylmethyl)-3H-pyrido[3,2,1-kl]phenoxazin-3-one
(2) 9-bromo-5-(3-hydroxypropyloxy)-2-(3-pyridylmethyl)-3H-pyrido[3,2,1-kl]phenoxazin-3-one
(3) 10-bromo-5-(3-hydroxypropyloxy)-2-(3-pyridylmethyl)-3H-pyrido[3,2,1-kl]phenothiazin-3-one
(4) 9-bromo-5-(3-hydroxypropyloxy)-2-(3-pyridylmethyl)-3H-pyrido[3,2,1-kl]phenothiazin-3-one
(5) 10-bromo-5-(3-hydroxypropyloxy)-2-(3-pyridylmethyl)-3H,7H-pyrido[3,2,1-de]phenazin-3-one
(6) 9-bromo-5-(3-hydroxypropyloxy)-2-(3-pyridylmethyl)-3H,7H-pyrido[3,2,1-de]phenazin-3-one
(7) 7-acetyl-10-bromo-5-(3-hydroxypropyloxy)-2-(3-pyridylmethyl)-3H,7H-pyrido[3,2,1-de]phenazin-3-one
(8) 7-acetyl-9-bromo-5-(3-hydroxypropyloxy)-2-(3-pyridylmethyl)-3H,7H-pyrido[3,2,1-de]phenazin-3-one
(9) 10-bromo-5-(3-hydroxypropyloxy)-7-methyl-2-(3-pyridylmethyl)-3H,7H-pyrido[3,2,1-de]phenazin-3-one
(10) 9-bromo-5-(3-hydroxypropyloxy)-7-methyl-2-(3-pyridylmethyl)-3H,7H-pyrido[3,2,1-de]phenazin-3-one
(11) 10-bromo-5-(3-hydroxypropyloxy)-2-(3-pyridylmethyl)-3H,7H-pyrido[3,2,1-de]acridin-3,7-dione
(12) 9-bromo-5-(3-hydroxypropyloxy)-2-(3-pyridylmethyl)-3H,7H-pyrido[3,2,1-de]acridin-3,7-dione
(13) 10-bromo-7-hydroxy-5-(3-hydroxypropyloxy)-2-(3-pyridylmethyl)-3H,7H-pyrido[3,2,1-de]acridin-3-one
(14) 9-bromo-7-hydroxy-5-(3-hydroxypropyloxy)-2-(3-pyridylmethyl)-3H,7H-pyrido[3,2,1-de]acridin-3-one
(15) 10-bromo-7-(hydroxyimino)-5-(3-hydroxypropyloxy)-2-(3-pyridylmethyl)-3H,7H-pyrido[3,2,1-de]acridin-3-one
(16) 9-bromo-7-(hydroxyimino)-5-(3-hydroxypropyloxy)-2-(3-pyridylmethyl)-3H,7H-pyrido[3,2,1-de]acridin-3-one
(17) 9-bromo-2-(3-hydroxypropyloxy)-5-(3-pyridylmethyl)-4H-indolo[3,2,1-de][1,5]naphthyridin-4-one
(18) 10-bromo-2-(3-hydroxypropyloxy)-5-(3-pyridylmethyl)-4H-indolo[3,2,1-de][1,5]naphthyridin-4-one

(19) 9-bromo-2-(3-hydroxypropyloxy)-5-(3-pyridylmethyl)-4H[7]-azaindolo[3,2,1-ij]quinolin-4-one
(20) 10-bromo-2-(3-hydroxypropyloxy)-5-(3-pyridylmethyl)-4H[7]-azaindolo[3,2,1-ij]quinolin-4-one
(21) 9-bromo-2-(3-hydroxypropyloxy)-5-(3-pyridylmethyl)-4H[5]-azaindolo[3,2,1-ij]quinolin-4-one
(22) 10-bromo-2-(3-hydroxypropyloxy)-5-(3-pyridylmethyl)-4H[6]-azaindolo[3,2,1-ij]quinolin-4-one
(23) 9-bromo-2-(3-hydroxypropyloxy)-5-(3-pyridylmethyl)-4H[4]-azaindolo[3,2,1-ij]quinolin-4-one
(24) 10-bromo-2-(3-hydroxypropyloxy)-5-(3-pyridylmethyl)-4H[4]-azaindolo[3,2,1-ij]quinolin-4-one
<A=O>
(25) 10-bromo-5-(3-pyridylmethyl)-2-(3-pyridylmethy)-3H-pyrido[3,2,1-kl]phenoxazin-3-one
(26) 5-(1-benzotriazolylmethyloxy)-10-bromo-2-(3-pyridylmethyl)-3H-pyrido[3,2,1-kl]phenoxazin-3-one
(27) 10-bromo-5-(2-(1-piperidyl)ethyloxy)-2-(3-pyridylmethyl)-3H-pyrido[3,2,1-kl]phenoxazin-3-one
(28) 9-bromo-5-(3-pyridylmethyloxy)-2-(3-pyridylmethyl)-3H-pyrido[3,2,1-kl]phenoxazin-3-one
(29) 5-(1-benzotriazolylmethyloxy)-9-bromo-2-(3-pyridylmethyl)-3H-pyrido[3,2,1-kl]phenoxazin-3-one
(30) 9-bromo-5-(2-(1-piperidyl)ethyloxy)-2-(3-pyridylmethyl)-3H-pyrido[3,2,1-kl]phenoxazin-3-one
<A=S>
(31) 10-bromo-2-(3-pyridylmethyl)-5-(3-pyridylmethyloxy)-3H-pyrido[3,2,1-kl]phenothiazin-3-one
(32) 5-(1-benzotriazolylmethyloxy)-10-bromo-2-(3-pyridylmethyl)-3H-pyrido[3,2,1-kl]phenothiazin-3-one
(33) 10-bromo-5-(2-(1-piperidyl)ethyloxy)-2-(3-pyridylmethyl)-3H-pyrido[3,2,1-kl]phenothiazin-3-one
(34) 9-bromo-2-(3-pyridylmethyl)-5-(3-pyridylmethyloxy)-3H-pyrido[3,2,1-kl]phenothiazin-3-one
(35) 9-bromo-5-(1-benzotriazolylmethyloxy)-2-(3-pyridylmethyl)-3H-pyrido[3,2,1-kl]phenothiazin-3-one
(36) 9-bromo-5-(2-(1-piperidyl)ethyloxy)-2-(3-pyridylmethyl)-3H-pyrido[3,2,1-kl]phenothiazin-3-one
<A=NH>
(37) 10-bromo-2-(3-pyridylmethyl)-5-(3-pyridylmethyloxy)-3H,7H-pyrido[3,2,1-de]phenazin-3-one
(38) 5-(1-benzotriazolylmethyloxy)-10-bromo-2-(3-pyridylmethyl)-3H,7H-pyrido[3,2,1-de]phenazin-3-one
(39) 10-bromo-5-(2-(1-piperidyl)ethyloxy)-2-(3-pyridylmethyl)-3H,7H-pyrido[3,2,1-de]phenazin-3-one
(40) 9-bromo-2-(3-pyridylmethyl)-5-(3-pyridylmethyloxy)-3H,7H-pyrido[3,2,1-de]phenazin-3-one
(41) 9-bromo-5-(1-benzotriazolylmethyloxy)-2-(3-pyridylmethyl)-3H,7H-pyrido[3,2,1-de]phenazin-3-one
(42) 9-bromo-5-(2-(1-piperidyl)ethyloxy)-2-(3-pyridylmethyl)-3H,7H-pyrido[3,2,1-de]phenazin-3-one
<A=N—Ac>
(43) 7-acetyl-10-bromo-2-(3-pyridylmethyl)-5-(3-pyridylmethyloxy)-3H,7H-pyrido[3,2,1-de]phenazin-3-one
(44) 7-acetyl-5-(1-benzotriazolylmethyloxy)-10-bromo-2-(3-pyridylmethyl)-3H,7H-pyrido[3,2,1-de]phenazin-3-one
(45) 7-acetyl-10-bromo-5-(2-(1-piperidyl)ethyloxy)-2-(3-pyridylmethyl)-3H,7H-pyrido[3,2,1-de]phenazin-3-one
(46) 7-acetyl-9-bromo-2-(3-pyridylmethyl)-5-(3-pyridylmethyloxy)-3H,7H-pyrido[3,2,1-de]phenazin-3-one
(47) 7-acetyl-5-(1-benzotriazolylmethyloxy)-9-bromo-2-(3-pyridylmethyl)-3H,7H-pyrido[3,2,1-de]phenazin-3-one
(48) 7-acetyl-9-bromo-5-(2-(1-piperidyl)ethyloxy)-2-(3-pyridylmethyl)-3H,7H-pyrido[3,2,1-de]phenazin-3-one
<A=N—Me>
(49) 10-bromo-7-methyl-2-(3-pyridylmethyl)-5-(3-pyridylmethyloxy)-3H,7H-pyrido[3,2,1-de]phenazin-3-one
(50) 5-(1-benzotriazolylmethyloxy)-10-bromo-7-methyl-2-(3-pyridylmethyl)-3H,7H-pyrido[3,2,1-de]phenazin-3-one
(51) 10-bromo-7-methyl-5-(2-(1-piperidyl)ethyloxy)-2-(3-pyridylmethyl)-3H,7H-pyrido[3,2,1-de]phenazin-3-one
(52) 9-bromo-7-methyl-2-(3-pyridylmethyl)-5-(3-pyridylmethyloxy)-3H,7H-pyrido[3,2,1-de]phenazin-3-one
(53) 5-(1-benzotriazolylmethyloxy)-9-bromo-7-methyl-2-(3-pyridylmethyl)-3H,7H-pyrido[3,2,1-de]phenazin-3-one
(54) 9-bromo-7-methyl-5-(2-(1-piperidyl)ethyloxy)-2-(3-pyridylmethyl)-3H,7H-pyrido[3,2,1-de]phenazin-3-one
<A=CO>
(55) 10-bromo-2-(3-pyridylmethyl)-5-(3-pyridylmethyloxy)-3H,7H-pyrido[3,2,1-de]acridin-3,7-dione
(56) 5-(1-benzotriazolylmethyloxy)-10-bromo-2-(3-pyridylmethyl)-3H,7H-pyrido[3,2,1-de]acridin-3,7-dione
(57) 10-bromo-5-(2-(1-piperidyl)ethyloxy)-2-(3-pyridylmethyl)-3H,7H-pyrido[3,2,1-de]acridin-3,7-dione
(58) 9-bromo-2-(3-pyridylmethyl)-5-(3-pyridylmethyloxy)-3H,7H-pyrido[3,2,1-de]acridin-3,7-dione
(59) 5-(1-benzotriazolylmethyloxy)-9-bromo-2-(3-pyridylmethyl)-3H,7H-pyrido[3,2,1-de]acridin-3,7-dione
(60) 9-bromo-5-(2-(1-piperidyl)ethyloxy)-2-(3-pyridylmethyl)-3H,7H-pyrido[3,2,1-de]acridin-3,7-dione
<A=CH—OH>
(61) 10-bromo-7-hydroxy-2-(3-pyridylmethyl)-5-(3-pyridylmethyloxy)-3H,7H-pyrido[3,2,1-de]acridin-3-one
(62) 5-(1-benzotriazolylmethyloxy)-10-bromo-7-hydroxy-2-(3-pyridylmethyl)-3H,7H-pyrido[3,2,1-de]acridin-3-one
(63) 10-bromo-7-hydroxy-5-(2-(1-piperidyl) ethyloxy)-2-(3-pyridylmethyl)-3H,7H-pyrido[3,2,1-de]acridin-3-one
(64) 9-bromo-7-hydroxy-2-(3-pyridylmethyl)-5-(3-pyridylmethyloxy)-3H,7H-pyrido[3,2,1-de]acridin-3-one
(65) 5-(1-benzotriazolylmethyloxy)-9-bromo-7-hydroxy-2-(3-pyridylmethyl)-3H,7H-pyrido[3,2,1-de]acridin-3-one
(66) 9-bromo-7-hydroxy-5-(2-(1-piperidyl)ethyloxy)-2-(3-pyridylmethyl)-3H,7H-pyrido[3,2,1-de]acridin-3-one
<A=N—OH>
(67) 10-bromo-7-(hydroxyimino)-2-(3-pyridylmethyl)-5-(3-pyridylmethyloxy)-3H,7H-pyrido[3,2,1-de]acridin-3-one
(68) 5-(1-benzotriazolylmethyloxy)-10-bromo-7-(hydroxyimino)-2-(3-pyridylmethyl)-3H,7H-pyrido[3,2,1-de]acridin-3-one
(69) 10-bromo-7-(hydroxyimino)-5-(2-(1-piperidyl)ethyloxy)-2-(3-pyridylmethyl)-3H,7H-pyrido[3,2,1-de]acridin-3-one
(70) 9-bromo-7-(hydroxyimino)-2-(3-pyridylmethyl)-5-(3-pyridylmethyloxy)-3H,7H-pyrido[3,2,1-de]acridin-3-one
(71) 9-bromo-7-(hydroxyimino)-5-(1-benzotriazolylmethyloxy)-2-(3-pyridylmethyl)-3H,7H-pyrido[3,2,1-de]acridin-3-one
(72) 9-bromo-7-(hydroxyimino)-5-(2-(1-piperidyl)ethyloxy)-2-(3-pyridylmethyl)-3H,7H-pyrido[3,2,1-de]acridin-3-one
(73) 10-bromo-5-hydroxy-2-(3-pyridylmethyl)-3H-pyrido[3,2,1-kl]phenothiazin-3-one
(74) 2-benzyl-10-bromo-5-(3-hydroxypropyloxy)-3H-pyrido[3,2,1-kl]phenothiazin-3-one

(75) 2-benzyl-10-bromo-5-(3-pyridylmethyloxy)-3H-pyrido[3,2,1-kl]phenothiazin-3-one
(76) 2-benzyl-10-bromo-5-(1-benzotriazolylmethyloxy)-3H-pyrido[3,2,1-kl]phenothiazin-3-one
(77) 2-benzyl-10-bromo-5-(2-(1-piperidyl)ethyloxy)-3H-pyrido[3,2,1-kl]phenothiazin-3-one
(78) 10-bromo-5-(3-hydroxypropyloxy)-2-(5-pyrimidinylmethyl)-3H-pyrido[3,2,1-kl]phenothiazin-3-one
(79) 10-bromo-5-(3-pyridylmethyloxy)-2-(5-pyrimidinylmethyl)-3H-pyrido[3,2,1-kl]phenothiazin-3-one
(80) 5-(1-benzotriazolylmethyloxy)-10-bromo-2-(5-pyrimidinylmethyl)-3H-pyrido[3,2,1-kl]phenothiazin-3-one
(81) 10-bromo-5-(2-(1-piperidyl)ethyloxy)-2-(5-pyrimidinylmethyl)-3H-pyrido[3,2,1-kl]phenothiazin-3-one.

In the formula (VI), $R^{11}$ represents a hydrogen atom, a halogen atom, a cyano group, an optionally protected carboxyl group, an optionally protected carboxymethyl group, an alkoxycarbonyl group having 1–4 carbon atoms, a carbamoyl group, an acetylamino group, an optionally protected hydroxyl group, an optionally protected mercapto group, a straight- or branched-chain alkyl group having 1–4 carbon atoms which may be substituted by one hydroxyl group, an amino group which may be mono- or disubstituted by an alkyl group having 1–4 carbon atoms, an alkylthio group having 1–3 carbon atoms or a straight-chain alkoxy group having 1–6 carbon atoms which may be substituted by a 4-methoxyphenoxy group; $R^{12}$ represents a hydrogen atom, a halogen atom, an optionally protected hydroxyl group, an optionally protected mercapto group, an optionally protected amino group, a cyano group, a nitro group, a trifluoromethyl group, a trifluoromethoxy group, an optionally protected carboxyl group, a straight- or branched-chain alkanoyl group having 1–4 carbon atoms, a straight- or branched-chain alkyl group having 1–4 carbon atoms or a straight- or branched-chain alkoxy group having 1–4 carbon atoms; $R^{13}$ represents a hydrogen atom, a halogen atom, an optionally protected hydroxyl group or a straight- or branched-chain alkoxy group having 1–4 carbon atoms; $R^{19}$ represents a hydrogen atom, a halogen atom, a group: —M—G (where M represents an oxygen atom, an imino group or a group: —N(CH$_3$)—, and G represents a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group), an a-hydroxybenzyl group, a methyl group or a halogenomethyl group.

More specifically, the substituents $R^{11}$, $R^{12}$, $R^{13}$ and $R^{19}$ are expressed by the definitions given to the specific examples of the relevant substituents which are represented by $R^1$, $R^2$, $R^3$ and $R^4$, respectively, in the formula (I) and which are specifically described hereinabove.

Referring to the formula (XVII) which will be set forth later in connection with production of the claimed compounds, $R^{22}$ represents a hydrogen atom, a methyl group, a cyclic alkyl group having 3–6 carbon atoms, a phenyl group which may be mono- or disubstituted in the benzene ring by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyridyl group which may be monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a morpholyl group, a triazolyl group, a furyl group, a thienyl group, a pyrimidinyl group, a pyrazinyl group, a pyrrolyl group, an imidazolyl group, a quinolyl group, an indolyl group or a naphthyl group.

More specifically, the "cyclic alkyl group having 3–6 carbon atoms" refers to a cyclopropyl group, a cyclohexyl group or the like; the "phenyl group which may be mono- or disubstituted in the benzene ring by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group" refers to a 2-fluorophenyl group, a 2-chlorophenyl group, a 2-bromophenyl group, a 3-fluorophenyl group, a 3-chlorophenyl group, a 3-bromophenyl group, a 4-fluorophenyl group, a 4-chlorophenyl group, a 4-bromophenyl group, a 2-hydroxyphenyl group, a 3-hydroxyphenyl group, a 4-hydroxyphenyl group, a 2-mercaptophenyl group, a 3-mercaptophenyl group, a 4-mercaptophenyl group, a 2-methoxyphenyl group, a 3-methoxyphenyl group, a 4-methoxyphenyl group, a 2-ethoxyphenyl group, a 3-ethoxyphenyl group, a 4-ethoxyphenyl group, a 2-n-propoxyphenyl group, a 3-n-propoxyphenyl group, a 4-n-propoxyphenyl group, a 2-i-propoxyphenyl group, a 3-i-propoxyphenyl group, a 4-i-propoxyphenyl group, a 2-n-butoxyphenyl group, a 3-n-butoxyphenyl group, a 4-n-butoxyphenyl group, a 2-t-butoxyphenyl group, a 3-t-butoxyphenyl group, a 4-t-butoxyphenyl group, a 2-methylthiophenyl group, a 3-methylthiophenyl group, a 4-methylthiophenyl group, a 2-ethylthiophenyl group, a 3-ethylthiophenyl group, a 4-ethylthiophenyl group, a 2-methoxycarbonylphenyl group, a 3-methoxycarbonylphenyl group, a 4-methoxycarbonylphenyl group, a 2-ethoxycarbonylphenyl group, a 3-ethoxycarbonylphenyl group, a 4-ethoxycarbonylphenyl group, a 2-t-butoxycarbonylphenyl group, a 3-t-butoxycarbonylphenyl group, a 4-t-butoxycarbonylphenyl group, a 2-acetylaminophenyl group, a 3-acetylaminophenyl group, a 4-acetylaminophenyl group, a 2-carboxyphenyl group, a 3-carboxyphenyl group, a 4-carboxyphenyl group, a 2-aminophenyl group, a 3-aminophenyl group, a 4-aminophenyl group, a 2-cyanophenyl group, a 3-cyanophenyl group, a 4-cyanophenyl group, a 2-nitrophenyl group, a 3-nitrophenyl group, a 4-nitrophenyl group, a 2-methylaminophenyl group, a 3-methylaminophenyl group, a 4-methylaminophenyl group, a 2-ethylaminophenyl group, a 3-ethylaminophenyl group, a 4-ethylaminophenyl group, a 2-dimethylaminophenyl group, a 3-dimethylaminophenyl group, a 4-dimethylaminophenyl group, a 2-diethylaminophenyl group, a 3-diethylaminophenyl group, a 4-diethylaminophenyl group, a 2-hydroxymethylphenyl group, a 3-hydroxymethylphenyl group, a 4-hydroxymethylphenyl group, a 2-acetoxymethylphenyl group, a 3-acetoxymethylphenyl group, a 4-acetoxymethylphenyl group, a 2-carbamoylphenyl group, a 3-carbamoylphenyl group, a 4-carbamoylphenyl group, a 2-methylphenyl group, a 3-methylphenyl group, a 4-methylphenyl group, a 2-ethylphenyl group, a 3-ethylphenyl group, a 4-ethylphenyl group, a 2-(n-propyl)phenyl group, a 3-(n-propyl)phenyl group, a 4-(n-propyl)phenyl group, a 2-(i-propyl)phenyl group, a 3-(i-propyl)phenyl group, a 4-(i-propyl)phenyl group, a 2-(n-butyl)phenyl group, a 3-(n-butyl)phenyl group, a 4-(n-butyl)phenyl group, a 2-(t-butyl)phenyl group, a 3-(t-butyl)phenyl group, a 4-(t-butyl)phenyl group, a 2,3-difluorophenyl group, a 2,4-difluorophenyl group, a 2,5-difluorophenyl group, a 3,4-difluorophenyl group, a 3,5-difluorophenyl group, a 2,3-dichlorphenyl group, a 2,4-dichlorphenyl group, a 2,5-dichlorphenyl group, a 3,4-dichlorphenyl group, a 3,5-dichlorphenyl group, a 2,3-dibromophenyl group, a 2,4-dibromophenyl group, a 2,5-dibromophenyl group, a 3,4-dibromophenyl group, a 3,5-dibromophenyl group, a 2,3-dihydroxyphenyl group, a 2,4-dihydroxyphenyl group, a 2,5-dihydroxyphenyl group, a 3,4-dihydroxyphenyl group, a 3,5-dihydroxyphenyl group, a 2,3-dimethoxyphenyl group, a 2,4-dimethoxyphenyl group, a 2,5-dimethoxyphenyl group, a 3,4-dimethoxyphenyl group, a 3,5-dimethoxyphenyl group, a 2,3-diethoxyphenyl group, a 2,4-diethoxyphenyl group, a 2,5-diethoxyphenyl group, a 3,4-diethoxyphenyl group, a 3,5-diethoxyphenyl group, a 2-fluoro-3-methoxyphenyl group, a 2-fluoro-4-methoxyphenyl group, a 2-fluoro-5-methoxyphenyl group, a 3-fluoro-4-methoxyphenyl group, a 3-fluoro-5-methoxyphenyl group, a 3-fluoro-2-methoxyphenyl group, a 4-fluoro-2-methoxyphenyl group, a 5-fluoro-2-methoxyphenyl group, a 4-fluoro-3-methoxyphenyl group, a 5-fluoro-3-methoxyphenyl group, a 2-chloro-3-methoxyphenyl group, a 2-chloro-4-methoxyphenyl group, a 2-chloro-5-methoxyphenyl group, a 3-chloro-4-methoxyphenyl group, a 3-chloro-5-methoxyphenyl group, a 3-chloro-2-methoxyphenyl group, a 4-chloro-2-methoxyphenyl group, a 5-chloro-2-methoxyphenyl group, a 4-chloro-3-methoxyphenyl group, a 5-chloro-3-methoxyphenyl group, a 2-bromo-3-methoxyphenyl group, a 2-bromo-4-methoxyphenyl group, a 2-bromo-5-methoxyphenyl group, a 3-bromo-4-methoxyphenyl group, a 3-bromo-5-methoxyphenyl group, a 3-bromo-2-methoxyphenyl group, a 4-bromo-2-methoxyphenyl group, a 5-bromo-2-methoxyphenyl group, a 4-bromo-3-methoxyphenyl group, a 5-bromo-3-methoxyphenyl group, a 2-cyano-3-methoxyphenyl group, a 2-cyano-4-methoxyphenyl group, a 2-cyano-5-methoxyphenyl group, a 3-cyano-4-methoxyphenyl group, a 3-cyano-5-methoxyphenyl group, a 3-cyano-2-methoxyphenyl group, a 4-cyano-2-methoxyphenyl group, a 5-cyano-2-methoxyphenyl group, a 4-cyano-3-methoxyphenyl group, a 5-cyano-3-methoxyphenyl group, or the like; the "pyridyl group which may be monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group" refers to a 2-pyridyl group, a 3-pyridyl group, a 4-pyridyl group, a 5-methyl-3-pyridyl group, a 6-methyl-2-pyridyl group, a 5-ethyl-3-pyridyl group, a 6-ethyl-2-pyridyl group, a 5-hydroxymethyl-3-pyridyl group, a 5-t-butyl-3-pyridyl group, a 6-hydroxymethyl-2-pyridyl group, a 5-acetoxymethyl-3-pyridyl group, a 6-acetoxymethyl-2-pyridyl group, a 5-methoxycarbonyl-3-pyridyl group, a 5-ethoxycarbonyl-3-pyridyl group, a 6-methoxycarbonyl-2-pyridyl group, a 5-carboxy-3-pyridyl group, a 6-carboxy-2-pyridyl group, a 4-amino-2-pyridyl group, a 5-amino-3-pyridyl group, a 2-amino-4-pyridyl group, a 4-carboxy-2-pyridyl group, a 4-acetylamino-2-pyridyl group, a 5-acetylamino-3-pyridyl group, a 2-acetylamino-4-pyridyl group, a 4-methylthio-2-pyridyl group, a 5-methylthio-3-pyridyl group, a 3-methylthio-4-pyridyl group, a 4-mercapto-2-pyridyl group, a 5-mercapto-3-pyridyl group, a 3-mercapto-4-pyridyl group, a 4-methoxy-2-pyridyl group, a 5-methoxy-3-pyridyl group, a 3-methoxy-4-pyridyl group, a 4-hydroxy-2-pyridyl group, a 5-hydroxy-3-pyridyl group, a 3-hydroxy-4-pyridyl group, a 4-fluoro-2-pyridyl group, a 5-fluoro-2-pyridyl group, a 4-fluoro-3-pyridyl group, a 5-fluoro-3-pyridyl group, a 2-fluoro-4-pyridyl group, a 2-fluoro-4-pyridyl group, a 4-chloro-2-pyridyl group, a 5-chloro-2-pyridyl group, a 4-chloro-3-pyridyl group, a 5-chloro-3-pyridyl group, a 2-chloro-4-pyridyl group, a 2-chloro-4-pyridyl group, a 4-bromo-2-pyridyl group, a 5-bromo-2-pyridyl group, a 4-bromo-3-pyridyl group, a 5-bromo-3-pyridyl group, a 2-bromo-4-pyridyl group, a 2-bromo-4-pyridyl group, a 4-cyano-2-pyridyl group, a 5-cyano-2-pyridyl group, a 4-cyano-3-pyridyl group, a 5-cyano-3-pyridyl group, a 2-cyano-4-pyridyl group, a 2-cyano-4-pyridyl group, a 4-nitro-2-pyridyl group, a 5-nitro-3-pyridyl group, a 4-dimethylamino-2-pyridyl group, a 5-dimethylamino-3-pyridyl group, a 4-carbamoyl-2-pyridyl group, a 5-carbamoyl-3-pyridyl group, or the like.

Preferably, $R^{22}$ represents a 2-pyrimidinyl group, a 4-pyrimidinyl group, a 5-pyrimidinyl group, a 2-pyridyl group, a 3-pyridyl group, a 4-pyridyl group, a 5-methyl-3-pyridyl group or a 6-methyl-2-pyridyl group.

More preferably, $R^{22}$ represents a 5-pyrimidinyl group, a 2-pyridyl group, a 3-pyridyl group or a 4-pyridyl group.

Further, $R^{23}$ in the formula (XVIII) represents an alkoxycarbonyl group having 1–4 carbon atoms, a 3-carboxy-1-propenyl group, a 2,2-diethoxyethyl group, a straight- or branched-chain alkanoyl group having 1–4 carbon atoms, a carbonyl group substituted by a phenyl group or a pyridyl group, or a group: —$(CH_2)_n$—Q (where Q represents a hydrogen atom, a carboxyl group, an alkoxy group having 1 or 2 carbon atoms which may be substituted by one hydroxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or one mercapto group, a piperidinylcarbonyl group which may be substituted by one carboxyl group or alkoxycarbonyl group having 1 or 2 carbon atoms, a morpholylcarbonyl group, a hydroxyl group, a mercapto group, a group: —$NR^{24}R^{24}$ ($R^{24}$ represents a hydrogen atom or an alkyl group having 1–4 carbon atoms; the two $R^{24}$s may be the same or different, or may combine each other to form a ring), a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyridyl group which may be monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyrazinyl group, a pyrimidinyl group, a furyl group, a thienyl group, an oxadiazolyl group, a 4-methoxyphenoxy group, a 1-benzotriazolyl group, a 4-morpholinyl group, or 2-benzimidazolyl group; n is 1–6).

More specifically, the "alkoxycarbonyl group having 1–4 carbon atoms" refers to a methoxycarbonyl group, an ethoxycarbonyl group, a n-propoxycarbonyl group, an i-propoxycarbonyl group, a cyclopropoxycarbonyl group, a n-butoxycarbonyl group, a t-butoxycarbonyl group, or the like; the "straight- or branched-chain alkanoyl group having 1–4 carbon atoms" refers to an acetyl group, a propionyl group, a butyryl group, a pivaloyl group, or the like; the "carbonyl group substituted by a phenyl group or a pyridyl group" refers to a benzoyl group, a nicotinoyl group, an isonicotinoyl group, or the like; the group: —(CH2)$_n$—Q (where Q represents a hydrogen atom, a carboxyl group, an alkoxy group having 1 or 2 carbon atoms which may be substituted by one hydroxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or one mercapto group, a piperidinylcarbonyl group which may be substituted by one carboxyl group or alkoxycarbonyl group having 1 or 2 carbon atoms, a morpholylcarbonyl group, a hydroxyl group, a mercapto group, a group: —NR$^{24}$R$^{24}$ (R$^{24}$ represents a hydrogen atom or an alkyl group having 1–4 carbon atoms; the two R$^{24}$s may be the same or different, or may combine each other to form a ring), a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyridyl group which may be monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyrazinyl group, a pyrimidinyl group, a furyl group, a thienyl group, an oxadiazolyl group, a 4-methoxyphenoxy group, a 1-benzotriazolyl group, a 4-morpholinyl group, or 2-benzimidazolyl group; n is 1–6) refers to a methyl group, an ethyl group, a n-propyl group, an i-propyl group, a n-butyl group, a t-butyl group, a n-pentyl group, a n-hexyl group, a carboxymethyl group, a 2-carboxyethyl group, a 3-carboxypropyl group, a methoxymethyl group, an ethoxymethyl group, a 2-methoxyethyl group, a 2-ethoxyethyl group, a 2-(2-hydroxyethoxy)ethyl group, a methoxycarbonylmethyl group, a n ethoxycarbonylmethyl group, a n-propoxycarbonylmethyl group, an i-propoxycarbonylmethyl group, a n-butoxycarbonylmethyl group, a t-butoxycarbonylmethyl group, a n-pentyloxycarbonylmethyl group, a n-hexyloxycarbonylmethyl group, a cyclopropyloxycarbonylmethyl group, a cyclohexyloxycarbonylmethyl group, a 2-(methoxycarbonyl)ethyl group, a 2-(ethoxycarbonyl)ethyl group, a 2-(n-propoxycarbonyl)ethyl group, a 2-(i-propoxycarbonyl)ethyl group, a 2-(n-butoxycarbonyl)ethyl group, a 2-(t-butoxycarbonyl)ethyl group, a 2-(n-pentyloxycarbonyl)ethyl group, a 2-(n-hexyloxycarbonyl)ethyl group, a 2-(cyclopropyloxycarbonyl)ethyl group, a 2-(cyclohexyloxycarbonyl)ethyl group, a 3-(methoxycarbonyl)propyl group, a 3-(ethoxycarbonyl)propyl group, a 3-(n-propoxycarbonyl)propyl group, a 3-(i-propoxycarbonyl)propyl group, a 3-(n-butoxycarbonyl)propyl group, a 3-(t-butoxycarbonyl)propyl group, a 3-(n-pentyloxycarbonyl)propyl group, a 3-(n-hexyloxycarbonyl)propyl group, a 3-(cyclopropyloxycarbonyl)propyl group, a 3-(cyclohexyloxycarbonyl)propyl group, a N-hydroxymethylcarbamoylmethyl group, a N-methylcarbamoylmethyl group, a N,N-dimethylcarbamoylmethyl group, a N-ethylcarbamoylmethyl group, a N,N-diethylcarbamoylmethyl group, a N-n-propylcarbamoylmethyl group, a N-n-butylcarbamoylmethyl group, a 3-hydroxy-2-oxopropyl group, a 4-hydroxy-3-oxobutyl group, a 5-hydroxy-4-oxopentyl group, a 4-hydroxy-2-oxobutyl group, a 5-hydroxy-2-oxopentyl group, a 6-hydroxy-2-oxohexyl group, a 5-mercapto-2-oxopentyl group, a 4-carboxy-1-piperidinylcarbonylmethyl group, a 4-methoxycarbonyl-1-piperidinylcarbonylmethyl group, a 4-ethoxycarbonyl-1-piperidinylcarbonylmethyl group, a 4-morpholylcarbonylmethyloxy group, a 2-hydroxyethyl group, a 3-hydroxypropyl group, a 4-hydroxybutyl group, a 2-mercaptoethyl group, a 3-mercaptopropyl group, a 4-mercaptobutyl group, a 2-aminoethyl group, a 3-aminopropyl group, a 4-aminobutyl group, 2-N,N-dimethylaminoethyl group, 3-N,N-dimethylaminopropyl group, 4-N,N-dimethylaminobutyl group, 2-N,N-diisopropylaminoethyl group, 3-N,N-diisopropylaminopropyl group, 4-N,N-diisopropylaminobutyl group,2-(1-piperidyl)ethyl group, 3-(1-piperidyl)propyl group, 4-(1-piperidyl)butyl group, a benzyl group, a 2-fluorobenzyl group, a 2-chlorobenzyl group, a 2-bromobenzyl group, a 3-fluorobenzyl group, a 3-chlorobenzyl group, a 3-bromobenzyl group, a 4-fluorobenzyl group, a 4-chlorobenzyl group, a 4-bromobenzyl group, a 2-hydroxybenzyl group, a 3-hydroxybenzyl group, a 4-hydroxybenzyl group, a 2-mercaptobenzyl group, a 3-mercaptobenzyl group, a 4-mercaptobenzyl group, a 2-methoxybenzyl group, a 3-methoxybenzyl group, a 4-methoxybenzyl group, a 2-ethoxybenzyl group, a 3-ethoxybenzyl group, a 4-ethoxybenzyl group, a 2-methylthiobenzyl group, a 3-methylthiobenzyl group, a 4-methylthiobenzyl group, a 2-ethylthiobenzyl group, a 3-ethylthiobenzyl group, a 4-ethylthiobenzyl group, a 2-methoxycarbonylbenzyl group, a 3-methoxycarbonylbenzyl group, a 4-methoxycarbonylbenzyl group, a 2-ethoxycarbonylbenzyl group, a 3-ethoxycarbonylbenzyl group, a 4-ethoxycarbonylbenzyl group, a 2-t-butoxycarbonylbenzyl group, a 3-t-butoxycarbonylbenzyl group, a 4-t-butoxycarbonylbenzyl group, a 2-acetylaminobenzyl group, a 3-acetylaminobenzyl group, a 4-acetylaminobenzyl group, a 2-carboxybenzyl group, a 3-carboxybenzyl group, a 4-carboxybenzyl group, a 2-aminobenzyl group, a 3-aminobenzyl group, a 4-aminobenzyl group, a 2-cyanobenzyl group, a 3-cyanobenzyl group, a 4-cyanobenzyl group, a 2-nitrobenzyl group, a 3-nitrobenzyl group, a 4-nitrobenzyl group, a 2-methylaminobenzyl group, a 3-methylaminobenzyl group, a 4-methylaminobenzyl group, a 2-ethylaminobenzyl group, a 3-ethylaminobenzyl group, a 4-ethylaminobenzyl group, a 2-dimethylaminobenzyl group, a 3-dimethylaminobenzyl group, a 4-dimethylaminobenzyl group, a 2-diethylaminobenzyl group, a 3-diethylaminobenzyl group, a 4-diethylaminobenzyl group, a 2-hydroxymethylbenzyl group, a 3-hydroxymethylbenzyl group, a 4-hydroxymethylbenzyl group, a 2-acetoxymethylbenzyl group, a 3-acetoxymethylbenzyl group, a 4-acetoxymethylbenzyl group, a 2-carbamoylbenzyl group, a 3-carbamoylbenzyl group, a 4-carbamoylbenzyl group, a 2-methylbenzyl group, a 3-methylbenzyl group, a 4-methylbenzyl group, a 2-ethylbenzyl group, a 3-ethylbenzyl group, a 4-ethylbenzyl group, a 2-(n-propyl)benzyl group, a 3-(n-propyl)benzyl group, a 4-(n-propyl)benzyl group, a 2-(i-propyl)benzyl group, a 3-(i-propyl)benzyl group, a 4-(i-propyl)benzyl group, a 2-(n-butyl)benzyl group, a 3-(n-butyl)benzyl group, a 4-(n-butyl)benzyl group, a 2-(t-butyl)benzyl group, a 3-(t-butyl)benzyl group, a 4-(t-butyl)benzyl group, a 2,3-difluorobenzyl group, a 2,4-difluorobenzyl group, a 2,5-difluorobenzyl group, a 3,4-difluorobenzyl group, a 3,5-difluorobenzyl group, a 2,3-dichlorbenzyl group, a 2,4-dichlorbenzyl group, a 2,5-dichlorbenzyl group, a 3,4-dichlorbenzyl group, a 3,5-dichlorbenzyl group, a 2,3-dibromobenzyl group, a 2,4-dibromobenzyl group, a 2,5-dibromobenzyl group, a 3,4-dibromobenzyl group, a 3,5-dibromobenzyl group, a 2,3-dihydroxybenzyl group, a 2,4-dihydroxybenzyl group, a 2,5-dihydroxybenzyl group, a 3,4-dihydroxybenzyl group, a 3,5-dihydroxybenzyl group, a 2,3-dimethoxybenzyl group, a 2,4-dimethoxybenzyl group, a 2,5-dimethoxybenzyl group, a 3,4-dimethoxybenzyl group, a 3,5-dimethoxybenzyl group, a 2,3-diethoxybenzyl group, a 2,4-diethoxybenzyl group, a 2,5-diethoxybenzyl group, a 3,4-diethoxybenzyl group, a 3,5-diethoxybenzyl group, a 2-fluoro-3-methoxybenzyl group, a 2-fluoro-4-methoxybenzyl group, a 2-fluoro-5-methoxybenzyl group, a 3-fluoro-4-methoxybenzyl group, a 3-fluoro-5-methoxybenzyl group, a 3-fluoro-2-methoxybenzyl group, a 4-fluoro-2-methoxybenzyl group, a 5-fluoro-2-methoxybenzyl group, a 4-fluoro-3-methoxybenzyl group, a 5-fluoro-3-methoxybenzyl group, a 2-chloro-3-methoxybenzyl group, a 2-chloro-4-methoxybenzyl group, a 2-chloro-5-methoxybenzyl group, a 3-chloro-4-methoxybenzyl group, a 3-chloro-5-methoxybenzyl group, a 3-chloro-2-methoxybenzyl group, a 4-chloro-2-methoxybenzyl group, a 5-chloro-2-methoxybenzyl group, a 4-chloro-3-methoxybenzyl group, a 5-chloro-3-methoxybenzyl group, a 2-bromo-3-methoxybenzyl group, a 2-bromo-4-methoxybenzyl group, a 2-bromo-5-methoxybenzyl group, a 3-bromo-4-methoxybenzyl group, a 3-bromo-5-methoxybenzyl group, a 3-bromo-2-methoxybenzyl group, a 4-bromo-2-methoxybenzyl group, a 5-bromo-2-methoxybenzyl group, a 4-bromo-3-methoxybenzyl group, a 5-bromo-3-methoxybenzyl group, a 2-cyano-3-methoxybenzyl group, a 2-cyano-4-methoxybenzyl group, a 2-cyano-5-methoxybenzyl group, a 3-cyano-4-methoxybenzyl group, a 3-cyano-5-methoxybenzyl group, a 3-cyano-2-methoxybenzyl group, a 4-cyano-2-methoxybenzyl group, a 5-cyano-2-methoxybenzyl group, a 4-cyano-3-methoxybenzyl group, a 5-cyano-3-methoxybenzyl group, a 2-phenethyl group, a 3-phenylpropyl group, a 5-hydroxymethyl-3-pyridylmethyl group, a 5-acetoxymethyl-3-pyridylmethyl group, a 6-hydroxymethyl-2-pyridylmethyl group, a 6-acetoxymethyl-2-pyridylmethyl group, a 5-methyl-3-pyridylmethyl group, a 6-methyl-2-pyridylmethyl group, a 5-ethyl-3-pyridylmethyl group, a 5-t-butyl-3-pyridylmethyl group, a 5-methoxycarbonyl-3-pyridylmethyl group, a 5-ethoxycarbonyl-3-pyridylmethyl group, a 2-pyridylmethyl group, a 3-pyridylmethyl group, a 4-pyridylmethyl group, a 6-ethyl-2-pyridylmethyl group, a 6-methoxycarbonyl-2-pyridylmethyl group, a 5-carboxy-3-pyridylmethyl group, a 6-carboxy-2-pyridylmethyl group, a 4-amino-2-pyridylmethyl group, a 5-amino-3-pyridylmethyl group, a 2-amino-4-pyridylmethyl group, a 4-carboxy-2-pyridylmethyl group, a 4-acetylamino-2-pyridylmethyl group, a 5-acetylamino-3-pyridylmethyl group, a 2-acetylamino-4-pyridylmethyl group, a 4-methylthio-2-pyridylmethyl group, a 5-methylthio-3-pyridylmethyl group, a 3-methylthio-4-pyridylmethyl group, a 4-mercapto-2-pyridylmethyl group, a 5-mercapto-3-pyridylmethyl group, a 3-mercapto-4-pyridylmethyl group, a 4-methoxy-2-pyridylmethyl group, a 5-methoxy-3-pyridylmethyl group, a 3-methoxy-4-pyridylmethyl group, a 4-hydroxy-2-pyridylmethyl group, a 5-hydroxy-3-pyridylmethyl group, a 3-hydroxy-4-pyridylmethyl group, a 4-fluoro-2-pyridylmethyl group, a 5-fluoro-2-pyridylmethyl group, a 4-fluoro-3-pyridylmethyl group, a 5-fluoro-3-pyridylmethyl group, a 2-fluoro-4-pyridylmethyl group, a 2-fluoro-4-pyridylmethyl group, a 4-chloro-2-pyridylmethyl group, a 5-chloro-2-pyridylmethyl group, a 4-chloro-3-pyridylmethyl group, a 5-chloro-3-pyridylmethyl group, a 2-chloro-4-pyridylmethyl group, a 2-chloro-4-pyridylmethyl group, a 4-bromo-2-pyridylmethyl group, a 5-bromo-2-pyridylmethyl group, a 4-bromo-3-pyridylmethyl group, a 5-bromo-3-pyridylmethyl group, a 2-bromo-4-pyridylmethyl group, a 2-bromo-4-pyridylmethyl group, a 4-cyano-2-pyridylmethyl group, a 5-cyano-2-pyridylmethyl group, a 4-cyano-3-pyridylmethyl group, a 5-cyano-3-pyridylmethyl group, a 2-cyano-4-pyridylmethyl group, a 2-cyano-4-pyridylmethyl group, a 4-nitro-2-pyridylmethyl group, a 5-nitro-3-pyridylmethyl group, a 4-dimethylamino-2-pyridylmethyl group, a 5-dimethylamino-3-pyridylmethyl group, a 4-carbamoyl-2-pyridylmethyl group, a 5-carbamoyl-3-pyridylmethyl group, a 2-pyrazinylmethyl group, a 2-pyrimidinylmethyl group, a 4-pyrimidinylmethyl group, a 5-pyrimidinylmethyl group, a 2-furylmethyl group, a 3-furylmethyl group, a 2-thienylmethyl group, a 3-thienylmethyl group, a 3-oxadiazolylmethyl group, a 2-(4-methoxyphenoxy)ethyl group, a 3-(4-methoxyphenoxy)propyl group, a 4-(4-methoxyphenoxy)butyl group, a 1-benzotriazolylmethyl group, 2-(1-benzotriazolyl)ethyl group, a 3-(1-benzotriazolyl)propyl group, a 4-(1-benzotriazolyl)butyl group, a 4-morpholylmethyl group, 2-(4-morpholyl)ethyl group, a 3-(4-morpholyl)propyl group, a 4-(4-morpholyl)butyl group, a 2-benzimidazolylmethyl group, 2-(2-benzimidazolyl)ethyl group, a 3-(2-benzimidazolyl)propyl group, a 4-(2-benzimidazolyl)butyl group, or the like.

Preferably, $R^{23}$ represents a carboxymethyl group, a 2-carboxyethyl group, a 3-carboxypropyl group, a methoxycarbonylmethyl group, an ethoxycarbonylmethyl group, a n-propoxycarbonylmethyl group, an i-propoxycarbonylmethyl group, a n-butoxycarbonylmethyl group, a t-butoxycarbonylmethyl group, a N-hydroxymethylcarbamoylmethyl group, a N-ethylcarbamoylmethyl group, a 4-hydroxy-2-oxobutyl group, a 5-hydroxy-2-oxopentyl group, a 2-hydroxyethyl group, a 3-hydroxypropyl group, a 4-hydroxybutyl group, a 3-aminopropyl group, a 4-aminobutyl group,2-N,N-dimethylaminoethyl group, 3-N,N-dimethylaminopropyl group, 4-N,N-dimethylaminobutyl group,2-N,N-diisopropylaminoethyl group, 3-N,N-diisopropylaminopropyl group, 4-N,N-diisopropylaminobutyl group, 2-(1-piperidyl)ethyl group, 3-(1-piperidyl)propyl group, 4-(1-piperidyl)butyl group, a benzyl group, a 5-hydroxymethyl-3-pyridylmethyl group, a 5-acetoxymethyl-3-pyridylmethyl group, a 6-hydroxymethyl-2-pyridylmethyl group, a 6-acetoxymethyl-2-pyridylmethyl group, a 5-methyl-3-pyridylmethyl group, a 6-methyl-2-pyridylmethyl group, a 5-ethyl-3-pyridylmethyl group, a 6-ethyl-2-pyridylmethyloxy group, a 5-t-butyl-3-pyridylmethyl group, a 6-t-butyl-2-pyridylmethyloxy group, a 5-methoxycarbonyl-3-pyridylmethyl group, a 5-ethoxycarbonyl-3-pyridylmethyl group, a 2-pyridylmethyl group, a 3-pyridylmethyl group, a 4-pyridylmethyl group, a 2-pirazinylmethyl group, a 2-pyrimidinylmethyl group, a 4-pyrimidinylmethyl group or a 5-pyrimidinylmethyl group, a 1-benzotriazolylmethyl group, 2-(1-benzotriazolyl)ethyl group, a 3-(1-benzotriazolyl)propyl group, a 4-(1-benzotriazolyl)butyl group, a 4-morpholylmethyl group, 2-(4-morpholyl)ethyl group, a 3-(4-morpholyl)propyl group, a 4-(4-morpholyl)butyl group, a 2-benzimidazolylmethyl group, 2-(2-benzimidazolyl)ethyl group, a 3-(2-benzimidazolyl)propyl group, a 4-(2-benzimidazolyl)butyl group.

More preferably, $R^{23}$ represents a carboxymethyl group, a 2-carboxyethyl group, a 3-carboxypropyl group, a N-hydroxymethylcarbamoylmethyl group, a N-ethylcarbamoylmethyl group, a 4-hydroxy-2-oxobutyl group, a 5-hydroxy-2-oxopentyl group, a 2-hydroxyethyl group, a 3-hydroxypropyl group, a 4-hydroxybutyl group, 2-N,N-dimethylaminoethyl group, 3-N,N-dimethylaminopropyl group, 4-N,N-dimethylaminobutyl group, 2-N,N-diisopropylaminoethyl group, 3-N,N-diisopropylaminopropyl group, 4-N,N-diisopropylaminobutyl group, 2-(1-piperidyl)ethyl group, 3-(1-piperidyl)propyl group, 4-(1-piperidyl)butyl group, a benzyl group, a 5-hydroxymethyl-3-pyridylmethyl group, a 5-acetoxymethyl-3-pyridylmethyl group, a 6-hydroxymethyl-2-pyridylmethyl group, a 6-acetoxymethyl-2-pyridylmethyl group, a 5-methyl-3-pyridylmethyl group, a 6-methyl-2-pyridylmethyl group, a 5-ethyl-3-pyridylmethyl group, a 6-ethyl-2-pyridylmethyloxy group, a 5-t-butyl-3-pyridylmethyl group, a 6-t-butyl-2-pyridylmethyloxy group, a 5-methoxycarbonyl-3-pyridylmethyl group, a 5-ethoxycarbonyl-3-pyridylmethyl group, a 2-pyridylmethyl group, a 3-pyridylmethyl group, a 4-pyridylmethyl group, a 2-pirazinylmethyl group, a 2-pyrimidinylmethyl group, a 4-pyrimidinylmethyl group or a 5-pyrimidinylmethyl group, a 1-benzotriazolylmethyl group, 2-(1-benzotriazolyl)ethyl group, a 3-(1-benzotriazolyl)propyl group, a 4-(1-benzotriazolyl)butyl group, a 4-morpholylmethyl group, 2-(4-morpholyl)ethyl group, a 3-(4-morpholyl)propyl group, a 4-(4-morpholyl)butyl group, a 2-benzimidazolylmethyl group, 2-(2-benzimidazolyl)ethyl group, a 3-(2-benzimidazolyl)propyl group, a 4-(2-benzimidazolyl)butyl group.

$R^{24}$ represents a hydrogen atom, or an alkyl group having 1–4 carbon atoms. Typical alkyl groups having 1–4 carbon atoms include methyl group, ethyl group, n-propyl group, i-propyl group, n-butyl group, t-butyl group and the like.

Throughout the specification, the number of carbon atoms indicated for the alkoxycarbonyl group, alkanoyloxy group or alkanoyl group refers to that of carbon atoms in the corresponding alkoxy, alkyl or alkyl group.

Aside from the protective groups specifically mentioned herein for the optionally protected substituents, the following may be mentioned: Protective groups for the hydroxyl group include alkyl-type protective groups such as a methyl group, a t-butyl group, a benzyl group, a trityl group and a methoxymethyl group, silyl-type protective groups such as a trimethylsilyl group and a t-butyldimethylsilyl group, acyl-type protective groups such as a formyl group, an acetyl group and a benzoyl group, carbonate-type protective groups such as a methoxycarbonyl group and a benzyloxycarbonyl group, and the like.

Protective groups for the carboxyl group include ester-type protective groups such as a methyl group, an ethyl group, a t-butyl group, a benzyl group and a methoxymethyl group, and the like.

Protective groups for the amino group include alkyl-type protective groups such as a benzyl group, a trityl group and a methoxymethyl group, acyl-type protective groups such as a formyl group, an acetyl group and a benzoyl group, carbamate-type protective groups such as a t-butoxycarbonyl group and a benzyloxycarbonyl group, and the like.

The compounds of the invention can form salts with inorganic or organic acids. Examples of such salts include inorganic acid salts such as hydrochlorides, sulfates and nitrates, and organic acid salts such as acetates, oxalates, maleates, tartrates, p-toluenesulfonates, methanesulfonates and citrates. Depending on the types of the substituents used, salts may be formed with inorganic or organic bases. Examples include salts with inorganic bases such as sodium carbonate and potassium carbonate, as well as salts with organic bases such as triethylamine, diethylamine and pyridine. These salts can be obtained in the usual manner, as by mixing an equivalent amount of a compound of the invention with a solution containing an acid or base of interest and obtaining the desired salt by filtration or evaporating the solvent.

The compounds of the invention or salts thereof can form solvates with water, ethanol, glycerol or the like, and these solvates are also included in the invention. It should be noted that the solvates of the invention are not limited thereto.

The compounds of the invention represented by the formula (I) can be produced by processes represented by the reaction schemes to be set forth below. The compounds shown in the Reaction Schemes 1 and 2 to be set forth below, the compounds represented by the formulae set forth herein, i.e. the formulae (I), (I)-a, (I)-b, (II), (VI), (XIV), (XV), (XVI), (XVII) and (XVIII), as well as the definitions of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{19}$, $R^{22}$, $R^{23}$, $R^{24}$, A, A', Q, X, $Y^1$–$Y^3$, $Z^1$–$Z^4$ are respectively the same as already discussed above. The compounds represented by the formulae set forth below, i.e. the formulae (III), (IV), (V), (VII), (VIII), (IX), (X), (XI), (XII) and (XIII), as well as the definitions of $R^{14}$, $R^{15}$, $R^{16}$, $R^{17}$, $R^{18}$, $R^{20}$, $R^{21}$ are discussed in these formulae. The condensed tetracyclic hetero-ring compounds represented by the formula (I) or salts thereof which are the compounds of the invention can be produced in accordance with Process I shown in FIG. 1 and Process I shown in FIG. 2 from compounds of the formula (III) which can easily be prepared from either documented or commercial compounds, or from salts of such compounds. The compounds of the formula (I) can also be produced in accordance with Process 2 shown in FIG. 1 and Process 1 shown in FIG. 2.

The processes for producing the compounds of the invention are described below in detail.

(Process 1)

A compound represented by the formula (III) or a salt thereof:

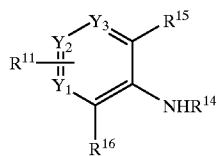

(III)

(where $R^{11}$ and $Y^1$–$Y^3$ have the same meanings as defined above; $R^{14}$ represents a hydrogen atom, a group: —$COR^{17}$ (where $R^{17}$ represents a hydrogen atom or a straight- or branched-chain alkyl group having 1–4 carbon atoms, which is more specifically exemplified by a methyl group, an ethyl group, a n-propyl group, a n-butyl group, a t-butyl group and so forth)) or a compound represented by the formula (IX) or a salt thereof:

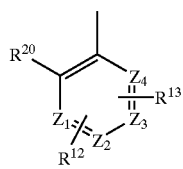

(IX)

where $R^{12}$, $R^{13}$ and $Z^1$–$Z^4$ have the same meanings as defined above; $R^{20}$ represents a hydrogen atom, a hydroxyl group, a group: —$NHR^{21}$ (where $R^{21}$ represents a hydrogen atom or a group: —$COR^{17}$), a thiol group, a carboxyl group, a halogen atom, a group: —$B(OH)_2$, a group: —$Sn(CH_3)_3$ or a group: —$Sn(Bu)_3$; $R^{15}$ represents a hydrogen atom, a cyano group or a group: —$COOR^{17}$; $R^{16}$ represents a hydrogen atom, a hydroxyl group, a group: —$NHR^{21}$, a thiol group, a carboxyl group, a halogen atom, a group: —$B(OH)_2$, a group: —$Sn(CH_3)_3$, a group: —$Sn(Bu)_3$ or the formula (IX)) is subjected to a ring closure reaction to yield a compound represented by the following formula (IV):

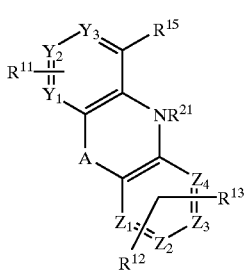

(IV)

(where $R^{11}$, $R^{12}$, $R^{13}$, $R^{15}$, $R^{21}$, $Y^1$–$Y^3$, $Z^1$–$Z^4$, A, as well as $R^6$, $R^7$, $R^8$, $R^9$ and $R^{10}$ defined in A have the same meanings as defined above). The condensed tricyclic hetero-ring compound represented by the formula (IV) is such that the method of constructing its backbone is known in the literature and, hence, it can be synthesized by application of that technique.

The following are non-limiting examples of the methods of synthesizing the compounds of the invention.

Consider first the case where A is a carbonyl group. The carboxyl group is converted to an acid halide by reaction with a thionyl halide reagent such as thionyl chloride or bromide in a halogenated hydrocarbon solvent typified by chloroform or methylene chloride or an aromatic hydrocarbon solvent such as benzene or toluene, preferably using methylene chloride as a solvent, at a temperature ranging from the one obtained by cooling with ice to the one where the reaction mixture is heated under reflux, preferably at room temperature, for a sufficient time to ensure adequate progress of the reaction, specifically for 15 min to 1 h; thereafter, the acid halide is subjected to Friedel-Crafts reaction in the presence of a Lewis acid such as aluminum chloride, tin chloride or zinc chloride without solvents or using nitrobenzene, carbon disulfide or a halogenated hydrocarbon solvent such as dichloromethane, carbon tetrachloride or 1,2-dichloroethane, preferably using carbon disulfide or methylene chloride, at a temperature ranging from −78° C. to the one where the reaction mixture is heated under reflux, preferably at room temperature, for a sufficient time to ensure adequate progress of the reaction, specifically for 15 min to 3 h; the acid halide may alternatively be reacted with trifluoroacetic anhydride in an aromatic hydrocarbon solvent such as benzene, toluene or xylene, preferably using toluene as a solvent, at a temperature ranging from room temperature to the one where the reaction mixture is heated under reflux, preferably at the temperature where heating under reflux is effected, for a sufficient time to ensure adequate progress of the reaction, specifically for 3 h to 10 h; alternatively, the acid halide is reacted with a phosphorylating reagent such as phosphorus pentoxide, polyphosphoric acid or a polyphosphate ester in the absence of solvents, optionally using an aromatic hydrocarbon solvent such as benzene or toluene, a halogenated hydrocarbon solvent such as chlorobenzene, chloroform or methylene chloride, preferably using chloroform as a solvent, at a temperature ranging from room temperature to the one where the reaction mixture is heated under reflux, preferably at the temperature where heating under reflux is effected, for a sufficient time to ensure adequate progress of the reaction, specifically for 1 h to 12 h, whereby the end product can be obtained.

In the case where A is an oxygen atom, a sulfur atom, a group: —$N(R^6)$— or the like, the starting material is subjected to Ullmann reaction in the presence of a copper powder, copper oxide or an iron powder, preferably in the presence of copper oxide, with an inorganic base such as potassium hydroxide or potassium carbonate or an alkali metal reagent such as a sodium alkoxide or sodium hydroxide, preferably using potassium carbonate, without solvents or using a suitable high-boiling point solvent such as N,N-dimethylformamide (DMF), dimethylsulfoxide (DMSO), 1,2-dimethoxyethane (DME), dibutylether, xylene, decalin or 1,3-dimethyl-2-imidazolidone (DMI), preferably without using any solvents, at a temperature of 100–200° C., preferably 180–190° C., for a sufficient time to ensure adequate progress of the reaction, specifically for 1 h to 12 h, whereby the end product can be obtained.

The end product can also be obtained by subjecting the corresponding alcohol, thiol, amine and halogen to the reaction for removing a hydrogen halide using a base.

It should be particularly mentioned that if A is a sulfur atom, direct ring closure can be accomplished using sulfur and iodine in dichlorbenzene.

Alternatively, a compound represented by the formula (X):

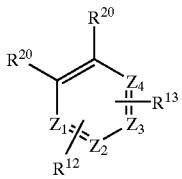

(X)

(where $R^{12}$, $R^{13}$, $R^{20}$ as well as $Z^1$–$Z^4$ have the same meanings as defined above) may be treated by the method described in Tetrahedron, Vol. 49, No. 1, pp. 49–64, 1993 or Tetrahedron Letters, Vol. 34, No. 13, pp. 2127–2130, 1993 or the like and the resulting intermediate is subjected to ring closure to derive the end compound. Known methods of synthesizing an α-, β-, γ- and δ-carboline backbones are other useful ways to synthesize the compound of the formula (IV). Depending on the positions of substituents, the end compound may be synthesized by other methods such as the conversion of substituents in commercial tricyclic compounds.

Then, a compound represented by the formula (IV) or a salt thereof:

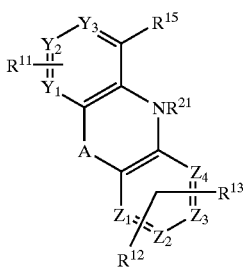

(IV)

is reacted with a compound represented by the following formula (XI):

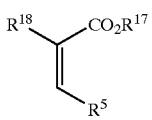

(XI)

(where $R^5$ and $R^{17}$ have the same meanings as defined above; $R^{18}$ represents a hydrogen atom or a methyl group) or the following formula (XII):

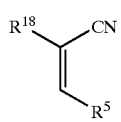

(XII)

(where $R^5$ and $R^{18}$ have the same meanings as defined above) or the following formula (XIII):

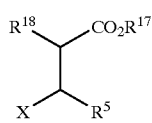

(XIII)

(where $R^5$, $R^{17}$, $R^{18}$ and X have the same meanings as defined above) and, if necessary, hydrolysis is performed to yield a compound represented by the following formula (V):

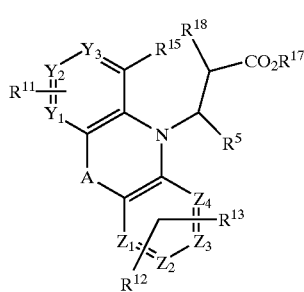

(V)

(where $R^5$, $R^{11}$, $R^{12}$, $R^{13}$, $R^{15}$, $R^{17}$, $R^{18}$, $Y^1$–$Y^3$, $Z^1$–$Z^4$, and A, as well as $R^6$, $R^7$, $R^8$, $R^9$ and $R^{10}$ defined in A have the same meanings as defined above).

Stated more specifically, the compound of the formula (IV) and the compound of the formula (XI) or (XII) are subjected to a Michael addition reaction in the presence or absence of copper acetate, N-benzyltrimethylammonium hydroxide (Triton B™) or the like, preferably in the presence of Triton B™, either without solvents or using water, a ketone-based solvent such as acetone or methyl ethyl ketone or an ether-based solvent such as tetrahydrofuran (THF), dioxane or 1,2-dimethoxyethane (DME), preferably using acetone as a solvent at a temperature ranging from the one obtained by cooling with ice to the one where the reaction mixture is heated under reflux, preferably at room temperature for a sufficient time to ensure adequate progress of the reaction, specifically for 15 min to 1 h and, if necessary, hydrolysis is performed in either an acidic aqueous solution such as dilute hydrochloric acid or sulfuric acid or a basic aqueous solution such as dilute aqueous sodium hydroxide or potassium hydroxide, preferably in dilute aqueous hydrochloric acid or sodium hydroxide at a temperature ranging from room temperature to the one where the reaction mixture is heated under reflux, preferably at room temperature for a sufficient time to ensure adequate progress of the reaction, specifically from 15 min to 12 h; alternatively, the compound of the formula (IV) and the compound of the formula (XIII) are subjected to an addition reaction in the presence of an inorganic base such as potassium carbonate, cesium carbonate, calcium carbonate or sodium hydride or an organic base such as triethylamine, pyridine or N,N-dialkylaniline, preferably in the presence of sodium hydride using a polar solvent such as acetonitrile or dimethylformamide (DMF), a halogenated hydrocarbon solvent typified by chloroform or methylene chloride or an ether-based solvent typified by ether or tetrahydrofuran (THF), preferably using DMF as a solvent at a temperature ranging from room temperature to the one where the reaction mixture is heated under reflux, preferably at the temperature where heating under reflux is effected, for a sufficient time to ensure adequate progress of the reaction, specifically for 15 min to 3 h and, if necessary, hydrolysis is performed in either an acidic aqueous solution such as dilute hydrochloric acid or sulfuric acid or a basic aqueous solution such as dilute aqueous sodium hydroxide or potassium hydroxide, preferably in a dilute aqueous hydrochloric acid or sodium hydroxide solution at a temperature ranging from room temperature to the one where the reaction mixture is heated under reflux, preferably at room temperature for a sufficient time to ensure adequate progress of the reaction, specifically for 15 min to 12 h. By either method, the compound of the formula (V) can be produced.

Subsequently, the compound of the formula (V) is converted to an acid halide by reaction in the presence of a thionyl halide reagent such as thionyl chloride or thionyl bromide using a halogenated hydrocarbon solvent typified by chloroform or methylene chloride or an aromatic hydrocarbon-based solvent such as benzene or toluene, preferably using methylene chloride as a solvent at a temperature ranging from the one obtained by cooling with ice to the one where the reaction mixture is heated under reflux, preferably at room temperature for a sufficient time to ensure adequate progress of the reaction, specifically for 15 min to 1 h; thereafter, the resulting acid halide is subjected to Friedel-Crafts reaction in the presence of a Lewis acid such as aluminum chloride, tin chloride or zinc chloride either without solvents or using nitrobenzene, carbon disulfide or a halogenated hydrocarbon-based solvent such as dichloromethane, carbon tetrachloride or 1,2-dichloroethane, preferably using carbon disulfide or methylene chloride as a solvent at a temperature ranging from −78° C. to the one where the reaction mixture is heated under reflux, preferably at room temperature for a sufficient time to ensure adequate progress of the reaction, specifically for 15 min to 3 h; alternatively, the acid halide is subjected to reaction in the presence of trifluoroacetic anhydride using an aromatic hydrocarbon-based solvent such as benzene, toluene or xylene, preferably using toluene as a solvent at a temperature ranging from room temperature to the one where the reaction mixture is heated under reflux, preferably at the temperature where heating under reflux is effected, for a sufficient time to ensure adequate progress of the reaction, specifically for 3 h to 10 h; alternatively, the acid halide is subjected to reaction in the presence of a phosphorylating agent such as phosphorus pentoxide, polyphosphoric acid or polyphosphate ester either without solvents or optionally using an aromatic hydrocarbon-based solvent such as benzene or toluene or a halogenated hydrocarbon-based solvent such as chlorobenzene, chloroform or methylene chloride, preferably using chloroform as a solvent at a temperature ranging from room temperature to the one where the reaction mixture is heated under reflux, preferably at the temperature where heating under reflux is effected, for a sufficient time to ensure adequate progress of the reaction, specifically for 1 h to 12 h; by either approach, a compound of the following formula (VI) can be produced:

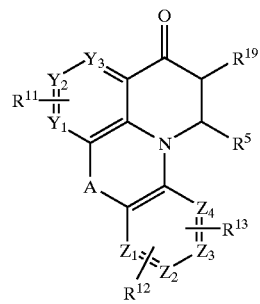

(VI)

The above-described reaction for ring closure (cyclization) has such selectivity that on account of the difference in electronic environment between the substituents $R^{11}$ and $R^{12}$ (or $R^{13}$) on the two benzene rings, cyclization favors the substituent which is relatively more effective electron donor. In order to achieve cyclization in the desired direction by taking advantage of this propensity, those substituents which can be changed or removed after cyclization can be used effectively.

If the selectivity in cyclization is so low as to produce a mixture, purification may optionally be performed by separation through recrystallization or column chromatography.

For achieving particularly selective ring closure, introducing a cyano group or a carboxyl group into $R^{15}$ may also be an effective method.

In one typical case, ring closure is performed with sodium hydride in an aromatic hydrocarbon solvent such as benzene, toluene or xylene, preferably using toluene as a solvent, at a temperature ranging from room temperature to the one where the reaction mixture is heated under reflux, preferably at the temperature where heating under reflux is effected, for a sufficient time to ensure adequate progress of the reaction, specifically for 3 h to 10 h; thereafter, the reaction is continued in an acidic aqueous solution such as concentrated hydrochloric acid, concentrated sulfuric acid or concentrated hydrobromic acid, preferably using 48% hydrobromic acid as a solvent, at a temperature ranging from room temperature to the one where the reaction mixture is heated under reflux, preferably at the temperature where heating under reflux is effected, for a sufficient time to ensure adequate progress of the reaction, specifically for 30 min to 3 h. Alternatively, the product of ring closure is converted to a sodium salt using sodium hydrogencarbonate, sodium carbonate or the like and, thereafter, the reaction is performed with sodium acetate in acetic anhydride at a temperature ranging from room temperature to the one where the reaction mixture is heated under reflux, preferably at 60–80° C., for a sufficient time to ensure adequate progress of the reaction, specifically for 1 h to 5 h, thereby yielding the desired compound of the formula (VI).

If $R^{11}$, $R^{12}$ and $R^{13}$ in the compound represented by the formula (VI) are groups included within the definitions of $R^1$, $R^2$ and $R^3$ in the compound represented by the formula (I), $R^{19}$ may be changed to $R^4$ in the manner to be described below, whereby the compound of the formula (VI) is directly derivated to the compound of the formula (I).

Subsequently, the compound represented by the formula (VI) is derivated to the compound represented by the formula (I) as set forth in FIG. 1 and the changes of substituents that are effected in the derivation are shown in FIG. 2 and described below in detail.

The compound of the formula (VI) is subjected to an aldol condensation reaction with aldehyde represented by the formula (XVII):

$$R^{22}\text{—CHO} \quad \text{(XVII)}$$

optionally in the presence of an inorganic base such as potassium hydroxide, sodium hydroxide or potassium carbonate or an organic base such as piperazine, piperidine, morpholine or n-BuLi, preferably in the presence of sodium hydroxide in an alcoholic solvent such as methanol or ethanol or an ether-based solvent such as ether, THF or dioxane, preferably using ethanol as a solvent at a temperature ranging from room temperature to the one where the reaction mixture is heated under reflux, preferably at room temperature for a sufficient time to ensure adequate progress of the reaction, specifically for 3 h to 12 h. The resulting compound is not isolated but dehydrated in situ to produce an enone which has the double bond subsequently isomerized in the ring, followed by oxidation in the manner described below. Alternatively, the reaction compound is isolated and subjected to oxidation reaction (dehydrogenation) in the presence of an oxidizing agent such as chloranil, dichlorodicyanobenzoquinone (DDQ) or 5% palladium on carbon, preferably DDQ, using an aromatic hydrocarbon-based nonpolar solvent such as benzene, toluene or xylene, an ether-based solvent such as THF, DME or dioxane or an alcoholic solvent such as ethylene glycol, preferably using dioxane as a solvent at a temperature ranging from room temperature to the one where the reaction mixture is heated under reflux, preferably at room temperature for a sufficient time to ensure adequate progress of the reaction, specifically from 1 h to 12 h; alternatively, the isolated reaction product is halogenated in the presence or absence of light, azobisisobutyronitrile (AIBN) or a peroxide such as benzoyl peroxide (BPO), preferably in their absence, using a suitable halogenating agent such as chlorine gas, bromine, copper bromide, N-bromosuccinimide (NBS), N-chlorosuccinimide (NCS), trihalogenomethanesulfonyl halogenide or trichlorobromomethane, preferably copper bromide, and also using a halogenated hydrocarbon solvent such as carbon tetrachloride, chloroform or methylene chloride, an aromatic hydrocarbon-based nonpolar solvent such as benzene or toluene, acetic acid or carbon disulfide solvent or an ester-based solvent such as ethyl acetate, preferably using chloroform or ethyl acetate as a solvent at a temperature ranging from room temperature to the one where the reaction mixture is heated under reflux, preferably at the temperature where heating under reflux is effected, for a sufficient time to ensure adequate progress of the reaction, specifically for 1 h to 12 h so as to yield a reactive derivative, which is thereafter subjected to the following replacement reaction with phenol, aniline, N-methylaniline, triazole, imidazole, morpholine or the like, optionally in the presence of an inorganic base such as potassium carbonate, cesium carbonate or calcium carbonate or an organic base such as triethylamine, pyridine or N,N-dialkylaniline, preferably cesium carbonate, and also optionally using a polar solvent such as acetonitrile or dimethylformamide (DMF), a halogenated hydrocarbon solvent typified by chloroform or methylene chloride or an ether-based solvent typified by ether or tetrahydrofuran (THF), preferably without using solvents, at a temperature ranging from room temperature to the one where the reaction mixture is heated under reflux, preferably at room temperature for a sufficient time to ensure adequate progress of the reaction, specifically for 30 min to 12 h; thereafter, the reaction product is oxidized (dehydrogenated) with an oxidizing agent such as chloranil or DDQ, preferably DDQ, using an aromatic hydrocarbon-based nonpolar solvent such as benzene, toluene or xylene or an ether-based solvent such as THF, DME or dioxane, preferably using dioxane as a solvent at a temperature ranging from room temperature to the one where the reaction mixture is heated under reflux, preferably at room temperature for a sufficient time to ensure adequate progress of the reaction, specifically for 1 h to 12 h; if desired, the replacement reaction may be bypassed and the reaction derivative obtained by halogenation is directly oxidized (dehydrogenated) under the conditions described above. In either way, the compound represented by the formula (XIV) can be produced.

Subsequently, the compound of the formula (XIV) may be subjected to substituent changes as required. If $R^{11}$, $R^{12}$ or $R^{13}$ is a protected hydroxyl group, it is deprotected by treatment in an aqueous solution of hydrochloric acid or hydrofluoric acid, preferably in an aqueous solution of hydrochloric acid, at a temperature ranging from the one obtained by cooling with ice to the one where the reaction mixture is heated under reflux, preferably at room temperature for a sufficient time to ensure adequate progress of the reaction, specifically for 15 min to 12 h; if $R^{11}$, $R^{12}$ or $R^{13}$ is a methoxy group, deprotection is performed by treatment in the presence of boron tribromide, aluminum chloride or hydrobromic acid, preferably in the presence of boron tribromide, using a halogenated hydrocarbon-based solvent such as methylene chloride or chloroform or acetic acid solvent, preferably using methylene chloride as a solvent at a temperature ranging from the one obtained by cooling with ice to the one where the reaction mixture is heated under reflux, preferably at room temperature for a sufficient time to ensure adequate progress of the reaction, specifically for 3 h to 24 h; if $R^{11}$, $R^{12}$ or $R^{13}$ is a benzyloxy group, deprotection is performed by treatment in the presence of palladium and sodium acetate in acetic acid solvent at a temperature ranging from room temperature to the one where the reaction mixture is heated under reflux, preferably at the temperature where heating under reflux is effected, for a sufficient time to ensure adequate progress of the reaction, specifically for 1 h to 12 h; by either method of deprotection, the compound (XIV) can be converted to a hydroxy form.

The compound represented by the formula (XIV) where $R^{11}$ is a hydroxyl group is reacted with a reactive halogen derivative represented by the following formula (XVIII):

$$R^{23}\text{—X} \quad \text{(XVIII)}$$

in the presence or absence of KI using an inorganic base such as potassium carbonate, cesium carbonate or calcium carbonate or an organic base such as triethylamine, pyridine or N,N-dialkylaniline, preferably using potassium carbonate, and also using a polar solvent such as acetonitrile, dimethylformamide (DMF) or dimethyl sulfoxide (DMSO) or an ether-based solvent such as THF, dioxane or DME, preferably using DMSO as a solvent at a temperature ranging from room temperature to 80° C., preferably at room temperature for a sufficient time to ensure adequate progress of the reaction, specifically for 1 h to 12 h so as to yield a compound represented by the formula (XV). The compound of (XIV) may be reacted with acetyl chloride or a bromoacetic acid ester if $R^{12}$ is a hydroxyl group, or with acetyl chloride if $R^{13}$ is a hydroxyl group.

Alternatively, the compound represented by the general formula (XIV) may have substituents changed to suitable ones to yield a compound represented by the general formula (XVI) and if $R^{11}$ in this compound is a straight-chain alkyl group having 1–6 carbon atoms which may be substituted by a 4-methoxyphenoxy group, specifically exemplified by a 2-(4-methoxyphenoxy)ethyloxy group, a 3-(4-methoxyphenoxy)propyloxy group or a 4-(4- methoxyphenoxy)butyloxy group, deprotection may be performed in the presence of cerium ammonium nitrate (CAN) in acetonitrile either alone or in admixture with water, preferably using the mixture of acetonitrile and water as a solvent system, at a temperature ranging from the one as obtained by cooling with ice to the one where the reaction mixture is heated under reflux, preferably at 0° C. for a sufficient time to ensure adequate progress of the reaction, specifically for 15 min to 4 h so as to derivate a compound represented by the general formula (I), specifically one in which $R^1$ is a 2-hydroxyethyloxy group, a 3-hydroxypropyloxy group, a 4-hydroxybutyloxy group or the like.

Other substituent changes that can be effected in the compound of the formula (XIV) are as follows: if $R^{11}$ or $R^{12}$ is a halogen atom, they may be changed to an amino group by reaction in the presence of copper or copper iodide in aqueous ammonia at a temperature of 150–200° C., preferably at a temperature of 180–190° C. for a sufficient time to ensure adequate progress of the reaction, specifically for 3 h to 12 h; alternatively $R^{11}$ or $R^{12}$ may be changed to a cyano group by reaction in the presence of copper cyanide in DMF at a temperature of 100–200° C., preferably at a temperature of 120–140° C. for a sufficient time to ensure adequate progress of the reaction, specifically for 1 h to 12 h.

If $R^{11}$ or $R^{12}$ is a nitro group, they may be changed to an amino group by reaction in the presence of copper using dilute sulfuric acid as a solvent at a temperature ranging from room temperature to the one where the reaction mixture is heated under reflux, preferably at 50° C. for a sufficient time to ensure adequate progress of the reaction, specifically for 30 min to 3 h.

If $R^{11}$ or $R^{12}$ is an amino group, they may be changed to a hydroxyl group by reaction in the presence of sodium nitrite using dilute sulfuric acid as a solvent at a temperature ranging from the one obtained by cooling with ice to the one where heating under reflux is effected, preferably at the temperature where heating under reflux is effected, for a sufficient time to ensure adequate progress of the reaction, specifically for 5 min to 3 h.

If $R^{11}$ or $R^{12}$ is an acetyl group, halogenation may be performed in the presence or absence of light, AIBN or a peroxide such as benzoyl peroxide (BPO), preferably in their absence using a suitable halogenating agent such as chlorine gas, bromine, copper bromide, N-bromosuccinimide (NBS), N-chlorosuccinimide (NCS), trihalogenomethanesulfonyl halogenide, trichlorobromomethane or phenyltrimethylammonium tribromide (PTT), preferably PTT, and also using a halogenated hydrocarbon solvent such as carbon tetrachloride, chloroform or methylene chloride, an aromatic hydrocarbon-based nonpolar solvent such as benzene or toluene, an ether-based solvent such as THF, dioxane or DME, acetic acid or carbon disulfide solvent, preferably using THF as a solvent at a temperature ranging from room temperature to the one where the reaction mixture is heated under reflux, preferably at the temperature where heating under reflux is effected, for a sufficient time to ensure adequate progress of the reaction, specifically for 1 h to 12 h; thereafter, the resulting halide is reacted with aniline, N-methylaniline, morpholine or the like using an inorganic base such as potassium carbonate, cesium carbonate, calcium carbonate or sodium hydrogencarbonate or an organic base such as triethylamine, pyridine or N,N-dialkylaniline, preferably using sodium hydrogencarbonate, and also using a polar solvent such as acetonitrile or dimethylformamide (DMF), a halogenated hydrocarbon solvent typified by chloroform or methylene chloride, an ether-based solvent typified by ether or THF or an alcoholic solvent such as methanol or ethanol, preferably using ethanol as a solvent at a temperature ranging from room temperature to the one where the reaction mixture is heated under reflux, preferably at the temperature where heating under reflux is effected, for a sufficient time to ensure adequate progress of the reaction, specifically for 1 h to 12 h.

If $R^{11}$ or $R^{12}$ is a halogen atom, dehalogenation may be performed in the presence of palladium using acetic acid as a solvent at a temperature ranging from room temperature to the one where the reaction mixture is heated under reflux, preferably at the temperature where heating under reflux is effected, for a sufficient time to ensure adequate progress of the reaction, specifically for 1 h to 12 h. The substituent changes described above may also be applied to $R^{13}$.

If necessary, further substituent changes may be performed so as to produce the compound of the formula (I) or a salt thereof:

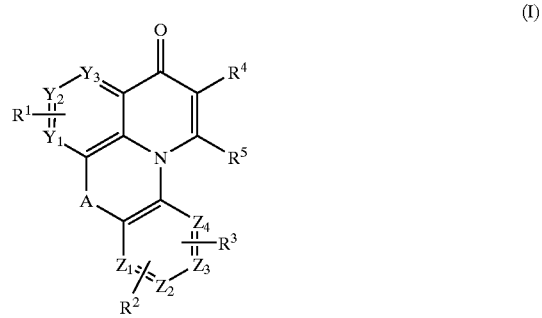

(I)

According to another method of producing the compound of the formula (I) or a salt thereof, $R^{11}$, $R^{12}$ and $R^{13}$ in the compound of the formula (XIV) may be changed to other substituents by the same reactions as described above to prepare the compound represented by the formula (XVI) which is then reacted with the reactive halogen derivative of the formula (XVIII) in the manner already described above.

(Process 2)

Depending on the positions, types and number of substituents and the selectivity in ring closure (cyclization), the compound of the formula (I) may occasionally be synthesized more efficiently by Process 2.

In the same manner as employed to achieve transformation from the formula (IV) to (V) in Process 1, a compound represented by the following formula (III) or a salt thereof:

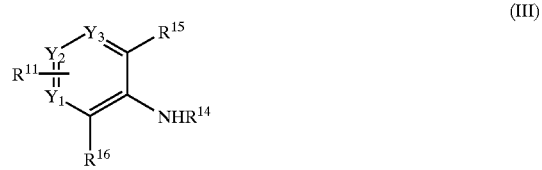

(III)

can be derivated to the following formula (VII):

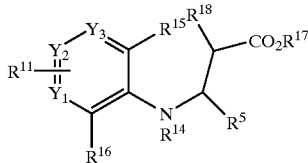
(VII)

(where $R^5$, $R^{11}$, $R^{14}$, $R^{15}$, $R^{16}$, $R^{17}$, $R^{18}$, and $Y^1$–$Y^3$ have the same meanings as defined above).

A compound of the formula (VII) may be subjected to the same procedure as employed to achieve ring-closing reaction from the formula (III) to (IV) in Process 1, thereby giving an intermediate of the formula (V). Subsequently, the same procedure as in Process 1 can be repeated to yield a compound of the formula (I) or a salt thereof.

Alternatively, the same procedure as employed to achieve transformation from the formula (V) to (VI) in Process 1 is repeated to perform cyclization, thereby yielding a compound of the following formula (VIII):

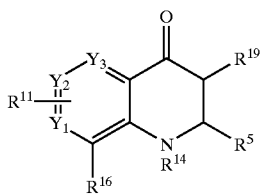
(VIII)

(where $R^5$, $R^{11}$, $R^{14}$, $R^{16}$, $R^{19}$ and $Y^1$–$Y^3$ have the same meanings as defined above).

This compound and a compound represented by the following formula (X)

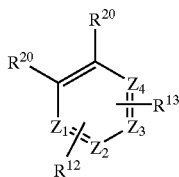
(X)

are subjected as required to Ullmann reaction in the presence of a copper powder, copper oxide or an iron powder, preferably in the presence of copper oxide, using an inorganic base such as potassium hydroxide or potassium carbonate or an alkali metal reagent such as sodium alkoxide or sodium hydroxide, preferably using potassium carbonate either without solvents or using a suitable high-boiling point solvent such as DMF, DMSO, DME, dibutyl ether, xylene, decalin or 1,3-dimethyl-2-imidazolidone (DMI), preferably in the absence of solvents, at 100–200° C., preferably at 180–190° C. for a sufficient time to ensure adequate progress of the reaction, specifically for 1 h to 12 h, or to a general substitution reaction of $R^{16}$ thereby introducing a desired substituent; thereafter, the same procedure as employed to achieve transformation from the formula (III) to (IV) as described in Process 1 of the Reaction Scheme 1 is repeated to derivate a compound of the formula (VI):

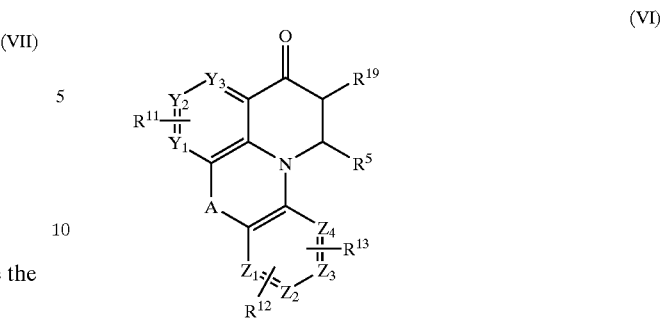
(VI)

Subsequently, the same procedure as in Process 1 can be used to yield a compound of the formula (I) or a salt thereof.

If the individual compounds synthesized by the processes described above contain reactive substituents such as a hydroxyl group, an amino group, a carboxyl group and a thiol group, they may be protected appropriately in the respective steps of reaction and later removed at appropriate stages. The methods of introducing and removing such protective groups may appropriately be selected in accordance with the types of the groups to be protected and the protective groups to be used and suitable methods may be found in the Overview in "Protective Groups in Organic Synthesis", 2nd Ed. 1991.

It should also be noted that the compounds prepared in the respective steps of each production process may have the functional groups optionally oxidized or reduced in the usual manner.

Experiments

On the pages that follow, the pharmacological action, toxicity and other features of representative compounds of the invention are described but it should be understood that the present invention will in no way be limited by the following description.

(Experiment 1)
[PDE Inhibiting Activity]
Method 1

On the basis of the method of Lugnier et al. (Biochem. Pharmacol., 35, 1743–1751, 1986), PDE was purified from the aorta in a dog. The canine aorta was minced and homogenized with a Waring Blender and a glass homogenizer in six volumes of a Tris-HCl buffer solution (pH 7.5, 20 mM) containing 2 mM magnesium acetate, 5 mM ethylenediaminetetraacetic acid (EDTA), 100 μg/mL of phenylmethylsulforyl fluoride and 15 mM 2-mercaptoethanol (2-ME), and centrifuged at 1200× g for 30 min. The supernatant was separated and salted out with ammonium sulfate which was added to 45% saturation. The resulting precipitated fraction was resuspended in a Tris-HCl buffer solution (pH 7.5, 20 mM) containing 2 mM magnesium acetate and 1 mM 2-ME, dialyzed overnight and applied to a DEAE-trisacryl column (DEAE TRISACRYL M:IBF). By elution with a sodium chloride gradient (0–0.4 M), PDE types V and III were separated from the other isozymes. The supernatant fraction of 45% saturated ammonium sulfate was further mixed with ammonium sulfate to 65% saturation and salted out. The resulting precipitated fraction was similarly applied to the DEAE-trisacryl column and eluted by a sodium chloride gradient (0–0.4 M) so as to separate PDE type I.
Method 2

PDE type VI was purified from bovine eyeballs which was purchased from a butchery. Isolation of the retina, rod outer segments, disk membranes and PDE was done on ice in a darkroom illuminated by dim red light as follows.

Muscles and connecting tissues were removed from eyeballs and the part containing the lens was cut off with a razor and surgical scissors. Remaining eye cups were incised in a radial manner and turned inside out, and the exposed surface was weakly rubbed with tweezers and the stripped retina was collected in a centrifugation tube. The collected retina was suspended in a phosphate buffer solution, pH 6.1 (1/15 M) and gently shaken for 15 sec and centrifuged at 7000× g for 10 min. After the supernatant was separated, the precipitate was resuspended in a phosphate buffer solution, pH 4.7 (1/15 M) and gently shaken for 15 sec and centrifuged at 7000× g for 10 min. The precipitate was resuspended in 43% sucrose-phosphate buffer solution (pH 6.1, 1/15 M) containing 5 mM $MgSO_4$ and mixed in an upside-down manner for about 2 min so that rod outer segments were released. The suspension was centrifuged at 25000× g for 20 min and the red suspension of rod outer segments floating on the buffer solution was collected. The suspension was diluted by the addition of 100 mM Tris-HCl buffer (pH 7.5) containing 5 mM $MgSO_4$. Outer segment plasma membranes were disrupted and disks were released by three cycles of freezing and thawing and the suspension was centrifuged at 27000× g for 20 min and disks were precipitated. The precipitate was resuspended in 100 mM Tris-HCl buffer (pH 7.5) containing 5 mM $MgSO_4$ and centrifuged at 27000× g for 20 min so that disks were washed. After the precipitated fraction was resuspended in 10 mM Tris-HCl buffer (pH 7.5) containing 3.5 mM ethylenediaminetetraacetic acid (EDTA) it was mixed and left out, and PDE bound to disk membranes was released by decreasing the concentration of free $Mg^{2+}$. The suspension was centrifuged at 27000× g for 20 min and the supernatant was obtained as the crude fraction of PDE type VI.

The PDE solution was stored after addition of 0.1% bovine serum albumin and activated by trypsin before the measurement of activity. The crude fraction was diluted to one tenth and mixed with the equal volume of 0.1 mg/ml trypsin solution (20 mM Tris-HCl buffer containing 2 mM $MgCl_2$, pH 7.5) and activation was achieved at 4° C. for 30 min. The reaction was stopped by mixing this solution with the equal volume of 0.52 mg/ml soy bean trypsin inhibitor solution (20 mM Tris-HCl buffer containing 0.1% bovine serum albumin, pH 7.5).

Measurement of PDE Inhibiting Activity

The thus obtained PDE types V, III, I and VI were measured for their activity in accordance with the method of Thompson et al. (Adv. Cyclic Nucleotide Res., 10, 69–72, 1979) and the method of Wells et al. (Bioche. Biophys. Acta, 384, 430–443, 1975).

Specifically, a purified PDE(types V, III and I) or activated PDE (Type VI) sample was added to 50 mM Tris-HCl buffer solution (pH 7.5) containing 1 µM of substrate cGMP or cAMP (containing tritium-labelled cGMP or cAMP), 1 mM EGTA and 2 mM magnesium acetate. For PDE activity measurement, enzymatically produced 5' GMP or 5' AMP was further hydrolyzed into guanosine or adenosine with snake venom and separated from the substrate by means of an ion-exchange resin (Dowex 1-X2), followed by measuring with a scintillation counter. The activity of each test compound was determined as a percentage of the PDE activity measured when it was added as a dimethyl sulfoxide solution (DMSO) and its $IC_{50}$ (50% inhibition concentration) was calculated by the probit method. The final concentration of DMSO was adjusted to be no more than 2% in consideration of the effect on PDE activity. Results were shown in Table 1.

TABLE 1

PDE Inhibiting Activity

Inhibition Activity IC50 (µM)

| Ex. No. | Type V | Type III | Type I | Type VI |
|---|---|---|---|---|
| 34 | 0.0025 | >30 | >30 | 0.025 |
| 35 | 0.0018 | >30 | >30 | 0.015 |
| 39 | 0.0038 | >30 | >30 | 0.061 |
| 43 | 0.0028 | 23 | NT | 0.036 |
| 44 | 0.0041 | 7.7 | NT | 0.038 |
| 47 | 0.0045 | 14 | >30 | 0.071 |
| 50 | 0.011 | 4.3 | >30 | 0.25 |
| 51 | 0.011 | NT | NT | 0.18 |
| Sildenafil | 0.0018 | 13 | 0.46 | 0.0063 |

NT: not tested

All compounds of the invention had a marked PDE type V inhibitory action and a high selectivity in enzyme inhibition. Furthermore, the inhibitory action of the compounds of the invention against PDE type VI was shown at higher concentrations than that against PDE type V and difference in the potency of these actions was shown.

(Experiment 2)
[Absorption upon Intranasal Administration to Rats]

Eight-week-old male Wistar rats were anesthetized with intraperitoneal injection of urethane at 1 g/kg. The cervical portion was incised so that the trachea was exposed, and a polyethylene tube (SP120, Natsume) was inserted into the trachea. Then, a part of the esophagus was incised and a polyethylene tube with the same diameter was inserted into postnasal cavity, the tip was closed with absorbent cotton and glue. Leak of the drug solution from the nasoplatine was avoided by closing it with synthetic glue. Drugs were dissolved in 0.1% tartaric acid solution and administered through the nostrils at 500 µl/kg with micropipette and the nostrils were rapidly closed with glue. For the control, drugs were intravenously administered to rats. Constant volume of blood was intermittently collected from the tail vein into heparinized capillary after administration, and plasma was separated by centrifugation. Constant volume of plasma was extracted with t-butyl-methyl-ether three times and the organic phase was evaporated and dissolved in the HPLC initial phase. Constant volume of the organic phase was applied to the HPLC system equipped with an ultraviolet detector, and plasma drug concentration was determined with the reverse phase column. The time to reach the maximal concentration ($T_{max}$), the mean residence time (MRT) and the mean absorption time (MAT) were calculated from measured values. Results were shown in Table 2.

TABLE 2

Absorption by Intranasal Administration

| Ex. No. | Dose (mg/kg) | Tmax (hr) | MRT (hr) | MAT (hr) |
|---|---|---|---|---|
| Ex. 81 | 0.3 | 0.2 ~ 0.5 | 0.8 ~ 1 | 0.2 ~ 0.3 |

$T_{max}$ and MRT of a compound of example 81 were shortened in comparison with oral administration. Namely, rapid and effective absorption was shown by intranasal administration and there was no first-pass effect and proper duration was observed.

Moreover, a compound of example 39 showed no irritativeness from the observation at drug administration and no abnormalities in nasal mucosa were observed during the experimental period.

(Experiment 3)
[Toxicity Test]

Selected compounds of the invention were tested for their toxicity. Four weeks old male Wistar rats were perorally administered the compounds of Examples 4, 10, 14, 18 and 29 of the invention for 4 days at a daily dose of 100 mg/kg. After the end of administration, none of the animals were found to be dead until the next day and there was nothing abnormal in their body weights and general symptoms.

The experiments described above demonstrated that the compounds of the invention had a marked PDE type V inhibitory action and a high selectivity in enzyme inhibition and the inhibitory action of the compounds of the invention against PDE type VI was shown at higher concentrations than that against PDE type V and there is difference in the potency of these actions. Furthermore, the compounds of the invention have an enhancing action to smooth muscle relaxation of corpus cavernosum in vitro, and intravenous injection of the compounds of the invention enhance the elevation in intracavernous pressure induced by intracavernous injection of sodium nitroprusside in vivo.

Furthermore, the compounds of the invention were absorbed not only by the route of oral administration, but intranasal administration, and the rapid absorption and the proper duration were shown.

On the other hand, the compounds of the invention were shown to be low in toxicity since nothing abnormal was found in the result of the toxicity test. Moreover, the compounds of the invention have less effects on hemodynamics such as vertebral blood flow and common carotid blood flow and less binding affinity to adenosine receptors.

Thus, the condensed tetracyclic hetero-ring compounds of the invention had a marked PDE type V inhibitory action and an extremely high selectivity in enzyme inhibition, which shows the compounds contribute to increasing the cGMP level in a body. Therefore, they are effective in treating or preventing diseases against which the PDE type V inhibitory action is effective, such as pulmonary hypertension, ischemic heart diseases, erectile dysfunction or female sexual dysfunction. They are also useful as circulation regulators during or after surgical operation.

The compounds represented by the formula (I) of the invention have potent and highly selective action in the enzyme inhibition of PDE type V and weak action in lowering blood pressure, and have less side effects such as a headache. In addition, since the inhibitory action of the compounds of the invention against PDE type VI was shown at higher concentrations than that against PDE type V, the compounds of the invention have less side effects on the retina and cause less defects in vision such as changes in blue/green color and increased sensitivity to light.

"Pulmonary hypertension" refers to various diseases manifesting hypertension in the pulmonary artery, which include chronic bronchitis, peripheral lesions in the airway, pulmonary pneumatosis, bronchiectasis, sarcoidosis, sequelae of pulmonary tuberculosis, diffuse interstitial pneumonia, diffuse bronchiolitis, asthma, fibroid lung, collagenosis, pulmonary thromboembolism, pulmonary venous obstruction, pulmonary arteritis and primary pulmonary hypertension; also included in the category of pulmonary hypertension are diseases such as corpulmonale in a developed phase of pulmonary hypertension.

Patients manifesting pulmonary hypertension suffer from disorders in pulmonary circulation due to the obstruction of pulmonary vessels and experience cyanosis and dyspnea. They often complain of palpitation and pectoralgia, as well as coughing. The pharmaceutical compositions of the invention are effective against these symptoms.

The term "ischemic heart diseases" as used herein is a generic name for the diseases that occur as the result of disorders in coronary circulation due to various etiological causes and includes angina of effort, angina pectoris decubitus, unstable angina, variant angina pectoris, acute heart failure, chronic heart failure, myocardial infarction, cardiac edema and arrhythmia.

Patients with ischemic cardiac diseases suffer from transient or persisting anginal pains such as pectoralgia and pressure felt in the chest, which are accompanied by fatigue, dizziness, panting, vomiting and consciousness derangement. Heart failure involves dyspnea and cyanosis and, due to the marked drop in blood pressure, shocks also occur as exemplified by bradycardia, cold sweat, pallor of the face, etc. The pharmaceutical compositions of the invention are effective against these symptoms.

The compounds of the invention increase the cGMP level markedly and are also applicable to arteriosclerosis, post-PTCA restenosis and thrombosis (caused by, for example, injury of vascular walls, arteriosclerosis, angitis and platelet aggregation). Since all of these diseases of the coronary artery are of particular interest as etiological factors in ischemic heart diseases, the pharmaceutical compositions of the invention hold promise as highly effective agents for preventing and/or treating ischemic heart diseases.

The proliferation of vascular smooth muscle cells which is an etiological factor to the above-mentioned arteriosclerotic diseases in the coronary artery is believed to be closely involved in post-PTCA coronary restenosis and the arteriosclerotic thickening of blood vessels at other sites; hence, increased cGMP levels will contribute to retarding the proliferation of vascular smooth muscle cells in arteriosclerosis and post-PTCA restenosis, potentially preventing these diseases. Several of the diseases that eventually manifest pulmonary hypertension do not actually have the complication of pulmonary hypertension in the early period of their onset as in the case of pulmonary pneumatosis and bronchitis; however, it is generally held that as hypoventilation is prolonged, the thickening of pulmonary blood vessels, the growth of arteriolar smooth muscle and other factors cause disorders in pulmonary circulation, eventually developing to irreversible pulmonary hypertension. Hence, if the pharmaceutical compositions of the invention are administered at the initial stage of those diseases in a preventive manner in order to retard the growth of vascular smooth muscle cells, it is possible to retard the subsequent onset of pulmonary hypertension.

Aside from those listed above, the "diseases against which the cGMP-PDE inhibitory action is effective" include the following against which increased cGMP levels are believed to be effective: asthma, chronic obstructive pulmonary diseases (e.g. bronchitis and pulmonary pneumatosis), glomerular diseases including glomerular nephritis and diabetic nephropathy, renal failure, nephritic edema, diseases in urinary organs and genital system (e.g. prostatomegaly, impotence and incontinence), female sexual dysfunction, peripheral circulatory disorders, peripheral vascular diseases, cerebral circulatory disorders (e.g. cerebral infarction), brain dysfunction, dementia, allergic diseases (e.g. atopic dermatitis and allergic rhinitis) and hypertension. The pharmaceutical compositions of the invention are also applicable to these diseases, among which asthma, chronic obstructive pulmonary diseases (e.g. bronchitis and pulmonary pneumatosis), glomerular diseases including glomerular nephritis and diabetic nephropathy, renal failure, nephritic edema, diseases in urinary organs and genital system (e.g. prostatomegaly, impotence and incontinence) and female sexual dysfunction are worth particular mention.

Impotence may be defined as the lack of the ability to perform sexual intercourse on the part of a male sex. More specifically, impotence or erectile dysfunction may be defined as the condition where males cannot achieve or maintain an erection firm and long enough to accomplish intercourse. The mechanism of erection is generally held to involve the NO-cGMP system and since NO which is the entity of a vascular endothelial cell derived relaxing factor is known to manifest its vasodilating action as mediated by cGMP, erectile dysfunction can be ameliorated by suppressing the cGMP decomposing system so that the cGMP level is maintained.

Female sexual dysfunction means impaired sexual functions including orgasmic dysfunction associated with disorders in the clitoris. Female sexual dysfunction can be ameliorated by suppressing the cGMP decomposing system so that the cGMP level is maintained.

"Renal failure" refers to those pathologic and clinical symptoms which are manifested by defective function of the kidneys, i.e., the decrease in glomerular filtration rate (GFR) due to various etiological factors. In chronic renal failure, some glomeruli give a sclerotic image but the progress of the sclerosis to less affected glomeruli would bring the renal failure to developed phase. The dysfunction of glomeruli is etiologically variable in many ways but if the cGMP level is increased, the kinetics of renal blood circulation is improved to elevate the GFR and, as a result, the in vivo accumulation of various excreted substances is effectively retarded to alleviate uremia. In addition, polyuria and nocturia due to disordered concentrating ability can be alleviated. If inappropriate Na and water loading accompanies renal failure, reduced GFR prevents sufficient compensation, causing edema, pulmonary edema, congestive heart failure, hypertension, etc. These symptoms can also be alleviated. Increased cGMP levels retard the increase of mesangial cells and matrix and, hence, the sclerosis of glomeruli can effectively be retarded to slow down the progress of glomerular diseases and renal failure. Briefly, by increasing the cGMP level, the process of development from renal failure to an end-stage kidney which has heretofore been considered to be practically impossible to check by drug administration can be retarded to eventually circumvent the necessity of performing renal dialysis.

The pharmaceuticals of the invention are administered in the form of pharmaceutical compositions.

The pharmaceutical compositions of the invention may contain at least one of the compounds of the invention which are represented by the formula (I) and they are prepared by being combined with pharmaceutically acceptable vehicles. More specifically, excipients (e.g., lactose, sucrose, mannitol, crystalline cellulose and silicic acid), binders [e.g., crystalline cellulose, sugars (e.g., mannitol and sucrose, sorbitol, erythritol, xylitol), dextrin, hydroxypropyl cellulose (HPC), hydroxymethyl cellulose (HPMC), polyvinyl pyrrolidone (PVP) and macrogol], lubricants (e.g., magnesium stearate, calcium stearate and talc), coloring agents, flavoring agents, disintegrants (e.g., corn starch and carboxymethyl cellulose), antiseptics (benzalkonium chloride, p-hydroxybenzoate ester), isotonic vehicles(e.g., glycerol, sodium chloride, potassium chloride, mannitol, glucose), pH adjusting agents (sodium hydroxide, potassium hydroxide, sodium carbonate, hydrochloric acid, sulfuric acid, buffers such as phosphate buffer), stabilizers (e.g., sugar, sugar alcohol, xanthan gum), dispersants, antioxidants [e.g., ascorbic acid, butyl hydroxyanisole (BHA), propyl gallate and dl-α-tocopherol], buffering agents, preservatives (e.g., parabens, benzyl alcohol and benzalkonium chloride), fragrances (e.g., vanillin, 1-menthol and rose oil), solubilizers (e.g., polyoxyethylene cured castor oil, polysorbate 80, polyethylene glycol, phospholipid cholesterol and triethanolamine), absorption accelerators (e.g., sodium glycolate, sodium edetate, sodium caprate, acylcarnitines, limonene), suspending or emulsifying agents, and other common suitable additives or solvents may be combined appropriately with the compounds of the invention into various dosage forms.

Exemplary dosage forms include tablets, capsules, granules, powders, suppositories, vaginal suppositories, sublingual preparation, buccal preparations, disintegrators in oral cavity, chewable tablets, troche, jelly preraretions, paste preparations, oral mucosal patch preparations, syrups (e.g. oral liquids and emulsions), inhalants, external preparations (ointments, creams, jelly, gels etc.), paints(tapes, patchs, cataplasms), pellets, injections, intranasal preparations (liquids, powder), intraurethral preparations etc.; these can be administered to the patient either orally or parenterally (such as by intravenous, intra-arterial, subcutaneous, intramuscular, intrarectal, intravaginal, or intranasal administration, intraurethral administration, or by transcutaneous or transmucomembranous(oral mucomembrane, penile mucomembrane etc.)). Preferably, oral, intranasal, intraurethral, transcutaneous or transmucomembranous preparations can be administered to the patient. More preferably, oral, intranasal or intraurethral preparations are used.

The compositions of the invention may be administered by two methods, one is by applying them as required at one draft or dose and the other is by administering them continuously for a certain period on a-given-dose-a-day basis. In the former case, the compositions are preferably administered into the nasal cavity or oral cavity(oral mucomembrane), and anticipated to exhibit the intended effect in about a few to 30 minutes after the administration. If the compounds are to be administered continuously, the preferred route of administration is peroral or percutaneous. In the case of percutaneous administration, a slow and sustained drug absorption can be achieved to sustain a preparedness for erection in which natural erection is possible upon sexual stimulation.

These dosage forms are typically administered in daily doses of 0.1 mg–2.5 g, preferably 0.5 mg–1.0 g, more preferably 1 mg–500 mg, per adult although that may be appropiately increased or decreased depending upon symptom or the route of administration.

It is also possible that daily dose is administered at a time or on a divided in 2–6 portions by oral or parenteral administration; alternatively, continuous administration may be performed as by intravenous drip infusion.

In the case of intranasal administration, the composition is sucked by, dropped on or applied to nasal cavity using an appropiate administrating device such as a quantitative sprayer (e.g., spray pump, an aerosol applicator, a nebulizer or an atomizer) or a dripping vessel (e.g., dropper or a nasal dropping pipette) to adhere to nasal mucous membrane whereby the effective component is absorbed through nasal mucousmembrane. In the case of Liquids preparation for intranasal administration, it may be administered one to six times a day, each into one or both nostrils, in a dose of 20–300 μl, preferably 50–200 μl, more preferably 100–150 μl, per nostril. To apply powders for intranasal administration, a capsule filled with the powder is set in a needle-equipped sprayer and needles are pierced through the capsule wall to make a tiny hole in both the upper and lower parts of the capsule and air is subsequently forced into the capsule by a suitable means such as a rubber bulb so as to eject the powder into nostrils. Using this method, the drug can be administered one to six times a day, each into one or both nostrils, in a dose of 1–20 mg, preferably 5–10 mg, per nostril. Gels and other dosage forms for intranasal administration that have comparatively high viscosity may be directly coated from a tube onto the nasal mucosa in the nasal cavity or coated with a definite dosage into an administrating device onto the mucosa.

If desired, sterilizing disinfectants such as benzalkonium chloride may be added to the compositions for intranasal administration.

In the case of patients suffering from nasal stuffiness or inflammations in the nasal mucosa, an appropriate drug absorption is not attainable even if a sufficient dose is applied. To deal with this situation, the compounds of the invention may be administered either in combination or as mixtures with topical vasoconstrictors such as epinephrine, naphazoline nitrate, tramazoline hydrochloride and tetrazoline, antiallergics such as sodium cromoglicate and ketotifen fumarate, inhibitors of pituria secretion such as flutropium bromide and ipratropium bromide, or steroids such as prednisolone, flunisolide, fluticasone propionate, beclomethasone propionate, dexamethasone m-sulfobenzoate sodium and dexamethasone phosphate sodium.

The intranasal composition of the invention shows prompt absorption and suitable acting time for its pharmaceutical effect, and is not affected by first-pass effect in digestive system and liver. Further, it shows no irritation, congestion and engorgement to nasal mucous membrane and, in addition, it shows no side effect in digestive organs. In the case of using for preventing or treating erectile dysfunction, it shows no side effect such as priapism, and unlike the injection to corpus cavernosum, the composition of the present invention can be administered by himself/herself whereby burden of patients and doctors is little and there is no side effect such as damage or corporal fibrosis of penis. Unlike the oral administration, affection of drug absorption by food which has been known in sildenafil is not observed. Further, it is difficult to administer too much amount at a time and, accordingly, the use of too much amount by patients with an expectation of prompt effect and far better effect can be prevented.

For percutaneous administration, the compounds of the invention may be applied in various dosage forms including ointments, creams, gels or paints such as tapes, patches and cataplasms. If desired, drug delivery systems employing absorption accelerators or iontophoresis may also be used. Paints are preferred since one replacement in one to several days is sufficient to achieve sustained drug efficacy.

A composition for percutaneous administration in accordance with the invention is able to afford a gradual and long-acting absorption. In the case of using for preventing or treating erectile dysfunction, it is able to keep a state of preparatory erection whereby a natural erection is possible by sexual stimulation. Also it is not affected by first-pass effect in digestive system and liver, and there is no disadvantage of side effect in digestive organs and side effect such as priapism. Unlike the injection to corpus cavernosum, the composition of the present invention can be administered by himself/herself whereby burden of patients and doctors is little and there is no side effect such as damage or corporal fibrosis of penis. Unlike the oral administration, affection of drug absorption by food which has been known in sildenafil is not observed. Further, the administering route is a simple as compared with other preparations.

In the case of the administration into oral cavity in the transmucomenbranous administration, the compounds of the invention may be applied in various dosage forms including sublingal preparations, buccal preparations, disintegrators in oral cavity, chewable tablets, troches, jelly preraretions, paste preparations, oral mucosal patch. Preferably, sublingal preparations or disintegrators in oral cavity are used, and more preferably, disintegrators in oral cavity are used. They can be used by being combined with absorption accelerators, pH adjusting agents, fragrances, flavoring agents or disintegrants.

For transmucomenbranous administration, the drug may be applied to the inner surfaces of condoms or the like so that it is absorbed into the penis.

The transmucomenbranous composition of the invention shows prompt absorption and suitable acting time for its pharmaceutical effect, and is not affected by first-pass effect in digestive system and liver and exhibits high bioavailability. In the case of using for preventing or treating erectile dysfunction, there is no disadvantage of side effect in digestive organs and side effect such as prolonged erection, and unlike the injection to corpus cavernosum, the composition of the present invention can be administered by himself/herself whereby burden of patients and doctors is little and there is no side effect such as damage or corporal fibrosis of penis. Further it can be dosed with sublingual preparations or disintegrators in oral cavity without a water or with a little water with a simple methods, and is suitable for a patient for limited drinking water. Further it is expected that the composition shows a good dissolubility or absorbency and have a short-action. Further it can be easily dosed for a patient with a lower swallowing function.

In the case of intraurethral administration, the compounds of the invention may be applied in various dosage forms including intraurethral suppositories, intraurethral creams, intraurethral ointments, intraurethral pastes, intraurethral gels, intraurethral suspensions, intraurethral dispersants or intraurethral pellets etc. The intraurethral compositions of the invention may contain at least one of the compounds of the invention which are represented by the formula (I) and they are prepared by being combined with pharmaceutically acceptable vehicles. More specifically, bases as fats and fatty oils(hardfats, macrogol(polyethylenegrycol)), emulsifying agents, thickeners, adhesive agents, dispersants, stabilizers (e.g., sugar, sugar alcohol, xanthan gum), absorption accelerators (e.g., sodium glycolate, sodium edetate, sodium caprate, acylcarnitines, limonene), solubilizers (e.g., polyoxyethylene cured castor oil, polysorbate 80, polyethylene glycol, phospholipid cholesterol and triethanolamine), or suspending agents etc, and other common suitable additives or solvents may be combined appropriately with the compounds of the invention into intraurehtral dosage forms.

In the case of intraurethral suppositories, they take the form of a long and narrow pencil, and have a suitable shape for inserting into urethra with a little fine on one end, are used with a length of 7–14 cm for men or 5–7 cm for women. Further, a pharmaceutical composition of solid or semisolid was formed with a suitable volume for intraurethreal administration, and then may be formed with a length of 1 cm and below.

The pharmaceutical composition for intraurethral administration of the present invention is administered with a definite dosage into urethra by directly or using a flexible tube, a squeeze bottle, or a device which is possible to insert into urethra when necessary.

These dosage forms are typically administered 1 mg–1000 mg, preferably 5 mg–500 mg, more preferably 10 mg–300 mg, per one dosage, may be appropriately increased or decreased depending upon a patient. It is also possible that one dosage is administered on a divided in 2–6 portions.

The volume per one dosage of the pharmaceutical composition for intraurethral administration of the present invention is administered with below 6 ml per one dosage, preferably 1–3 ml, and it is selected a suitable volume for a patient at a personal urethal permissive volume.

In the case of using for preventing or treating erectile dysfunction, a composition for intraurethral administration in accordance with the invention is able to afford a prompt, gradual and long-acting absorption and suitable acting time for its pharmaceutical effect, and it is able to keep a state of preparatory erection whereby a natural erection is possible by sexual stimulation, and will not cause a priapism. Unlike the injection to corpus cavernosum or the usual intrauresal preparations, there is no side effect such as pain or corporal fibrosis of penis, and the composition of the present invention can be administered by himself/herself whereby burden of patients and doctors is little. Also it is not affected by first-pass effect by digestive system and liver, and there is no disadvantage of side effect in digestive organs. Unlike the oral administration, affection of drug absorption by food which has been known in sildenafil is not observed. Further, there is no systemic action of such as hypotension, and the administering route is a simple as compared with other preparations.

Further, it may be a dosage form uniformly coated a pharmaceutical composition for intraurethal administration on the solid (base) which is dissolved at body temperature or the suitable insert. The insert itself may be made from any pharmacologically acceptable material and although it may be rigid, it is preferred that the device be relatively soft and flexible for purposes of comfort, merely having sufficient rigidity to facilitate insertion. More specifically, it is suitable for the insert, for example, various pharmaceutically acceptable natural or synthetic rubber or polymeric materials such as natural rubber, silicone rubber, ethylene vinyl acetate (EVA) copolymer, polyethylene, polypropylene, polycarbonate, polyester, polyurethane, polyisobutylene polymers, and polyoxyethylene polymers such as Delrin™ manufactured by Du Pont.

The following examples are provided for the purpose of further illustrating the present invention but are in no way to be taken as limiting.

NMR measurements were performed with JEOL JNM-EX270 FT-NMR (product of JEOL Ltd.), JEOL JNM-LA300 FT-NMR (product of JEOL Ltd.; the data taken with this model are preceded by an asterisk), or JEOL FX90A FT-NMR (product of JEOL Ltd.; the data taken with this model are preceded by a sharp); IR measurements with HORIBA FT-200 (product of HORIBA Ltd.); and m.p. measurements with Mettler FP-80, FP-82, FP-81HT or FP-90 (each produced by Mettler Instruments AG). In the following examples, the yield of each "title compound" is parenthesized in both absolute and relative terms.

EXAMPLE 1

Synthesis of 5,9-dichloro-2-(3-pyridylmethyl)-3H-pyrido[3,2,1-kl]phenoxazin-3-one <Step 1> Synthesis of 4-chloro-2-(2,5-dichlorophenoxy)aniline-N-β-propionic acid 4-chloro-2-(2,5-dichlorophenoxy)aniline (33.9 g) prepared by the procedure described in J. Heterocycl. Chem., 16, 1121 (1979) and acrylic acid (8.3 mL) were suspended in water (30.2 mL) and the suspension was heated under reflux for 1 hour under an argon atmosphere and allowed to cool. The reaction mixture was adjusted with 1N aqueous solution of sodium hydroxide to pH 12. The mixture was washed with ether (30 mL). The aqueous layer was adjusted with 6N hydrochloric acid to pH 3, followed by extraction with ethyl acetate. The ethyl acetate layer was dried over anhydrous sodium sulfate, and the solvent was evaporated under reduced pressure to obtain the title compound (39.3 g; 91%).

IR spectrum (KBr) vcm$^{-1}$:2953, 1711, 1512, 1471, 1396, 1232

NMR spectrum (#CDCl$_3$) δ ppm:7.35 (1H, d), 7.25–6.86 (3H, m), 6.75–6.63 (2H, m), 3.80–3.17 (2H, m), 3.49 (2H, t)

<Step 2> Synthesis of 6-chloro-8-(2,5-dichlorophenoxy)-1,2,3,4-tetrahydroquinolin-4-one To the compound (1 g) obtained in step 1 was added polyphosphoric acid (9.6 g) and the mixture was heated at 120° C. for 1.5 hours under an argon atmosphere and allowed to cool. After addition of water (30 mL), the mixture was extracted with ether. The ether layer was successively washed with 1N aqueous solution of sodium hydroxide and brine, and dried over anhydrous sodium sulfate. The solvent was evaporated under reduced pressure. The residue was purified by silica gel column chromatography (eluent: hexane/ethyl acetate=7:1) to obtain the title compound (0.25 g; 26%).

m.p.:169.5–171.3° C.

IR spectrum (KBr) vcm$^{-1}$:3389, 1660, 1521, 1233

NMR spectrum (#DMSO-d$_6$) δ ppm:7.66 (1H, d), 7.41–7.10 (3H, m), 6.90–6.80 (2H, m), 3.51 (2H, t), 2.61 (2H, t)

<Step 3> Synthesis of 5,9-dichloro-1,2-dihydro-3H-pyrido[3,2,1-kl]phenoxazin-3-one The compound (500 mg) obtained in step 2, copper (II) oxide (32 mg) and potassium carbonate (200 mg) were heated at 170° C. for 3.5 hours under an argon atmosphere and allowed to cool. Ethyl acetate (100 mL) was added and the insoluble material was separated by filtration. The filtrate was concentrated under reduced pressure and the residue was purified by silica gel column chromatography (eluent: hexane/ethyl acetate=7:1) to obtain the title compound (90 mg; 20%).

m.p.: 201.8–204.8° C.

IR spectrum (KBr) vcm$^{-1}$: 1670, 1479, 1275, 1260

NMR spectrum (#DMSO-d$_6$) δ ppm: 7.20–6.90 (3H, m), 6.83–6.68 (2H, m), 3.83 (2H, t), 2.77 (2H, t)

<Step 4> Synthesis of 5,9-dichloro-2-(3-pyridylmethyl)-3H-pyrido[3,2,1-kl]phenoxazin-3-one The compound (100 mg) obtained in step 3 was suspended in ethanol (5 mL) and pyridine-3-aldehyde (49 μl) and sodium hydroxide (100 mg) which was dissolved in water (0.5 mL) were added to the suspension at room temperature and the mixture was heated under reflux for 15 minutes under an argon atmosphere. After allowing to cool, the precipitated crystals were recovered by filtration and washed with ethanol. The resulting crude crystals were dissolved in chloroform under heating and reprecipitated from hexane to obtain the title compound (102 mg; 79%).

EXAMPLE 2

Synthesis of 5,9-dichloro-2-benzyl-3H-pyrido[3,2,1-kl]phenoxazin-3-one

According to Example 1<step 4>, the compound (500 mg) produced in Example 1<step 3> was reacted with benzaldehyde (260 μl) to obtain the title compound (508 mg; 81%).

EXAMPLE 3

Synthesis of 5,9-dichloro-3H-pyrido[3,2,1-kl]phenoxazin-3-one

The compound (100 mg) obtained in Example 1, step 3 was suspended in anhydrous dioxane (6 mL) and to the suspension was added DDQ (8.9 mg). The mixture was heated under reflux for 3 hours under an argon atmosphere. Another portion of DDQ (15 mg) was added during heating. The reaction mixture was allowed to cool and added to 1N aqueous solution of sodium hydroxide (10 mL). The mixture was extracted with ethyl acetate. The ethyl acetate layer was successively washed with 1N aqueous solution of sodium hydroxide and brine, and dried over anhydrous sodium sulfate. The solvent was evaporated under reduced pressure. The resulting crude crystals were recrystallized from ethyl acetate to obtain the title compound (60 mg; 62%).

EXAMPLE 4

Synthesis of 2-(3-pyridylmethyl)-3H-pyrido[3,2,1-kl]phenoxazin-3-one

According to Example 1<step 4>, 1,2-dihydro-3H-pyrido[3,2,1-kl]phenoxazin-3-one (1 g) prepared by the procedure described in literature (J. Org. Chem., 24, 1699 (1959)) was reacted with pyridine-3-aldehyde (0.7 g) to obtain the title compound (1.2 g; 88%). The chemical structure thereof is shown below.

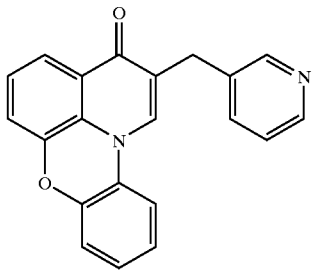

EXAMPLE 5

Synthesis of 5,9-dichloro-2-(3-pyridylmethyl)-3H-pyrido[3,2,1-kl]phenothiazin-3-one <Step 1> Synthesis of 3,7-dichlorophenothiazine-N-β-propionitrile 3,7-dichlorophenothiazine (200 mg) prepared by the procedure described in J. Pract. Chem., 353, (1976) was added to acrylonitrile (20 mL) and the mixture was cooled to 0° C. in an ice bath, followed by addition of Triton B™ (1 mL). The mixture was stirred for 5 minutes and thereafter the acrylonitrile was evaporated under reduced pressure. The residue was purified by silica gel column chromatography (eluent: hexane/ethyl acetate=4:1) to obtain the title compound (180 mg; 75%).

IR spectrum (KBr) νcm$^{-1}$: 2251, 1459, 1253, 1119, 814
NMR spectrum (DMSO-d$_6$) δ ppm: 7.32–7.18 (4H, m), 7.09 (2H, d), 4.19 (2H, t), 2.90 (2H, t)

<Step 2> Synthesis of 3,7-dichlorophenothiazine-N-β-propionic acid

The compound (3.5 g) obtained in step 1 was suspended in methanol (116 mL). To the suspension was added dropwise sodium hydroxide (2.8 g) dissolved in water (12 mL) at room temperature. The mixture was heated under reflux for 7 hours and allowed to cool. Water and ether were added to the mixture to separate the aqueous layer, which was adjusted to pH 2 with 4N hydrochloric acid. The aqueous layer was extracted with ethyl acetate, washed with brine and dried over anhydrous sodium sulfate. Then, the solvent was evaporated under reduced pressure. The residue was purified by silica gel column chromatography (eluent: ethyl acetate) to obtain the title compound (276 mg; 7%).

m.p.: 145.5–153.1° C.

IR spectrum (KBr) ν cm$^{-1}$: 3051, 1707, 1460, 810

NMR spectrum (DMSO-d$_6$) δ ppm: 7.31–7.22 (4H, m), 7.05 (2H, d), 4.09 (2H, t), 2.63 (2H, t)

<Step 3> Synthesis of 5,9-dichloro-1,2-dihydro-3H-pyrido[3,2,1-kl]phenothiazin-3-one The compound (272 mg) obtained in step 2 was suspended in benzene (9 mL). To the suspension was added dropwise trifluoroacetic anhydride (0.34 mL). The mixture was heated under reflux for 2 hours and allowed to cool. After addition of saturated sodium carbonate, the mixture was extracted with ethyl acetate, washed with brine, and dried over anhydrous sodium sulfate. The solvent was evaporated under reduced pressure. The residue was purified by silica gel column chromatography (eluent: hexane/ethyl acetate=4:1). The crude product was successively washed with methanol and ether and recovered by filtration to obtain the title compound (112 mg; 35%).

m.p.: 183.9–184.7° C.

IR spectrum (KBr) ν cm$^{-1}$: 1680, 1446, 1225, 866

NMR spectrum (DMSO-d$_6$) δ ppm: 7.49–7.47 (2H, m), 7.32–7.28 (2H, m), 7.18 (1H, d), 4.10 (2H, t), 2.84 (2H, t)

<Step 4> Synthesis of 5,9-dichloro-2-(3-pyridylmethyl)-3H-pyrido[3,2,1-kl]phenothiazin-3-one According to Example 1<step 4>, the compound (30 mg) produced in step 3 was reacted with pyridine-3-aldehyde (14 μl) to obtain the title compound (29 mg; 76%).

EXAMPLE 6

Synthesis of 2-benzyl-5,9-dichloro-3H-pyrido[3,2,1-kl]phenothiazin-3-one

According to Example 1<step 4>, the compound (30 mg) produced in Example 5<step 3 >was reacted with benzaldehyde (15 μl) to obtain the title compound (23 mg; 60%).

EXAMPLE 7

Synthesis of 5,9-dichloro-3H-pyrido[3,2,1-kl]phenothiazin-3-one

According to Example 3, the compound (85 mg) produced in Example 5<step 3> was reacted to obtain the title compound (44 mg; 52%).

EXAMPLE 8

Synthesis of 2-(3-pyridylmethyl)-3H-pyrido[3,2,1-kl]phenothiazin-3-one

According to Example 1<step 4>, 1,2-dihydro-3H-pyrido[3,2,1-kl]phenothiazin-3-one (20 mg) prepared by the procedure described in literature( J. Heterocycl. Chem., 29, 675 (1992)) was reacted with pyridine-3-aldehyde (12 μl) to obtain the title compound (17 mg; 83%). The chemical structure thereof is shown below.

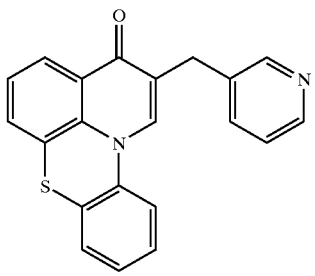

EXAMPLE 9

Synthesis of 7-acetyl-2-(3-pyridylmethyl)-3H,7H-pyrido[3,2,1-de]phenazin-3-one

<Step 1> Synthesis of 10-acetyl-5,10-dihydrophenazine-5-β propionic acid methyl ester According to Example 5<step 1>, 5-acetyl-5,10-dihydrphenazine (157 g) prepared by the procedure described in literature (JP-B 42-16629) was reacted with methyl acrylate (500 mL) to obtain the title compound (43 g; 20%).

m.p.: 143.1–144.3° C.

IR spectrum (KBr) ν cm$^{-1}$: 2952, 1736, 1672, 1479, 1329, 1265, 770

NMR spectrum (CDCl$_3$) δ ppm: 7.36 (2H, d), 7.25–7.15 (2H, m), 7.05–6.90 (4H, m), 4.19 (2H, t), 3.72 (3H, s), 2.83 (2H, t), 2.19 (3H, s)

<Step 2> Synthesis of 10-acetyl-5,10-dihydrophenazine-5-β-propionic acid

The compound (43.3 g) obtained in step 1 was dissolved in methanol (350 mL) and to the solution was added dropwise 0.2 N aqueous solution of lithium hydroxide (100 mL) at room temperature. The mixture was stirred overnight at room temperature. After addition of water (500 mL), the mixture was washed with ether. the aqueous layer was adjusted with iN hydrochloric acid to pH 3, followed by extraction with ethyl acetate. The ethyl acetate layer was washed with brine and dried over anhydrous sodium sulfate. The solvent was evaporated under reduced pressure to obtain the title compound (36.8 g; 89%).

m.p.: 197.5–201.7° C.

IR spectrum (KBr) ν cm$^{-1}$: 2881, 1736, 1633, 1479, 1348, 1269, 1038, 760

NMR spectrum (CDCl$_3$) δ ppm: 7.38–6.94 (8H,m), 4.21 (2H, t), 2.87 (2H, t), 2.18 (3H, s)

<Step 3> Synthesis of 7-acetyl-1,2-dihydro-3H,7H-pyrido[3,2,1-de]phenazin-3-one

According to Example 5<step 3>, the compound (36.8 g) produced in step 2 was reacted to obtain the title compound (27.2 g; 79%).

m.p.: 188.6–191.1° C.

IR spectrum (KBr) ν cm$^{-1}$: 1668, 1610, 1475, 1273, 1108,

NMR spectrum (CDCl$_3$) δ ppm: 7.78 (1H, dd), 7.56 (1H, dd), 7.40 (1H, dd), 7.27 (1H, ddd), 7.14 (1H, ddd), 7.05 (1H, dd), 7.02 (1H, dd), 4.00–3.80 (2H, m), 2.97 (2H, t), 2.25 (3H, s)

<Step 4> Synthesis of 7-acetyl-2-(3-pyridylmethyl)-3H,7H-pyrido[3,2,1-de]phenazin-3-one The compound (6 g) obtained in step 3 was suspended in ethanol (240 mL) and to the suspension were added piperidine (1.8 mL) and pyridine-3-aldehyde (3.7 g). The mixture was heated under reflux for 16 hours under an argon atmosphere and allowed to cool. The solvent was evaporated under reduced pressure. The residue was purified by silica gel column chromatography (eluent: hexane/ethyl acetate= 1:1) to obtain the title compound (1.3 g; 17%).

EXAMPLE 10

Synthesis of 7-acetyl-2-benzyl-3H,7H-pyrido[3,2,1-de]phenazin-3-one

According to Example 9<step 4>, the compound (5 g) produced in Example 9<step 3>was reacted with benzaldehyde (3 mL) to obtain the title compound (2.4 g; 36%).

EXAMPLE 11

Synthesis of 7-acetyl-3H,7H-pyrido[3,2,1-de]phenazin-3-one

According to Example 3, the compound (5 g) produced in Example 9<step 3>was reacted to obtain the title compound (11.0 g; 24%).

EXAMPLE 12

Synthesis of 2-(3-pyridylmethyl)-3H,7H-pyrido[3,2,1-de]phenazin-3-one

The compound (500 mg) obtained in Example 9 was suspended in ethanol (20 mL) and to the suspension was added piperidine (2 mL). The mixture was heated under reflux for 30 hours under an argon atmosphere and allowed to cool. The solvent was evaporated under reduced pressure. The residue was purified by silica gel column chromatography (eluent: hexane/ethyl acetate =1:1) to obtain the title compound (115 mg; 26%)

EXAMPLE 13

Synthesis of 2-benzyl-3H,7H-pyrido[3,2,1-de]phenazin-3-one

According to Example 12, the compound (2.4 g) produced in Example 10 was reacted to obtain the title compound (0.2 g; 10%).

EXAMPLE 14

Synthesis of 3H,7H-pyrido[3,2,1-depphenazin-3-one

According to Example 12, the compound (400 mg) produced in Example 11 was reacted to obtain the title compound (85 mg; 25%).

EXAMPLE 15

Synthesis of 7-methyl-2-(3-pyridylmethyl )-3H,7H-pyrido[3,2,1-de]phenazin-3-one

<Step 1> Synthesis of 10-methyl-5,10-dihydrophenazine-5-β-propionic acid methyl ester 5-methyl-5,10-dihydrophenazine (100 mg) prepared by the procedure described in J. Heterocycl., Chem., 26, 435 (1989) was dissolved in acetone (1 mL) and to the solution was added methyl acrylate (0.5 mL). The mixture was cooled to 0° C. in an ice bath, followed by addition of Triton B™ (10 μl). The mixture was stirred overnight at room temperature and the solvent was evaporated under reduced pressure. The residue was purified by silica gel column chromatography (eluent: hexane/ethyl acetate=10:1) to obtain the title compound (37 mg; 60%).

m.p.: 96.8–97.6° C.

IR spectrum (KBr) ν cm$^{-1}$: 2949, 1720, 1483, 1271, 1180, 1149, 1047, 750

NMR spectrum (CDCl$_3$) δ ppm: 6.74–6.67 (4H, m), 6.46–6.34 (4H, m), 3.90 (3H, t), 3.74 (3H, s), 2.99 (3H, s), 2.74 (2H, t)

<Step 2> Synthesis of 10-methyl-5,10-dihydrophenazine-5-8-propionic acid

According to Example 5<step 2>, the compound (25 mg) produced in step 1 was reacted to obtain the title compound (23 mg; 93%).

m.p.: 141.2–143.7° C.

IR spectrum (KBr) ν cm$^{-1}$: 3053, 1697, 1485, 1383, 1215, 1045, 735

NMR spectrum (CDCl$_3$) δ ppm: 7.40–5.70 (8H,m), 3.20–2.50 (4H, m), 2.05 (3H, s)

<Step 3> Synthesis of 7-methyl-1,2-dihydro-3H,7H-pyrido[3,2,1-de]phenazin-3-one

According to Example 5<step 3>, the compound (200 mg) produced in step 2 was reacted to obtain the title compound (48 mg; 23%).

m.p.: 136.1–141.2 C.

IR spectrum (KBr) ν cm$^{-1}$:1684, 1479, 1354, 1273, 1101, 785, 739

NMR spectrum (DMSO-d$_6$) δ ppm: 7.20–6.30 (7H, m), 3.80–3.50 (2H, m), 3.30–2.80 (2H, m), 2.18 (3H, s)

<Step 4> Synthesis of 7-methyl-2-(3-pyridylmethyl)-3H,7H-pyrido[3,2,1-de]phenazin-3-one According to Example 1<step 4>, the compound (100 mg) produced in step 3 was reacted with pyridine-3-aldehyde (60 μl) to obtain the title compound (73 mg; 54%).

EXAMPLE 16

Synthesis of 2-benzyl-7-methyl-3H,7H-pyrido[3,2,1-de]phenazin-3-one

According to Example 1<step 4>, the compound (200 mg) produced in Example 15<step 3> was reacted with benzaldehyde (0.13 mL) to obtain the title compound (102 mg; 30%).

EXAMPLE 17

Synthesis of 7-methyl-3H,7H-pyrido[3,2,1-de]phenazin-3-one

According to Example 3, the compound (40 mg) produced in Example 15<step 3> was reacted to obtain the title compound (25 mg; 63%).

EXAMPLE 18

Synthesis of 2-(3-pyridylmethyl)-3H,7H-pyrido[3,2,1-de]acridin-3,7-dione

<Step 1> Synthesis of 9(10H)-acridone-N-β-propionic acid

According to Example 5<steps 1 and 2>,9(10H)-acridone (10 g) was reacted with methyl acrylate (11.5 mL) to obtain the title compound (1.8 g; 13%).

m.p.: 265.5–268.0° C.

IR spectrum (KBr) ν cm$^{-1}$: 3020, 1724, 1591, 1562, 1174

NMR spectrum (DMSO-d6) δ ppm: 12.62 (1H, s), 8.36 (2H, d), 7.92–7.87 (4H, m), 7.43–7.30 (2H, m), 4.73 (2H, m), 2.90–2.78 (2H, m)

<Step 2> Synthesis of 1,2-dihydro-3H,7H-pyrido[3,2,1-de]acridin-3,7-dione

According to Example 1<step 2>, the compound (1.5 g) produced in step 1 was reacted to obtain the title compound (0.6 g; 43%).

m.p.: 252.8–245.3° C.

IR spectrum (KBr) ν cm$^{-1}$:1691, 1632, 1608, 1495, 1292, 752

NMR spectrum (DMSO-d$_6$) δ ppm: 8.58 (1H, dd), 8.38 (1H, dd), 8.30 (1H, dd), 8.07–7.85 (2H, m), 7.48–7.38 (2H, m), 4.72 (2H, t), 3.10 (2H, t)

<Step 3> Synthesis of 2-(3-pyridylmethyl)-3H,7H-pyrido[3,2,1-de]acridin-3,7-dione According to Example 1<step 4>, the compound (200 mg) obtained in step 2 was reacted with pyridine-3-aldehyde (0.12 mL) to obtain the title compound (25 mg; 9.2%).

EXAMPLE 19

Synthesis of 2-benzyl-3H,7H-pyrido[3,2,1-de]acridin-3,7-dione

According to Example 1<step 4>, the compound (200 mg) obtained in Example 18<step 2>was reacted with benzaldehyde (0.13 mL) to obtain the title compound (194 mg; 72%).

EXAMPLE 20

Synthesis of 3H,7H-pyrido[3,2,1-de]acridin-3,7-dione

According to Example 3, the compound (100 mg) produced in Example 18<step 2> was reacted to obtain the title compound (74 mg; 75%).

EXAMPLE 21

Synthesis of 10-chloro-5-(3-pyridylmethyl)-4H-indolo[3,2,1-ij][1,6]naphthyridin-4-one <Step 1> Synthesis of 8-chloro-4-cyano-5H-pyrido[4,3-b]indole-5-propionic acid methyl ester According to Example 5<step 1>, 8-chloro-4-cyano-5H-pyrido[4,3-b]indole (1.26 g) prepared from 5-chloro-2-cyanomethylindole by the procedure described in literature (Synthesis, 743 (1992) and Chem. Pharm. Bull., 29, 1280 (1981)) was reacted with ethyl acrylate (1.8 mL) to obtain the title compound (850 mg; 47%).

m.p.: 196.4° C. (dec.)

IR spectrum (KBr) ν cm$^{-1}$: 1716, 1581, 1323, 1203

NMR spectrum (#DMSO-d$_6$) δ ppm: 9.65 (1H, s), 8.94 (1H, s), 8.53 (1H, d), 7.93 (1H, d), 7.67 (1H, dd), 4.95 (2H, t), 3.99 (2H, q), 2.99 (2H, t), 1.06 (3H, t)

<Step 2> Synthesis of 4-carbamoyl-8-chloro-5H-pyrido[4,3-b]indole-5-propionic acid The compound (5.9 g) obtained in step 1 was suspended in ethyl cellosolve (180 mL) and to the suspension was added 1N aqueous solution of potassium hydroxide (51.3 mL). The mixture was heated under reflux for 2 hours under an argon atmosphere and allowed to cool. The solvent was evaporated under reduced pressure and to the residue was added ethanol. The precipitated crystals were recovered by filtration and washed with ether. The resulting crystals were dissolved in water (20 mL), followed by adjustment with iN hydrochloric acid to pH 7. The insoluble material was recovered by filtration and successively washed with ethanol and ether to obtain the title compound (5.2 g; 90%).

m.p.: 297.7° C. (dec.)

IR spectrum (KBr) ν cm$^{-1}$: 3390, 1662, 1616, 1473

NMR spectrum (#DMSO-d$_6$) δ ppm: 9.47-(1H, s), 8.54 (1H, s), 8.44 (1H, d), 8.34 (1H, s), 8.08–7.57 (2H, m), 7.57 (1H, dd), 4.72 (2H, t), 2.72 (2H, t)

<Step 3> Synthesis of 4-carboxy-8-chloro-5H-pyrido[4,3-b]indole-5-β-propionic acid The compound (5 g) obtained in step 2 was dissolved in con. nitric acid (200 mL) and to the solution was added sodium nitrite (21.7 g) under cooling with ice. The mixture was stirred for 1 hour at room temperature and poured into water (800 mL). The precipitated crystals were recovered by filtration to obtain the title compound (5.9 g; 100%).

m.p.: 265.3° C. (dec.)

IR spectrum (KBr) ν cm$^{-1}$: 1711, 1464, 1398, 1354

NMR spectrum (#DMSO-d$_6$) δ ppm: 9.86 (1H, s), 9.11 (1H, s), 8.67 (1H, d), 8.07 (1H, d), 7.81 (1H, dd), 5.27–4.71 (2H, m), 3.11–2.57 (2H, m)

<Step 4> Synthesis of 10-chloro-5,6-dihydro-4H-indolo[3,2,1-ij][1,6]naphthyridin-4-one The compound (500 mg) obtained in step 3 was suspended in water (30 mL) and to the suspension was added sodium hydrogencarbonate (290 mg) at room temperature. The solvent was evaporated under reduced pressure. Then, acetic anhydride (20 mL) and sodium acetate (257 mg) were added and the mixture was heated at 80° C. for 3 hours and allowed to cool. The layers were separated by addition of water and ethyl acetate. The organic layer was washed with saturated aqueous solution of sodium hydrogencarbonate and dried over anhydrous sodium sulfate. The solvent was evaporated under reduced pressure. The residue was purified by silica gel column chromatography (eluent: hexane/ethyl acetate=3:2) to obtain the title compound (60 mg; 15%).

m.p.: 259.6° C. (dec.)

IR spectrum (KBr) ν cm.$^{-1}$: 1684, 1466, 1273, 1221

NMR spectrum (#DMSO-d$_6$) δ ppm: 9.49 (1H, s), 8.76 (1H, s), 8.45 (1H, d), 7.79 (1H, d), 7.63 (1H, dd), 4.65 (2H, t), 3.29–3.06 (2H, m)

<Step 5> Synthesis of 10-chloro-5-(3-pyridylmethyl)-4H-indolo[3,2,1-ij][1,6]naphthyridin-4-one According to Example 1<step 4>, the compound (120 mg) produced in step 4 was reacted with pyridine-3-aldehyde (70 μl) to obtain the title compound (27 mg; 17%).

EXAMPLE 22

Synthesis of 10-chloro-4H-indolo[3,2,1-ij][1,6]naphthyridin-4-one

<Step 1> Synthesis of 4-acetoxy-10-chloro-6H-indolo[3,2,1-ij][1,6]naphthyridine

The title compound obtained (20 mg; 7%) was a by-product which was obtained by silica gel column chromatography (eluent: hexane/ethyl acetate=2:3) in the process of Example 21, step 4.

m.p.: 203.2° C. (dec.)

IR spectrum (KBr) ν cm$^{-1}$: 1763, 1211, 1174, 1070

NMR spectrum (#DMSO-d6) δ ppm: 9.14 (1H, s), 8.57–8.14 (1H, m), 8.09 (1H, s), 7.78–7.36 (2H, m), 5.70–5.66 (1H, m), 5.34 (2H, d), 2.37 (3H, s)

<Step 2> Synthesis of 10-chloro-4H-indolo[3,2,1-ij][1,6]naphthyridin-4-one

According to Example 3, the compound (150 mg) produced in step 1 was reacted to obtain the title compound (50 mg; 39%).

EXAMPLE 23

Synthesis of 10-chloro-5-(3-pyridylmethyl)-4H-indolo[3,2,1-de][1,5]naphthyridin-4-one <Step 1> Synthesis of 6-chloro-l-cyano-9H-pyrido[3,4-b]indole 1-cyano-9H-pyrido[3,4-b]indole (1 g) prepared by the procedure described in J. Am. Chem. Soc., 109, 3378 (1987) was suspended in methylene chloride (40 mL) and to the suspension was added 1-chlorobenzotriazole (J. Chem. Soc. (C), 1474 (1969)) (0.8 g) at room temperature. The mixture was stirred overnight. After addition of ethyl acetate, the mixture was washed with 3% aqueous solution of sodium hydroxide and dried over anhydrous sodium sulfate. The solvent was evaporated under reduced pressure and the residue was successively washed with ethyl acetate and ether to obtain the title compound (1 g; 85%).

m.p.: 313.3° C. (dec.)

IR spectrum (KBr) ν cm$^{-1}$:2227, 1493, 1456, 1234, 834

NMR spectrum (DMSO-d$_6$) δ ppm: 12.67 (1H, s), 8.57–8.47 (3H, m), 7.78–7.61 (2H, m)

<Step 2> Synthesis of 6-chloro-1-cyano-9H-pyrido[3,4-b]indole-9-p-propionic acid ethyl ester According to Example 5<step 1>, the compound (500 mg) produced in step 1 was reacted with ethyl acrylate (0.48 mL) to obtain the title compound (480 mg; 67%).

m.p.: 232.9° C. (dec.)

IR spectrum (KBr) ν cm$^{-1}$: 2220, 1736, 1473, 1203, 1186

NMR spectrum (#DMSO-d$_6$) δ ppm: 8.75–8.30 (3H, m), 8.16–7.46 (2H, m), 4.97 (2H, t), 3.96 (2H, q), 2.97 (2H, t), 1.04 (3H, t)

<Step 3> Synthesis of 4-amino-10-chloro-6H-indolo[3,2,1-de][1,5]naphthyridine-5-carboxylic acid ethyl ester The compound (400 mg) obtained in step 2 was dissolved in toluene (120 mL) and to the solution was added sodium hydride (312 mg) at room temperature. The mixture was heated under reflux for 14 hours and allowed to cool. The mixture was extracted by addition of water and ethyl acetate, and dried over anhydrous sodium sulfate. The solvent was evaporated under reduced pressure. The residue was purified by silica gel column chromatography (eluent: hexane/ethyl acetate=20:1) to obtain the title compound (200 mg; 50%).

m.p.: 170.4° C. (dec.)

IR spectrum (KBr) ν cm$^{-1}$: 3423, 3311, 1682, 1612, 1259

NMR spectrum (#DMSO-d$_6$) δ ppm: 8.61–8.26 (2H, m), 8.08 (1H, d), 7.86–7.44 (2H, m), 5.15 (2H, s), 4.23 (2H, q), 1.32 (3H, t)

<Step 4> Synthesis of 10-chloro-5,6-dihydro-4H-indolo[3,2,1-de][1,5]naphthyridin-4-one The compound (1.48 g) obtained in step 3 was suspended in 48% hydrogen bromide (75 mL). The suspension was heated at 80° C. for 4 hours and allowed to cool. After addition of water (100 mL), the mixture was adjusted with 3N aqueous solution of sodium hydroxide to pH 9 and the precipitated crystals were recovered by filtration to obtain the title compound (900 mg; 78%).

m.p.: 168.6–176.7° C.

IR spectrum (KBr) ν cm$^{-1}$: 1684, 1504, 1464, 1271, 1209

NMR spectrum (#DMSO-d$_6$) δ ppm: 8.80–8.11 (4H, m), 7.98–7.53 (1H, m), 4.66 (2H, t), 3.33–2.98 (2H, m)

<Step 5> Synthesis of 10-chloro-5-(3-pyridylmethyl)-4H-indolo[3,2,1-de][1,5]naphthyridin-4-one According to Example 1<step 4>, the compound (138 mg) produced in step 4 was reacted with pyridine-3-aldehyde (80 μl) to obtain the title compound (18 mg; 10%).

EXAMPLE 24

Synthesis of 5-benzyl-10-chloro-4H-indolo[3,2,1-de][1,5]naphthyridin-4-one

According to Example 1<step 4>, the compound (200 mg) produced in Example 23<step 4> was reacted with benzaldehyde (132 mg) to obtain the title compound (43 mg; 16%).

EXAMPLE 25

Synthesis of 10-chloro-4H-indolo[3,2,1-de][1,5]naphthyridin-4-one

According to Example 3, the compound (300 mg) produced in Example 23<step 4> was reacted to obtain the title compound (111 mg; 37%).

EXAMPLE 26

Synthesis of 5-(3-pyridylmethyl)-4H-indolo[3,2,1-de][1,5]naphthyridin-4-one

<Step 1> Synthesis of 4-amino-6H-indolo[3,2,1-de][1,5]naphthyridine-5-carboxylic acid ethyl ester According to Example 23<step 3>, 1-cyano-9H-pyrido[3,4-b]indole-9-β-propionic acid ethyl ester (3.3 g) prepared by the procedure described in literature (J. Am. Chem. Soc., 109, 3378 (1987)) was reacted to obtain the title compound (2.0 g; 61%).

m.p.: 172.8° C. (dec.)

IR spectrum (KBr) ν cm$^{-1}$: 3427, 3315, 1682, 1612, 1263

NMR spectrum (#DMSO-d$_6$) δ ppm: 8.54–8.21 (2H, m), 8.08 (1H, d), 7.99–7.14 (3H, m), 5.20 (2H, s), 4.25 (2H, q), 1.32 (3H, t)

<Step 2> Synthesis of 5,6-dihydro-4H-indolo[3,2,1-de][1,5]naphthyridin-4-one

According to Example 23<step 4>, the compound (1.2 g) produced in step 1 was reacted to obtain the title compound (0.8 g; 86%).

m.p.: 190.1° C. (dec.)

IR spectrum (KBr) ν cm$^{-1}$: 1687, 1626, 1506, 1306

NMR spectrum (#DMSO-d$_6$) δ ppm: 8.55 (1H, d), 8.42–8.08 (2H, m), 7.96–7.08 (3H, m), 4.65 (2H, t), 3.26 (2H, t) <Step 3> Synthesis of 5-(3-pyridylmethyl)-4H-indolo[3,2,1-de][1,5]naphthyridin-4-one According to Example 1<step 4>, the compound (200 mg) produced in step 2 was reacted with pyridine-3-aldehyde (0.14 mL) to obtain the title compound (30 mg; 11%).

EXAMPLE 27

Synthesis of 5-benzyl-4H-indolo[3,2,1-de][1,5]naphthyridin-4-one

According to Example 1<step 4>, the compound (200 mg) produced in Example 26<step 2> was reacted with benzaldehyde (153 mg) to obtain the title compound (116 mg; 42%).

EXAMPLE 28

Synthesis of 5-(3-pyridylmethyl)-4H[6]-azaindolo[3,2,1-ij]quinolin-4-one

<Step 1> Synthesis of 5,6-dihydro-4H[6]-azaindolo(3,2,1-ij]quinolin-4-one

According to Example 1<step 2>, 9H-pyrido[3,4-b]indole-9-:-propionic acid (12.8 g) prepared by the procedure described in US 285051 to obtain the title compound (2.8 g; 24%).

m.p.: 174.8–175.8° C.

IR spectrum (KBr) ν cm$^{-1}$: 1676, 1450, 1441, 1323

NMR spectrum (DMSO-d$_6$) δ ppm: 9.12 (1H, s), 8.54 (1H, d), 8.49 (1H, d), 8.23 (1H, d), 7.93 (1H, d), 7.44–7.34 (1H, m), 4.72 (2H, t), 3.18 (2H, t)

<Step 2> Synthesis of 5-(3-pyridylmethyl)-4H[6]-azaindolo[3,2,1-ij]quinolin-4-one According to Example 1<step 4>, the compound (50 mg) produced in step 1 was reacted with pyridine-3-aldehyde (50 mg) to obtain the title compound (80 mg; 100%).

EXAMPLE 29

Synthesis of 5-benzyl-4H[6]-azaindolo[3,2,1-ij]quinolin-4-one

According to Example 1<step 4>, the compound (2 g) produced in Example 28<step 1> was reacted with benzaldehyde (2 g) to obtain the title compound (2 g; 71%).

EXAMPLE 30

Synthesis of 4H[6]-azaindolo[3,2,1-ij]quinolin-4-one

According to Example 3, the compound (180 mg) produced in Example 28<step 1> was reacted to obtain the title compound (12 mg; 7%).

EXAMPLE 31

Synthesis of 10-bromo-5-methoxy-2-(3-pyridylmethyl)-3H-pyrido[3,2,1-kl]phenoxazin-3-one <Step 1> Synthesis of 3-(2,4-dibromophenoxy)-4-nitroanisole 3-chloro-4-nitroanisole (7.0 g) prepared by the procedure described in J. Org. Chem., 17, 1475 (1952) and 2,4-dibromophenol (9.4 g) were melted at 120 to 125° C. under an argon atmosphere, followed by dropwise addition of 10N aqueous solution of potassium hydroxide (3.5 mL) over 2 hours. Then, the mixture was stirred at 140 to 145° C. for 3 hours and cooled to 100° C. Thereafter, 30% aqueous solution of sodium hydroxide (14 mL) and water (140 mL) were successively added. The mixture was allowed to cool and extracted with methylene chloride. The methylene chloride layer was washed with 1N aqueous solution of sodium hydroxide and dried over anhydrous sodium sulfate. The solvent was evaporated under reduced pressure. The resulting crude crystals were washed with hexane to obtain the title compound (12.7 g; 84%).

m.p.: 49.7–50.9° C.

IR spectrum (KBr) ν cm$^{-1}$: 1589, 1514, 1338, 1288, 1043

NMR spectrum (DMSO-d$_6$) δ ppm: 8.19 (1H, d), 8.03 (1H, d), 7.58 (1H, dd), 7.07–6.96 (2H, m), 6.64 (1H, d), 3.84 (3H, s)

<Step 2> Synthesis of 2-(2,4-dibromophenoxy)-4-methoxyaniline

Tin (II) chloride dihydrate (16.8 g) was dissolved in con. hydrochloric acid (33 mL) and to the solution were added successively the compound (6.0 g) obtained in step 1 and ethanol (48 mL). The mixture was heated at 80° C. for 1 hour under an argon atmosphere and allowed to cool. The solvent was evaporated under reduced pressure. After addition of 20% sodium hydroxide, the mixture was extracted with ether. The ether layer was washed with brine and dried over anhydrous sodium sulfate. The solvent was evaporated under reduced pressure to obtain the title compound (4.6 g; 84%).

IR spectrum (neat) ν cm$^{-1}$ : 1512, 1466, 1232, 1134, 1041

NMR spectrum (DMSO-d6) δ ppm: 7.91 (1H, d), 7.49 (1H, dd), 6.79 (1H, d), 6.70–6.59 (2H, m), 6.43 (1H, d), 3.62 (3H, s)

<Step 3> Synthesis of 2-(2,4-dibromophenoxy)-4-methoxyaniline-N-β-propionic acid According to Example 1<step 1>, the compound (4.4 g) produced in step 2 was reacted with acrylic acid (0.81 mL) to obtain the title compound (3.9 g; 75%).

IR spectrum (neat) ν cm$^{-1}$:1734, 1711, 1520, 1468, 1443, 1423, 1078

NMR spectrum (DMSO-d6) δ ppm: 12.48–11.80 (1H, m), 7.93 (1H, d), 7.50 (1H, dd), 6.83–6.67 (3H, m), 6.39 (1H, d), 4.97–4.48 (1H, m), 3.62 (3H, s), 3.28 (2H, t), 2.48 (2H, t)

Step 4> Synthesis of 8-(2,4-dibromophenoxy)-6-methoxy-1,2,3,4-tetrahydroquinolin-4-one According to Example 1<step 2 >, the compound (6.3 g) produced in step 3 was reacted to obtain the title compound (0.21 g) as a crude product.

NMR spectrum (*DMSO-$d_6$) δ ppm: 7.80 (1H, d), 7.44–7.38 (1H, m), 7.14 (1H, d), 6.89 (1H, d), 6.48 (1H, d), 3.75 (3H, s), 3.61 (2H, t), 2.75 (2H, t)

Step 5> Synthesis of 10-bromo-1,2-dihydro-5-methoxy-3H-pyrido[3,2,1-kl]phenoxazin-3-one According to Example 1<step 3>, the crude compound (210 mg) produced in step 4 was reacted to obtain the title compound (4.5 mg).

m.p.: 187.8–194.9° C.

IR spectrum (KBr) ν $cm^{-1}$:1660, 1633, 1489, 1325, 1288

NMR spectrum ($CDCl_3$) δ ppm: 6.93–6.82 (2H, m), 6.76 (1H, d), 6.61 (1H, d), 6.53 (1H, d), 3.76 (3H, s), 3.68 (2H, t), 2.83 (2H, t)

Step 6> Synthesis of 10-bromo-5-methoxy-2-(3-pyridylmethyl)-3H-pyrido[3,2,1-kl]phenoxazin-3-one According to Example 1<step 4>, the compound (4.0 mg) produced in step 5 was reacted with pyridine-3-aldehyde (1.7 μl) to obtain the title compound (3.4 mg; 68%). The chemical structure thereof was shown below.

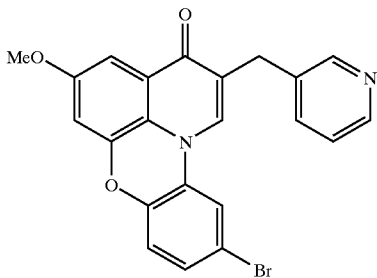

EXAMPLE 32

Synthesis of 10-bromo-5-methoxy-2-(3-pyridylmethyl)-3H,7H-pyrido[3,2,1-de]acridin-3,7-dione Step 1> Synthesis of 6-bromo-2-methoxy-10H-acridine-9one-N-β-propionic acid According to Example 5<steps 1 and 2>, 6-bromo-2-methoxy-10H-acridin-9-one (13.5 g) prepared by the procedure described in D.R.P. 565411 was reacted with methyl acrylate (200 mL) to obtain the title compound (145 mg; 1%).

m.p.: 247.3–248.7° C.

IR spectrum (KBr) ν $cm^{-1}$: 1718, 1610, 1587, 1566, 1506, 1385

NMR spectrum (*DMSO-$d_6$) δ ppm: 8.24 (1H, d), 8.13–8.07 (1H, m), 7.84 (1H, d), 7.74 (1H, d), 7.51 (1H, dd), 7.46 (1H, dd), 4.70 (2H, t), 3.88 (3H, s), 2.75 (2H, t)

Step 2> Synthesis of 10-bromo-1,2-dihydro-5-methoxy-3H,7H-pyrido[3,2,1-de]acridin-3,7-dione The compound (145 mg) obtained in step 1 was suspended in anhydrous chloroform (10 mL) and to the suspension was added PPE (1g) dissolved in anhydrous chloroform (10 mL). The mixture was heated under reflux for 15 hours under an argon atmosphere and allowed to cool. Water (20 mL) was added and the mixture was stirred for 30 minutes. The insoluble material was recovered by filtration and extracted with methylene chloride. The methylene chloride layer was washed with brine and dried over anhydrous sodium sulfate. The solvent was evaporated under reduced pressure. The residue was purified by silica gel column chromatography (eluent: hexane/ethyl acetate=4:1) to obtain the title compound (12 mg; 9%).

m.p.: 255.8–257.2° C.

IR spectrum (KBr) ν $cm^{-1}$: 1689, 1628, 1589, 1495, 1471

NMR spectrum (*DMSO-$d_6$) δ ppm: 8.44 (1H, d), 8.22 (1H, d) 8.02 (1H, d), 7.78 (1H, d), 7.47 (1H, dd), 4.56 (2H, t), 3.96 (3H, s), 3.13 (2H, t)

Step 3> Synthesis of 10-bromo-5-methoxy-2-(3-pyridylmethyl)-3H,7H-pyrido[3,2,1-de]acridin-3,7-dione According to Example 1<step 4>, the compound (26 mg) produced in step 2 was reacted with pyridine-3-aldehyde (11 μl) to obtain the title compound (3 mg; 9%).

EXAMPLE 33

Synthesis of 10-bromo-5-hydroxy-2-(3-pyridylmethyl)-3H,7H-pyrido[3,2,1-de]acridin-3,7-dione The compound (100 mg) obtained in Example 32 was suspended in acetic acid (3 mL) and to the suspension was added 47% hydrobromic acid (3 mL). The mixture was heated under reflux for 20 hours. After allowing to cool, the mixture was alkalized with 6N-sodium hydroxide and extracted with ethyl acetate. The ethyl acetate layer was washed with brine and dried over anhydrous sodium sulfate. The solvent was evaporated under reduced pressure. The residue was purified by silica gel column chromatography (eluent: ethyl acetate) to obtain the title compound (69 mg; 71%).

EXAMPLE 34

Synthesis of 10-bromo-5-(3-hydroxypropyloxy)-2-(3-pyridylmethyl)-3H,7H-pyrido[3,2,1-de]acridin-3,7-dione The compound (47 mg) obtained in Example 33 was suspended in DMF (2 mL) and to the suspension was added 3-bromopropanol (11 μL) and potassium carbonate (19 mg) The mixture was stirred at room temperature overnight. After addition of water, the mixture was extracted with ethyl acetate. The ethyl acetate layer was washed with brine and dried over anhydrous sodium sulfate. The solvent was evaporated under reduced pressure. The residue was purified by silica gel column chromatography (eluent: methylene chloride:methanol=100:0~10:1) to obtain the title compound (27 mg; 51%).

EXAMPLE 35

Synthesis of 10-bromo-2-(3-pyridylmethyl)-5-(3-pyridylmethyloxy)-3H,7H-pyrido[3,2,1-de]acridin-3,7-dione According to Example 34, the compound (10 mg) produced in Example 33 was reacted with 3-chloropyridine hydrochloride (6 mg) to obtain the title compound (12 mg; 100%).

EXAMPLE 36

Synthesis of 10-bromo-5-methoxy-2-(3-pyridylmethyl)-3H-pyrido[3,2,1-kl]phenothiazin-3-one Step 1> Synthesis of 2-bromo-7-methoxyphenothiazin-N-β-propionic acid 2-Bromo-7-methoxyphenothiazine(30.8 g) prepared by the literature (Can. J. Chem., 45, 761 (1967)) was dissolved in acetone(1 L) and to the solution were added methyl acrylate(30 mL) and Triton B™ (20 mL) under cooling with ice and the mixture was stirred at room temperature overnight. The solvent was evaporated under reduced pressure.

The residue was purified by silica gel column chromatography (eluent: hexane:ethyl acetate=5:1~0:1) to obtain the methyl ester derivative. The obtained crystal was dissolved in methanol/THF (1:1)(800 mL) and to the solution was added a solution of sodium hydroxide (88 g) in water (88 mL) and the mixture was stirred for 2 hours at room temperature. The solvent was evaporated and the residue was diluted with water and washed with ether. The water layer was further washed with ether and adjusted with 6N-hydrochloric acid to pH 1 and extracted with ethyl acetate. The ethyl acetate layer was washed with brine and dried over anhydrous sodium sulfate. The solvent was evaporated under reduced pressure to obtain the title compound (36.8 g; 59%).

m.p.: 168.9–172.6° C.

IR spectrum (KBr) ν cm$^{-1}$:1707, 1493, 1460, 1286, 1221

NMR spectrum (*CDCl$_3$) δ ppm: 7.08–6.97 (3H, m), 6.84–6.70 (3H, m), 4.14 (2H, t), 3.76 (3H, s),2.87 (2H, t)

Step 2> Synthesis of 10-bromo-5-methoxy-1,2-dihydro-3H-pyrido[3,2,1-kl]phenothiazin-3-one The compound (36.8 g) obtained in <Step 1> was suspended in chloroform (1 L) and to the suspension was added PPE(250 g) in chloroform (1 L) at room temperature. The mixture was heated under reflux for 15 minutes. After allowing to cool, water was added to the mixture, and chloroform layer was separated and aqueous layer was extracted with methylene chloride. The combined organic layer was washed with brine and dried over anhydrous sodium sulfate. The solvent was evaporated under reduced pressure. The residue was washed with hexane:ethyl acetate (1:1) to obtain the title compound and then the filtrate was condensed, washed with ether to obtain the title compound (Total yield: 22.5 g; 64%).

m.p.: 169.5–172.9° C.

IR spectrum (KBr) ν cm$^{-1}$:1684, 1606, 1454, 1431, 1155

NMR spectrum (*DMSO-d$_6$) δ ppm:7.33 (1H, d), 7.19–7.15 (1H, m), 7.13 (1H, d), 7.09–7.05 (2H, m), 4.11 (2H, t), 3.74 (3H, s),2.81(2H, t)

Step 3> Synthesis of 10-bromo-5-methoxy-2-(3-pyridylmethyl)-3H-pyrido[3,2,1-kl]phenothiazin-3-one According to Example 1 <step4>, the compound (12 g) produced in step 2 was reacted with pyridine-3-aldehyde (5 mL) to obtain the title compound (10.3 g; 69%).

EXAMPLE 37

Synthesis of 10-bromo-5-hydroxy-2-(3-pyridylmethyl)-3H-pyrido[3,2,1-kl]phenothiazin-3-one According to Example 33, the compound (10.3 g) produced in Example 36 was reacted to obtain the title compound (10.5 g; 100%).

EXAMPLE 38

Synthesis of 10-bromo-5-(3-hydroxypropyloxy)-2-(3-pyridylmethyl)-3H-pyrido[3,2,1-kl]phenothiazin-3-one According to Example 34, the compound (300 mg) produced in Example 37 was reacted with 3-bromopropanol (78 μL) to obtain the title compound (210 mg; 73%).

EXAMPLE 39

Synthesis of 10-bromo-2-(3-pyridylmethyl)-5-(3-pyridylmethyloxy)- 3H-pyrido[3,2,1-kl]phenothiazin-3-one According to Example 34, the compound (300 mg) produced in Example 37 was reacted with 3-chloromethylpyridine hydrochloride (142 mg) to obtain the title compound (140 mg; 46%).

EXAMPLE 40

Synthesis of 10-bromo-5-(5-methyl-3-pyridylmethyloxy)-2-(3-pyridylmethyl)-3H-pyrido[3,2,1-kl]phenothiazin-3-one According to Example 34, the compound (150 mg) produced in Example 37 was reacted with 3-chloromethyl-5-methylpyridine synthesized from 3,5-dimethylpyridine (500 mg) to obtain the title compound (180 mg; 10%).

EXAMPLE 41

Synthesis of 5-(5-acetoxymethyl-3-pyridylmethyloxy)-10-bromo-2-(3-pyridylmethyl)-3H-pyrido[3,2,1-kl]phenothiazin-3-one According to Example 34, the compound (250 mg) produced in Example 37 was reacted with 3-chloromethyl-5-acetoxymethylpyridine (175 mg) to obtain the title compound (260 mg; 77%).

EXAMPLE 42

Synthesis of 10-bromo-5-(5-hydroxymethyl-3-pyridylmethyloxy)-2-(3-pyridylmethyl)-3H-pyrido[3,2,1-kl]phenothiazin-3-one The compound (220 mg) obtained in Example 41 was suspended in methanol(10 mL) and to the suspension was added dropwise a solution of sodium hydroxide (90 mg) in water (1 mL). The mixture was stirred at room temperature overnight. After the end of reaction, the precipitate crystals were collected by filtration and washed with methanol and ether in turns to obtain the title compound (180 mg; 91%).

EXAMPLE 43

Synthesis of 10-bromo-2-(3-pyridylmethyl)-5-(4-pyridylmethyloxy)-3H-pyrido[3,2,1-kl]phenothiazin-3-one According to Example 34, the compound (150 mg) produced in Example 37 was reacted with 4-chloromethylpyridine hydrochloride (84 mg) to obtain the title compound (98 mg; 54%).

EXAMPLE 44

Synthesis of 10-bromo-2-(3-pyridylmethyl)-5-(2-pyridylmethyloxy)-3H-pyrido[3,2,1-kl]phenothiazin-3-one According to Example 34, the compound (150 mg) produced in Example 37 was reacted with 2-chloromethylpyridine hydrochloride (84 mg) to obtain the title compound (12 mg; 67%).

EXAMPLE 45

Synthesis of 10-bromo-5-benzyloxy-2-(3-pyridylmethyl)-3H-pyrido[3,2,1-kl]phenothiazin-3-one According to Example 34, the compound (100 mg) produced in Example 37 was reacted with benzyl chloride (39 μl) to obtain the title compound (58 mg; 48%).

EXAMPLE 46

Synthesis of 10-bromo-5-(3-dimethylaminopropyloxy)-2-(3-pyridylmethyl)-3H-pyrido[3,2,1-kl]phenothiazin-3-one According to Example 34, the compound (100 mg) produced in Example 37 was reacted with dimethylaminopropylchroride hydrochloride (54 mg) to obtain the title compound (105 mg; 100%).

EXAMPLE 47

Synthesis of 5-(1-benzotriazolylmethyloxy)-10-bromo-2-(3-pyridylmethyl)-3H-pyrido[3,2,1-kl]phenothiazin-3-one According to Example 34, the compound (100 mg) produced in Example 37 was reacted with 1-chloromethyl-benzotriazole (38 mg) to obtain the title compound (90 mg; 84%).

EXAMPLE 48

Synthesis of 10-bromo-5-(1-methyl-hexahydroazepin-4-yloxy)-2-(3-pyridylmethyl)-3H-pyrido[3,2,1-kl]phenothiazin-3-one.

According to Example 34, the compound (100 mg) produced in Example 37 was reacted with 2-(2-chloroethyl)-1-methylpyrrolidine hydrochloride (54 mg) to obtain the ring expanding title compound (46 mg; 37%).

EXAMPLE 49

Synthesis of 10-bromo-5-(2-(4-morpholinyl)ethyloxy)-2-(3-pyridylmethyl)-3H-pyrido[(3,2,1-kl]phenothiazin-3-one According to Example 34, the compound (100 mg) produced in Example 37 was reacted with N-chloroethyl-morpholine (70 mg) to obtain the title compound (60 mg; 56%).

EXAMPLE 50

Synthesis of 10-bromo-5-(2-(1-piperidyl)ethyloxy)-2-(3-pyridylmethyl)-3H-pyrido[(3,2,1-kl]phenothiazin-3-one According to Example 34, the compound (100 mg) produced in Example 37 was reacted with 1-(2-chloroethyl)piperidine (71 mg) to obtain the title compound (48 mg; 45%).

EXAMPLE 51

Synthesis of 10-bromo-5-(2-diisopropylaminoethyloxy-2-(3-pyridylmethyl)-3H-pyrido[3,2,1-kl]phenothiazin-3-one According to Example 34, the compound (100 mg) produced in Example 37 was reacted with diisopropylchloroethylamine hydrochloride (77 mg) to obtain the title compound (45 mg; 41%).

EXAMPLE 52

Synthesis of 5-(2-benzimidazolylmethyloxy)-10-bromo-2-(3-pyridylmethyl)-3H-pyrido [3,2,1-kl]phenothiazin-3-one According to Example 34, the compound (500 mg) produced in Example 37 was reacted with 2-chloromethyl-benzimidazole (243 mg) to obtain the title compound (10 mg; 0.2%).

EXAMPLE 53

Synthesis of 9-bromo-5-methoxy-2-(3-pyridylmethyl)-3H-pyrido[3,2,1-kl]phenothiazin-3-one <Step 1> Synthesis of 3-bromo-7-methoxyphenothiazin-N-β-propionic acid According to Example 36 <stepcoi 3-bromo-7-methoxyphenothiazine(2.4g) prepared by the literature (*Can. J. Chem.*, 45, 761 (1967) ) was converted to the title compound (500 mg; 20%).

m.p.: 157.2–158.9 ° C.

IR spectrum (KBr) ν cm$^{-1}$: 1711, 1493, 1460, 1292, 1261, 1219

NMR spectrum (*DMSO-d$_6$) δ ppm: 7.38–7.32 (2H, m), 6.98 (1H, d), 6.95 (1H, d), 6.83–6.78 (2H, m), 4.05 (2H, t), 3.70 (3H, s),2.62 (2H, t)

<Step 2> Synthesis of 9-bromo-5-methoxy-1,2-dihydro-3H-pyrido[3,2,1-kl]phenothiazin-3-one According to Example 36 <step2>, the compound (100 mg) produced in step 1 was converted to the title compound (540 mg; 71%).

m.p.: 166.7–168.8 ° C.

IR spectrum (KBr) ν cm$^{-1}$: 1678, 1458, 1429, 1213, 1153

NMR spectrum (*DMSO-d6) δ ppm:7.41–7.36 (2H, m), 7.10–7.04 (3H, m), 4.05 (2H, t), 3.72 (3H, s),2.80(2H, t)

<Step 3> Synthesis of 9-bromo-5-methoxy-2-(3-pyridylmethyl)-3H-pyrido[3,2,1-kl]phenothiazin-3-one According to Example 1 <step4>, the compound (540 mg) produced in step 2 was reacted with pyridine-3-aldehyde (0.3 mL) to obtain the title compound (650 mg; 96%).

EXAMPLE 54

Synthesis of 9-bromo-5-hydroxy-2-(3-pyridylmethyl)-3H-pyrido[3,2,1-kl]phenothiazin-3-one According to Example 33, the compound (650 mg) produced in Example 53 was converted to the title compound (460 mg; 72%).

EXAMPLE 55

Synthesis of 9-bromo-5-(3-hydroxypropyloxy)-2-(3-pyridylmethyl)-3H-pyrido[3,2,1-kl]phenothiazin-3-one According to Example 34, the compound (120 mg) produced in Example 54 was reacted with 3-bromopropanol (0.04 mL) to obtain the title compound (72 mg; 53%).

EXAMPLE 56

Synthesis of 9-bromo-2-(3-pyridylmethyl)-5-(3-pyridylmethyloxy)-3H-pyrido[3,2,1-kl]phenothiazin-3-one According to Example 34, the compound (120 mg) produced in Example 54 was reacted with 3-chloromethyl-pyridine hydrochloride (68 mg) to obtain the title compound (138 mg; 95%).

EXAMPLE 57

Synthesis of 10-bromo-5-methoxy-3H-pyrido[3,2,1-kl]phenothiazin-3-one

The compound (2 g) obtained in Example 36 <step 2> was suspended in dioxane (110 mL) and to the suspension was added DDQ (1.88 g). The mixture was heated under reflux for 3 hours. After allowing to cool, to the mixture were added 1N-sodium hydroxide (20 mL) and ethyl acetate(50 mL). The precipitate crystals were collected by filtration and washed with water and ethanol in turns to obtain the title compound (1.41 g; 71%).

EXAMPLE 58

Synthesis of 10-bromo-5-hydroxy-3H-pyrido[3,2,1-kl]phenothiazin-3-one

According to Example 33, the compound (1.4 g) produced in Example 57 was converted to the title compound (1.08 g; 80%).

EXAMPLE 59

Synthesis of l0-bromo-5-(3-hydroxypropyloxy)-3H-pyrido[3,2, 1-kl]phenothiazin-3-one According to Example 34, the compound (145 mg) produced in Example 58 was reacted with 3-bromopropanol (65 µl) to obtain the title compound (62 mg; 36%).

EXAMPLE 60

Synthesis of 10-bromo-5-(3-pyridylmethyloxy)-3H-pyrido [3,2, 1-kl]phenothiazin-3-one According to Example 34, the compound (170 mg) produced in Example 58 was reacted with 3-chloromethylpyridine hydrochloride (155 mg) to obtain the title compound (155 mg; 72%).

EXAMPLE 61

Synthesis of 5-(1-benzotriazolylmethyloxy)-10-bromo-3H-pyrido[3,2,1-kl]phenothiazin-3-one According to Example 34, the compound (120 mg) produced in Example 58 was reacted with 1-chloromethylbenztriazole (87 mg) to obtain the title compound (102 mg; 62%).

EXAMPLE 62

Synthesis of 10-bromo-5-(2-(1-piperidyl) ethyloxy)-3H-pyrido [3,2,1-kl]phenothiazin-3-one According to Example 34, the compound (170 mg) produced in Example 58 was reacted with 1-(2-chloroethyl) piperidine (169 mg) to obtain the title compound (194 mg; 86%).

EXAMPLE 63

Synthesis of 10-bromo-5-methoxy-2-methyl-3H-pyrido [3,2,1-kl]phenothiazin-3-one

A solution of sodium hydride(840 mg) in DMSO(200 mL) was stirred at 60–70° C. for 30 min. After addition of THF (60 mL), the mixture was cooled down to 0° C. To the mixture were added dropwise a solution in DMSO of the compound (7g) obtained in Example 36 <step 2>, then methyl iodide (1.33 mL). After stirring for 1 hour, the mixture was diluted with water and extracted with ethyl acetate. The organic layer was washed with water and brine and dried over anhydrous sodium sulfate. The solvent was evaporated under reduced pressure. The residue was suspended in dioxane (5 mL) and to the suspension was added DDQ (1.22 g). The mixture was heated under reflux for 3 hours. After allowing the reaction mixture to cool to room temperature, IN sodium hydroxide (20 mL) and ethyl acetate (50 mL) were added. The precipitated crystals were collected by filtration and washed with water and ethanol. The resultant compound (1.1 g) was suspended in dioxane (60 mL) and to the suspension was added DDQ (1.2 g). The mixture was heated under reflux for 3 hours. After allowing the reaction mixture to cool to room temperature, to the mixture were added 1N-sodium hydroxide (20 mL) and ethyl acetate(50 mL). The precipitated crystals were collected by filtration and washed with water and ethanol to obtain the title compound (1.1 g; 11%).

EXAMPLE 64

Synthesis of 10-bromo-5-hydroxy-2-methyl-3H-pyrido[3,2,1-kl]phenothiazin-3-one

According to Example 33, the compound (1.1 g) produced in Example 63 was converted to the title compound (717 mg; 67%).

EXAMPLE 65

Synthesis of 10-bromo-5-(3-hydroxypropyloxy)-2-methyl-3H-pyrido[3,2,1-kl]phenothiazin-3-one According to Example 34, the compound (230 mg) produced in Example 64 was reacted with 3-bromopropanol (83,Ul) to obtain the title compound (154 mg; 58%).

EXAMPLE 66

Synthesis of 10-bromo-2-methyl-5-(3-pyridylmethyloxy)-3H-pyrido [3, 2,1-kl] phenothiazin-3-one According to Example 34, the compound (130 mg) produced in Example 64 was converted to the title compound (122 mg; 75%).

EXAMPLE 67

Synthesis of 5-(1-benzotriazolylmethyloxy)-10-bromo-2-methyl-3H-pyrido [3,2,1-kl]phenothiazin-3-one According to Example 34, the compound (100 mg) produced in Example 64 was converted to the title compound (99 mg; 72%).

EXAMPLE 68

Synthesis of 10-bromo-2-methyl-5-(2-(1-piperidyl)-ethyloxy)-3H-pyrido[3,2,1-kl]phenothiazin-3-one According to Example 34, the compound (120 mg) produced in Example 64 was converted to the title compound (117 mg; 74%).

EXAMPLE 69

Synthesis of 2-benzyl-10-bromo-5-methoxy-3H-pyrido[3,2,1-kl]phenothiazin-3-one

According to Example 1 <step 4>, the compound (3 g) produced in Example 36 <step 2> was reacted with benzaldehyde (1.25 mL) to obtain the title compound (1.73 g; 46%).

EXAMPLE 70

Synthesis of 2-benzyl-10-bromo-5-hydroxy-3H-pyrido[3,2,1-kl]phenothiazin-3-one

According to Example 33, the compound (1.72 g) produced in Example 69 was converted to the title compound (1.38 g; 83%).

EXAMPLE 71

Synthesis of 2-benzyl-10-bromo-5-(3-hydroxypropyloxy)-3H-pyrido[3,2,1-kl] phenothiazin-3-one According to Example 34, the compound (147 mg) produced in Example 70 was reacted with 3-bromopropanol (42 µl) to obtain the title compound (57 mg; 34%).

EXAMPLE 72

Synthesis of 2-benzyl-10-bromo-5-(3-pyridylmethyloxy)-3H-pyrido[3,2,1-kl]phenothiazin-3-one According to Example 34, the compound (200 mg) produced in Example 70 was reacted with 3-chloromethylpyridine hydrochloride (145 mg) to obtain the title compound (149 mg; 62%).

EXAMPLE 73

Synthesis of 5-(1-benzotriazolylmethyloxy)-2-benzyl-10-bromo-3H-pyrido[3,2,1-kl]phenothiazin-3-one According to Example 34, the compound (150 mg) produced in Example 70 was reacted with 1-chloromethylbenzotriazole (86 mg) to obtain the title compound (131 mg; 67%).

EXAMPLE 74

Synthesis of 2-benzyl-10-bromo-5-(2-(1-piperidyl)ethyloxy)-3H-pyrido[3,2,1-kl]phenothiazin-3-one According to Example 34, the compound (200 mg) produced in Example 70 was reacted with 1-(2-chloroethyl)piperidine (158 mg) to obtain the title compound (151 mg; 60%).

EXAMPLE 75

Synthesis of 10-bromo-5-methoxy-2-(5-pyrimidinylmethyl)-3H-pyrido[3,2,1-kl]phenothiazin-3-one According to Example 1 <step 4>, the compound (2 g) produced in Example 36 <step 2> was reacted with pyrimidine-5-aldehyde (3.11 g) to obtain the title compound (1.8 g; 72%).

EXAMPLE 76

Synthesis of 10-bromo-5-hydroxy-2-(5-pyrimidinylmethyl)-3H-pyrido[3,2,1-kl]phenothiazin-3-one According to Example 33, the compound (1.65 g) produced in Example 75 was converted to the title compound (640 mg; 40%).

EXAMPLE 77

Synthesis of 10-bromo-5-(3-hydroxypropyloxy)-2-(5-pyrimidinylmethyl)-3H-pyrido[3,2,1-kl]phenothiazin-3-one According to Example 34, the compound (150 mg) produced in Example 76 was reacted with 3-bromopropanol (50 µl) to obtain the title compound (64 mg; 38%).

EXAMPLE 78

Synthesis of 10-bromo-5-(3-pyridylmethyloxy)-2-(5-pyrimidinylmethyl)-3H-pyrido[3,2,1-kl]phenothiazin-3-one According to Example 34, the compound (109 mg) produced in Example 76 was reacted with 3-chloromethylpyridine hydrochloride (62 mg) to obtain the title compound (88 mg; 67%).

EXAMPLE 79

Synthesis of 5-(1-benzotriazolylmethyloxy)-10-bromo-2-(5-pyrimidinylmethyl)-3H-pyrido[3,2,1-kl]phenothiazin-3-one According to Example 34, the compound (120 mg) produced in Example 76 was reacted with 1-chloromethylbenzotriazole (69 mg) to obtain the title compound (118 mg; 76%).

EXAMPLE 80

Synthesis of 10-bromo-5-(2-(1-piperidyl)ethyloxy)-2-(5-pyrimidinylmethyl)-3H-pyrido[3,2,1-kl]phenothiazin-3-one According to Example 34, the compound (110 mg) produced in Example 76 was reacted with 1-(2-chloroethyl)piperidine (69 mg) to obtain the title compound (71 mg; 51%).

EXAMPLE 81

Synthesis of 10-bromo-2-(3-pyridylmethyl)-5-(3-pyridylmethyloxy)-3H-pyrido[3,2,1-kl]phenothiazin-3-one dimethanesulfonate The compound (9.34 g) obtained in Example 39 was suspended in methanol (360 mL) and to the suspension was added methanesulfonic acid (2.35 mL). The solution was condensed under reduced pressure and the residue was crystallized with a small amount of methanol to obtain title compound (12 g; 95%).

The physical data of the compounds in Examples 1 to 81 are shown in Table 3. The structural formulae of the compounds in Examples 1 to 3, 5 to 7 and 9 to 81 are shown in Tables 4 to 21, and Example 4, 8 and 81 are shown in FIG. 3.

| EX. No. | IR (KBr, cm-1) | NMR (ppm) (*: 300Hz, non-mark: 270 MHZ) | m.p. |
|---|---|---|---|
| 1 | 1606, 1556, 1479, 1340, 1326 | DMSO-d6: 8.97(1H, s), 8.60 (1H, d), 8.41–8.34(1H, m), 8.07(1H, d), 7.80–7.73(1H, m), 7.53(1H, d), 7.34–7.22 (3H, m), 7.13(1H, d), 3.84 (2H, s) | 296.7–299.0 |
| 2 | 1599, 1477, 1338, 1319, 1296 | DMSO-d6: 8.90(1H, s), 8.07 (1H, d), 7.52(1H, d), 7.39–7.08(8H, m), 3.84(2H, s) | 250.7–252.9 |
| 3 | 1647, 1612, 1477, 1340, 1315 | DMSO-d6: 8.73(1H, d), 7.98 (1H, d), 7.56(1H, d), 7.35 (1H, d), 7.37–7.12(2H, m), 6.24(1H, d) | >300.0 |
| 4 | 1597, 1560, 1491, 1323, 744 | DMSO-d6: 8.90(1H, s), 8.61 (1H, d), 8.36(1H, dd), 7.91–7.69(2H, m), 7.61(1H, dd), 7.33–7.09(6H, m), 3.86 (2H, s) | 244.3–244.8 |
| 5 | 1632, 1587, 1456, 1275, 789 | DMSO-d6: 8.77(1H, s), 8.60 (1H, d), 8.37(1H, dd), 7.79–7.70(3H, m), 7.61(1H, d), 7.59 (1H, d), 7.49(1H, dd) 7.27 (1H, dd), 3.89(2H, s) | 222.4–224.7 |
| 6 | 1618, 1587, 1576, 1460, 1286 | DMSO-d6: 8.66(1H, s), 7.78 (1H, d), 7.71(1H, d), 7.61 (1H, d), 7.55(1H, d), 7.48 (1H, dd), 7.38–7.11(5H, m), 3.88(2H, s) | 186.9–188.5 |
| 7 | 1645, 1628, 1589, 1541, 1485, 1284 | DMSO-d6: 8.57(1H, d), 7.80 (1H, d), 7.77(1H, d), 7.63 (1H, d), 7.51(1H, d), 7.45 (1H, dd), 6.36(1H, d) | >300.0 |
| 8 | 1620, 1595, 1470, 1279, 744 | DMSO-d6: 8.75(1H, s), 8.62 (1H, s), 8.37(1H, d), 7.88 (1H, dd), 7.82–7.73(1H, m 7.60–7.25(7H, m), 3.91(2H, s) | 199.8–201.5 |

-continued

| EX. No. | IR (KBr, cm-1) | NMR (ppm) (*: 300Hz, non-mark: 270 MHZ) | m.p. |
|---|---|---|---|
| 9 | 1666, 1633, 1599, 1481, 1296 | DMSO-d6: 8.95(1H, s), 8.64 (1H, d), 8.43–8.32(1H, m), 7.94(1H, dd), 7.87(1H, dd), 7.85–7.69(3H, m), 7.54–7.31 (3H, m), 7.28(1H, dd), 3.93 (2H, s), 2.21(3H, s) | 232.3 (dec.) |
| 10 | 1674, 1595, 1483, 1296, 752 | DMSO-d6: 8.83(1H, s), 7.94 (1H, dd), 7.87(1H, dd), 7.76–7.68(2H, m), 7.52–7.32 (5H, m), 7.25(2H, dd), 7.15 (1H, t), 3.91 (2H, s), 2.21 (3H, s) | 190.6–192.1 |
| 11 | 1682, 1630, 1591, 1556, 1367, 1286 | DMSO-d6: 8.74(1H, s), 7.95 (1H, dd), 7.91(1H, d), 7.74 (1H, dd), 7.68(1H, d), 7.55–7.33(3H, m), 6.36(1H, d), 2.23(3H, s) | 275.0 (dec.) |
| 12 | 1551, 1514, 1491, 1317, 739 | DMSO-d6: 9.28 (1H, bs), 8.70 (1H, s), 8.64(1H, s), 8.42 (1H, d), 7.89(1H, d), 7.57 (1H, dd), 7.39(1H, dd), 7.20 (1H, d), 7.08–6.88(2H, m), 6.80(1H, dd), 6.64(1H, d), 6.55(1H, d), 3.86(2H, s) | 235.0 (dec.) |
| 13 | 3248, 1549, 1512, 1309, 735 | DMSO-d6: 9.20(1H, s), 8.56 (1H, s), 7.51(1H, d), 7.39–6.66(9H, m), 6.63(1H, dd), 6.53(1H, dd), 3.82(2H, s) | 271.9 (dec.) |
| 14 | 3425, 1572, 1551, 1510, 1296, 741 | DMSO-d6: 9.24(1H, s), 8.46 (1H, s), 7.47(1H, d), 7.19 (1H, dd), 7.09–6.94(2H, m) 6.81–6.55(3H, m), 6.08(1H, d) | 235.2 (dec.) |
| 15 | 1552, 1365, 1319, 1279, 737 | DMSO-d6: 8.74(1H, s), 8.60 (1H, d), 8.40–8.33(1H, m), 7.77–7.71(1H, m), 7.57(1H, d), 7.33(1H, dd), 7.28–7.10 (3H, m), 6.99–6.93(2H, m), 6.79(1H, dd), 3.86(2 H, s), 3.18(3H, s) | 217.8–219.3 |
| 16 | 1570, 1551, 1489, 1367, 1279, 735 | DMSO-d6: 8.63(1H, s), 7.52 (1H, d), 7.36–6.92(10H, m), 6.79(1H, s), 3.85(2H, s), 3.18(3H, s) | 254.1–256.5 |
| 17 | 1618, 1579 1367, 1277, 735 | CDCl3: 8.01(1H, d), 7.66(1H, m), 7.26–7.01(3H, m), 6.96–6.89(1H, m), 6.80(1H, d) 6.66(1H, d), 6.46(1H, d), 3.23(3H, s) | 232.8–234.5 |
| 18 | 1628, 1471, 1327, 1265, 768 | DMSO-d6: 9.52(1H, s), 8.73–8.63(3H, m), 8.56(1H, d), 8.45–8.37(2H, m), 8.08–8.00 (1H, m), 7.84–7.78(2H, m), 7.64(1H, dd), 7.29(1H, dd), 4.00(2H, s) | 233.7–234.9 |
| 19 | 1632, 1593, 1329, 1267, 756 | DMSO-d6: 9.41(1H, s), 8.70 (1H, dd), 8.64(1H, dd), 8.53 (1H, d), 8.40(1H, dd), 8.06–7.98(1H, m), 7.80(1H, dd) 7.62(1H, dd), 7.45–7.40(2H, m), 7.30–7.23(2H, m), 7.16 (1H, t), 3.36(2H, s) | 209.0–211.6 |
| 20 | 1630, 1471, 1329, 1257, 760 | DMSO-d6: 9.32(1H, d), 8.73 (1H, dd), 8.67(1H, dd) 8.47–8.38(2H, m), 8.04–7.96 (1H, m), 7.84(1H, dd), 7.63 (1H, dd), 6.53(1H, d) | >300.0 |
| 21 | 1657, 1622, 1500, 1329, 802 | DMSO-d6: 9.62(1H, s), 9.26 (2H, s), 8.64(1H, d), 8.56 (1H, d), 8.39(1H, dd), 8.19 (1H, d), 7.83–7.75(2H, m), 7.29(1H, dd), 3.91(2H, s) | 204.0 (dec.) |
| 22 | 1662, 1628, 1497, 1227, 814 | DMSO-d6: 9.65(1H, s), 9.26 (1H, s), 9.05(1H, d), 8.55 (1H, d), 8.23(1H, d), 7.78 (1H, dd), 6.54(1H, d) | 280.0 (dec.) |
| 23 | 1506, 1462, 1329, 1223 | DMSO-d6: 9.18(1H, s), 9.01 (1H, d), 8.64(1H, d), 8.57 (1H, d), 8.50(1H, d), 8.39 (1H, dd), 8.18(1H, d), 7.86 (1H, dd), 7.82–7.75(1H, m), 7.29(1H, dd), 3.92(2H, s) | 263.9–273.2 |
| 24 | 1608, 1579, 1506, 1460, 1219 | DMSO-d6: 9.11(1H, s), 9.00 (1H, d), 8.54(1H, d), 8.48 (1H, d), 8.18(1H, d), 7.84 (1H, dd), 7.39(2H, d), 7.27 (2H, dd), 7.17(1H, t), 3.91 (2H, s) | 289.8–292.7 |
| 25 | 1649, 1616, 1552, 1504, 829 | DMSO-d6: 9.01(1H, d), 8.97 (1H, d), 8.55(1H, d), 8.50 (1H, d), 8.22(1H, d), 7.84 (1H, dd), 6.53(1H, d) | 350.0 (dec.) |
| 26 | 1608, 1566, 1514, 1441, 1331 | DMSO-d6: 9.21(1H, s), 8.99 (1H, d), 8.65(1H, d), 8.48 (1H, d), 8.44–8.37(2H, m) 8.17(1H, d), 7.86–7.77(2H, m), 7.54(1H, dd), 7.29(1H, dd), 3.94(2H, s) | 251.8 (dec.) |
| 27 | 1603, 1566, 1510, 1333, 704 | DMSO-d6: 9.14(1H, s), 8.99 (1H, d), 8.47(1H, d), 8.39 (1H, d), 8.17(1H, d), 7.80 (1H, dd), 7.53(1H, dd), 7.40 (2H, d), 7.27(2H, dd), 7.17 (1H, t), 3.93(2H, s) | 260.6 (dec.) |
| 28 | 1643, 1574, 1506, 1439, 1321 | DMSO-d6: 9.48(1H, s), 9.32 (1H, s), 8.80–8.56(3H, m), 8.49–8.35(1H, m), 8.33(1H, dd), 8.28(1H, d), 7.88–7.70 (2H, m), 7, 29(1H, dd), 3.93 (2H, s) | 216.8–218.6 |
| 29 | 1641, 1601, 1574, 1506, 1435, 1317 | DMSO-d6: 9.47(1H, s), 9.24 (1H, s), 8.75–8.60(2H, m), 8.34–8.21(2H, m), 7.77(1H, dd), 7.41(2H, dd), 7.27(2H, dd), 7.17(1H, t), 3.92(2H, s) | 199.8–203.2 |
| 30 | 1641, 1504, 1454, 1308, 798 | DMSO-d6: 9.51(1H, s), 9.10 (1H, d), 8.74–8.63(2H, m), 8.44–8.36(2H, m), 7.81(1H, dd), 6.49(1H, d) | 211.3 (dec.) |
| 31 | 1603, 1485, 1429, 1325, 1242 | DMSO-d6: 8.92(1H, s), 8.61 (1H, s), 8.35(1H, d), 8.16 (1H, s), 7.80–7.72(1H, m), 7.36(1H, d), 7.26(1H, dd), 7.13–7.00(2H, m), 6.91–6.84 (1H, m), 3.84(2H, s), 3.80 (3H, s) | 277.1–280.3 |
| 32 | 1630, 1589, 1473, 1271 | *DMSO-d6: 9.48(1H, s), 8.85 (1H, s), 8.65(1H, s), 8.36 (1H, d), 8.26(1H, d), 8.13 (1H, d), 8.07(1H, d), 7.85–7.75(2H, m), 7.28(1H, dd), 3.96(5H, s) | 247.5–251.1 |
| 33 | 3400, 1622, 1581, 1462, 1336, 1259 | *DMSO-d6: 9.41(1H, s), 8.80 (1H, s), 8.65(1H, s), 8.42–8.32(1H, m), 8.24–8.16(1H, m), 8.00(1H, d), 7.95(1H, d), 7.82–7.66(2H, m), 7.32–7.21(1H, m), 3.93(2H, s) | >300 |
| 34 | 3425, 1624, 1591, 1460, 1419, 1330, 1267 | *DMSO-d6: 9.41(1H, s), 8.78 (1H, s), 8.66(1H, s), 8.41–8.33(1H, m), 8.22–8.14(1H, m), 8.03(1H, d), 8.00(1H, d), 7.84–7.64(2H, m), 7.33–7.23(1H, m), 4.67–4.57(1H, m), 4.26–4.14(2H, m), 3.94 (2H, s), 3.64–3.52(2H, m), 1.98–1.86(2H, m) | 165.0 (dec.) |
| 35 | 3421, 1626, 1591, 1468, 1419, 1329, 1317, 1267 | *DMSO-d6: 9.50(1H, s), 8.87 (1H, s), 8.74(1H, s), 8.68 (1H, s), 8.61–8.53(1H, m), 8.41–8.33(1H, m), 8.31–8.23 | 262.4–264.6 |

| EX. No. | IR (KBr, cm-1) | NMR (ppm) (*: 300Hz, non-mark: 270 MHZ) | m.p. |
|---|---|---|---|
| | | (2H, m), 8.21–8.16(1H, m), 7.98–7.92(1H, m), 7.84–7.76 (2H, m), 7.49–7.42(1H, m), 7.32–7.25(1H, m), 5.43(2H, s), 3.98(2H, s) | |
| 36 | 1595, 1572, 1425, 1292, 1117, 1045 | *DMSO-$d_6$: 8.78(1H, s), 8.61 (1H, d), 8.36(1H, dd), 7.85 (1H, d), 7.78–7.72(1H, m), 7.52–7.46(1H, m), 7.37(1H, d), 7.31–7.23(3H, m), 3.91 (2H, s), 3.82(3H, s) | 185.7–187.4 |
| 37 | 3122, 1541, 1468, 1427, 1290, 930 | *DMSO-d6: 10.18(1H, brs), 8.95 (1H, s), 8.83(1H, s), 8.75 (1H, d), 8.57(1H, d), 7.99–7.92(1H, m), 7.90(1H, d), 7.53–7.47(1H, m), 7.38(1H, d), 7.17(1H, d), 7.06(1H, d), 4.06(2H, s) | 297.4 (dec.) |
| 38 | 3404, 1574, 1549, 1462, 1055 | DMSO-d6: 8.76(1H, s), 8.59 (1H, d), 8.35(1H, dd), 7.82 (1H, d), 7.77–7.69(1H, m), 7.46(1H, dd), 7.33(1H, d), 7.30–7.12(3H, m), 4.57(1H, t), 4.08(2H, t), 3.89(2H, s), 3.58–3.46(2H, m), 1.92–1.78(2H, m) | 189.1–191.3 |
| 39 | 1618, 1592, 1574, 1462, 1292, 716 | *DMSO-d6: 8.77(1H, s), 8.66 (1H, d), 8.59(1H, d), 8.53 (1H, dd), 8.35(1H, dd), 7.89–7.82(2H, m), 7.76–7.71(1H, m), 7.47(1H, dd), 7.45–7.32 (4H, m), 7.28–7.23(1H, m), 5.23(2H, s), 3.89(2H, s) | 170.8–172.1 |
| 40 | 1620, 1595, 1574, 1551, 1462 | *DMSO-d6: 8.79(1H, s), 8.63–8.58(1H, m), 8.51–8.45(1H, m), 8.42–8.34(2H, m), 7.88–7.83(1H, m), 7.78–7.67(2H, m), 7.52–7.24(5H, m), 5.20 (2H, s), 3.91(2H, s), 2.31 (3H, s) | 172.4–173.6 |
| 41 | 1734, 1622, 1599, 1576, 1460, 1244 | *DMSO-d6: 8.78(1H, s), 8.64 (1H, s), 8.61(1H, s), 8.57 (1H, s), 8.37(1H, d), 7.89 (1H, s), 7.84(1H, s), 7.75 (1H, d), 7.48(1H, d), 7.43–7.41(3H, m), 7.27(1H, dd), 5.25(2H, s), 5.14(2H, s), 3.91(2H, s), 2.07(3H, s) | 181.0–182.9 |
| 42 | 3392, 1618, 1597, 1574, 1551, 1462 | *DMSO-d6: 8.76(1H, s), 8.61 (1H, d), 8.55(1H, d), 8.51–8.46(1H, m), 8.38–8.31(1H, m), 7.87–7.83(1H, m), 7.81 (1H, m), 7.75(1H, d), 7.52–7.46(1H, m), 7.42–7.33(3H, m), 7.30–7.23(1H, m), 5.38 (1H, t), 5.24(2H, s), 4.55 (2H, d), 3.91(2H, s) | 232.5–233.1 |
| 43 | 1620, 1595, 1574, 1551, 1462 | *DMSO-d6: 8.78(1H, s), 8.63–8.55(3H, m), 8.38–8.34(1H, m), 7.84(1H, d), 7.77–7.71 (1H, m), 7.52–7.32(6H, m), 7.26(1H, dd), 5.28(2H, s), 3.90(2H, s) | 194.2–196.1 |
| 44 | 1620, 1599, 1589, 1572, 1551, 1462, 1433 | *DMSO-d6: 8.78(1H, s), 8.63–8.55(2H, m), 8.36(1H, dd), 7.87–7.71(3H, m), 7.54–7.30 (6H, m), 7.27(1H, dd), 5.27 (2H, s), 3.89(2H, s) | 94.6–96.4 |
| 45 | 1622, 1595, 1574, 1551, 1462 | *DMSO-d6: 8.78(1H, s), 8.60 (1H, d), 8.36(1H, dd), 7.84 (1H, d), 7.73–7.72(1H, m), 7.52–7.24(10H, m), 5.19(2H, s), 3.90(2H, s) | 174.9–176.0 |
| 46 | 1620, 1595, 1574, 1462, 1385 | *DMSO-$d_6$: 8.77(1H, s), 8.59 (1H, d), 8.35(1H, dd), 7.83 (1H, d), 7.77–7.70(1H, m), | 160.3–163.3 |
| | | 7.47(1H, dd), 7.36(1H, d), 7.29–7.21(3H, m), 4.05(2H, t), 3.89(2H, s), 2.37(2H, t), 2.15(6H, s), 1.90–1.80 (2H, m) | |
| 47 | 1620, 1599, 1462, 1288, 1051 | *DMSO-d6: 8.78(1H, s), 8.61 (1H, d), 8.37(1H, dd), 8.10 (1H, d), 7.98(1H, d), 7.83 (1H, d), 7.74(1H, d), 7.67–7.58(2H, m), 7.51–7.33(4H, m), 7.28(1H, dd), 6.87(2H, s), 3.90(2H, s) | 252.5–255.1 |
| 48 | 2929, 1618, 1593, 1572, 1462 | *CDCl3: 8.61(1H, d), 8.48 (1H, dd), 7.81(1H, s), 7.72 (1H, dt), 7.42(1H, d), 7.29 (1H, dd), 7.24(1H, dd), 7.15 (1H, d), 7.08(1H, d), 6.97 (1H, d), 4.73–4.62(1H, m), 3.98(2H, s), 2.72(1H, ddd), 2.64–2.57(2H, m), 2.51(1H, ddd), 2.36(1H, dd), 2.28–1.77 (5H, m), 1.73–1.57(1H, m) | 162.3–165.8 |
| 49 | 1618, 1593, 1574, 1549, 1462, 1117 | *DMSO-d6: 8.78(1H, s), 8.60 (1H, d), 8.36(1H, dd), 7.85 (1H, d), 7.75(1H, ddd), 7.49 (1H, dd), 7.38(1H, d), 7.30–7.23(3H, m), 4.15(2H, t), 3.91(2H, s), 3.56(4H, t), 2.68(2H, t), 2.50–2.40(4H, m) | 173.5–175.0 |
| 50 | 2935, 1620, 1595, 1574, 1549, 1460, 1290 | *CDCl3: 8.62(1H, d), 8.49 (1H, dd), 7.80(1H, s), 7.72 (1H, ddd), 7.46(1H, d), 7.31 (1H, dd), 7.26–7.22(1H, m), 7.15(1H, d), 7.11(1H, d), 7.04(1H, d), 4.18(2H, t), 3.99(2H, s), 2.78(2H, t), 2.53–2.46(4H, m), 1.70–1.40 (6H, m) | 166.5–169.0 |
| 51 | 2966, 1620, 1597, 1574, 1460 | *CDCl3: 8.62(1H, d), 8.48 (1H, dd), 7.80(1H, s), 7.73 (1H, ddd), 7.48(1H, d), 7.31 (1H, dd), 7.26–7.24(1H, m), 7.15(1H, d), 7.11(1H, d), 7.00(1H, d), 3.99(2H, s), 3.97(2H, t), 3.11–2.96(2H, m), 2.83(2H, t), 1.03(12H, d) | 169.0–171.0 |
| 52 | 3338, 1630, 1589, 1423, 1261 | *DMSO-d6: 8.54–8.48(2H, m), 8.28(1H, d), 7.67–7.64(1H, m), 7.55–7.45(2H, m), 7.40–7.31(3H, m), 7.25–7.11(2H, m), 7.09–6.98(3H, m), 4.86 (2H, s), 3.80(2H, s) | 203.0 (dec.) |
| 53 | 1618, 1591, 1489, 1466 | *DMSO-d6: 8.69(1H, s), 8.59 (1H, d), 8.35(1H, d), 7.73 (1H, d), 7.68(1H, d), 7.58 (1H, dd), 7.50(1H, d), 7.28–7.21(3H, m), 3.87(2H, s) 3.80(3H, s) | 137.3–138.1 |
| 54 | 3429, 1616, 1572, 1468, 1313, 1290 | *DMSO-d6: 10.15(1H, s), 8.66 (1H, s), 8.59(1H, d), 8.37 (1H, d), 7.74(1H, ddd), 7.68 (1H, d), 7.58(1H, dd), 7.49 (1H, d), 7.27(1H, dd), 7.19 (1H, d), 7.03(1H, d), 3.86 (2H, s) | >300 |
| 55 | 3433, 1618, 1591, 1464, 1277 | *DMSO-d6: 8.71(1H, s), 8.60 (1H, dd), 8.37(1H, dd), 7.77–7.72(1H, m), 7.70(1H, d) 7.59(1H, dd), 7.51(1H, d), 7.29–7.23(3H, m), 4.58(1H, t), 4.10(2H, t), 3.88(2H, s), 3.54(2H, dt), 1.86(2H, tt) | 215.7–218.4 |

| EX. No. | IR (KBr, cm-1) | NMR (ppm) (*: 300Hz, non-mark: 270 MHZ) | m.p. |
|---|---|---|---|
| 56 | 1622, 1599, 1576, 1466, 1427 | *DMSO-d6: 8.71(1H, s), 8.68 (1H, d), 8.60(1H, d), 8.55 (1H, dd), 8.37(1H, dd), 7.90–7.85(1H, m), 7.77–7.72(1H, m), 7.71(1H, d), 7.60(1H, dd), 7.52(1H, d), 7.43(1H, dd), 7.39(1H, d), 7.36(1H, d), 7.27(1H, d), 5.24(2H, s), 3.89(2H, s) | 226.5–228.1 |
| 57 | 1637, 1602, 1573, 1551, 1464 | DMSO-d6: 8.49(1H, d), 7.67 (1H, d), 7.45(1H, dd), 7.36–7.30(2H, m), 7.21(1H, d), 6.26(1H, d), 3.85(3H, s) | >300.0 |
| 58 | 3176, 1656, 1610, 1591, 1466 | *DMSO-d6: 10.19(1H, s), 8.52 (1H, d), 7.71–7.68(1H, m), 7.50–7.44(1H, m), 7.35(1H, d), 7.21(1H, dd), 7.06 (1H, dd), 6.20(1H, d) | >300.0 |
| 59 | 3392, 1628, 1603, 1593, 1460 | *DMSO-d6: 8.57(1H, d), 7.73 (1H, d), 7.49(1H, dd), 7.38 (1H, d), 7.29(1H, d), 7.27 (1H, d), 6.26(1H, d), 4.60 (1H, t), 4.12(2H, t), 3.61–3.51 (2H, m), 1.93–1.83(2H, m) | 221.8–223.6 |
| 60 | 1647, 1626, 1599, 1576, 1462 | DMSO-d6: 8.70(1H, bs), 8.63–8.51(2H, m), 7.90(1H, d), 7.71(1H, bs), 7.53–7.31(5H, m), 6.27(1H, d), 5.27(2H, s) | 209.2–212.5 |
| 61 | 1632, 1606, 1576, 1547, 1460 | *DMSO-d6: 8.58(1H, d), 8.10 (1H, d), 8.00(1H, d), 7.71 (1H, s), 7.68–7.61(2H, m), 7.52–7.43(3H, m), 7.37(1H, d), 6.91(2H, s), 6.28(1H, d) | 120.6–124.7 |
| 62 | 2933, 1632, 1603, 1574, 1458 | DMSO-d6: 8.56(1H, d), 7.71 (1H, d), 7.47(1H, dd), 7.36 (1H, d), 7.28(1H, d), 7.27 (1H, d), 6.25(1H, d), 4.15 (2H, t), 2.66(2H, t), 2.47–2.35(4H, m), 1.57–1.31(6H, m) | 131.8–144.3 |
| 63 | 1624, 1597, 1574, 1554, 1462 | DMSO-d6: 8.50(1H, s), 7.77 (1H, d), 7.44(1H, dd), 7.33 (1H, d), 7.29(1H, d), 7.23 (1H, d), 3.82(3H, s), 2.08 (3H, s) | 231.7–233.7 |
| 64 | 3288, 1618, 1572, 1489, 1462 | *DMSO-d6: 10.09(1H, s), 8.47 (1H, s), 7.79–7.75(1H, m), 7.47–7.42(1H, m), 7.33(1H, d), 7.22(1H, d), 7.02(1H, d), 2.07(3H, s) | >300.0 |
| 65 | 3396, 1630, 1622, 1594, 1574 | *DMSO-d6: 8.51(1H, s), 7.79 (1H, d), 7.45(1H, dd), 7.34 (1H, d), 7.29(1H, d), 7.22(1H, d), 4.61–4.56(1H, m), 4.14–4.06(2H, m), 3.61–3.52(2H, m), 2.09(3H, s), 1.93–1.82(2H, m) | 188.9–197.8 |
| 66 | 1626, 1597, 1574, 1551, 1462 | *DMSO-d6: 8.74(1H, d), 8.60 (1H, dd), 8.53(1H, s), 8.01–7.95(1H, m), 7.88(1H, d), 7.54–7.44(2H, m), 7.42(1H, d), 7.38–7.34(2H, m), 5.28 (2H, s), 2.09(3H, s) | 148.3–158.0 |
| 67 | 1630, 1603, 1574, 1552, 1462 | *DMSO-d6: 8.52(1H, s), 8.10 (1H, d), 8.00(1H, d), 7.78 (1H, d), 7.67–7.61(2H, m), 7.50–7.40(3H, m), 7.35(1H, d), 6.90(2H, s), 2.08(3H, s) | 205.9–215.5 |
| 68 | 2933, 1630, 1622, 1595, 1574 | *DMSO-d6: 8.51(1H, s), 7.79 (1H, d), 7.45(1H, dd), 7.34 (1H, d), 7.29(1H, d), 7.24 (1H, d), 4.14(2H, t), 2.66 (2H, t), 2.47–2.39(4H, m), 2.09(3H, s), 1.55–1.34(6H, m) | 184.1–186.0 |
| 69 | 1626, 1593, 1574, 1549, 1466 | DMSO-d6: 8.68(1H, s), 7.79 (1H, d), 7.48(1H, dd), 7.38–7.32(3H, m), 7.30–7.21(4H, m), 7.18–7.11(1H, m), 3.91 (2H, s), 3.82(3H, s) | 218.1–219.3 |
| 70 | 3230, 1618, 1591, 1574, 1549 | DMSO-d6: 8.62(1H, s), 7.76 (1H, d), 7.46(1H, dd), 7.37–7.31(3H, m), 7.29–7.11(4H, m), 7.02(1H, d), 3.89(2H, s) | 268.1–274.3 |
| 71 | 3348, 1620, 1591, 1574, 1549 | *DMSO-d6: 8.68(1H, s), 7.79 (1H, d), 7.47(1H, dd), 7.38–7.33(3H, m), 7.29–7.22(4H, m), 7.18–7.12(1H, m), 4.59 (1H, t), 4.10(2H, t), 3.91 (2H, s), 3.59–3.50(2H, m), 1.92–1.81(3H, m) | 152.0–168.3 |
| 72 | 1622, 1595, 1574, 1551, 1460 | *DMSO-d6: 8.71–8.67(2H, m), 8.55(1H, dd), 7.81–7.70(1H, m), 7.80(1H, d), 7.50–7.32 (7H, m), 7.28–7.22(2H, m), 7.18–7.12(1H, m), 5.25(2H, s), 3.91(2H, s) | 158.3–160.5 |
| 73 | 1622, 1595, 1572, 1552, 1458 | *DMSO-d6: 8.68(1H, s), 8.09 (1H, d), 7.99(1H, d), 7.77 (1H, d), 7.66–7.59(2H, m), 7.49–7.43(2H, m), 7.40(1H, d), 7.35(3H, d), 7.29–7.23 (2H, m), 7.18–7.12(1H, m), 6.88(2H, s), 3.90(2H, s) | 232.1–233.6 |
| 74 | 2933, 1630, 1622, 1599, 1572 | *DMSO-d6: 8.67(1H, s), 7.79 (1H, d), 7.47(1H, dd), 7.38–7.32(3H, m), 7.28–7.21(4H, m), 7.18–7.11(1H, m), 4.12 (2H, t), 3.91(2H, s), 2.64 (2H, t), 2.46–2.38(4H, m), 1.52–1.32(6H, m) | 174.9–176.4 |
| 75 | 1622, 1597, 1572, 1464, 1406 | *DMSO-d6: 8.99(1H, s), 8.84–8.80(3H, m), 7.87(1H, d), 7.47(1H, dd), 7.33(1H, d), 7.25(1H, d), 7.21(1H, d), 3.90(2H, s), 3.81(3H, s) | 206.6–210.7 |
| 76 | 3230, 1618, 1570, 1464 | *DMSO-d6: 10.16(1H, s), 9.00 (1H, s), 8.82(2H, s), 8.78 (1H, s), 7.87(1H, s), 7.50–7.45(1H, m), 7.35(1H, d) 7.18(1H, d), 7.03(1H, d), 3.88(2H, s) | >300.0 |
| 77 | 3433, 1618, 1589, 1573, 1461 | DMSO-d6: 8.99(1H, s), 8.82 (3H, s), 7.89(1H, d), 7.49 (1H, dd), 7.37(1H, d), 7.37–7.34(2H, m), 4.57(1H, t), 4.15–4.05(2H, m), 3.90(2H, s), 3.58–3.31(2H, m), 1.92–1.79(2H, m) | 192.2–229.2 |
| 78 | 1622, 1595, 1576, 1551, 1460 | *DMSO-d6: 9.00(1H, s), 8.82 (3H, s), 8.68–8.66(1H, m), 8.56–8.54(1H, m), 7.92–7.86 (2H, m), 7.53–7.48(1H, m), 7.47–7.36(5H, m), 5.21(2H, s), 3.90(2H, s) | 98.9–102.0 |
| 79 | 1620, 1599, 1576, 1554, 1462 | *DMSO-d6: 9.00(1H, s), 8.82 (3H, s), 8.09(1H, d), 7.98 (1H, d), 7.89–7.87(1H, m), 7.67–7.60(2H, m), 7.53–7.37 (4H, m), 6.88(2H, s), 3.89 (2H, s) | 249.9–257.1 |
| 80 | 2935, 1621, 1589, 1583, 1460 | DMSO-d6: 8.99(1H, s), 8.82 (3H, s), 7.89(1H, d), 7.49 (1H, dd), 7.37(1H, d), 7.26 (2H, s), 4.12(2H, t), 3.87 (2H, s), 2.64(2H, t), 2.48–2.38(4H, m), 1.67–1.30(6H, m) | 80.5–83.7 |
| 81 | 3433, 1614, 1591, 1570, 1552, 1466, | CD3OD: 9.03(1H, s), 8.94(1H, s), 8.89–8.65(5H, m), 8.19–8.11(1H, m), 8.05–7.96(1H, | 238.7–242.3 |

-continued
| EX. No. | IR (KBr, cm-1) | NMR (ppm) (*: 300Hz, non-mark: 270 MHZ) | m.p. |
|---|---|---|---|
| | 1209, 1192, 1057, 787 | m), 7.82(1H, d), 7.53–7.44 (2H, m), 7.37(1H, d), 7.29 (1H, d), 5.44(2H, s), 4.21 (2H, s), 2.69(6H, s) | |
TABLE 4
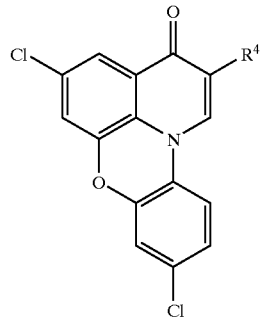
| EX. No. | R⁴ |
|---|---|
| 1 | 3-pyridyl-CH₂ |
| 2 | benzyl |
| 3 | H |
TABLE 5
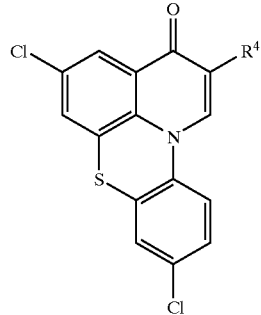
| EX. No. | R⁴ |
|---|---|
| 5 | 3-pyridyl-CH₂ |
| 6 | benzyl |
| 7 | H |
TABLE 6
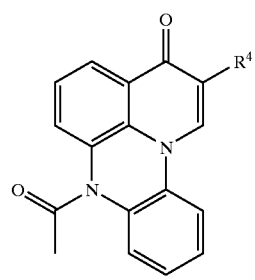
| EX. No. | R⁴ |
|---|---|
| 9 | 3-pyridyl-CH₂ |
| 10 | benzyl |
| 11 | H |
TABLE 7
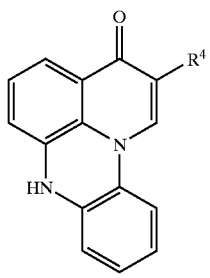
| EX. No. | R⁴ |
|---|---|
| 12 | 3-pyridyl-CH₂ |
| 13 | benzyl |
| 14 | H |

TABLE 8
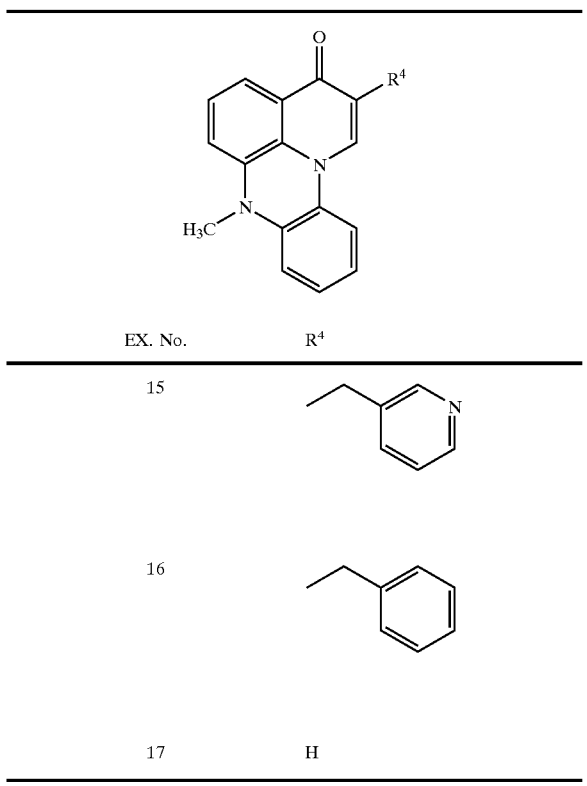
| EX. No. | R⁴ |
|---|---|
| 15 | 3-pyridylmethyl |
| 16 | benzyl |
| 17 | H |
TABLE 9
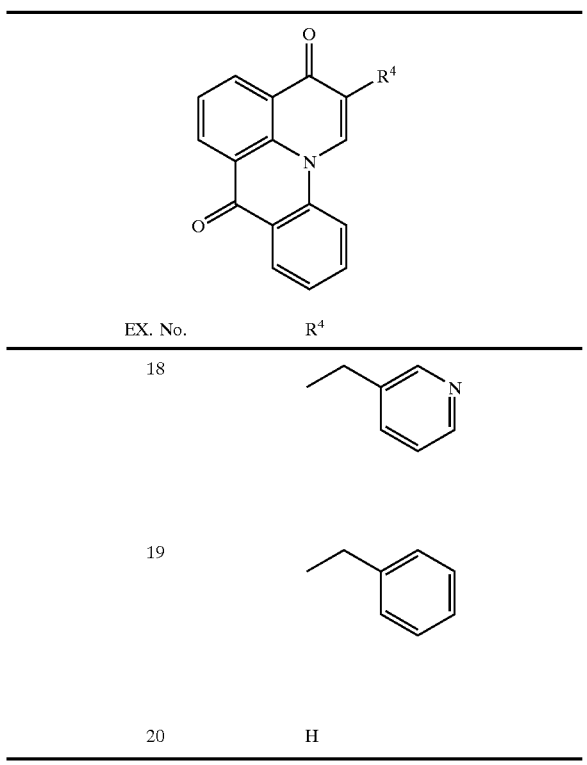
| EX. No. | R⁴ |
|---|---|
| 18 | 3-pyridylmethyl |
| 19 | benzyl |
| 20 | H |
TABLE 10
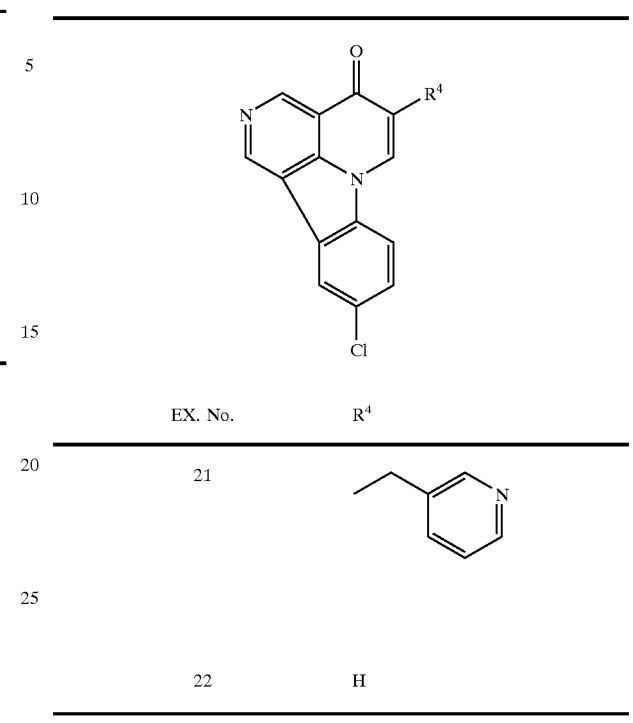
| EX. No. | R⁴ |
|---|---|
| 21 | 3-pyridylmethyl |
| 22 | H |
TABLE 11
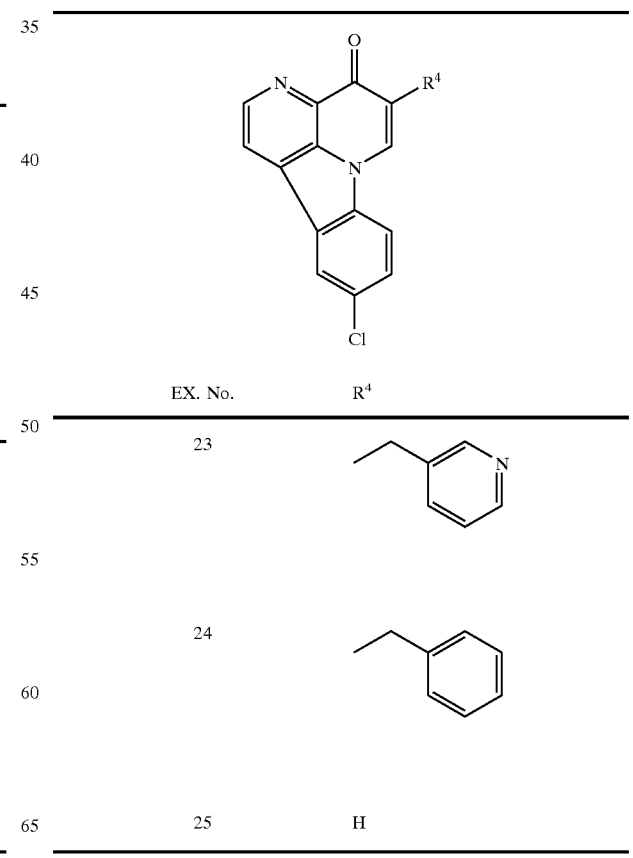
| EX. No. | R⁴ |
|---|---|
| 23 | 3-pyridylmethyl |
| 24 | benzyl |
| 25 | H |

TABLE 12
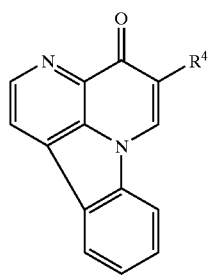
| EX. No. | R⁴ |
|---|---|
| 26 | 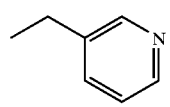 |
| 27 | 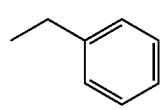 |
TABLE 13
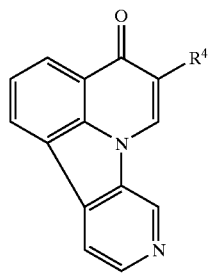
| EX. No. | R⁴ |
|---|---|
| 28 | 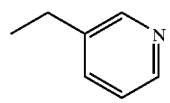 |
| 29 | 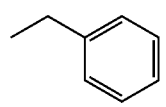 |
| 30 | H |
TABLE 14
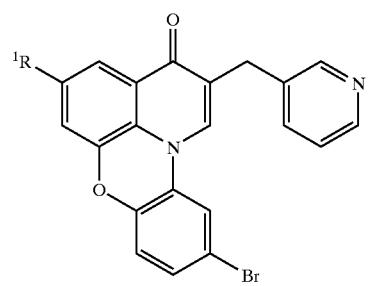
| EX. No. | R¹ |
|---|---|
| 31 | OCH₃ |
TABLE 15
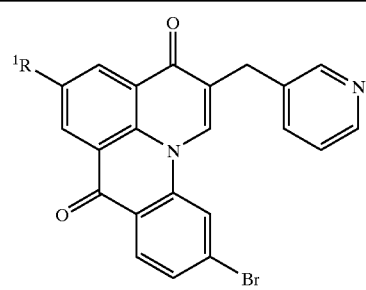
| EX. No. | R¹ |
|---|---|
| 32 | OCH₃ |
| 33 | OH |
| 34 | OCH₂CH₂CH₂OH |
| 35 | 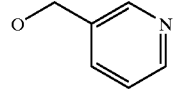 |
TABLE 16
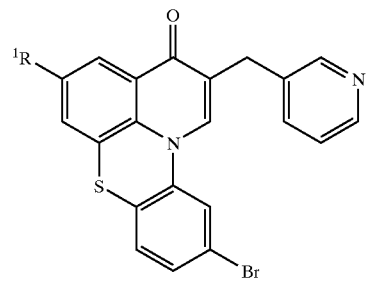
| EX. No. | R¹ |
|---|---|
| 36 | OCH₃ |
| 37 | OH |
| 38 | OCH₂CH₂CH₂OH |
| 39 | 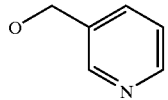 |

TABLE 16-continued
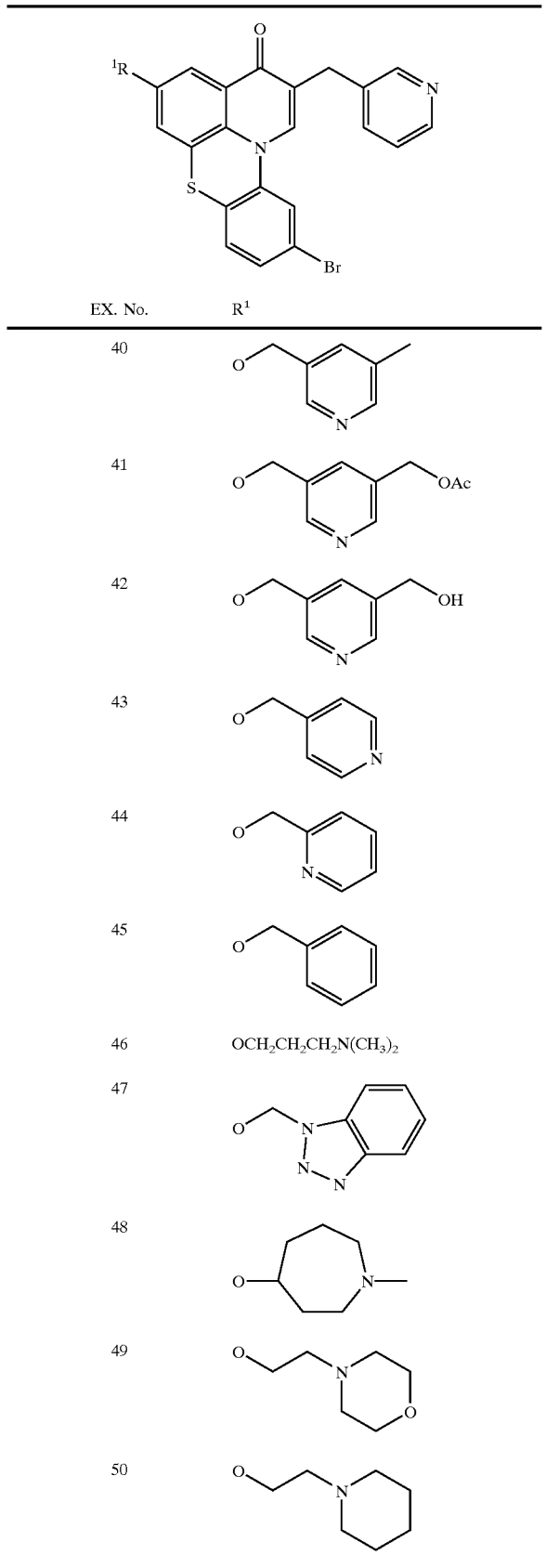
TABLE 16-continued
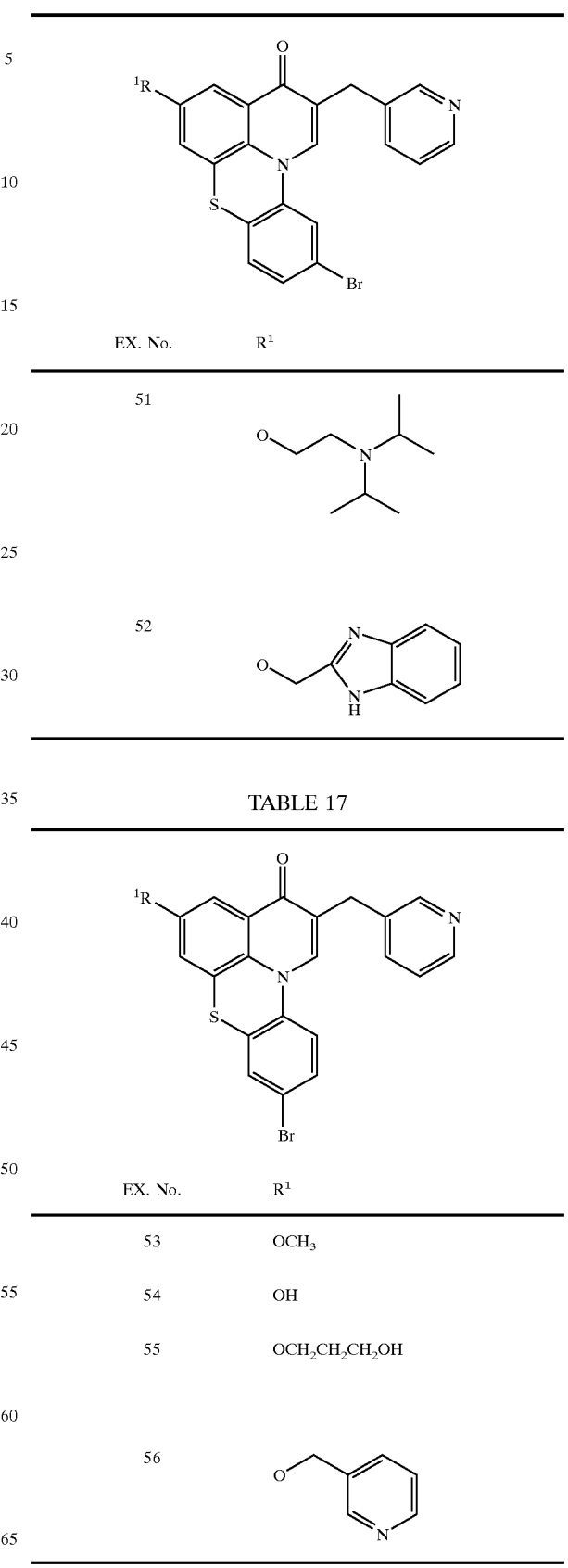
TABLE 17

TABLE 18
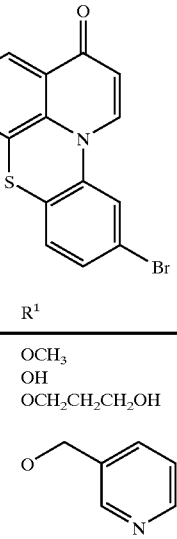
| EX. No. | R¹ |
|---|---|
| 57 | OCH₃ |
| 58 | OH |
| 59 | OCH₂CH₂CH₂OH |
| 60 | 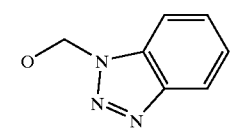 |
| 61 | 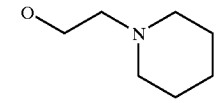 |
| 62 | 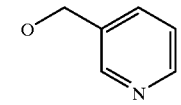 |
TABLE 19
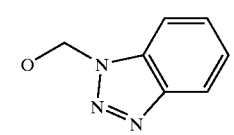
| EX. No. | R¹ |
|---|---|
| 63 | OCH₃ |
| 64 | OH |
| 65 | OCH₂CH₂CH₂OH |
| 66 | 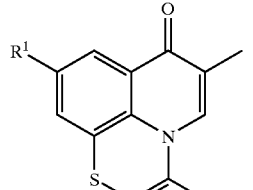 |
| 67 | 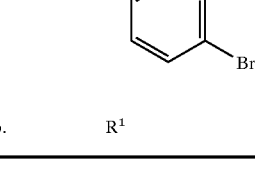 |
TABLE 19-continued
| EX. No. | R¹ |
|---|---|
| 68 | 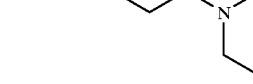 |
TABLE 20
| EX. No. | R¹ |
|---|---|
| 69 | OCH₃ |
| 70 | OH |
| 71 | OCH₂CH₂CH₂OH |
| 72 | 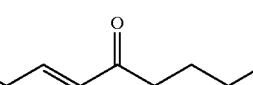 |
| 73 | 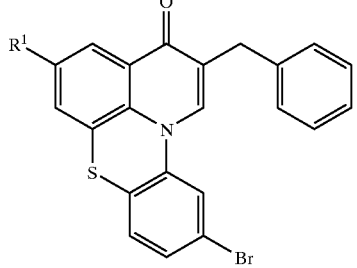 |
| 74 | 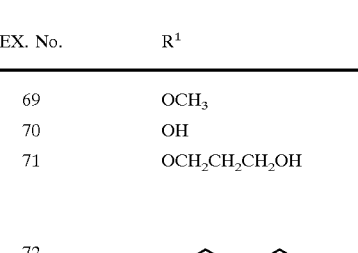 |

TABLE 21

| EX. No. | R¹ |
|---|---|
| 75 | OCH₃ |
| 76 | OH |
| 77 | OCH₂CH₂CH₂OH |
| 78 | (3-pyridylmethoxy) |
| 79 | (benzotriazol-1-ylmethoxy) |
| 80 | (2-piperidinoethoxy) |

The following are non-limiting examples of the pharmaceutical formulations containing the compounds of the invention.

| (Formulation 1: Tablet) | |
|---|---|
| Compound of Example 34 | 100 g |
| Lactose | 350 g |
| Potato starch | 120 g |
| Polyvinyl alcohol | 15 g |
| Magnesium stearate | 15 g |

The above components were weighed and then the compound of Example 34, lactose and potato starch were mixed uniformly. An aqueous polyvinyl alcohol solution was added to the mixture and granules were prepared by wet granulation method. The granules were dried, mixed with magnesium stearate and compressed to tablets each weighing 300 mg.

| (Formulation 2: Capsule) | |
|---|---|
| Compound of Example 50 | 50 g |
| Lactose | 435 g |
| Magnesium stearate | 15 g |

The above components were weighed and then mixed uniformly. By means of a capsule-filling machine, the mixture was filled into suitable hard capsules in 300-mg portions to prepare capsules.

| (Formulation 3: Injection) | |
|---|---|
| Compound of Example 26 | 2 g |
| Propylene glycol | 200 g |
| Water for injection | q.s. |

The above components were weighed and then the compound of Example 26 was dissolved in propylene glycol. The sterile water for injection was added to make a total of 1,000 mL; following sterilizing filtration, the solution was put in 5-mL portions into 10-mL ampules, which were fused and sealed to prepare injections.

| (Formulation 4: Suppository) | |
|---|---|
| Compound of Example 8 | 100 g |
| Polyethylene glycol 1500 | 180 g |
| Polyethylene glycol 4000 | 720 g |

The compound of Example 8 was sufficiently ground in a mortar to prepare a fine powder, which was then prepared into suppositories, each of 1 g, by a fusing method.

| (Formulation 5: Powder) | |
|---|---|
| Compound of Example 4 | 200 g |
| Lactose | 790 g |
| Magnesium stearate | 10 g |

The above components were weighed and then mixed uniformly to prepare a 20% powder.

| (Formulation 6: liquid for intranasal administration) | |
|---|---|
| Compound of Example 26 | 3 g |
| Citric acid | 6 g |
| Benzalkonium chloride | 50 mg |

The above components were weighed and dissolved in purified water uniformly to make a total of 100 mL. The solution was filtered through a 0.2-μm filter and dispensed in 3.0-mL portions into quantitative sprayer capable of spraying 0.05–0.1 mL of the solution per stroke.

| (Formulation 7: liquid for intranasal administration) | |
|---|---|
| Compound of Example 26 | 3 g |
| HCO-60 | 10 g |
| Benzalkonium chloride | 50 mg |

The above components were weighed and the preparation was manufactured by the same manner as in Formulation 6.

| (Formulation 8: liquid for intranasal administration) | |
|---|---|
| Compound of Example 26 | 3 g |

This component was weighed and dissolved uniformly in glycerin to make a total of 100 mL.

| (Formulation 9: powder for intranasal administration) | |
|---|---|
| Compound of Example 39 | 300 mg |
| Crystalline cellulose | 9.7 g |

The above components were weighed and mixed uniformly. For assisting in setting on a nasal sprayer, the mixture was dispensed in 20-mg portions into hard gelatin capsules.

| (Formulation 10: powder for intranasal administration) | |
|---|---|
| Compound of Example 39 | 300 mg |
| Hydroxypropyl cellulose | 9.7 g |

The above components were weighed and the preparation was manufactured by same manner as in Formulation 9 to make a powder for intranasal administration.

| (Formulation 11: powder for intranasal administration) | |
|---|---|
| Compound of Example 39 | 300 mg |
| Lactose | 9.7 g |

The above components were weighed and the preparation was manufactured by same manner as in Formulation 9 to make a powder for intranasal administration.

| (Formulation 12: oil-base ointment) | |
|---|---|
| Compound of Example 47 | 5 g |
| Propylene glycol | 50 g |
| Propylene glycol monostearate | 7.5 g |
| Isopropyl adipate | 5 g |
| White soft paraffine | 32.5 g |

Compound of Example 47 was dissolved in propylene glycol and then other components were added thereto. The mixture was warmed at about 60° C. with vigorous stirring to mix homogeneously.

| (Formulation 13: oil-base ointment) | |
|---|---|
| Compound of Example 26 | 5 g |
| Glycerin | 50 g |
| Propylene glycol monostearate | 7.5 g |
| Isopropyl adipate | 5 g |
| White soft paraffine | 32.5 g |

The above components were weighed and mixed uniformly.

| (Formulation 14: water-soluble ointment) | |
|---|---|
| Compound of Example 26 | 5 g |
| Glycerin | 70 g |
| Starch | 10 g |
| Methylparaben | 0.1 g |
| Propylparaben | 0.1 g |

The above components were weighed and all components except starch were homogeneously mixed. To the mixture was added starch little by little with stirring. Purified water was added to make a total of 100 g.

| (Formulation 15: water-soluble gel) | |
|---|---|
| Compound of Example 26 | 10 g |
| Citric acid | 6 g |
| Hydroxypropylmethylcellulose 2208 (nominal viscosity: 4000) | 1.5 g |
| Methylparaben | 0.1 g |
| Propylparaben | 0.1 g |

The above components were weighed and all components except hydroxypropylmethylcellulose 2208 were homogeneously mixed. The mixture was dissolved in about 70 g of purified water and then hydroxypropylmetylcellulose 2208 was added thereto little by little with stirring. Purified water was added to make a total of 100 g.

| (Formulation 16: Disintegrators in oral cavity) | |
|---|---|
| Compound of Example 55 | 50 g |
| Xylitol | 1100 g |
| Maltitol | 200 g |
| Corn starch | 626 g |
| Aspartame | 4 g |
| Acacia | 20 g |

The above components were weighed and were mixed for one minute by a stirring granulator, and then 32 ml of water was added and the mixture was kneaded. About 800 tablets were obtained by compressing at a pressure of 10 Kg/cm$^2$ (power: 30 kg) using a flat end punch of $\phi$ 20mm in a single punch tableting machine.

(Formulation 17: Disintegrators in Oral Cavity)

Granulation was performed in a fluidized bed granulator using 8 kg of mannitol and 2.67 kg of 15% maltose aqueous solution and the granules were dried. At this time, fine particle coating was performed at an atomizing pressure of 3.0 kg/cm$^2$ until the amount of maltose aqueous solution reached 1.0 kg, after which granulation was performed. 0.9 g of the compound of Example 56, 0.2 g of gelatin and 0.9 g of mannitol were weighed and mixed in a mortar. After being combined with 7 g of previously granulated mannitol, the mixture was compressed at a pressure of 20 kg/cm$^2$ using a punch of $\phi$ 8 mm and 9.6 mmR in a hydraulic press to obtain tablets each weighing 300 mg.

| (Formulation 18: Intraurethral suppository) | |
|---|---|
| Compound of Example 81 | 58.2 g |
| Polyethylene glycol 1500 | 180 g |
| Polyethylene glycol 4000 | 720 g |

The compound of Example 81 was sufficiently ground in a mortar to prepare fine powder, and then polyethylene glycol 1500 (180g) and polyethylene glycol 4000 (720 g) were melted at 120° C., and then the mixture was combined homogeneously. The mixture was cooled to 40° C., and then was filled in a polyethylene tube ($\phi$ 3 mm), and after it became solid by cooling, was cut into 7.0 cm portions. Each of the thus prepared suppositories contains 30 mg of the compound of Example 81.

| (Formulation 19: Intraurethral cream) | |
|---|---|
| Compound of Example 81 | 1.2 g |
| Propylene glycol | 12 g |
| Stearyl alcohol | 20 g |
| White vaserine | 25 g |
| HCO-60 | 4 g |
| Glyceryl monostearate | 1 g |
| Methylparaben | 0.1 g |
| Propylparaben | 0.1 g |

Stearyl alcohol, white vaseline, HCO-60, and glycerol monosterate were dissolved by heating at about 75° C. In the meanwhile, compound of Example 81, methyl paraben and propyl paraben were dissolved in propylene glycol, 20g of pure water was added thereto, and the mixture was heated at about 75° C. and added to the above-prepared mixture followed by stirring to give an emulsion. This was gradually cooled with stirring.

INDUSTRIAL APPLICABILITY

The condensed tetracyclic hetero-ring compounds of the invention exhibit an extremely high isozyme selectivity for inhibiting PDE type V and the inhibitory action of the compounds of the invention against PDE type VI was shown at higher concentrations than that against PDE type V and there is difference in the potency of these actions. Furthermore, the compounds of the invention have an enhancing action to smooth muscle relaxation of corpus cavernosum in vitro, and intravenous injection of the compounds of the invention enhances the elevation in intracavernous pressure induced by intracavernous injection of sodium nitroprusside in vivo.

On the other hand, the compounds of the invention were shown to be low in toxicity since nothing abnormal was found in the result of the toxicity test. Moreover, the compounds of the invention have less effects on hemodynamics such as vertebral blood flow and common carotid blood flow and less binding affinity to adenosine receptors.

Therefore, they have an extremely low toxicity, and are useful as pharmaceuticals both clinically and in animals and expected to be particularly effective in preventing and/or treating pulmonary hypertension, ischemic heart diseases, erectile dysfunction, female sexual dysfunction or other diseases against which the cGMP-PDE inhibitory action is effective.

The compounds represented by the formula (I) of the invention have potent and highly selective action in the enzyme inhibition of PDE type V and weak action in lowering blood pressure, and have less side effects such as a headache. In addition, since the inhibitory action of the compounds of the invention against PDE type VI was shown at higher concentrations than that against PDE type V, the compounds of the invention have less side effects on the retina and cause less defects in vision such as changes in blue/green color and increased sensitivity to light. The compound of the invention by intranasal administration shows prompt and efficient absorption and suitable acting time for its pharmaceutical effect. Further, it shows no irritation, congestion and engorgement to nasal mucous membrane and, in addition, it shows no side effect in digestive organs.

The pharmaceutical compositions of the invention are also effective in treating or preventing pulmonary hypertension, ischemic heart diseases, erectile dysfunction, female sexual dysfunction and other diseases against which the cGMP-PDE inhibitory action is effective. "Pulmonary hypertension" is a generic term for the various diseases that manifest hypertension in the pulmonary artery and it includes chronic bronchitis, peripheral lesions in the airway, pulmonary pneumatosis, bronchiectasis, sarcoidosis, sequelae of pulmonary tuberculosis, diffuse interstitial pneumonia, diffuse bronchiolitis, asthma, fibroid lung, collagenosis, pulmonary thromboembolism, pulmonary venous obstruction, pulmonary arteritis and primary pulmonary hypertension, as well as diseases such as cor pulmonale that are in a developed stage of pulmonary hypertension. Patients manifesting pulmonary hypertension suffer from disorders in pulmonary circulation due to the obstruction of pulmonary vessels and experience cyanosis and dyspnea. They often complain of palpitation and pectoralgia, as well as coughing. The pharmaceutical compositions of the invention are effective against these symptoms.

The term "ischemic heart diseases" as used herein refers to all diseases that occur as the result of disorders in coronary circulation due to various causes and it covers angina of effort, angina pectoris decubitus, unstable angina, variant angina pectoris, acute heart failure, chronic heart failure, myocardial infarction, cardiac edema and arrhythmia. Patients with ischemic heart diseases suffer from transient or sustained anginal pains such as pectoralgia and a feel of pressure in the chest, frequently accompanied by a feel of fatigue, vertigo, breathlessness, vomiting and impaired consciousness. In heart failure, dyspnea and cyanosis are manifested and due to a marked drop in blood pressure, shock symptoms such as bradycardia, cold sweat and pallor of the face are also manifested. The pharmaceutical compositions of the invention are effective against the various symptoms described above.

Further, the pharmaceutical compositions of the invention increase the cGMP level markedly and are also applicable to arteriosclerosis, post-PTCA restenosis and thrombosis (caused by, for example, injury of vascular walls, arteriosclerosis, arterits and platelet aggregation).

In addition, aside from those listed above, the "diseases against which the cGMP-PDE inhibitory action is effective" include the following against which increased CGMP levels are believed to be effective: asthma, chronic obstructive pulmonary diseases (e.g. bronchitis and pulmonary pneumatosis), glomerular diseases including glomerular nephritis and diabetic nephropathy, renal failure, nephritic edema, diseases in urinary organs and genital system (e.g. prostatomegaly, impotence and incontinence), female sexual dysfunction, peripheral circulatory disorders, peripheral vascular diseases, cerebral circulatory disorders (e.g., cerebral infarction), brain dysfunction, dementia, allergic diseases (e.g. atopic dermatitis and allergic rhinitis) and hypertension. The pharmaceutical compositions of the invention are also applicable to these diseases, among which asthma, chronic obstructive pulmonary diseases (e.g. bronchitis and pulmonary pneumatosis), glomerular diseases including glomerular nephritis and diabetic nephropathy, renal failure, nephritic edema, diseases in urinary organs and genital system (e.g. prostatomegaly, impotence and incontinence), and female sexual dysfunction are worth particular mention.

Impotence may be defined as the lack of the ability to perform sexual intercourse on the part of a male sex. More specifically, impotence or erectile dysfunction may be defined as the condition where males cannot achieve or maintain an erection firm and long enough to accomplish intercourse. The mechanism of erection is generally held to involve the NO-cGMP system and since NO which is the entity of a vascular endothelial cell derived relaxing factor is known to manifest its vasodilating action as mediated by cGMP, erectile dysfunction can be ameliorated by suppressing the cGMP decomposing system so that the cGMP level is maintained.

Female sexual dysfunction means impaired sexual functions including orgasmic dysfunction associated with disorders in the clitoris. Female sexual dysfunction can be ameliorated by suppressing the cGMP decomposing system so that the cGMP level is maintained.

"Renal failure" refers to those pathologic and clinical symptoms which are manifested by defective function of the kidneys, i.e., the decrease in glomerular filtration rate (GFR) due to various etiological factors. In chronic renal failure, some glomeruli give a sclerotic image but the progress of the sclerosis to less affected glomeruli would bring the renal failure to a developed phase. As a result, various excreted substances will accumulate in the body to cause "uremia". Polyuria and nocturia also occur due to disordered concentrating ability. If inappropriate Na and water loading accompanies renal failure, reduced GFR prevents sufficient compensation, causing edema, pulmonary edema, congestive heart failure, hypertension, etc. The pharmaceutical compositions of the invention are also effective against these symptoms as described above.

Using the production processes of the invention, one can produce condensed tetracyclic hetero-ring compounds which exhibit a PDE type V inhibitory action featuring an extremely high selectivity in enzyme inhibition.

What is claimed is:

1. A compound represented by the following formula (I) or a salt thereof:

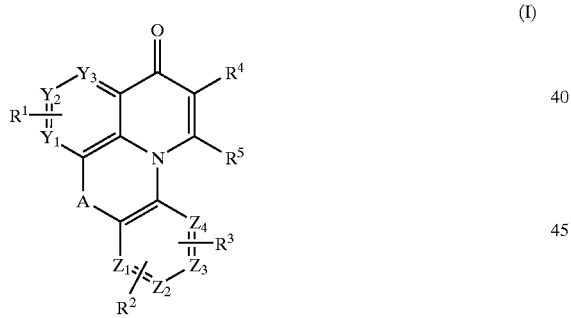

where:
A represents a carbonyl group, an oxygen atom, a group: —$SO_n$—(n is 0), a group: —$N(R^6)$—($R^6$ is a hydrogen atom, a straight- or branched-chain alkyl group having 1–4 carbon atoms or a straight- or branched-chain alkanoyl group having 1–4 carbon atoms);

$Y^1$–$Y^3$ and $Z^1$–$Z^4$ represent each a methine group;

$R^1$ represents a hydrogen atom, a halogen atom, a cyano group, an optionally protected carboxyl group, an optionally protected carboxymethyl group, an alkoxycarbonyl group having 1–4 carbon atoms, a carbamoyl group, an acetylamino group, a 3-carboxy-1-propenyl group, a 2-hydroxypentyloxy group, a 2,2-diethoxyethoxy group, an optionally protected hydroxyl group, an optionally protected mercapto group, a straight- or branched-chain alkanoyloxy group having 1–4 carbon atoms, a caronyloxy group substituted by a phenyl group or a pyridyl group, a straight- or branched-chain alkyl group having 1–4 carbon atoms which may be substituted by one hydroxyl group, an amino group which may be mono-or disubstituted by an alkyl group having 1–4 carbon atoms, an alkylthio group having 1–3 carbon atoms which may be monosubstituted by any group selected from the group consisting of a hydroxyl group, a carboxyl group, a phenyl group and a pyridyl group, a 1-methyl-hexahydroazepin-4-yl-oxy group, or is represented by the following formula (II):

wherein Q represents a hydrogen atom, a carboxyl group, an alkoxy group having 1 or 2 carbon atoms which may be substituted by one hydroxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or one mercapto group, a piperidinylcarbonyl group which may be substituted by one carboxyl group or alkoxycarbonyl group having 1 or 2 carbon atoms, a morpholylcarbonyl group, a hydroxyl group, a mercapto group, a group: —$NR^{24}R^{24}$ ($R^{24}$ represents a hydrogen atom or an alkyl group having 1–4 carbon atoms and the two $R^{24}$S may be the same or different, or may combine with each other to form a ring), a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyridyl group which may be monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyrazinyl group, a pyrimidinyl group, a furyl group, a thienyl group, an oxadiazolyl group or a 4-methoxyphenoxy group, a 1-benzotriazolyl group, a 4-morpholinyl group, or 2-benzimidazolyl group; and n is 1–6;

$R^2$ represents a hydrogen atom, a halogen atom, an optionally protected hydroxyl group, an optionally protected mercapto group, an optionally protected amino group, a cyano group, a nitro group, a trifluoromethyl group, a trifluoromethoxy group, an optionally protected carboxyl group, a 4-morpholylacetyl group, a straight- or branched-chain alkanoyloxy group having 1–4 carbon atoms, a straight- or branched-chain alkanoyl group having 1–4 carbon atoms, a straight- or branched-chain alkyl group having 1–4 carbon atoms, an alkylthio group having 1–3 carbon atoms which may be monosubstituted by any group selected from the group consisting of a hydroxyl group, a carboxyl group, a phenyl group and a pyridyl group, or a straight- or branched-chain alkoxy group having 1–4 carbon atoms which may be monosubstituted by any group selected from the group consisting of an alkoxycarbonyl group having 1–4 carbon atoms, a hydroxyl group, a carboxyl group, a phenyl group and a pyridyl group;

$R^3$ represents a hydrogen atom, a halogen atom, an optionally protected hydroxyl group or a straight- or branched-chain alkoxy group having 1–4 carbon atoms;

$R^4$ represents a hydrogen atom, a halogen atom, a group: —M—G wherein
  M represents an oxygen atom, an imino group or a group: —N(CH$_3$)—, and
  G represents a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, an alkyl group having 1 or 2 carbon atoms which may be substituted by a cyclic alkyl group having 3–6 carbon atoms, a benzyl group which may be mono- or disubstituted in the benzene ring by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxy group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyridylmethyl group which may be monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a morpholylmethyl group, a triazolylmethyl group, a furylmethyl group, a thienylmethyl group, a pyrimidinylmethyl group, a pyrazinylmethyl group, a pyrrolylmethyl group, an imidazolylmethyl group, a quinolylmethyl group, an indolylmethyl group, a naphthylmethyl group, a benzoyl group or an α-hydroxybenzyl group;

$R^5$ represents a hydrogen atom or a methyl group; and with the proviso that the compounds where A represents a sulfur atom, $Y^1$–$Y^3$ and $Z^1$–$Z^4$ represent a methine group, $R^1$, $R^2$, $R^3$ and $R^5$ represent respectively a hydrogen atom, and $R^4$ represents a hydrogen atom, a benzyl group, a 4-methoxybenzyl group, a 4-dimethylaminobenzyl group, a 4-chlorobenzyl group, a 3-nitrobenzyl group, or a bromine atom are excluded; and with the proviso that the compounds where A represents an oxygen atom;

$Y^1$–$Y^3$ and $Z^1$–$Z^4$ represent a methine group, $R^1$, $R^2$, $R^3$ and $R^5$ represent respectively a hydrogen atom, and $R^4$ represents a hydrogen atom, a benzyl group, a 4-methoxybenzyl group, a 4-dimethylaminobenzyl group, a 4-chlorobenzyl group, or a 3-nitrobenzyl group are excluded; and1 with the proviso that the compounds where A represents a carbonyl group;

$Y^1$–$Y^3$ and $Z^1$–$Z^4$ represent a methine group, $R^2 R^3$, $R^4$ and $R^5$ represent respectively a hydrogen atom, and $R^1$ represents a methoxy group at position 5 are excluded; and with the provision that the compounds where A represents a carbonyl group;

$Y^1$–$Y^3$ and $Z^1$–$Z^4$ represent a methine group, $R^1$, $R^4$ and $R^5$ represent respectively a hydrogen atom, and one of $R^2$ and $R^3$ represents a hydrogen atom and the other one of $R^2$ and $R^3$ represents a methoxy group at position 9 are excluded; and with the proviso that the compounds wherein A represents a group: $SO_n$ (n is 1);

$y^1$–$y^3$ and $Z^1$–$Z^4$ represent a methine group, and $R^1$, $R^2$, $R^3$, $R^4$ and $R^5$ represent respectively a hydrogen atom.

2. The compound according to claim 1, or a salt thereof, wherein A is a sulfur atom.

3. The compound according to claim 2, or a salt thereof, wherein
  $R^1$ is substituted at position 5,
  $R^2$ is a hydrogen atom, a halogen atom, a hydroxy group, a cyano group, a trifluoromethyl group or a straight- or branched-chain alkoxy group having 1–4 carbon atoms which is substituted at position 9 or 10, and
  $R^3$ is a hydrogen atom.

4. The compound according to claim 3, or a salt thereof, wherein $R^4$ is a hydrogen atom, an alkyl group having 1 or 2 carbon atoms, a pyrimidinylmethyl group, a pyridylmethyl group which may be substituted by a methyl group or a benzyl group.

5. The compound according to claim 4, or a salt thereof, wherein
  $R^1$ is substituted at position 5, and is either a hydroxyl group or represented by the following formula (II):

$$—O—(CH_2)_n—Q \qquad (II)$$

wherein
  Q represents a hydrogen atom, a hydroxyl group, a group: —NR$^{24}$R$^{24}$ (R$^{24}$ represents a hydrogen atom or an alkyl group having 1–4 carbon atoms and the two R$^{24}$S may be the same or different, or may combine with each other to form a ring), a phenyl group, a pyridyl group which may be monosubstituted by a hydroxymethyl group, an acetoxymethyl group or an alkyl group having 1–4 carbon atoms, or a 1-benzotriazolyl group; and n is 1–4;

$R^2$ is a halogen atom which is substituted at position 10;

$R^3$ is a hydrogen atom;

$R^4$ is a pyridylmethyl group; and $R^5$ is a hydrogen atom.

6. A compound of formula 10-bromo-2-(3-pyridylmethyl)-5-(3-pyridylmethyloxy)-3H-pyrido[3,2,1-k1] phenothiazin-3-one or a salt thereof.

7. The compound according to claim 1, or a salt thereof wherein

A is carbonyl group, $R^1$ is substituted at position 5, and is either a hydroxyl group or represented by the following formula (II):

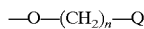   (II)

where

Q represents a hydrogen atom, a hydroxyl group, a group: —$NR^{24}R^{24}$ where $R^{24}$ represents a hydrogen atom or an alkyl group having 1–4 carbon atoms and the two $R^{24}$s may be the same or different, or may combine with each other to form a ring, a phenyl group, a pyridyl group which may be monosubstituted by a hydroxymethyl group, an acetoxymethyl group or an alkyl group having 1–4 carbon atoms or a 1-benzotriazolyl group; and n is 1–4;

$R^2$ is a halogen atom which is substituted at position 10;

$R^3$ is a hydrogen atom;

$R^4$ is a pyridylmethyl group; and $R^5$ is a hydrogen atom.

8. A compound or the salt thereof selected from the group consisting of:

1) 10-bromo-5-(3-hydroxypropyloxy)-2-(3-pyridylmethyl)-3H, 7H-pyrido(3,2,1-de)acridin-3,7-dione;

2) 10-bromo-2-(3-pyridylmethyl)-5-(3-pyridylmethyloxy)-3H, 7H-pyrido(3,2,1-de)acridin-3,7-dione;

3) 10-bromo-2-(3-pyridylmethyl)-5-(4-pyridylmethyloxy)-3H-pyrido(3,2,1-k1)phenothiazin-3-one;

4) 10-bromo-2-(3-pyridylmethyl)-5-(2-pyridylmethyloxy)-3H-pyrido(3,2,1-k1)phenothiazin-3-one;

5) 5-(1-benzotriazolylmethyloxy)-10-bromo-2-(3-pyridylmethyl)-3H-pyrido(3,2,1-k1)phenothiazin-3-one;

6) 10-bromo-5-(2-(1-piperidyl)ethyloxy)-2-(3-pyridylmethyl)-3H-pyrido(3,2,1-k1)phenothiazin-3-one; and 7) 10-bromo-5-(2-diisopropylaminoethyloxy)-2-(3-pyridylmethyl)-3H-pyrido(3,2,1-k1)phenothiazin-3-one.

9. A compound or a salt thereof which is useful for the synthesis of compounds of said formula (I) or salts thereof, said compound being represented by the following formula (VI):

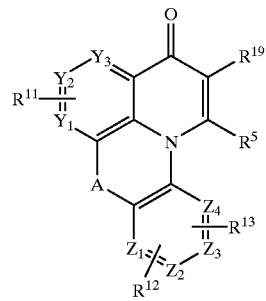   (VI)

wherein

A represents a carbonyl group, an oxygen atom, a group: —$SO_n$—(n is 0), a group: —$N(R^6)$—;

$Y^1$–$Y^3$ and $Z^1$–$Z^4$ represent each a methine group;

$R^5$ represents a hydrogen atom;

$R^6$ represents a hydrogen atom, a straight- or branched-chain alkyl group having 1–4 carbon atoms or a straight- or branched-chain alkanoyl group having 1–4 carbon atoms;

$R^{11}$ represents a hydrogen atom, a halogen atom, a cyano group, an optionally protected carboxyl group, an optionally protected carboxymethyl group, an alkoxycarbonyl group having 1–4 carbon atoms, a carbamoyl group, an acetylamino group, an optionally protected hydroxyl group, an optionally protected mercapto group, a straight- or branched-chain alkyl group having 1–4 carbon atoms which may optionally be substituted by one hydroxyl group, an amino group which may optionally be mono- or disubstituted by an alkyl group having 1–4 carbon atoms, an alkylthio group having 1–3 carbon atoms, or a straight-chain alkoxy group having 1–6 carbon atoms which may optionally be substituted by a 4-methoxyphenoxy group;

$R^{12}$ represents a hydrogen atom, a halogen atom, an optionally protected hydroxyl group, an optionally protected mercapto group, an optionally protected amino group, a cyano group, a nitro group, a trifluoromethyl group, a trifluoromethoxy group, an optionally protected carboxyl group, a straight- or branched-chain alkanoyl group having 1–4 carbon atoms, a straight- or branched-chain alkyl group having 1–4 carbon atoms, or a straight- or branched-chain alkoxy group having 1–4 carbon atoms;

$R^{13}$ represents a hydrogen atom, a halogen atom, an optionally protected hydroxyl group or a straight- or branched-chain alkoxy group having 1–4 carbon atoms;

$R^{19}$ represents a hydrogen atom, a halogen atom, a group: —M—G where

M represents an oxygen atom, an imino group or a group: —$N(CH_3)$—, and

G represents a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group), an α-hydroxybenzyl group, a methyl group or a halogenomethyl group with the proviso that the compounds wherein, A represents an oxygen atom or a group: —SO$_n$—(n is 0), Y$^1$–Y$^3$ and Z$^1$–Z$^4$ represent a methine group, and all of R$^5$, R$^{11}$, R$^{12}$, R$^{13}$ and R$^{19}$ represent respectively a hydrogen atom are excluded; and with the proviso that the compounds wherein, A represents a sulfur atom, Y$^1$–Y$^3$ and Z$^1$–Z$^4$ represent a methine group, R$^5$, R$^{11}$ and R$^{19}$ represent respectively a hydrogen atom, and one of R$^{12}$ and R$^{13}$ represents a hydrogen atom and the other one of R$^{12}$ and R$^{13}$ represents a fluorine atom, a chlorine atom or a bromine atom at position 10, or a chlorine atom at position 11 are excluded; and with the proviso that the compounds wherein, A represents a sulfur atom, Y$^1$–Y$^3$ and Z$^1$–Z$^4$ represent a methine group, R$^5$, R$^{11}$, R$^{12}$ and R$^{13}$ represent respectively a hydrogen atom, and R$^{19}$ represents a bromine atom or a methyl group are excluded; and with the proviso that the compounds wherein, A represents a sulfur atom, Y$^1$–Y$^3$ and Z$^1$–Z$^4$ represent a methine group, R$^5$, R$^{12}$, R$^{13}$ and R$^{19}$ represent respectively a hydrogen atom, and R$^{11}$ represents a chlorine atom at position 4 are excluded; and with the proviso that the compounds wherein, A represents a sulfur atom, Y$^1$–Y$^3$ and Z$^1$–Z$^4$ represent a methine group, R$^5_1$, R$^{11}$, R$^{13}$ and R$^{19}$ represent respectively a hydrogen atom, and R$^{12}$ represents a trifluoromethyl group at position 9, 10 or 11 are excluded, and with the proviso that the compounds wherein, A represents a sulfur atom, Y$^1$–Y$^3$ and Z$^1$–Z$^4$ represent a methine group, R$^5$, R$^{13}$, and R$^{19}$ represent respectively a hydrogen atom, R$^{11}$ represents a methyl group at position 4, and R$^{12}$ represents a trifluoromethyl group at position 10.

10. The compound according to claim 9 or salt thereof, wherein in the compound represented by the formula (VI), A represents a carbonyl group or a sulfur atom;

R$^{11}$ represents an optionally protected hydroxyl group or a straight-chain alkoxy group having 1–6 carbon atoms;

R$^{12}$ represents a hydrogen atom or a halogen atom;

R$^{13}$ represents a hydrogen atom; and

R$^{19}$ represents a hydrogen atom.

11. A process for producing derivative compounds of formula (I) or a salt thereof of claim 1:

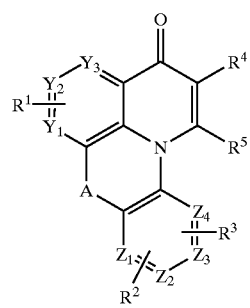

(I)

comprising:

1) optionally reacting under basic conditions a compound represented by the following formula (VI) or a salt thereof:

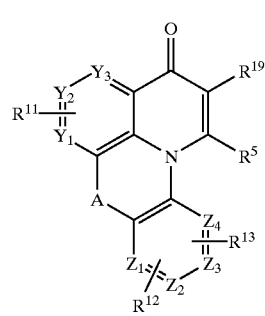

(VI)

wherein

A represents a carbonyl group, an oxygen atom, a group: —SO$_n$—(n is 0), a group: —N(R$^6$) (R$^6$ is a hydrogen atom, a straight- or branched-chain alkyl group having 1–4 carbon atoms or a straight- or branched-chain alkanoyl group having 1–4 carbon atoms);

Y$^1$–Y$^3$ and Z$^1$–Z$^4$ represent each a methine group;

R$^5$ represents a hydrogen atom or a methyl group;

R$^{11}$ represents a hydrogen atom, a halogen atom, a cyano group, an optionally protected carboxyl group, an optionally protected carboxylmethyl group, an alkoxycarbonyl group having 1–4 carbon atoms, a carbamoyl group, an acetylamino group, an optionally protected hydroxyl group, an optionally protected mercapto group, a straight- or branched-chain alkyl group having 1–4 carbon atoms which may optionally be substituted by one hydroxyl group, an amino group which may optionally be mono- or disubstituted by an alkyl group having 1–4 carbon atoms, an alkylthio group having 1–3 carbon atoms, or a straight-chain alkoxy group having 1–6 carbon atoms which may optionally be substituted by a 4-methoxyphenoxy group;

R$^{12}$ represents a hydrogen atom, a halogen atom, an optionally protected hydroxyl group, an optionally protected mercapto group, an optionally protected amino group, a cyano group, a nitro group, a trifluoromethyl group, a trifluoromethyloxy group, an optionally protected carboxyl group, a straight- or branched-chain alkanoyl group having 1–4 carbon atoms, a straight- or branched-chain alkyl group having 1–4 carbon atoms, or a straight- or branched-chain alkoxy group having 1–4 carbon atoms;

$R^{13}$ represents a hydrogen atom, a halogen atom, an optionally protected hydroxyl group or a straight- or branched-chain alkoxy group having 1–4 carbon atoms;

$R^{19}$ represents a hydrogen atom, a halogen atom, a group: —M—G wherein
  M represents an oxygen atom, an imino group or a group: —N(CH$_3$)—, and
  G represents a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, an α-hydroxybenzyl group, a methyl group or a halogenomethyl group, with an aldehyde derivative represented by the following formula (XVII):

$$R^{22}\text{—CHO} \quad \quad \text{(XVII)}$$

wherein
  $R^{22}$ represents a hydrogen atom, a methyl group, a cyclic alkyl group having 3–6 carbon atoms, a phenyl group which may be mono- or disubstituted in the benzene ring by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyridyl group which may be monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group, an acetoxymethyl group, a morpholyl group, a triazolyl group, a furyl group, a thienyl group, a pyrimidinyl group, a pyrazinyl group, a pyrrolyl group, an imidazolyl group, a quinolyl group, an indolyl group or a naphthyl group;

2) isolating or dehydrating the reaction product to yield an enone, which has the double bond subsequently isomerized in the ring;

3) subjecting the reaction product to an oxidation, either immediately or after reaction with phenol, aniline, N-methylaniline, triazole, imidazole, morpholine;

4) deriving a compound represented by the following formula (XIV):

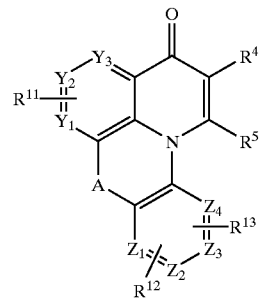

(XIV)

wherein $R^4$, $R^5$, $R^6$, $R^{11}$, $R^{12}$, $R^{13}$, $Y^1$–$Y^3$, $Z^1$–$Z^4$ and A have the same meanings as defined in claim 1 or claim 9, and said compound (XIV) is optionally subjected to a suitable substituents change and, after optional deprotection of $R^{11}$, reacted with a reactive halogen derivative represented by the following formula (XVIII):

$$R^{23}\text{—X} \quad \quad \text{(XVIII)}$$

wherein
X is a halogen atom, and
$R^{23}$ represents an alkoxycarbonyl group having 1–4 carbon atoms, a 3-carboxy-1-propenyl group, a 2,2-diethoxyethyl group, a straight- or branched-chain alkanoyl group having 1–4 carbon atoms, a carbonyl group substituted by a phenyl group or a pyridyl group, or a group: —(CH$_2$)$_n$—Q wherein
Q represents a hydrogen atom, a carboxyl group, an alkoxy group having 1 or 2 carbon atoms which may be substituted by one hydroxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or one mercapto group, a piperidinylcarbonyl group which may be substituted by one carboxyl group or alkoxycarbonyl group having 1 or 2 carbon atoms, a morpholylcarbonyl group, a hydroxyl group, a mercapto group, a group: —NR$^{24}$R$^{24}$ wherein $R^{24}$ represents a hydrogen atom or an alkyl group having 1–4 carbon atoms and the two $R^{24}$s may be the same or different, or may combine with each other to form a ring, a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyridyl group which may be monosubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group, an amino group, a cyano group, a nitro group, an amino group mono- or disubstituted by a lower alkyl group, a carbamoyl group, an alkyl group having 1–4 carbon atoms, a hydroxymethyl group and an acetoxymethyl group, a pyrazinyl group, a pyrimidinyl group, a furyl group, a thienyl group, an oxadiazolyl group, a 4-methoxyphenoxy group, a 1-benzotriazolyl group, a 4-morpholinyl group, or 2-benzimidazolyl group;

n is 1–6 to yield a compound represented by the following formula (XV):

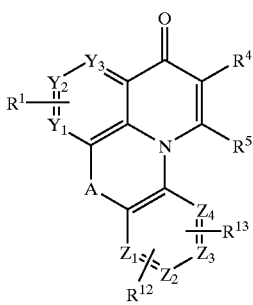

(XV)

wherein $R^1$, $R^4$, $R^5$, $R^6$, $R^{12}$, $R^{13}$, $Y^1$–$Y^3$, $Z^1$–$Z^4$ and A have the same meanings as defined in claim 1 or claim 9, which is subjected to a suitable substituents change, or alternatively, the compound represented by the formula (XIV) is subjected to a suitable substituent change to yield a compound represented by the following formula (XVI):

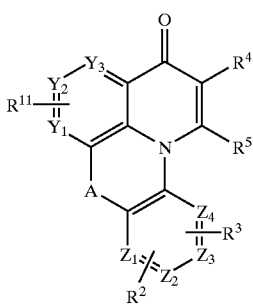

(XVI)

wherein $R^2$, $R^3$, $R^4$, $R^5$, $R^{11}$, $Y^1$–$Y^3$, $Z^1$–$Z^4$ and A have the same meanings as defined in claim 1 or claim 9, which is optionally subjected to deprotection of $R^{11}$, when $R^{11}$ is reacted with the reactive halogen derivative represented by said formula (XVIII).

12. The process according to claim 11 in the compound represented by the formula (VI) or a salt thereof, wherein A represents a carbonyl group or a sulfur atom;

$R^{11}$ represents an optionally protected hydroxyl group or a straight-chain alkoxy group having 1–6 carbon atoms;

$R^{12}$ represents a hydrogen atom or a halogen atom;

$R^{13}$ represents a hydrogen atom; and $R^{19}$ represents a hydrogen atom.

13. A pharmaceutical composition comprising an effective amount of at least one of the compounds of claims 1, 5,or 8 or pharmaceutically acceptable salts thereof as an active ingredient; and a pharmaceutically acceptable carrier.

14. A pharmaceutical composition, comprising:

an effective amount of 10-bromo-2-(3-pyridylmethyl)-5-(3-pyridylmethyloxy)-3H-pyrido[3,2,1-k1]phenothiazin-3-one or salt thereof as an active ingredient; and a pharmaceutically acceptable carrier.

15. A method for preventing or treating erectile dysfunction, comprising:

administering the composition of claim 13 to a patient.

16. A method for preventing or treating diseases against which the cGMP-PDE inhibitory action is effective, comprising:

administering the composition of claim 13 to a patient.

17. The method according to any one of claims 15–16, wherein the composition is administered to the patient by a dosage form of oral preparations.

18. The method according to any one of claims 15–16, which is administered to the patient by a dosage form of intranasal preparations.

19. The method according to any one of claims 15–16, which is administered to the patient by a dosage form of intraurethral preparations.

20. A method for preventing or treating erectile dysfunction comprising:

administering the composition of claim 14 to a patient.

21. A method for preventing or treating diseases against which the cGMP-PDE inhibitory action is effective, comprising:

administering the composition of claim 14 to a patient.

22. The method according to any one of claims 20 or 21, wherein the composition is administered to a patient by a dosage form of oral preparation.

23. The method according to any one of claims 20 or 21, wherein the composition is administered to a patient by a dosage form of intranasal preparation.

24. The method according to any one of claims 20 or 21, wherein the composition is administered to a patient by a dosage form of intraurethral preparation.

* * * * *